United States Patent
Maddaford et al.

(10) Patent No.: US 7,989,447 B2
(45) Date of Patent: *Aug. 2, 2011

(54) 1,5 AND 3,6-SUBSTITUTED INDOLE COMPOUNDS HAVING NOS INHIBITORY ACTIVITY

(75) Inventors: Shawn Maddaford, Mississauga (CA); Jailall Ramnauth, Brampton (CA); Suman Rakhit, Mississauga (CA); Joanne Patman, Mississauga (CA); Paul Renton, Toronto (CA); Subhash C. Annedi, Mississauga (CA)

(73) Assignee: NeurAxon, Inc., Mississauga (CA)

(*) Notice: Subject to any disclaimer, the term of this patent is extended or adjusted under 35 U.S.C. 154(b) by 265 days.

This patent is subject to a terminal disclaimer.

(21) Appl. No.: 11/787,167

(22) Filed: Apr. 13, 2007

(65) Prior Publication Data

US 2007/0254940 A1 Nov. 1, 2007

Related U.S. Application Data

(60) Provisional application No. 60/791,846, filed on Apr. 13, 2006.

(51) Int. Cl.
*C07D 409/14* (2006.01)
*C07D 407/14* (2006.01)
*A61K 31/439* (2006.01)
*A61K 31/405* (2006.01)
*A61K 31/454* (2006.01)
*A61K 31/5377* (2006.01)
*A61K 31/55* (2006.01)
*A61P 25/00* (2006.01)

(52) U.S. Cl. ............ 514/217.08; 514/235.5; 514/304; 514/305; 514/326; 514/361; 514/415; 540/602; 544/163; 546/126; 546/133; 546/201; 548/467; 548/468

(58) Field of Classification Search .................. None
See application file for complete search history.

(56) References Cited

U.S. PATENT DOCUMENTS

| | | | |
|---|---|---|---|
| 4,324,790 A | 4/1982 | Guillaume et al. | |
| 4,816,470 A | 3/1989 | Dowle et al. | |
| 4,816,560 A | 3/1989 | Verdini et al. | |
| 4,839,377 A * | 6/1989 | Bays et al. | 514/415 |
| 4,894,387 A | 1/1990 | Butina et al. | |
| 4,994,483 A | 2/1991 | Oxford et al. | |
| 5,037,845 A | 8/1991 | Oxford | |
| 5,070,102 A | 12/1991 | Traber et al. | |
| 5,103,020 A | 4/1992 | Albinson et al. | |
| 5,200,410 A | 4/1993 | Traber et al. | |
| 5,234,942 A | 8/1993 | Bernstein et al. | |
| 5,270,333 A | 12/1993 | Bays et al. | |
| 5,331,005 A | 7/1994 | Calderó Ges et al. | |
| 5,399,574 A | 3/1995 | Robertson et al. | |
| 5,466,699 A | 11/1995 | Robertson et al. | |
| 5,468,768 A | 11/1995 | Cipollina et al. | |
| 5,708,008 A | 1/1998 | Audia et al. | |
| 5,863,935 A | 1/1999 | Robertson et al. | |
| 5,874,427 A | 2/1999 | Filla et al. | |
| 5,998,438 A | 12/1999 | Slassi et al. | |
| 6,090,839 A | 7/2000 | Adams et al. | |
| 6,093,716 A | 7/2000 | Davis et al. | |
| 6,242,447 B1 | 6/2001 | Demopulos et al. | |
| 6,255,334 B1 | 7/2001 | Sands | |
| 6,380,201 B1 | 4/2002 | Johnson et al. | |
| 6,750,242 B1 | 6/2004 | Gurley et al. | |
| 6,861,443 B2 | 3/2005 | Gurley et al. | |
| 7,141,595 B2 | 11/2006 | Ramnauth et al. | |
| 7,375,219 B2 | 5/2008 | Maddaford et al. | |
| 2003/0064991 A1 | 4/2003 | Harriman et al. | |
| 2003/0203055 A1 | 10/2003 | Rao et al. | |
| 2004/0142935 A1 | 7/2004 | Schiemann et al. | |
| 2004/0259891 A1 | 12/2004 | Agarwal et al. | |
| 2005/0032791 A1 | 2/2005 | Merc-Vidal et al. | |
| 2005/0075348 A1 | 4/2005 | Harriman et al. | |
| 2005/0244389 A1 | 11/2005 | Fioramonti et al. | |
| 2005/0256182 A1 | 11/2005 | Sutter et al. | |
| 2006/0009512 A1 | 1/2006 | Curwen et al. | |
| 2006/0258721 A1 | 11/2006 | Maddaford et al. | |
| 2007/0105943 A1 | 5/2007 | Nakamoto et al. | |
| 2008/0249302 A1 | 10/2008 | Maddaford et al. | |
| 2009/0131503 A1 * | 5/2009 | Annedi et al. | 514/414 |
| 2009/0163451 A1 | 6/2009 | Porreca et al. | |
| 2009/0192157 A1 | 7/2009 | Maddaford et al. | |

FOREIGN PATENT DOCUMENTS

| | | |
|---|---|---|
| CA | 2380775 | 2/2002 |
| CA | 2498644 | 2/2005 |
| EP | 0262873 | 4/1988 |
| EP | 0 438 230 | 7/1991 |
| EP | 0 574 618 | 12/1993 |
| EP | 1 571 142 | 9/2005 |
| JP | 6212151 | 8/1994 |
| JP | 2000280626 | 10/2000 |

(Continued)

OTHER PUBLICATIONS

Johnson et al, Chemical Abstracts, 128:192544, 1998.*
Johnson et al., Chemical Abstracts, 128:257330, 1998.*
Kitazawa et al., Chemical Abstracts, 129:302522, 1998.*
Kuyper et al., J. Med. Chem., 39(4), 892-903, 1996.*
Abdel-Magid et al., "Reductive Amination of Aldehydes and Ketones with Sodium Triacetoxyborohydride. Studies on Direct and Indirect Reductive Amination Procedures," *J.Org.Chem.*, 61: 3849-3862, 1996.
Adachi et al., "Aminohaloborane in Organic Synthesis. IX. Exclusive *ortho* Acylation Reaction of *N*-Monoaminoalkylanilines," *Chem. Pharm. Bull.*, 33: 1826-1835, 1985.

(Continued)

*Primary Examiner* — Fiona T Powers
(74) *Attorney, Agent, or Firm* — Clark & Elbing LLP

(57) ABSTRACT

The present invention features inhibitors of nitric oxide synthase (NOS), particularly those that selectively inhibit neuronal nitric oxide synthase (nNOS) in preference to other NOS isoforms. The NOS inhibitors of the invention, alone or in combination with other pharmaceutically active agents, can be used for treating or preventing conditions such as, for example, stroke, reperfusion injury, neurodegeneration, head trauma, CABG, migraine headache with and without aura, migraine with allodynia, central post-stroke pain (CPSP), neuropathic pain, or chronic pain.

20 Claims, 1 Drawing Sheet

FOREIGN PATENT DOCUMENTS

| | | |
|---|---|---|
| JP | 2005129430 | 5/2005 |
| WO | WO 91/18897 | 12/1991 |
| WO | WO 92/13856 | 8/1992 |
| WO | WO 93/11106 | 6/1993 |
| WO | WO 94/03446 | 2/1994 |
| WO | WO 97/47302 | 12/1997 |
| WO | WO 98/11895 | 3/1998 |
| WO | WO 00/00487 | 1/2000 |
| WO | WO 00/17198 | 3/2000 |
| WO | WO 00/38677 | 7/2000 |
| WO | WO 01/12187 | 2/2001 |
| WO | WO 01/32619 | 5/2001 |
| WO | WO 02/16318 | 2/2002 |
| WO | WO 03/051275 | 6/2003 |
| WO | WO 2004/014885 | 2/2004 |
| WO | WO 2005/013974 | 2/2005 |
| WO | WO 2005/024416 | 3/2005 |
| WO | WO 2005/090282 | 9/2005 |
| WO | WO 2007/118314 | 10/2007 |

OTHER PUBLICATIONS

Anderson et al., "Palladium-Catalyzed Amination of Aryl Nonaflates," *J.Org.Chem*,. 68: 9563-9573, 2003.

Antilla et al., "Copper-Catalyzed Coupling of Arylboronic Acids and Amines," *Organic Letters*, 3: 2077-2079, 2001.

Baati et al., "An Improved Method for the Preparation of Amidines Via Thiophenylimidic Esters," *Synthesis*, 927-929, 1999.

Blair et al., "Effect of Ring Fluorination on the Pharmacology of Hallucinogenic Tryptamines," *J. Med. Chem.*, 43:4701-4710, 2000.

Castro et al., "Enhancement of Oral Absorption in Selective 5-HT$_{1D}$ Receptor Agonists: Fluorinated 3-[3-(Piperidin-1-yl)propyl]indoles," *J. Med. Chem.*, 41: 2667-2670, 1998.

Coe et al., "Convenient preparation of N-Substituted Indoles by Modified Leimgruber-Batcho Indole Synthesis," *Tet. Lett.*, 37:6045-6048, 1996.

Cooper et al., 2-Aryl Indole NK$_1$ Receptor Antagonists: Optimisation of Indole Substitution, *Bioorg. Med. Chem. Lett.*, 11: 1233-1236, 2001.

Heaney et al., "1-Benzylindole," *Organic Syntheses*, *Coll.* vol. 6, p. 104, 1988.

Huang et al., "New Ammonia Equivalents for the Pd-Catalyzed Amination of Aryl Halides," *Org. Lett.*, 3: 3417-3419, 2001.

Kim et al., "An Experimental Model for Peripheral Neuropathy Produced by Segmental Spinal Nerve Ligation in the Rat," *Pain*, 50: 355-363, 1992.

Macor et al., "5-[(3-Nitropyrid-2-yl)amino]indoles: Novel Serotonin Agonists with Selectivity for the 5-HT$_{1D}$ Receptor. Variation of the C3 Substituent on the Indole Template Leads to Increased 5-HT$_{1D}$ Receptor Selectivity," *J. Med. Chem.*, 37: 2509-2512, 1994.

McKay, "The Preparation of N-Substituted-N$^1$-Nitroguanidines by the Reaction of Primary Amines with N-Alkyl-N-Nitroso-N$^1$-Nitroguanidines," *J. Am. Chem. Soc.*, 71: 1968-1970, 1949.

Perregaard et al., "Selective, Centrally Acting Serotonin 5-HT$_2$ Antagonists. 1. 2- and 6-Substituted 1-Phenyl-3-(4-piperidinyl)-1*H*-indoles," *J. Med. Chem.*, 35: 4813-4822, 1992.

Rowley et al., "3-(4-Fluoropiperidin-3-yl)-2-phenylindoles as High Affinity, Selective and Orally Bioavailable h5-HT$_{2A}$ Receptor Antagonists," *J. Med. Chem.*, 44: 1603-1614, 2001.

Russell et al., "3-[3-(Piperidin-1-yl)propyl]indoles as Highly Selective h5-HT$_{1D}$ Receptor Agonists," *J. Med. Chem.*, 42: 4981-5001, 1999.

Speeter et al., "The Action of Oxalyl Chloride on Indoles: A New Approach to Tryptamines," *J. Am. Chem. Soc.*, 76: 6208-6210, 1954.

Sternfeld et al., "Synthesis and Serotonergic Activity of 3-[2-(Pyrrolidin-1-yl)ethyl]indoles: Potent Agonists for the h5-HT$_{1D}$ Receptor with High Selectivity over the h5-HT$_{1B}$ Receptor," *J. Med. Chem.* 42: 677-690, 1999.

Suh et al., "Novel Potent Antagonists of Transient Receptor Potential Channel, Vanilloid Subfamiliy Member 1: Structure-Activity Relationship of 1,3-Diarylalkyl Thioureas Possessing New Vanilloid Equivalents," *J. Med. Chem.*, 48: 5823-5836, 2005.

Wiedenau et al., "Facile Synthesis of 2-Benzylindoles," *Synthetic Communications*, 27: 2033-2039, 1997.

Wolfe et al., "Simple, Efficient Catalyst System for the Palladium-Catalyzed Amination of Aryl Chlorides, Bromides, and Triflates," *J. Org. Chem.*, 65: 1158-1174, 2000.

Written Opinion of the International Searching Authority, (PCT/CA2007/000617) mailed Jul. 18, 2007.

Acton et al., "Benzoyl 2-Methyl Indoles as Selective PPAR$_\gamma$ Modulators," *Bioorg. Med. Chem. Lett.* 15:357-362 (2005).

Berridge, "The Mode of Action of 5-Hydroxytryptamine," *J. Exp. Biol.* 56:311-321 (1972).

Dörwald, "Side Reactions in Organic Synthesis," *Wiley-VCH* (2005).

Jordan, "Tamoxifen: A Most Unlikely Pioneering Medicine," *Nature Reviews.* 2:205-213 (2003).

Mahindroo et al., "Novel Indole-Based Peroxisome Proliferator-Activated Receptor Agonists: Design, SAR, Structural Biology, and Biological Activities," *J. Med. Chem.* 48:8194-8208 (2005).

Macor et al., "Use of 2,5-Dimethylpyrrole as an Amino-Protecting Group in an Efficient Synthesis of 5-Amino-3-[(N-methyl-pyrrolidin-2(R)-yl)methyl]indole," *J. Org. Chem.*, 59:7496-7498 (1994).

Non-Final Office Action for U.S. Appl. No. 12/272,656 on Jun. 11, 2009.

van Niel et al., "Fluorination of 3-(3-(Piperidin-1-yl)propyl)indoles and 3-(3-(Piperazin-1-yl)propyl)indoles Gives Selective Human 5-HT1D Receptor Ligands with Improved Pharmacokinetic Profiles," *J. Med. Chem.*, 42:2087-2104 (1999).

Egle et al., "3-(2-Pyrrolidin-1-ylethyl)-5-(1,2,3,6-Tetrahydropyridin-4-yl)-1H-indole Derivatives as High Affinity Human 5-HT(1B/1D) Ligands," *Bioorg. Med. Chem. Lett.* 14(3): 727-729, 2004.

Heuring and Peroutka, "Characterization of a Novel 3H-5-Hydroxytryptamine Binding Site Subtype in Bovine Brain Membranes," *J. Neurosci.* 7(3):894-903, 1987.

Hoyer et al., "Characterization of the 5-HT1B Recognition Site in Rat Brain: Binding Studies with (−)[125I]Iodocyanopindolol," *Eur. J. Pharmacol.* 118(1-2):1-12, 1985.

Humphrey and Kuethe, "Practical Methodologies for the Synthesis of Indoles," *Chem. Rev.* 106(7):2875-2911, 2006.

Srivastava and Banik, "Bismuth Nitrate-Catalyzed Versatile Michael Reactions," *J. Org. Chem.* 68(6):2109-2114, 2003.

Ahn and Basbaum, "Tissue Injury Regulates Serotonin 1D Receptor Expression: Implications for the Control of Migraine and Inflammatory Pain," J. Neurosci. 26(32):8332-8338, 2006.

Ahn and Basbaum, "Where do Triptans Act in the Treatment of Migraine?" Pain 115(1-2):1-6, 2005.

Al-Chaer et al., "A New Model of Chronic Visceral Hypersensitivity in Adult Rats Induced by Colon Irritation During Postnatal Development," Gastroenterology 119(5):1276-1285, 2000.

Arvieu et al., "Sumatriptan Inhibits the Release of CGRP and Substance P from the Rat Spinal Cord," Neuroreport. 7(12):1973-1976, 1996.

Azpiroz et al., "Mechanisms of Hypersensitivity in IBS and Functional Disorders," Neurogastroenterol. Motil. 19(1 Suppl):62-88, 2007.

Bartsch et al., "Activation of 5-HT(1B/1D) Receptor in the Periaqueductal Gray Inhibits Nociception," Ann. Neurol. 56(3):371-381, 2004.

Bingham et al., "Inhibition of Inflammation-Induced Thermal Hypersensitivity by Sumatriptan Through Activation of 5-HT(1B/1D) Receptors," Exp. Neurol. 167(1):65-73, 2001.

Bornman et al., "Pathogenesis of Pain in Chronic Pancreatitis: Ongoing Enigma," World J. Surg. 27(11):1175-1182, 2003.

Bourdu et al., "Rectal Instillation of Butyrate Provides a Novel Clinically Relevant Model of Noninflammatory Colonic Hypersensitivity in Rats," Gastroenterology 128(7):1996-2008, 2005.

Bruinvels et al., "Localization of 5-HT1B, 5-HT1D alpha, 5-HT1E and 5-HT1F Receptor Messenger RNA in Rodent and Primate Brain," Neuropharmacology 33(3-4):367-386, 1994.

Bueno et al., "Serotonergic and non-serotonergic targets in the pharmacotherapy of visceral hypersensitivity," Nuerogastroenterol Motil 19(Suppl. 1):89-119, 2007.

Burgess et al., "Time-Dependent Descending Facilitation from the Rostral Ventromedial Medulla Maintains, but does not Initiate, Neuropathic Pain," J. Neurosci. 22(12):5129-5136, 2002.

Buscher et al., "Chronic Pancreatitis Patients Show Hyperalgesia of Central Origin: A Pilot Study," Eur. J. Pain 10(4):363-370, 2006.

Castro et al., "Differential Distribution of [3H]Sumatriptan Binding Sites (5-HT1B, 5-HT1D and 5-HT1F Receptors) in Human Brain: Focus on Brainstem and Spinal Cord," Neuropharmacology 36(4-5):535-542, 1997.

Cervero and Laird, "Visceral Pain," Lancet 353(9170):2145-2148, 1999.

De Ponti and Tonini, "Irritable Bowel Syndrome: New Agents Targeting Serotonin Receptor Subtypes," Drugs 61(3):317-332, 2001.

Dimcevski et al., "Assessment of Experimental Pain from Skin, Muscle, and Esophagus in Patients with Chronic Pancreatitis," Pancreas 35(1):22-29, 2007.

Dimcevski et al., "Pain in Chronic Pancreatitis: The Role of Reorganization in the Central Nervous System," Gastroenterology 132(4):1546-1556, 2007.

Ekbom, "Treatment of Cluster Headache: Clinical Trials, Design and Results," Cephalalgia 15(Suppl 15):33-36, 1995.

Ghelardini et al., "Involvement of Central Cholinergic System in Antinociception Induced by Sumatriptan in Mouse," Int. J. Clin. Pharmacol. Res. 17(2-3):105-109, 1997.

Giamberardino, "Referred Muscle Pain/Hyperalgesia and Central Sensitization," J. Rehabil. Med. (41 Suppl):85-88, 2003.

Hauer et al., "Gabapentin Successfully Manages Chronic Unexplained Irritability in Children with Severe Neurologic Impairment," Pediatrics 119(2):e519-522, 2007.

Humphrey and Goadsby, "The Mode of Action of Sumatriptan is Vascular? A Debate," Cephalalgia 14(6):401-410, 1994.

Jain and Kulkarni, "Antinociceptive Effect of Sumatriptan in Mice," Indian J. Exp. Biol. 36(10):973-979, 1998.

Jennings et al., "Effects of Sumatriptan on Rat Medullary Dorsal Horn Neurons," Pain 111(1-2):30-37, 2004.

Kayser et al., "The Antimigraine 5-HT 1B/1D Receptor Agonists, Sumatriptan, Zolmitriptan and Dihydroergotamine, Attenuate Pain-Related Behaviour in a Rat Model of Trigeminal Neuropathic Pain," Br. J. Pharmacol. 137(8):1287-1297, 2002.

Levy et al., "Disruption of Communication Between Peripheral and Central Trigeminovascular Neurons Mediates the Antomigraine Action of 5HT 1B/1D Receptor Agonists," Proc. Natl. Acad. Sci. USA 101(12):4274-4279, 2004.

Li et al., "Voltage-Dependent Calcium Currents in Bulbospinal Neurons of Neonatal Rat Rostral Ventrolateral Medulla: Modulation by Alpha2-Adrenergic Receptors," J. Neurophysiol. 79(2):583-594, 1998.

Nicholas et al., "Cellular Localization of Messenger RNA for beta-1 and beta-2 Adrenergic Receptors in Rat Brain: An In Situ Hybridization Study," Neuroscience 56(4):1023-1039, 1993.

Nikai et al., "Profund Reduction of Somatic and Visceral Pain in Mice by Intrathecal Administration of the Anti-Migraine Drug, Sumatriptan" Pain 139 (2008) 533-540.

Ottani et al., "Effect of Sumatriptan in Different Models of Pain in Rats," Eur. J. Pharmacol. 497(2):181-186, 2004.

Potrebic et al., "Peptidergic Nociceptors of Both Trigeminal and Dorsal Root Ganglia Express Serotonin 1D Receptors: Implications for the Selective Antimigraine Action of Triptans," J. Neurosci. 23(34):10988-10997, 2003.

Rényi et al., "Biochemical and Behavioural Effects of Isamoltane, a beta-Adrenoceptor Antagonist with Affinity for the 5-HT1B Receptor of Rat Brain," Naunyn. Schmiedebergs. Arch. Pharmacol. 343(1):1-6, 1991.

Sparmann et al., "Pancreatic Fibrosis in Experimental Pancreatitis Induced by Dibutyltin Dichloride," Gastroenterology 112(5):1664-1672, 1997.

Stepanović-Petrović et al., "The Antinociceptive Effects of Anticonvulsants in a Mouse Visceral Pain Model," Anesth. Analg. 106(6):1897-1903, 2008.

Tack et al., "Role of tension receptors in dyspeptic patients with hypersensitivity to gastric distention," Gastroenterology 127(4):1058-1066, 2004.

Vera-Portocarrero and Westlund, "Attenuation of Nociception in a Model of Acute Pancreatitis by an NK-1 Antagonist," Pharmacol. Biochem. Behay. 77(3):631-640, 2004.

Vera-Portocarrero et al., "Descending Facilitation from the Rostral Ventromedial Medulla Maintains Visceral Pain in Rats with Experimental Pancreatitis," Gastroenterology 130(7):2155-2164, 2006.

Vera-Portocarrero et al., "Nociception in Persistent Pancreatitis in Rats: Effects of Morphine and Neuropeptide Alterations," Anesthesiology 98(2):474-484, 2003.

Vera-Portocarrero et al., "Reversal of Inflammatory and Noninflammatory Visceral Pain by Central or Peripheral Actions of Sumatriptan," Gastroenterology 135(4):1369-1378, 2008.

Verne et al., "Hypersensitivity to Visceral and Cutaneous Pain in the Irritable Bowel Syndrome," Pain 93(1):7-14, 2001.

Wick et al., "Transient Receptor Potential Vanilloid 1, Calcitonin Gene-Related Peptide, and Substance P Mediate Nociception in Acute Pancreatitis," Am. J. Physiol. Gastrointest. Liver Physiol. 290(5):G959-G969, 2006.

Winston et al., "Acute Pancreatitis Results in Referred Mechanical Hypersensitivity and Neuropeptide Up-Regulation that can be Suppressed by the Protein Kinase Inhibitor k252a," J. Pain 4(6):329-337, 2003.

Zhuo and Gebhart, "Facilitation and Attenuation of a Visceral Nociceptive Reflex from the Rostroventral Medulla in the Rat," Gastroenterology 122(4):1007-1019, 2002.

Zhuo et al., "Biphasic Modulation of Spinal Visceral Nociceptive Transmission from the Rostroventral Medial Medulla in the Rat," J. Neurophysiol. 87(5):2225-2236, 2002.

Zochodne and Ho, "Sumatriptan Blocks Neurogenic Inflammation in the Peripheral Nerve Trunk," Neurology 44(1):161-163, 1994.

Supplementary European Search Report and Communication for European Application No. 07719544.4 (dated Jan. 12, 2010).

* cited by examiner

Experimental Design of the Chung Model of Neuropathic Pain. Measurement of Thermal Hyperalgesia Compound 107 reverses thermal hyperalgesia in rats with L5/L6 Spinal Nerve Ligation (SNL).

1,5 AND 3,6-SUBSTITUTED INDOLE COMPOUNDS HAVING NOS INHIBITORY ACTIVITY

CROSS-REFERENCE TO RELATED APPLICATIONS

This application claims benefit of U.S. provisional application No. 60/791,846, filed Apr. 13, 2006, which is hereby incorporated by reference.

BACKGROUND OF THE INVENTION

The present invention relates to novel 1,5 and 3,6-substituted indole compounds having nitric oxide synthase (NOS) inhibitory activity, to pharmaceutical and diagnostic compositions containing them, and to their medical use, particularly as compounds for the treatment of stroke, reperfusion injury, neurodegenerative disorders, head trauma, coronary artery bypass graft (CABG) associated neurological damage, migraine with and without aura, migraine with allodynia, chronic tension type headache (CTTH), neuropathic pain, central post-stroke pain (CPSP), and chronic pain.

Nitric oxide (NO) has diverse roles both in normal and pathological processes, including the regulation of blood pressure, in neurotransmission, and in the macrophage defense systems (Snyder et al., *Scientific American, May* 1992:68). NO is synthesized by three isoforms of nitric oxide synthase, a constitutive form in endothelial cells (eNOS), a constitutive form in neuronal cells (nNOS), and an inducible form found in macrophage cells (iNOS). These enzymes are homodimeric proteins that catalyze a five-electron oxidation of L-arginine, yielding NO and citrulline. The role of NO produced by each of the NOS isoforms is quite unique. Overstimulation or overproduction of individual NOS isoforms especially nNOS and iNOS, plays a role in several disorders, including septic shock, arthritis, diabetes, ischemia-reperfusion injury, pain, and various neurodegenerative diseases (Kerwin, et al., *J. Med. Chem.* 38:4343, 1995), while eNOS inhibition leads to unwanted effects such as enhanced white cell and platelet activation, hypertension and increased atherogenesis (Valance and Leiper, *Nature Rev. Drug Disc.* 2002, 1, 939).

NOS inhibitors have the potential to be used as therapeutic agents in many disorders. However, the preservation of physiologically important nitric oxide synthase function suggests the desirability of the development of isoform-selective inhibitors that preferentially inhibit nNOS over eNOS.

SUMMARY OF THE INVENTION

The invention features a compound having the formula:

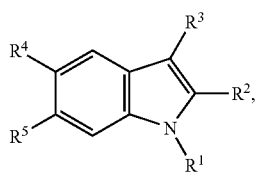

(I)

or a pharmaceutically acceptable salt or prodrug thereof, wherein, $R^1$ is H, optionally substituted $C_{1-6}$ alkyl, optionally substituted $C_{1-4}$ alkaryl, optionally substituted $C_{1-4}$ alkheterocyclyl, or optionally substituted $C_{2-9}$ heterocyclyl; each of $R^2$ and $R^3$ is, independently, H, Hal, optionally substituted $C_{1-6}$ alkyl, optionally substituted $C_{6-10}$ aryl, optionally substituted $C_{1-6}$ alkaryl, optionally substituted $C_{2-9}$ heterocyclyl, or optionally substituted $C_{1-4}$ alkheterocyclyl; $R^4$ is H, $R^{4A}C(NH)NH(CH_2)_{r4}$, or $R^{4A}NHC(S)NH(CH_2)_{r4}$, wherein r4 is an integer from 0 to 2, $R^{4A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, optionally substituted $C_{1-4}$ thioalkheterocyclyl, or optionally substituted amino; and $R^5$ is H, $R^{5A}C(NH)NH(CH_2)_{r5}$, or $R^{5A}NHC(S)NH(CH_2)_{r5}$, wherein r5 is an integer from 0 to 2, $R^{5A}$ is $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, optionally substituted $C_{1-4}$ thioalkheterocyclyl, or optionally substituted amino; wherein one, but not both, of $R^4$ and $R^5$ is H, and when $R^4$ is H, $R^1$ is H, and when $R^5$ is H, $R^3$ is H.

In certain embodiments, $R^1$ is H, optionally substituted $C_{1-6}$ alkyl, or optionally substituted $C_{2-9}$ heterocyclyl, each of $R^2$ and $R^3$ is, independently, H, optionally substituted $C_{1-6}$ alkaryl, optionally substituted $C_{6-10}$ aryl, or optionally substituted $C_{2-9}$ heterocyclyl; $R^4$ is H, or $R^{4A}C(NH)NH(CH_2)_{r4}$, wherein r4 is an integer from 0 to 1, $R^{4A}$ is optionally substituted $C_{2-9}$ heterocyclyl; or optionally substituted amino; and $R^5$ is H or $R^{5A}C(NH)NH(CH_2)_{r5}$, wherein r5 is an integer from 0 to 1, $R^5A$ is optionally substituted $C_{2-9}$ heterocyclyl, or optionally substituted amino.

In certain embodiments, each of $R^4$ and $R^5$ is, independently, H or the group

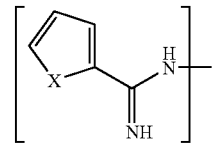

wherein X = O or S.

In certain embodiments, $R^1$ or $R^3$ is

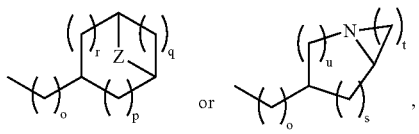

wherein Z is $NR^6$ and o is an integer from 0 to 3, p is an integer from 1 to 2, q is an integer from 0 to 2 and r is an integer from 0 to 1, s is an integer from 1 to 3, u is an integer from 0 to 1, and t is an integer from 5 to 7, and wherein the $R^1$ or $R^3$ substituent includes 0 to 6 carbon-carbon double bonds or 0 or 1 carbon-nitrogen double bonds.

In other embodiments, $R^3$ is H, $R^5$ is H, and $R^4$ is

wherein X=O or S. For such compounds, $R^1$ may also be optionally substituted alkheterocyclyl, optionally substituted heterocyclyl, or alkyl substituted with $NR^G R^H$, where each of $R^G$ and $R^H$ is, independently, selected from the group consisting of hydrogen; alkyl of one to six carbon atoms; cycloalkyl of three to eight carbon atoms; and alkcycloalkyl, where the cycloalkyl group is of three to eight carbon atoms, and the alkylene group is of one to ten carbon atoms. $R_2$ may also be $C_{1-6}$ alkyl, optionally substituted aryl, or optionally substituted alkaryl.

Alternatively, $R^1$ is H, $R^4$ is H, and $R^5$ is

wherein X=O or S. For such compounds, $R^3$ may be optionally substituted heterocyclyl or optionally substituted cycloalkyl.

Preferably, a compound of the invention selectively inhibits neuronal nitric oxide synthase (nNOS), and particularly nNOS, over endothelial nitric oxide synthase (eNOS) or inducible nitric oxide synthase (iNOS).

Preferably, a compound of the invention selectively inhibits neuronal nitric oxide synthase (nNOS) over endothelial nitric oxide synthase (eNOS) or inducible nitric oxide synthase (iNOS) or both in an in vitro assay. Preferably, the $IC_{50}$ or $K_i$ value observed for the compound when tested is at least 2 times lower in the nNOS assay than in the eNOS and/or iNOS assays. More preferably, the $IC_{50}$ or $K_i$ value is at least 5 times lower. Most preferably, the $IC_{50}$ or $K_i$ value is 20, or even 50 times lower. In one embodiment, the $IC_{50}$ or $K_i$ value is between 2 times and 50 times lower. In another embodiment, the $IC_{50}$ or $K_i$ in eNOS is greater than 10 μM. More preferably, eNOS $IC_{50}$ or $K_i$ is greater than 20 μM, most preferably eNOS $IC_{50}$ or $K_i$ is greater than 30 μM.

Specific exemplary compounds are described herein.

In another aspect, the invention features a pharmaceutical composition that includes a compound of the invention and a pharmaceutically acceptable excipient.

In another aspect, the invention features a method of treating or preventing a condition in a mammal, such as, for example, a human, caused by the action of nitric oxide synthase (NOS), and particularly nNOS, that includes administering an effective amount of a compound of the invention to the mammal. Examples of conditions that can be prevented or treated include migraine headache, migraine with allodynia, neuropathic pain, central post-stroke pain (CPSP), chronic tension type headache, chronic pain, acute spinal cord injury, diabetic nephropathy, an inflammatory disease, stroke, reperfusion injury, head trauma, cardiogenic shock, CABG associated neurological damage, HCA, AIDS associated dementia, neurotoxicity, Parkinson's disease, Alzheimer's disease, ALS, Huntington's disease, multiple sclerosis, metamphetamine-induced neurotoxicity, drug addiction, morphine/opioid induced tolerance, dependence, hyperalgesia or withdrawal, ethanol tolerance, dependence, or withdrawal, epilepsy, anxiety, depression, attention deficit hyperactive disorder, or psychosis. Compounds of the invention are particularly useful for treating stroke, reperfusion injury, neurodegeneration, head trauma, CABG, migraine headache with and without aura, migraine with allodynia, chronic tension type headache, neuropathic pain, central post-stroke pain (CPSP), morphine/opioid induced hyperalgesia or chronic pain. In particular, 1,5-substituted indole compounds are useful in the treatment of central post-stroke pain (CPSP).

A compound of the invention can also be used in combination with one or more other therapeutic agents for the prevention or treatment of one of the aforementioned conditions. Examples of classes of therapeutic agents and some specific examples that are useful in combination with a compound of the invention are listed in Table 1.

Other agents useful in combination with a compound of the invention, include opioids, antidepressants, antiepileptics, non-steroidal anti-inflammatory drugs (NSAIDs), antiarrhythmics, GABA-B antagonists, alpha-2-adrenergic receptor agonists, serotonin $5HT_{1B/1D}$ agonists, N-methyl-D-aspartate antagonists, cholecystokinin B antagonists, substance P antagonists (NK1), anti-inflammatory compounds, DHP-sensitive L-type calcium channel antagonists, omega-conotoxin-sensitive N-type calcium channel antagonists, P/Q-type calcium channel antagonists, adenosine kinase antagonists, adenosine receptor $A_1$ agonists, adenosine receptor $A_{2a}$ antagonists, adenosine receptor $A_3$ agonists, adenosine deaminase inhibitors, adenosine nucleoside transport inhibitors, vanilloid VR1 receptor agonists, cannabinoid CB1/CB2 agonists, AMPA receptor antagonists, kainate receptor antagonists, sodium channel blockers (e.g., Nav1.8 blocker for neuropathic pain), nicotinic acetylcholine receptor agonists, a $K_{ATP}$ potassium channel, $K_{v1.4}$ potassium channel, $Ca^{2+}$-activated potassium channel, SK potassium channel, BK potassium channel, IK potassium channel, or KCNQ2/3 potassium channel opening agents, muscarinic M3 antagonists, muscarinic M1 agonists, muscarinic M2/M3 partial agonists/antagonists, and antioxidants.

TABLE 1

Therapeutic agents useful in combination with compounds of the invention

| Class | Examples |
|---|---|
| Opioid | alfentanil, butorphanol, buprenorphine, codeine, dextromoramide, dextropropoxyphene, dezocine, dihydrocodeine, diphenoxylate, etorphine, fentanyl, hydrocodone, hydromorphone, ketobemidone, levorphanol, levomethadone, methadone, meptazinol, morphine, morphine-6-glucuronide, nalbuphine, naloxone, oxycodone, oxymorphone, pentazocine, pethidine, piritramide, remifentanil, sulfentanyl, tilidine, and tramadol |

TABLE 1-continued

Therapeutic agents useful in combination with compounds of the invention

| Class | Examples |
|---|---|
| Antidepressant (selective serotonin re-uptake inhibitor) | alaproclate, citalopram, chlomipramine, escitalopram, femoxetine, fluoxetine, fluvoxamine, paroxetine, sertraline, or zimelidine |
| Antidepressant (norepinephrine-reuptake inhibitor) | adinazolam, amiltriptylinoxide, amineptine, amoxapine, atomoxetine, bupropion, butriptyline, desipramine, doxepin, desipramine, maprotiline, nortriptyline (desmethylamitriptyline), demexiptiline, dothiepin, fluacizine, imipramine, imipramine oxide, iprindole, lofepramine, maprotiline, melitracen, metapramine, norclolipramine, noxiptilin, opipramol, perlapine, pizotyline, propizepine, quinupramine, reboxetine, or tianeptine, tomoxetine, trimipramine or viloxazine |
| Antidepressant (noradrenaline/ norepinephrine reuptake inhibitor) | atomoxetine, bupropion, reboxetine, or tomoxetine |
| Antidepressant (dual serotonin/ norepinephrine reuptake inhibitor) | duloxetine, milnacipran, mirtazapine, nefazodone, or venlafaxine |
| Antidepressant (monoamine oxidase inhibitor) | amiflamine, iproniazid, isocarboxazid, M-3-PPC (Draxis), moclobemide, pargyline, phenelzine, tranylcypromine, or vanoxerine |
| Antidepressant (reversible monoamine oxidase type A inhibitor) | bazinaprine, befloxatone, brofaromine, cimoxatone, or clorgyline |
| Antidepressant (tricyclic) | amitriptyline, amoxapine, buriptyline, clomipramine, desipramine, dibenzepin, dothiepin, doxepin, imipramine, iprindole, , lofepramine, melitracen, , opipramol, nortryptyline, protriptyline, or trimipramine |
| Antidepressant (other) | adinazolam, alaproclate, amineptine, amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, lithium, litoxetine; lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, trazodone, tofenacin, tofisopam, toloxatone, tomoxetine, veralipride, viloxazine, viqualine, zimelidine, zometapine |
| Antiepileptic | carbamazepine, flupirtine, gabapentin, lamotrigine, oxcarbazepine, phenyloin, pregabalin, retigabine, topiramate, or valproate |
| Nonsteroidal anti-inflammatory drug (NSAID) | acemetacin, aspirin, celecoxib, deracoxib, diclofenac, diflunisal, ethenzamide, etofenamate, etoricoxib, fenoprofen, flufenamic acid, flurbiprofen, lonazolac, lornoxicam, ibuprofen, indomethacin, isoxicam, kebuzone, ketoprofen, ketorolac, naproxen, nabumetone, niflumic acid, sulindac, tolmetin, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, suprofen, tiaprofenic acid, tenoxicam, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, and 2-(3,5-difluorophenyl)-3-[4-(methylsulfonyl)phenyl]-2-cyclopenten-1-one). |
| $5HT_{1B/1D}$ agonist | eletriptan, frovatriptan, naratriptan, rizatriptan, sumatriptan, almotriptan, donitriptan or zolmitriptan |
| Anti-inflammatory compounds | aspirin, celecoxib, cortisone, deracoxib, diflunisal, etoricoxib, fenoprofen, ibuprofen, ketoprofen, naproxen, prednisolone, sulindac, tolmetin, piroxicam, mefenamic acid, meloxicam, phenylbutazone, rofecoxib, suprofen, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)- |

TABLE 1-continued

Therapeutic agents useful in combination with compounds of the invention

| Class | Examples |
|---|---|
| N-methyl-D-aspartate antagonist and other glutamate receptor antagonists (e.g., AMPA/kainite (GluR5), MGluR, and iGluR) (Medicinal Research Reviews, 2007; 27(2): 239-278 and Basic & Clinical. Pharmacol. Toxicol. 2005, 97: 202-213) | pyridazinone, or 2-(3,5-difluorophenyl)-3-[4-(methylsulfonyl)phenyl]-2-cyclopenten-1-one amantadine; aptiganel; besonprodil; budipine; conantokin G; delucemine; dexanabinol; dextromethorphan; dextropropoxyphen; felbamate; fluorofelbamate; gacyclidine; glycine; ipenoxazone; kaitocephalin; ketamine; ketobemidone; lanicemine; licostinel; midafotel; memantine; D-methadone; D-morphine; milnacipran; neramexane; orphenadrine; remacemide; sulfazocine; FPL-12,495 (racemide metabolite); topiramate; (αR)-α-amino-5-chloro-1-(phosphonomethyl)-1H-benzimidazole-2-propanoic acid; 1-aminocyclopentane-carboxylic acid; [5-(aminomethyl)-2-[[[(5S)-9-chloro-2,3,6,7-tetrahydro-2,3-dioxo-1H-,5H-pyrido[1,2,3-de]quinoxalin-5-yl]acetyl]amino]phenoxy]-acetic acid; α-amino-2-(2-phosphonoethyl)-cyclohexanepropanoic acid; α-amino-4-(phosphonomethyl)-benzeneacetic acid; (3E)-2-amino-4-(phosphonomethyl)-3-heptenoic acid; 3-[(1E)-2-carboxy-2-phenylethenyl]-4,6-dichloro-1H-indole-2-carboxylic acid; 8-chloro-2,3-dihydropyridazino[4,5-b]quinoline-1,4-dione 5-oxide salt with 2-hydroxy-N,N,N-trimethyl-ethanaminium; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfinyl]phenyl]-guanidine; 6-chloro-2,3,4,9-tetrahydro-9-methyl-2,3-dioxo-1H-indeno[1,2-b]pyrazine-9-acetic acid; 7-chlorothiokynurenic acid; (3S,4aR,6S,8aR)-decahydro-6-(phosphonomethyl)-3-isoquinolinecarboxylic acid; (−)-6,7-dichloro-1,4-dihydro-5-[3-(methoxymethyl)-5-(3-pyridinyl)-4-H-1,2,4-triazol-4-yl]-2,3-quinoxalinedione; 4,6-dichloro-3-[(E)-(2-oxo-1-phenyl-3-pyrrolidinylidene)methyl]-1H-indole-2-carboxylic acid; (2R,4S)-rel-5,7-dichloro-1,2,3,4-tetrahydro-4-[[(phenylamino)carbonyl]amino]-2-quinolinecarboxylic acid; (3R,4S)-rel-3,4-dihydro-3-[4-hydroxy-4-(phenylmethyl)-1-piperidinyl-]-2H-1-benzopyran-4,7-diol; 2-[(2,3-dihydro-1H-inden-2-yl)amino]-acetamide; 1,4-dihydro-6-methyl-5-[(methylamino)methyl]-7-nitro-2,3-quinoxalinedione; [2-(8,9-dioxo-2,6-diazabicyclo[5.2.0]non-1(7)-en-2-yl)ethyl]-phosphonic acid; (2R,6S)-1,2,3,4,5,6-hexahydro-3-[(2S)-2-methoxypropyl]-6,11,11-trimethyl-2,6-methano-3-benzazocin-9-ol; 2-hydroxy-5-[[(pentafluorophenyl)methyl]amino]-benzoic acid; 1-[2-(4-hydroxyphenoxy)ethyl]-4-[(4-methylphenyl)methyl]-4-piperidinol; 1-[4-(1H-imidazol-4-yl)-3-butynyl]-4-(phenylmethyl)-piperidine; 2-methyl-6-(phenylethynyl)-pyridine; 3-(phosphonomethyl)-L-phenylalanine; efenprodil, CP101606, Ro256981, or 3,6,7-tetrahydro-2,3-dioxo-N-phenyl-1H,5H-pyrido[1,2,3-de]quinoxaline-5-acetamide |

Asymmetric or chiral centers may exist in any of the compounds of the present invention. The present invention contemplates the various stereoisomers and mixtures thereof. Individual stereoisomers of compounds of the present invention are prepared synthetically from commercially available starting materials which contain asymmetric or chiral centers or by preparation of mixtures of enantiometic compounds followed by resolution well-known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns. Alternatively, chiral compounds can be prepared by an asymmetric synthesis that favours the preparation of one enantiomer over the other. Alternatively a chiral pool synthesis (starting with an enantiomerically pure building block) can be used wherein the chiral group or center is retained in the intermediate or final product. Enantiomers are designated herein by the symbols "R," or "S," depending on the configuration of substituents around the chiral atom. Alternatively, enantiomers are designated as (+) or (−) depending on whether a solution of the enantiomer rotates the plane of polarized light clockwise or counterclockwise, respectively.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration, where the term "Z" represents substituents on the same side of the carbon-carbon double bond and the term "E" represents substituents on opposite sides of the carbon-carbon double bond. It is also recognized that for structures in which tautomeric forms are possible, the description of one tautomeric form is equivalent to the description of both, unless otherwise specified. For example, amidine structures of the formula $-C(=NR^Q)NHR^T$ and $-C(NHR^Q)=NR^T$, where $R^T$ and $R^Q$ are different, are equivalent tautomeric structures and the description of one inherently includes the other.

It is understood that substituents and substitution patterns on the compounds of the invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

Other features and advantages will be apparent from the following description and the claims.

Definitions

The terms "acyl" or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups include from 2 to 7 carbons.

The terms "$C_{x-y}$ alkaryl" or "$C_{x-y}$ alkylenearyl," as used herein, represent a chemical substituent of formula —RR', where R is an alkylene group of x to y carbons and R' is an aryl group as defined elsewhere herein. Similarly, by the terms "$C_{x-y}$ alkheteroaryl" "$C_{x-y}$ alkyleneheteroaryl," is meant a chemical substituent of formula —RR", where R is an alkylene group of x to y carbons and R" is a heteroaryl group as defined elsewhere herein. Other groups proceeded by the prefix "alk-" or "alkylene-" are defined in the same manner. Exemplary unsubstituted alkaryl groups are of from 7 to 16 carbons.

The term "alkcycloalkyl" represents a cycloalkyl group attached to the parent molecular group through an alkylene group.

The term "alkenyl," as used herein, represents monovalent straight or branched chain groups of, unless otherwise specified, from 2 to 6 carbons containing one or more carbon-carbon double bonds and is exemplified by ethenyl, 1-propenyl, 2-propenyl, 2-methyl-1-propenyl, 1-butenyl, 2-butenyl, and the like.

The term "alkheterocyclyl" represents a heterocyclic group attached to the parent molecular group through an alkylene group. Exemplary unsubstituted alkheterocyclyl groups are of from 2 or 3 to 14 carbons.

The term "alkoxy" represents a chemical substituent of formula —OR, where R is an alkyl group of 1 to 6 carbons, unless otherwise specified.

The term "alkoxyalkyl" represents an alkyl group which is substituted with an alkoxy group. Exemplary unsubstituted alkoxyalkyl groups include between 2 to 12 carbons.

The terms "alkyl" and the prefix "alk-," as used herein, are inclusive of both straight chain and branched chain saturated groups of from 1 to 6 carbons, unless otherwise specified. Alkyl groups are exemplified by methyl, ethyl, n- and isopropyl, n-, sec-, iso- and tert-butyl, neopentyl, and the like, and may be optionally substituted with one, two, three or, in the case of alkyl groups of two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) amino; (5) aryl; (6) arylalkoxy; (7) aryloyl; (8) azido; (9) carboxaldehyde; (10) cycloalkyl of three to eight carbon atoms; (11) halo; (12) heterocyclyl; (13) (heterocycle)oxy; (14) (heterocycle)oyl; (15) hydroxyl; (16) N-protected amino; (17) nitro; (18) oxo; (19) spiroalkyl of three to eight carbon atoms; (20) thioalkoxy of one to six carbon atoms; (21) thiol; (22) —$CO_2R^A$, where $R^A$ is selected from the group consisting of (a) alkyl, (b) aryl and (c) alkaryl, where the alkylene group is of one to six carbon atoms; (23) —C(O)$NR^BR^C$, where each of $R^B$ and $R^C$ is, independently, selected from the group consisting of (a) hydrogen, (b) alkyl, (c) aryl and (d) alkaryl, where the alkylene group is of one to six carbon atoms; (24) —$SO_2R^D$, where $R^D$ is selected from the group consisting of (a) alkyl, (b) aryl and (c) alkaryl, where the alkylene group is of one to six carbon atoms; (25) —$SO_2NR^ER^F$, where each of $R^E$ and $R^F$ is, independently, selected from the group consisting of (a) hydrogen, (b) alkyl, (c) aryl and (d) alkaryl, where the alkylene group is of one to six carbon atoms; and (26) —$NR^GR^H$, where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group. In other examples, an alkyl group may be substituted with one, two, three or, in the case of alkyl groups of two carbons or more, four substituents independently selected from the group consisting of: (27) acyl, (28) carboxyl, or (29) —$NR^GR^H$, where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms. Alkyl groups may also be substituted with one or more groups selected from (1)-(29).

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkylsulfinyl," as used herein, represents an alkyl group attached to the parent molecular group through an —S(O)— group. Exemplary unsubstituted alkylsulfinyl groups are of from 1 to 6 carbons.

The term "alkylsulfonyl," as used herein, represents an alkyl group attached to the parent molecular group through an —$SO_2$— group. Exemplary unsubstituted alkylsulfonyl groups are of from 1 to 6 carbons.

The term "alkylsulfinylalkyl," as used herein, represents an alkyl group, as defined herein, substituted by an alkylsulfinyl group. Exemplary unsubstituted alkylsulfinylalkyl groups are of from 2 to 12 carbons.

The term "alkylsulfonylalkyl," as used herein, represents an alkyl group, as defined herein, substituted by an alkylsulfonyl group. Exemplary unsubstituted alkylsulfonylalkyl groups are of from 2 to 12 carbons.

The term "alkynyl," as used herein, represents monovalent straight or branched chain groups of from two to six carbon atoms containing a carbon-carbon triple bond and is exemplified by ethynyl, 1-propynyl, and the like.

The term "amidine," as used herein, represents a —C(=NH)$NH_2$ group.

The term "amino," as used herein, represents an —$NH_2$ group, or an —$NHR^{N1}$ wherein $R^{N1}$ can be a OH, $NO_2$, $NH_2$, $NR^{N2}_2$, $SO_2OR^{N2}$, $SO_2R^{N2}$, $SOR^{N2}$, and wherein $R^{N2}$ can be a H, an alkyl group or an aryl group.

The term "aminoalkyl," as used herein, represents an alkyl group, as defined herein, substituted by an amino group.

The term "aryl," as used herein, represents a mono- or bicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) $-(CH_2)_qCO_2R^A$, where q is an integer of from zero to four, and $R^A$ is selected from the group consisting of (a) alkyl, (b) aryl, and (c) alkaryl, where the alkylene group is of one to six carbon atoms; (36) $-(CH_2)_qCONR^BR^C$, where q is an integer of from zero to four and where $R^B$ and $R^C$ are independently selected from the group consisting of (a) hydrogen, (b) alkyl, (c) aryl, and (d) alkaryl, where the alkylene group is of one to six carbon atoms; (37) $-(CH_2)_qSO_2R^D$, where q is an integer of from zero to four and where $R^D$ is selected from the group consisting of (a) alkyl, (b) aryl, and (c) alkaryl, where the alkylene group is of one to six carbon atoms; (38) $-(CH_2)_qSO_2NR^ER^F$, where q is an integer of from zero to four and where each of $R^E$ and $R^F$ is, independently, selected from the group consisting of (a) hydrogen, (b) alkyl, (c) aryl, and (d) alkaryl, where the alkylene group is of one to six carbon atoms; (39) $-(CH_2)_qNR^GR^H$, where q is an integer of from zero to four and where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy. In other examples, an aryl group may be substituted with one, two, three, four, or five substituents independently selected from the group consisting of: (47) carboxyl, (48) (alkanoyl)alkyl, where the alkylene group is of one to six carbon atoms, or (49) $-NR^GR^H$, where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms. Aryl groups may also be substituted with one or more groups selected from (1)-(49).

The term "arylalkoxy," as used herein, represents an alkaryl group attached to the parent molecular group through an oxygen atom. Exemplary unsubstituted arylalkoxy groups are of from 7 to 16 carbons.

The term "aryloxy" represents a chemical substituent of formula —OR', where R' is an aryl group of 6 to 18 carbons, unless otherwise specified.

The terms "aryloyl" and "aroyl" as used interchangeably herein, represent an aryl group that is attached to the parent molecular group through a carbonyl group. Exemplary unsubstituted aryloyl groups are of 7 or 11 carbons.

The term "azido" represents an $N_3$ group, which can also be represented as N=N=N.

The term "azidoalkyl" represents an azido group attached to the parent molecular group through an alkyl group.

The term "carbonyl," as used herein, represents a C(O) group, which can also be represented as C=O.

The term "carboxaldehyde" represents a CHO group.

The term "carboxaldehydealkyl" represents a carboxaldehyde group attached to the parent molecular group through an alkylene group.

The term "cycloalkyl," as used herein represents a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl groups of this invention can be optionally substituted with (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) $-(CH_2)_qCO_2R^A$, where q is an integer of from zero to four, and $R^A$ is selected from the group consisting of (a) alkyl, (b) aryl, and (c) alkaryl, where the alkylene group is of one to six carbon atoms; (36) $-(CH_2)_qCONR^BR^C$, where q is an integer of from zero to four and where $R^B$ and $R^C$ are independently selected from the group consisting of (a) hydrogen, (b) alkyl, (c) aryl, and (d) alkaryl, where the alkylene group is of one to six carbon atoms; (37) $-(CH_2)_qSO_2R^D$, where q is an integer of from zero to four and where $R^D$ is selected from the group consisting of (a) alkyl, (b) aryl, and (c) alkaryl, where the alkylene group is of one to six carbon atoms; (38) $-(CH_2)_qSO_2NR^ER^F$, where q is an integer of from zero to four and where each of $R^E$ and $R^F$ is, independently, selected from the group consisting of (a) hydrogen, (b) alkyl, (c) aryl, and (d)

alkaryl, where the alkylene group is of one to six carbon atoms; (39) —(CH₂)$_q$NR$^G$R$^H$, where q is an integer of from zero to four and where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy. In other examples, cycloalkyl group may be substituted with (47) carboxyl, (48) (alkonyl)alkyl, where the alkylene group is of one to six carbons, or (49) —NR$^G$R$^H$, where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms. Cycloalkyl groups may also be substituted with one or more groups selected from (1)-(49).

The terms "cycloalkyloxy" or "cycloalkoxy", as used interchangeably herein, represent a cycloalkyl group, as defined herein, attached to the parent molecular group through an oxygen atom. Exemplary unsubstituted cycloalkyloxy groups are of from 3 to 8 carbons.

The term an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is an inhibitor of NOS, an effective amount of an agent is, for example, an amount sufficient to achieve a reduction in NOS activity as compared to the response obtained without administration of the agent.

The terms "halide" or "halogen" or "Hal" or "halo," as used herein, represent bromine, chlorine, iodine, or fluorine.

The term "heteroaryl," as used herein, represents that subset of heterocycles, as defined herein, which are aromatic: i.e., they contain 4n+2 pi electrons within the mono- or multicyclic ring system.

The terms "heterocycle" or "heterocyclyl," as used interchangeably herein represent a 5-, 6- or 7-membered ring, unless otherwise specified, containing one, two, three, or four heteroatoms independently selected from the group consisting of nitrogen, oxygen and sulfur. The 5-membered ring has zero to two double bonds and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocycle" includes bicyclic, tricyclic and tetracyclic groups in which any of the above heterocyclic rings is fused to one, two, or three rings, e.g., an aryl ring, a cyclohexane ring, a cyclohexene ring, a cyclopentane ring, a cyclopentene ring and another monocyclic heterocyclic ring, such as indolyl, quinolyl, isoquinolyl, tetrahydroquinolyl, benzofuryl, benzothienyl and the like. Examples of fused heterocycles include tropanes and 1,2,3,5;8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Heterocyclic groups also include compounds of the formula

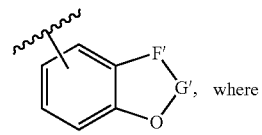

where

F' is selected from the group consisting of —CH₂—, —CH₂O— and —O—, and G' is selected from the group consisting of —C(O)— and —(C(R')(R''))$_v$—, where each of R' and R'' is, independently, selected from the group consisting of hydrogen or alkyl of one to four carbon atoms, and v is one to three and includes groups, such as 1,3-benzodioxolyl, 1,4-benzodioxanyl, and the like. The heterocycle groups mentioned herein may be optionally substituted with one, two, three, four or five substituents, depending on the type of heterocycle, independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH₂)$_q$CO₂R$^A$, where q is an integer of from zero to four, and R$^A$ is selected from the group consisting of (a) alkyl, (b) aryl, and (c) alkaryl, where the alkylene group is of one to six carbon atoms; (36) —(CH₂)$_q$ CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH₂)$_q$SO₂R$^D$, where q is an integer of from zero to four and where $R^D$ is selected from the group consisting of (a) alkyl, (b) aryl, and (c) alkaryl, where the alkylene group is of one to six carbon atoms; (38) —(CH$_2$)$_q$SO$_2$NR$^E$R$^F$, where q is an integer of from zero to four and where each of R$^E$ and R$^F$ is, independently, selected from the group consisting of (a) hydrogen, (b) alkyl, (c) aryl, and (d) alkaryl, where the alkylene group is of one to six carbon atoms; (39) —(CH$_2$)$_q$NR$^G$R$^H$, where q is an integer of from zero to four and where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy. In other examples, a heterocycle is substituted with (47) carboxyl, (48) (alkanoyl) alkyl, where the alkylene group is of one to six carbon atoms, or (49) —NR$^G$R$^H$, where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms. Heterocycle groups may also be substituted with one or more groups selected from (1)-(49). As is known in the art, heterocycles may be spiro compounds, where a heteroatom or a carbon atom is bound to two divalent radicals to form at least a bicyclic structure.

The terms "heterocyclyloxy" and "(heterocycle)oxy," as used interchangeably herein, represent a heterocycle group, as defined herein, attached to the parent molecular group through an oxygen atom.

The terms "heterocyclyloyl" and "(heterocycle)oyl," as used interchangeably herein, represent a heterocycle group, as defined herein, attached to the parent molecular group through a carbonyl group.

The term "hydroxy" or "hydroxyl," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group and is exemplified by hydroxymethyl, dihydroxypropyl, and the like.

The terms "inhibit" or "suppress" or "reduce," as relates to a function or activity, such as NOS activity, means to reduce the function or activity when compared to otherwise same conditions except for a condition or parameter of interest, or alternatively, as compared to another condition.

The term "N-protected amino," as used herein, refers to an amino group, as defined herein, to which is attached an N-protecting or nitrogen-protecting group, as defined herein.

The terms "N-protecting group" and "nitrogen protecting group," as used herein, represent those groups intended to protect an amino group against undesirable reactions during synthetic procedures. Commonly used N-protecting groups are disclosed in Greene, "Protective Groups In Organic Synthesis," 3$^{rd}$ Edition (John Wiley & Sons, New York, 1999), which is incorporated herein by reference. N-protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "oxo" as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, represents an alkoxy group, as defined herein, where each hydrogen radical bound to the alkoxy group has been replaced by a fluoride radical.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M Berge et al. describe pharmaceutically acceptable salts in detail in *J. Pharmaceutical Sciences* 66:1-19, 1977. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like.

Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "Ph" as used herein means phenyl.

The term "prodrug," as used herein, represents compounds which are rapidly transformed in vivo to the parent compound of the above formula, for example, by hydrolysis in blood. Prodrugs of the compounds of the invention may be conventional esters. Some common esters which have been utilized as prodrugs are phenyl esters, aliphatic ($C_8$-$C_{24}$) esters, acyloxymethyl esters, carbamates, and amino acid esters. For example, a compound of the invention that contains an OH group may be acylated at this position in its prodrug form. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins et al., *Synthetic Communications* 26(23):4351-4367, 1996, each of which is incorporated herein by reference. Additional prodrugs include $C_1$-$C_7$ aliphatic esters and cholesterol esters.

Each of the terms "selectively inhibits nNOS" or "a selective nNOS inhibitor" refers to a substance, such as, for example, a compound of the invention, that inhibits or binds the nNOS isoform more effectively than the eNOS and/or iNOS isoform by an in vitro assay, such as, for example, those assays described herein. Selective inhibition can be expressed in terms of an $IC_{50}$ value, a $K_i$ value, or the inverse of a percent inhibition value which is lower, or conversely a higher % inhibition, when the substance is tested in an nNOS assay than when tested in an eNOS and/or iNOS assay. Preferably, the $IC_{50}$ or $K_i$ value is 2 times lower. More preferably, the $IC_{50}$ or $K_i$ value is 5 times lower. Most preferably, the $IC_{50}$ or $K_i$ value is 10, or even 50 times lower.

The term "solvate" as used herein means a compound of the invention wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

The term "spiroalkyl," as used herein, represents an alkylene diradical, both ends of which are bonded to the same carbon atom of the parent group to form a spirocyclic group.

The term "sulfonyl," as used herein, represents an —S(O)$_2$— group.

The term "thioalkheterocyclyl," as used herein, represents a thioalkoxy group substituted with a heterocyclyl group.

The term "thioalkoxy," as used herein, represents an alkyl group attached to the parent molecular group through a sulfur atom. Exemplary unsubstituted alkylthio groups are of from 1 to 6 carbons.

The term "thiol" represents an —SH group.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. The term also includes prophylactic treatment.

DETAILED DESCRIPTION

Figure 1:
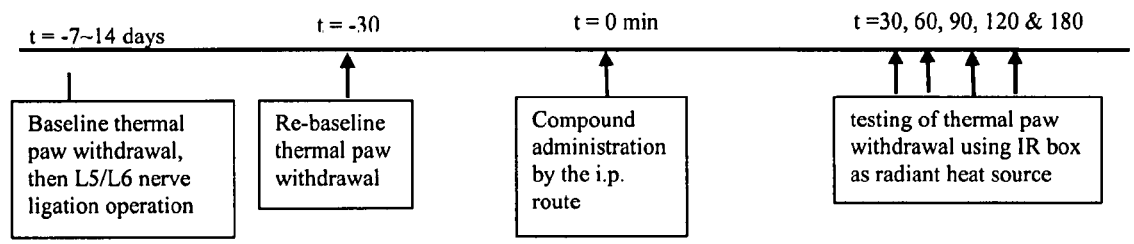
FIG. 1 shows flow charts of the experimental designs used in the Chung Spinal Nerve Ligation (SNL) model assays (tactile allodynia and thermal hyperalgesia) for neuropathic pain.

The invention features novel 1,5- and 3,6-substituted indole compounds having nitric oxide synthase (NOS) inhibitory activity, pharmaceutical and diagnostic compositions containing them, and their medical use, particularly as compounds for the treatment of stroke, reperfusion injury, neurodegenerative disorders, head trauma, coronary artery bypass graft (CABG) associated neurological damage, migraine with and without aura, migraine with allodynia, chronic tension type headache (CTTH), neuropathic pain, central post-stroke pain (CPSP), chronic pain, prevention or reduction of opioid-induced hyperalgesia, opioid induced tolerance and withdrawal, and chemical dependencies and addictions. Exemplary compounds of the invention are shown in Table 2.

TABLE 2

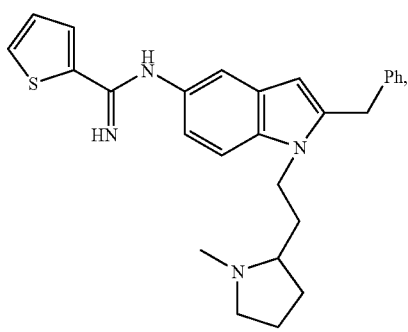

6

TABLE 2-continued
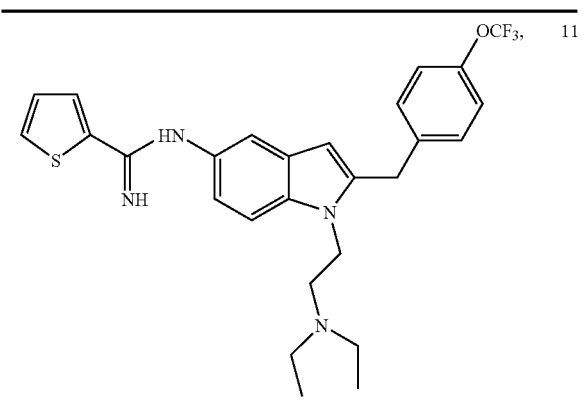 11
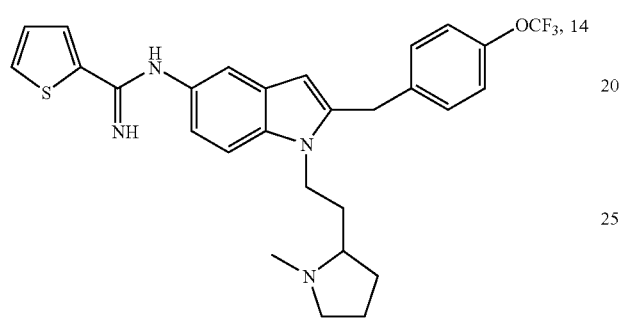 14
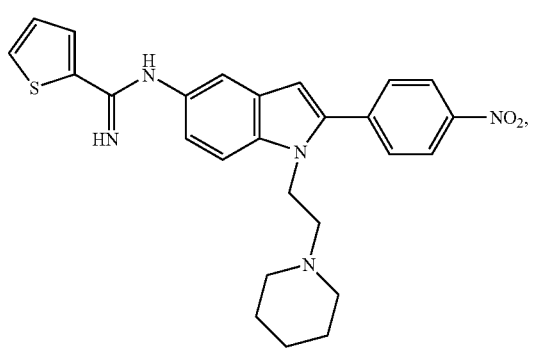 18
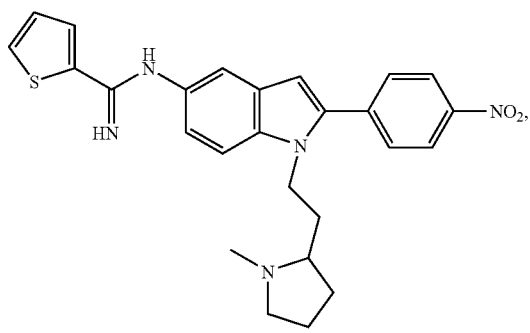 21
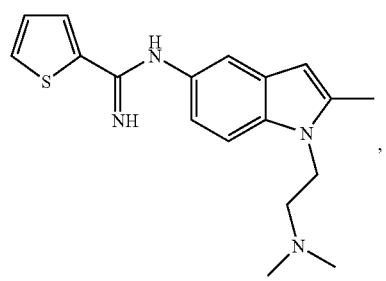 25
TABLE 2-continued
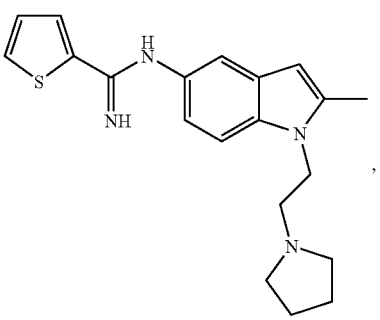 28
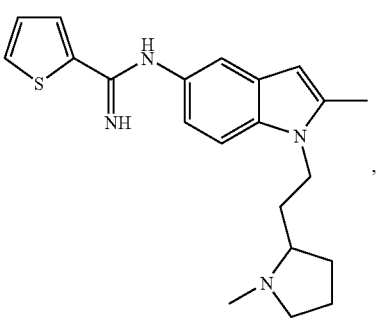 32
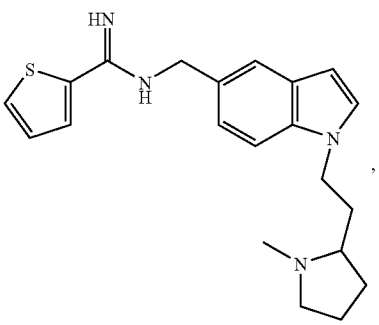 37
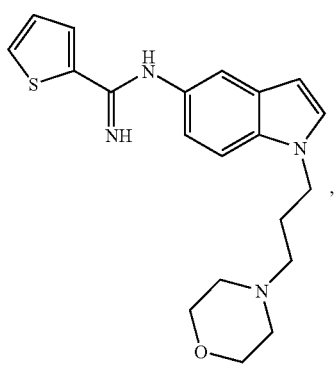 40

TABLE 2-continued
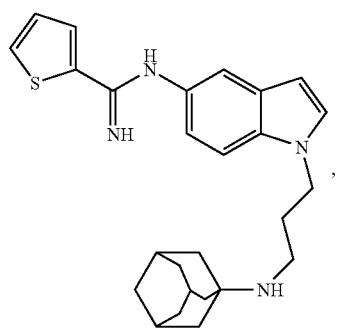
42
,
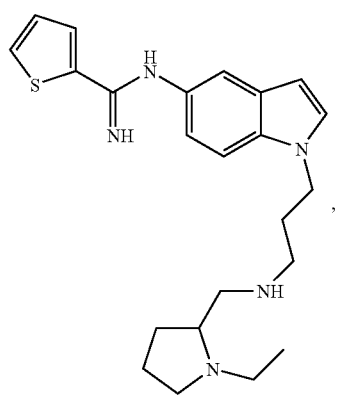
44
,
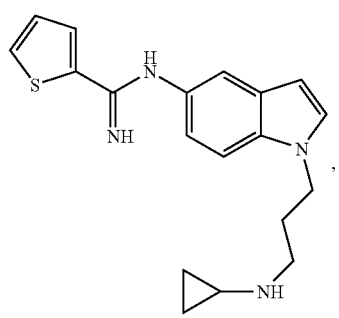
46
,
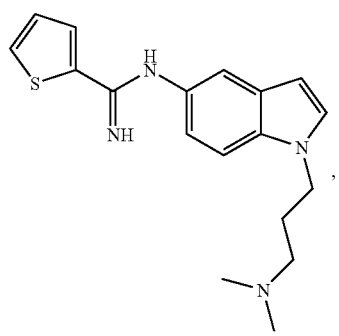
48
,
TABLE 2-continued
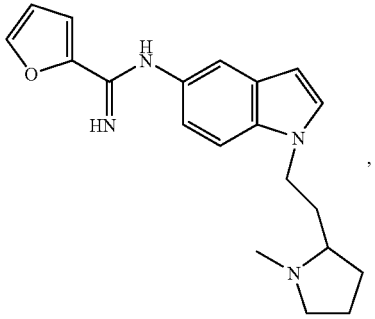
53
,
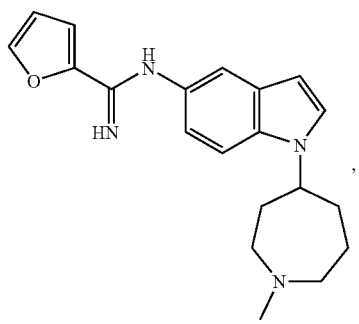
54
,
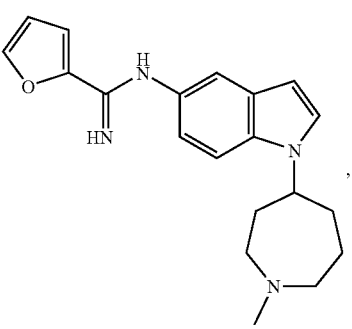
(+)-55
,
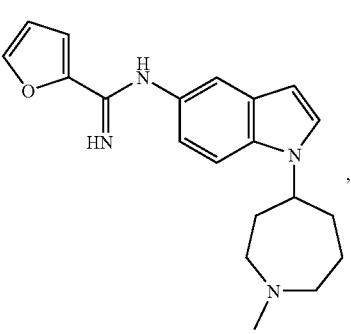
(−)-55
,
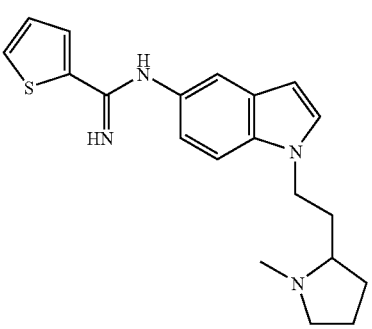
56
, TABLE 2-continued
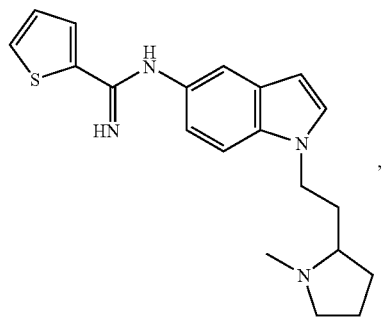
(+)-57
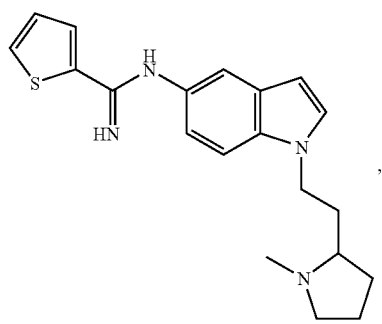
(−)-57
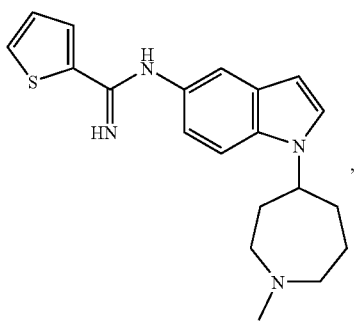
58
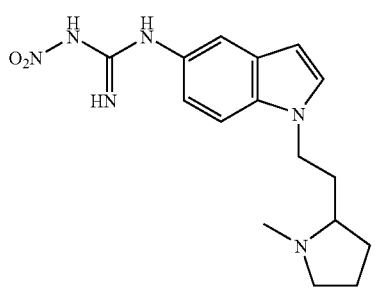
59
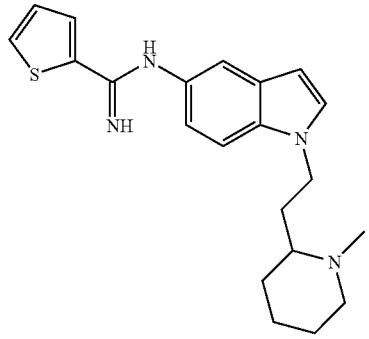
62
TABLE 2-continued
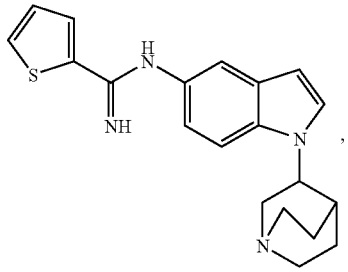
71
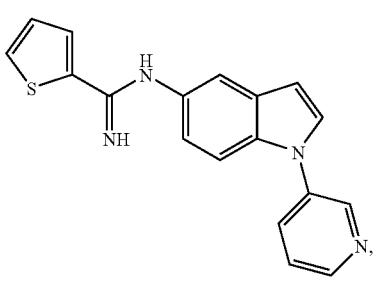
74
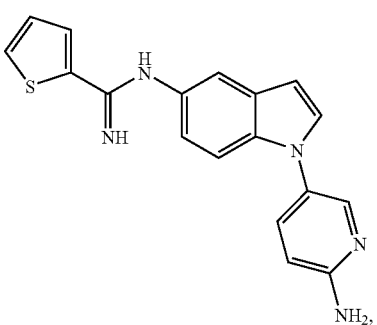
77
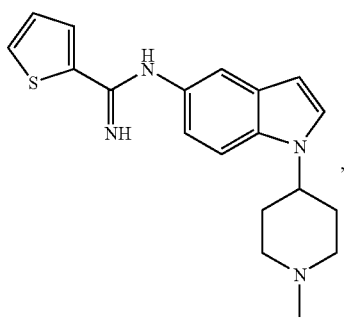
82
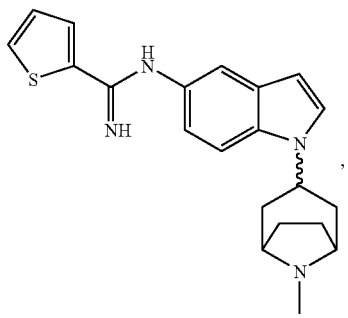
86

TABLE 2-continued
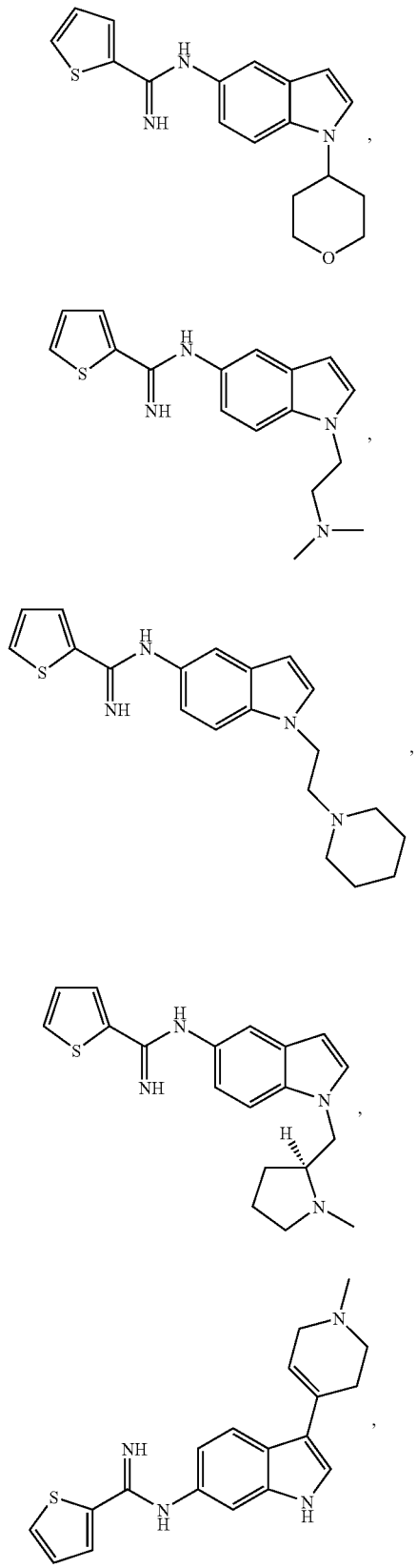
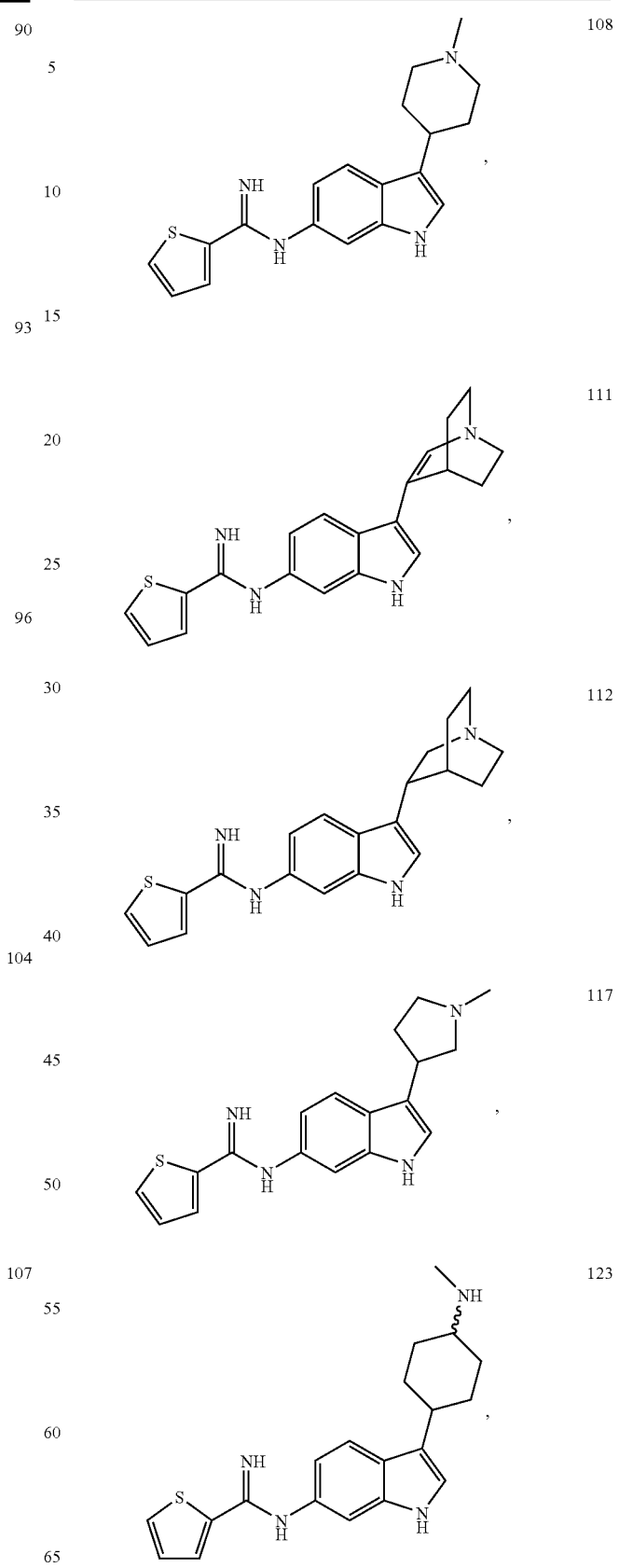

TABLE 2-continued

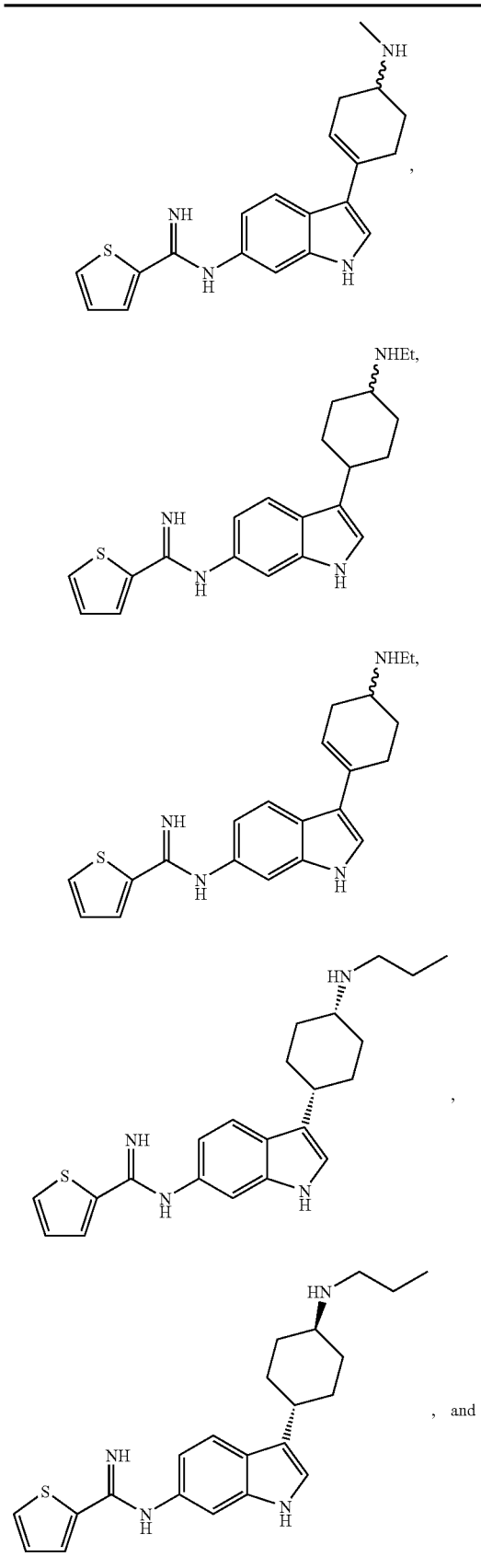

Methods of Preparing Compounds of the Invention

The compounds of the invention can be prepared by processes analogous to those established in the art, for example, by the reaction sequences shown in Schemes 1-12.

A compound of formula IV where $R^1$, $R^2$, and $R^3$ are as defined elsewhere herein, can be prepared under standard alkylating conditions by treating a compound of formula II with a compound of formula III, or a suitably protected derivative thereof, where $R^1$ is as defined above, with the exception that $R^1$ is not H, and "LG" is a leaving group, such as, for example, chloro, bromo, iodo, or sulfonate (e.g., mesylate, tosylate, or triflate). Conditions to effect the alkylation of a compound of formula II with a compound of formula III may include, for example, heating a compound of formula II and a compound of formula III, with or without a solvent, optionally in the presence of a suitable base (see Scheme 1).

Scheme 1

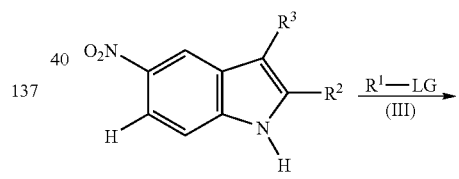

Alternatively, production of a compound of formula IV, or a suitably protected derivative thereof, where $R^2$ and $R^3$ are as defined herein for a compound formula I and $R^1$ is $(CH_2)_{m1}X^1$, where $X^1$ is

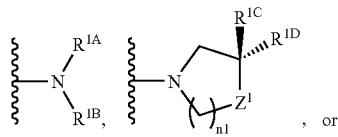

-continued

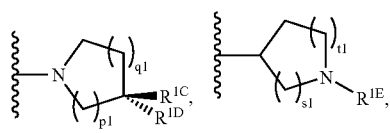

wherein each of $R^{1A}$ and $R^{1B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl; each of $R^{1C}$ and $R^{1D}$ is, independently, H, OH, $CO_2R^{1E}$, or $NR^{1F}R^{1G}$, wherein each of $R^{1E}$, $R^{1F}$, and $R^{1G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{1C}$ and $R^{1D}$ together with the carbon they are bonded to are C=O; $Z^1$ is $NR^{1H}$, $NC(O)R^{1H}$, $NC(O)OR^{1H}$, $NC(O)NHR^{1H}$, $NC(S)R^{1H}$, $NC(S)NHR^{1H}$, $NS(O)_2R^{1H}$, O, S, S(O), or $S(O)_2$, wherein $R^{1H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl; m1 is an integer of 2 to 6; n1 is an integer of 1 to 4; p1 is an integer of 0 to 2; q1 is an integer of 0 to 5; s1 is an integer of 0 to 2; and t1 is an integer of 0 to 5, and involves the reaction of a compound of formula V, wherein LG is a suitable leaving group, such as, for example, chloro, bromo, iodo, or sulfonate (e.g., mesylate, tosylate, or triflate), with compounds of formula VI, where $X^1$ is as defined above, under standard alkylation conditions as shown in Scheme 2. Alternatively, a compound of formula V, where LG represents an aldehyde, ester, or acylchloride group, may be reacted with a compound of formula VI. When LG is an aldehyde group, standard reductive amination conditions (Abdel-Majid et al. J. Org. Chem. 61: 3849-3862, 1996) may be employed using a suitable reducing agent, such as $NaBH_4$, $NaBH(OAc)_3$, $NaCNBH_4$, and the like, in an alcoholic solvent, such as ethanol, to produce a compound of formula VII. The reductive amination may be performed in one reaction or the imine resulting from mixing a compound of formula V with a compound of formula VI can be performed in situ, followed by sequential reduction with a suitable reducing agent. When LG is an acyl chloride or an ester group, preferably an active ester, such as, for example, pentafluorophenyl ester or hydroxysuccinimide ester, the reaction of a compound of formula V with a compound of formula $X^1$—H, or a suitably protected derivative thereof, is followed by reduction of the resulting amide using a suitable reducing agent, such as, for example, $BH_3$ to give compounds of formula VIII. Compounds of formula V may be prepared using standard methodologies, as described in WO 00/38677.

Scheme 2

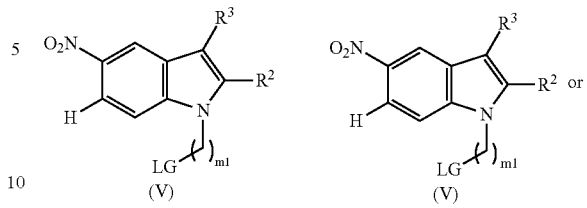

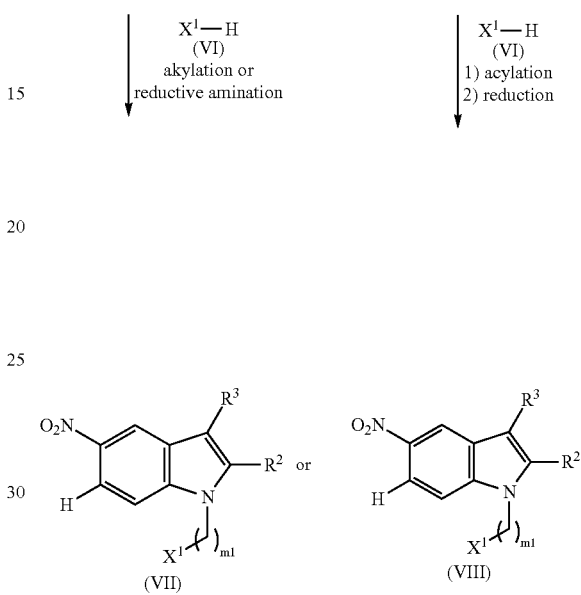

A compound of formula IV, or a suitably protected derivative thereof, where $R^2$ and $R^3$ are as defined herein for a compound formula I; LG is a suitable leaving group, such as, for example, chloro, bromo, iodo, or a sulfonate (e.g., mesylate, tosylate, or triflate); and $X^3$ is

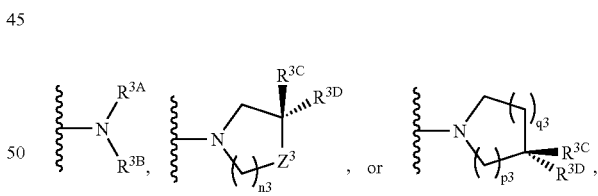

where $R^{3A}$, $R^{3B}$, $R^{3C}$, $R^{3D}$, $Z^3$, n3, p3, and q3 are defined as $R^{1A}$, $R^{1B}$, $R^{1C}$, $R^{1D}$, $Z^1$, n1, p1, and q1 above, can be prepared according to Scheme 3, for example, by treating a compound of Formula IX with oxalyl chloride in a suitable solvent, such as, for example, ether, to produce a compound of formula X. Subsequent reaction with amine $X^3$—H, followed by reduction with a reducing agent, such as $LiAlH_4$, according to standard procedures (Blair et. al., *J. Med. Chem.* 43:4701-4710, 2000; Speeter and Anthony, *J. Am. Chem. Soc.* 76:6208-6210, 1954) produces a compound of formula XI.

Scheme 3

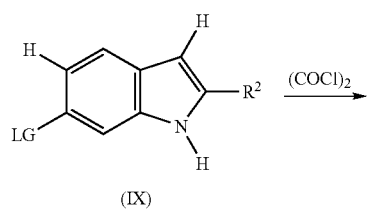

(IX)

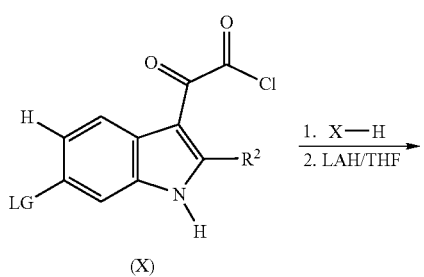

(X)

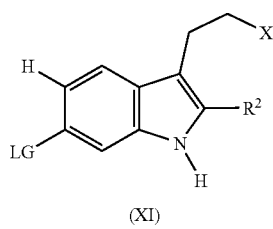

(XI)

Using standard methodologies as described in the literature (Russell et al., *J. Med. Chem.* 42:4981-5001, 1999; Cooper et al., *Bioorg. Med. Chem. Lett.* 11:1233-1236, 2001; Sternfeld et al., *J. Med. Chem.* 42:677-690, 1999), a compound of formula XIVa, XIVb, XVa, or XVb, or a suitably protected derivative thereof; $X^3$ is

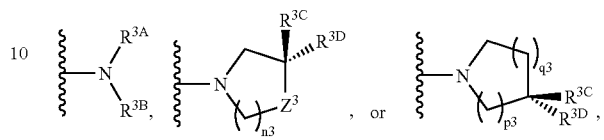

where $R^{3A}$, $R^{3B}$, $R^{3C}$, $R^{3D}$, $Z^3$, n3, p3, and q3 are as defined elsewhere herein; $X^2$ is

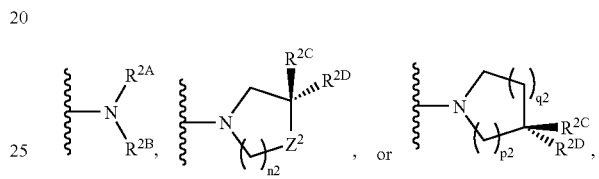

where $R^{2A}$, $R^{2B}$, $R^{2C}$, $R^{2D}$, $Z^2$, n2, p2, and q2 are as $R^{1A}$, $R^{1B}$, $R^{1C}$, $R^{1D}$, $Z^1$, n1, p1, and q1 above; r2 and r3 are as m1 above; and LG is a suitable leaving group, such as, for example, chloro, bromo, iodo, or triflate, can be prepared according to Scheme 4 by treating amine $X^3$—H or $X^2$—H with a compound of formula XII; or XIIIa or XIIIb, respectively, where Y is a suitable leaving group, such as, for example, chloro, bromo, iodo, or sulfonate (e.g., mesylate or tosylate). The Y group can be prepared from the appropriate alcohol (i.e., Y=OH) using standard techniques.

Scheme 4

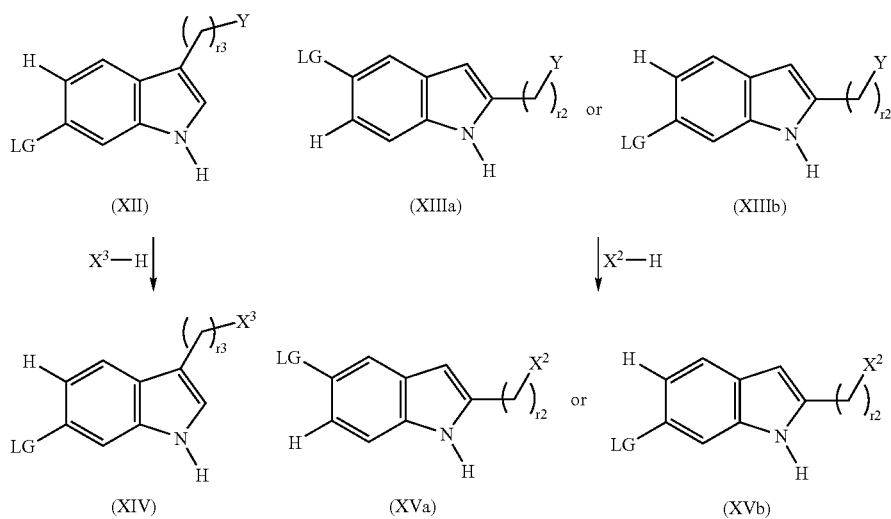

Compounds of formula XVIa and XVIb wherein $X^2$ is phenyl or aryl, X is a leaving group LG such as chloro, bromo, iodo, or sulfonate (e.g., mesylate, triflate or tosylate), or alternatively a nitro group or N-protected amino, can be prepared by reacting a compound of formula XVIa or XVIb with a suitable alkylating agent (r2 is 1) $X^2$—$(CH_2)_{r2}$Y where Y is a suitable leaving group, such as, for example, chloro, bromo, iodo, or sulfonate (e.g., mesylate, triflate or tosylate) in the presence of a base and a suitable solvent. An example of suitable base includes potassium or sodium hydroxide and the like in a polar solvent such as DMSO or DMF (Organic Syntheses, Col. Vol 6, p 104). Compounds of formula XVIIIa and XVIIIb where r2 is 1 and $X^2$ is phenyl or aryl and X is defined above can be prepared from XVIIa and XVIIb respectively by a 1,2-shift under conditions of heating in the presence of a catalyst, preferably polyphosphoric acid (PPA) as described in Synthetic Communications, 27(12), 2033-2039 (1997).

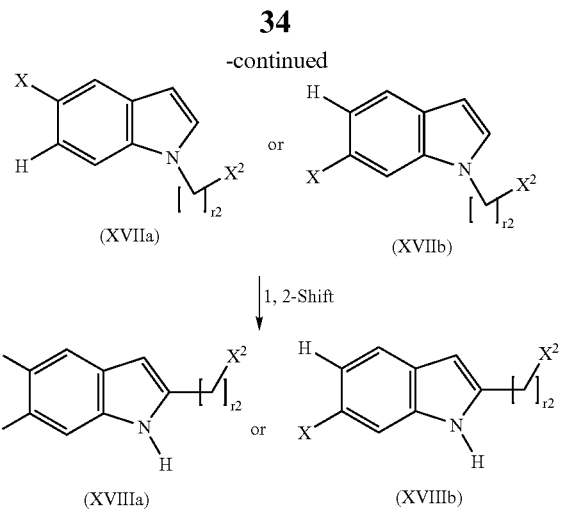

A compound of formula XXIVa or XXIVb, where LG, Z, o, p, q, s, t, and u are as defined elsewhere herein, can be prepared as shown in Scheme 6 by procedures analogous to those previously described (see, for example, Coe et al., *Tett. Lett.* 37(34):6045-6048, 1996). A compound of formula XIX can be reacted with dimethylformamide dimethylacetal with a suitable base such as pyrrolidine with heating in a suitable solvent such as DMF to give compound XX. When LG is halo such as chloro, bromo, or iodo, compound of XXI can be prepared by treatment of compound of formula XX with acidic methanol, preferably HCl in anhydrous methanol, followed by reduction of the nitro group. Suitable reducing conditions include sodium dithionite in refluxing ethanol.

Scheme 5

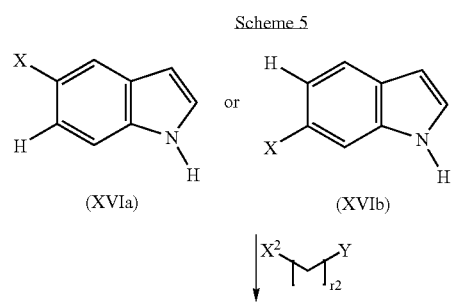

Scheme 6

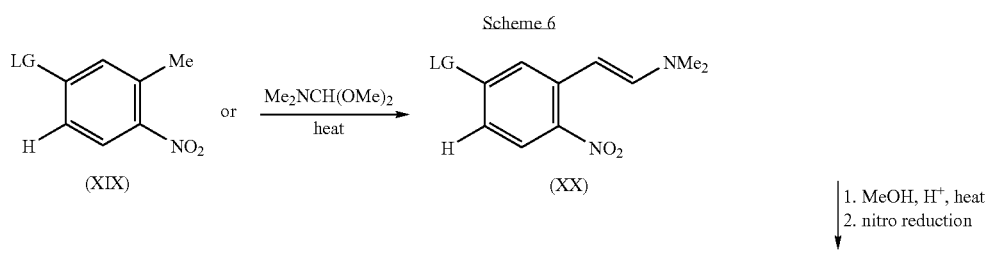

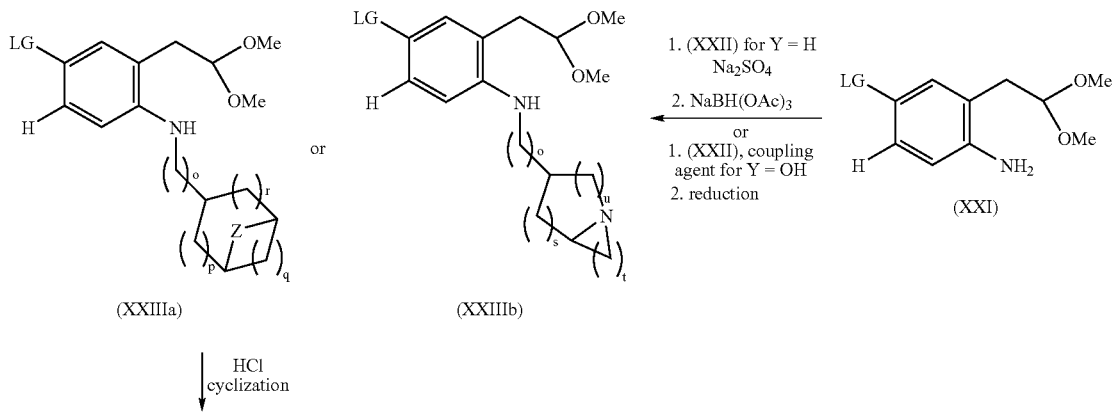

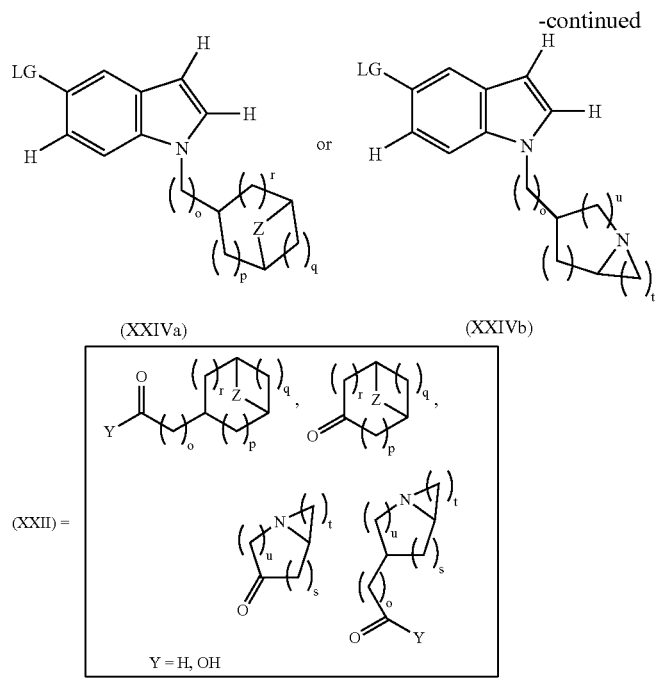

A compound of formula XXI can be converted to XXIIIa or XXIIIb by treatment with the appropriate aldehyde XXII (Y═H) or ketone XXII under standard reductive amination conditions (for example see: Abdel-Majid et al. *J. Org. Chem.* 61: 3849-3862, 1996). Alternatively, a compound of formula XXIIIa or XXIIIb can be prepared by coupling the amine XXI with the corresponding carboxylic acid XXII (Y═OH) under standard amide coupling conditions known in the art followed by reduction of the amide bond with a reducing agent such as LiAlH$_4$. Alternatively Y═OH can be converted to a suitable leaving group such as a mixed anhydride by reaction of XXII (Y═OH) with a chloroformate reagent. Suitable chloroformates include ethyl chloroformate and the like in aprotic solvents such as for example, THF, in the presence of a tertiary amine base such as triethylamine and the like. Compounds of formula XXIVa or XXIVb can be prepared by cyclization with a suitable protic acid in an alcoholic solvent. Preferably the conditions employ HCl in anhydrous methanol.

Alternatively, compound of formula XXIVa can be prepared according to Scheme 7. A compound of formula XXV can be coupled with a carboxylic acid of formula XXII (Y═OH)

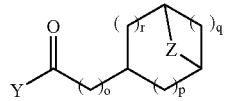

where Z, o, p, q and r and defined elsewhere, under standard amide bond forming conditions. Standard conditions include for example, EDCl in the presence of HOBT in a polar solvent such as DMF. Alternatively Y═OH can be converted to a suitable leaving group such as a mixed anhydride by reaction of XXII (Y═OH) with a chloroformate reagent. Suitable chloroformates include ethyl chloroformate and the like in aprotic solvents such as for example, THF, in the presence of a tertiary amine base such as triethylamine and the like. The amide bond of XXIV can be reduced to a compound of formula XXVII using a suitable reducing agent, such as lithium aluminum hydride for example, in a suitable non-protic solvent such as THF at room temperature to reflux. If Z is a N-protected nitrogen such as N-CBz for example, the protecting group may reduced to the corresponding methyl group. A compound of XXVII can be chloracetylated to give a compound of formula XXVIII according to procedures as described in the literature (Sugasawa et. al. *Chem. Pharm. Bull.* Vol 33, 1827-1835, 1985). A preferred chloracetylating conditions includes the use of chloroacetonitrole in the presence of a Lewis acid, for example boron trichloride followed by hydrolysis to the chloroketone XXVIII. Reduction and cyclization of a compound of formula XXVIII to XXIVa can be achieved using a reducing agent in the presence of a suitable base. The preferred conditions utilize sodium borohydride in ethanol with cooling.

Scheme 7

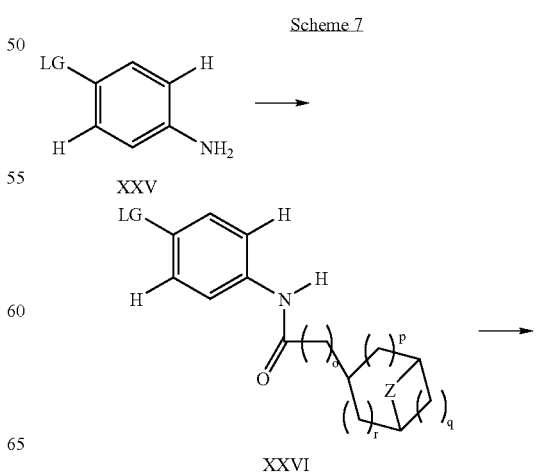

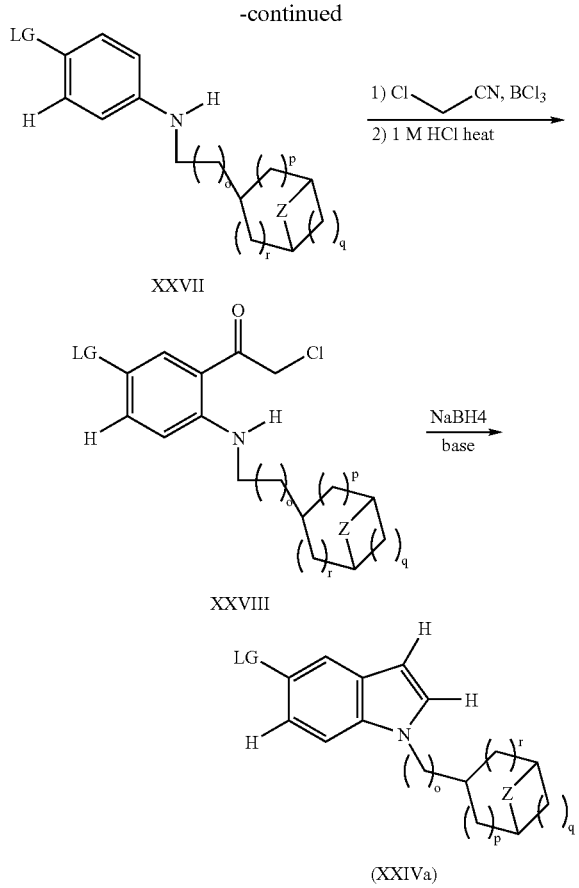

Accordingly, a compound of formula XXIX, XXX or XXXI, where, $Z^1$, Z, p1, and q1, o, p, q, r and s are as defined elsewhere herein can be prepared from a compound of formula XXVIII, as shown in Scheme 8, by procedures analogous to those previously described (see, for example, Perregaard et al., *J. Med. Chem.* 35:4813-4822, 1992; Rowley et al., *J. Med. Chem.* 44:1603-1614, 2001). Reaction of the appropriate ketone with indole XXVIII under suitable conditions will generate the corresponding compound with the double bond. Depending on the nature of the substrates, suitable conditions include heating the ketone and XXVIII in the presence of a suitable base such as pyrrolidine or KOH in a protic solvent such as ethanol or methanol. Depending on the presence of the protecting groups in the substrates, for example when an acid stable protecting group is used, acidic conditions can be employed. Suitable acidic conditions include heating the indole compound with the ketone in acetic acid in the presence of phosphoric acid ($H_3PO_4$). Reduction of the double bond in compounds of formula XXIX, XXX or XXXI can be accomplished by catalytic hydrogenation over Pd on carbon in suitable solvents such as ethanol, methanol and the like or by reduction with hydrazine hydrate in water in the presence of Raney-Nickel and a suitable co-solvent such as methanol or ethanol. Simultaneous reduction of both nitro and the double bond can be accomplished by hydrogenation with Pd on carbon. When reduction of only the nitro group is required without reduction of the double bond, hydrazine in the presence of Raney-Nickel is the preferred method. Preferably the reaction time is minimized to prevent over reduction of the double bond. Alternatively, palladium on calcium carbonate poisoned with Pb can be used to selectively reduce the nitro group without reduction of the double bond. In this case, the source of hydrogen can be hydrogen gas or from a transfer hydrogenation reagent such as formic acid, ammonium formate, or tetraalkylammonium formate.

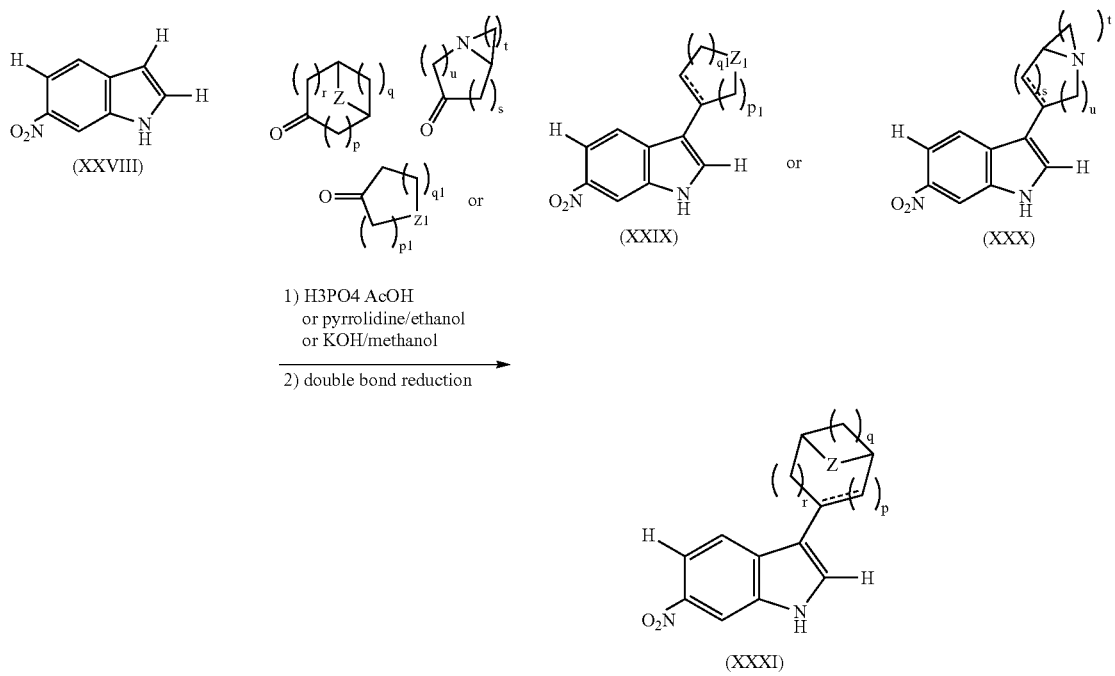

A compound of formula XXVa or XXVb, where $R^1$, $R^2$, and $R^3$ are as defined in formula I, can be prepared by reduction of the nitro group of a compound of formula XXIVa or XXIVb, respectively, or a suitably protected derivative, under standard conditions as shown in Scheme 7. In one example, standard reduction conditions include the use of $SnCl_2$ in a polar solvent, such as, for example, ethanol at refluxing temperatures. Alternatively, a compound of formula XXVa or XXVb can be prepared by the hydrogenation of a compound of formula XXIVa or XXIVb, respectively, using a suitable catalyst, such as palladium on charcoal in ethanol or another solvent or combinations of solvents.

More specific compounds of the invention of formula XXXIII wherein $Z^1$ is an alkyl group can be prepared by reaction a compound of formula XVIb where X is nitro, N-protected amino (eg NBz group) or halo with an N-alkyl-maleimide, for example, N-methylmaleimide, in refluxing acetic acid (Scheme 9; see Macor et. al. 37, 2509, 1994). Reduction of the amide bonds of XXXII can be accomplished with a reducing agent such as lithium aluminum hydride ($LiAlH_4$) in THF.

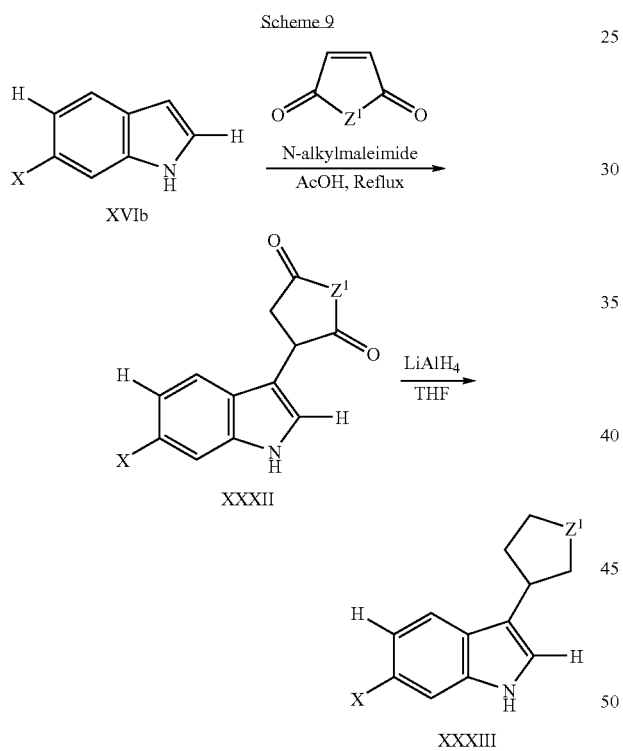

Specific compounds of the formula XXXV wherein X, preferably X is nitro, are defined previously and $R^8$ and $R^9$ are independently H or alkyl, can be prepared according to Scheme 10. Reaction of indole XVIb with 1,4-cyclohexadione monomethylene ketal in the presence of refluxing methanol or ethanol in the presence of a base such as KOH, NaOH, pyrrolidine and the like give compounds of formula XXXII. Hydrodrolysis of the ketal to give a compound of formula XXXIII can be achieved under acidic conditions. Preferred conditions include 10% HCl solution in acetone at room temperature. A compound of formula XXXIV can be prepared by standard reductive amination conditions with an amine of formula $NHR^8R^9$. When $R^8$ or $R^9$ is H, protection of the amine function of a compound of formula XXIV or XXXV can be accomplished by standard techniques. Suitable protecting groups include carbamates such as ethyl, t-butyl (Boc) and the like which can be removed when needed by standard deprotection techniques. A preferred protecting group is Boc protecting group. Compounds of formula XXXV wherein $R^8$ or $R^9$ are H, alkyl or N-protected, can be prepared by hydrogenation over Pd on carbon in a suitable solvent such as ethanol, methanol and the like. In the case of compounds of formula XXXV, a mixture of cis and trans diastereomers can occur. Separation of these diastereomers can be achieved by column chromatography or by HPLC.

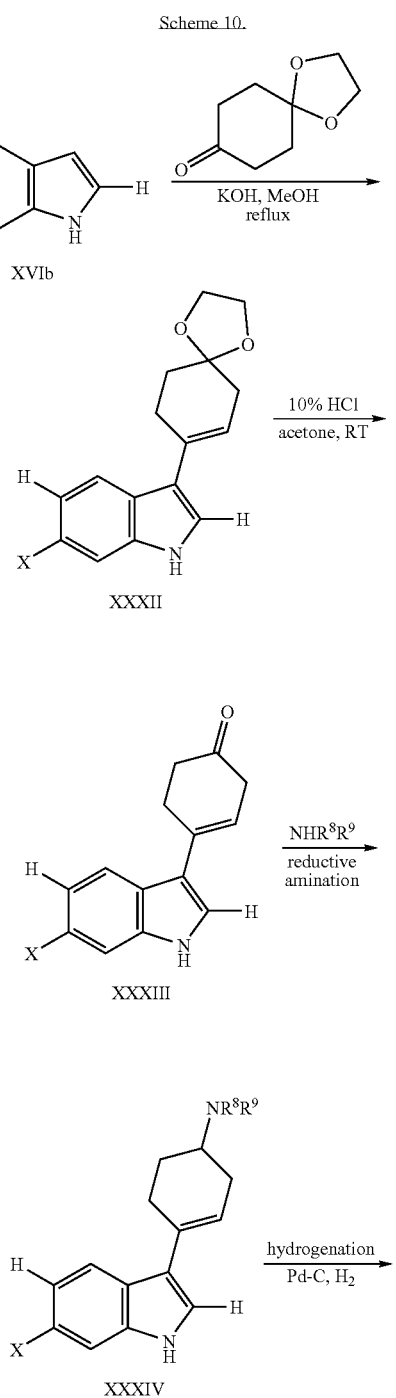

Compounds of formula XXXVIIa or XXVIIb where $R^1$, $R^2$, and $R^3$ are defined herein, can be prepared by reduction of the corresponding nitro group with $SnCl_2$ in refluxing ethanol or hydrogenation over Pd on carbon. Other techniques for reduction of nitro groups, for example using hydrazine hydrate and Raney-Ni, are known to those in the art.

As shown in Scheme 12, a compound of formula XXXVIIa or XXVIIb can also be prepared by metal catalyzed amination of compounds of a compound of formula XXVIa or XXVIb, respectively, where LG is chloro, bromo, iodo, or triflate (Wolfe, et al. *J. Org. Chem.* 65:1158-1174, 2000) in the presence of a suitable ammonia equivalent, such as benzophenone imine, $LiN(SiMe_3)_2$, $Ph_3SiNH_2$, $NaN(SiMe_3)_2$, or lithium amide (Huang and Buchwald, *Org. Lett.* 3(21):3417-3419, 2001). Examples of suitable metal catalysts include, for example, a palladium catalyst coordinated to suitable ligands. Alternatively a suitable leaving group for palladium catalyzed amination may be nonaflate (Anderson, et al., *J. Org. Chem.* 68:9563-9573, 2003) or boronic acid (Antilla and Buchwald, *Org. Lett.* 3(13):2077-2079, 2001) when the metal is a copper salt, such as Cu(II) acetate, in the presence of suitable additives, such as 2,6-lutidine. A preferred leaving group is bromo in the presence of palladium (0) or palladium (II) catalyst. Suitable palladium catalysts include tris-dibenzylideneacetone dipalladium ($Pd_2 dba_3$) and palladium acetate ($PdOAc_2$), preferably $Pd_2 dba_3$. Suitable ligands for palladium can vary greatly and may include, for example, XantPhos, BINAP, DPEphos, dppf, dppb, DPPP, (o-biphenyl)-$P(t-Bu)_2$, (o-biphenyl)-$P(Cy)_2$, $P(t-Bu)g 3$, $P(Cy)_3$, and others (Huang and Buchwald, *Org. Lett.* 3(21):3417-3419, 2001). Preferably the ligand is $P(t-Bu)_3$. The Pd-catalyzed amination is performed in a suitable solvent, such as THF, dioxane, toluene, xylene, DME, and the like, at temperatures between room temperature and reflux.

Compounds of formula XXXIXa or XXXIXb, where each of $R^{4A}$ or $R^{5A}$ is as defined elsewhere herein and Q is an aryl group (e.g., a phenyl group), a $C_1$ alkaryl group (e.g., a naphthylmethyl group), or an alkyl group (e.g., a methyl group) are either commercially available or may be prepared by reacting a cyano compound of formula XXXVIIIa or XXXVIIIb with thiol-containing compounds of formula XL (Scheme 13). Other examples of this transformation are described the art (see, for example, Baati et al., *Synlett* 6:927-9, 1999; EP 262873 1988, Collins et al., *J. Med. Chem.* 41:15, 1998).

As shown in Scheme 14, a compound of formula XLIa or XLIb, where $R^1$, $R^2$, $R^3$, $R^{4A}$, or $R^{5A}$ are as defined elsewhere herein, can be prepared by reacting a compound of formula XXXIXa or XXXIXb with a compound of formula XXXVIIa or XXXVIIb, respectively, where Q is defined as above. Compounds of formula XLIc can be prepared by reaction of a compound of formula XXXVIIa with 1-methyl-3-nitro-1-nitrosoguanidine.

Scheme 14

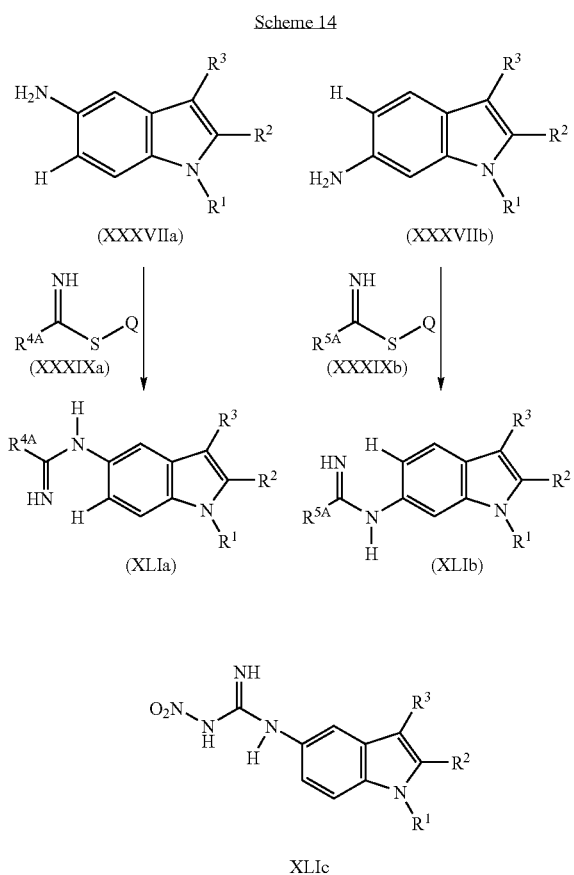

In some cases the chemistries outlined above may have to be modified, for instance, by the use of protective groups to prevent side reactions due to reactive groups, such as reactive groups attached as substituents. This may be achieved by means of conventional protecting groups as described in "Protective Groups in Organic Chemistry," McOmie, Ed., Plenum Press, 1973 and in Greene and Wuts, "Protective Groups in Organic Synthesis," John Wiley & Sons, $3^{rd}$ Edition, 1999.

The compounds of the invention, and intermediates in the preparation of the compounds of the invention, may be isolated from their reaction mixtures and purified (if necessary) using conventional techniques, including extraction, chromatography, distillation and recrystallization.

The formation of a desired compound salt is achieved using standard techniques. For example, the neutral compound is treated with an acid in a suitable solvent and the formed salt is isolated by filtration, extraction, or any other suitable method.

The formation of solvates of the compounds of the invention will vary depending on the compound and the solvate. In general, solvates are formed by dissolving the compound in the appropriate solvent and isolating the solvate by cooling or adding an antisolvent. The solvate is typically dried or azeotroped under ambient conditions.

Preparation of an Optical Isomer of a Compound of the Invention May be Performed by reaction of the appropriate optically active starting materials under reaction conditions which will not cause racemization. Alternatively, the individual enantiomers may be isolated by separation of a racemic mixture using standard techniques, such as, for example, fractional crystallization or chiral HPLC.

A radiolabeled compound of the invention may be prepared using standard methods known in the art. For example, tritium may be incorporated into a compound of the invention using standard techniques, such as, for example, by hydrogenation of a suitable precursor to a compound of the invention using tritium gas and a catalyst. Alternatively, a compound of the invention containing radioactive iodine may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, such as, for example, hexamethylditin in the presence of tetrakis(triphenylphosphine) palladium (0) in an inert solvent, such as dioxane, and at elevated temperatures, suitably 50-100° C.

Pharmaceutical Uses

The present invention features all uses for compounds of the invention, including use in therapeutic methods, whether alone or in combination with another therapeutic substance, their use in compositions for inhibiting NOS activity, their use in diagnostic assays, and their use as research tools.

The compounds of the invention have useful NOS inhibiting activity, and therefore are useful for treating, or reducing the risk of, diseases or conditions that are ameliorated by a reduction in NOS activity. Such diseases or conditions include those in which the synthesis or oversynthesis of nitric oxide plays a contributory part.

Accordingly, the present invention features a method of treating, or reducing the risk of, a disease or condition caused by NOS activity that includes administering an effective amount of a compound of the invention to a cell or animal in need thereof. Such diseases or conditions include, for example, migraine headache with and without aura, neuropathic pain, chronic tension type headache, chronic pain, acute spinal cord injury, diabetic neuropathy, diabetic nephropathy, an inflammatory disease, stroke, reperfusion injury, head trauma, cardiogenic shock, CABG associated neurological damage, HCA, AIDS associated dementia, neurotoxicity, Parkinson's disease, Alzheimer's disease, ALS, Huntington's disease, multiple sclerosis, metamphetamine-induced neurotoxicity, drug addiction, morphine/opioid induced tolerance, dependence, hyperalgesia or withdrawal, ethanol tolerance, dependence, or withdrawal, epilepsy, anxiety, depression, attention deficit hyperactivity disorder, central post-stroke pain (CPSP), and psychosis.

The following description is a summary and a basis for the link between NOS inhibition and some of these conditions.

Migraine

The first observation by Asciano Sobrero in 1847 that small quantities of nitroglycerine, an NO releasing agent, causes severe headache lead to the nitric oxide hypothesis of migraine (Olesen et al., *Cephalagia* 15:94-100, 1995). Serotonergic 5HT$_{1D/1B}$ agonists, such as sumatriptan, which are used clinically in the treatment of migraine, are known to prevent the cortical spreading depression in the lissencephalic and gyrencephalic brain during migraine attack, a process resulting in widespread release of NO. Indeed, it has been shown that sumatriptan modifies the artificially enhanced cortical NO levels following infusion of glyceryl trinitate in rats (Read et al., *Brain Res.* 847:1-8, 1999; ibid, 870(1-2):44-53, 2000). In a human randomized double-blinded clinical trial for migraine, a 67% response rate after single i.v. administration of L-N$^G$ methylarginine hydrochloride (L-NMMA, an NOS inhibitor) was observed. The effect was not attributed to a simple vasoconstriction since no effect was observed on transcranial doppler determined velocity in the middle cerebral artery (Lassen et al., *Lancet* 349:401-402, 1997). In an open pilot study using the NO scavenger hydroxycobalamin, a reduction in the frequency of migraine attack of 50% was observed in 53% of the patients and a reduction in the total duration of migraine attacks was also observed (van der Kuy et al., *Cephalgia* 22(7):513-519, 2002).

Migraine with Allodynia

Clinical studies have shown that as many as 75% of patients develop cutaneous allodynia (exaggerated skin sensitivity) during migraine attacks and that its development during migraine is detrimental to the anti-migraine action of triptan $5HT_{1B/1D}$ agonists (Burstein et al., *Ann. Neurol.* 47:614-624, 2000; Burstein et al., *Brain*, 123:1703-1709, 2000). While the early administration of triptans such as sumatriptan can terminate migraine pain, late sumatriptan intervention is unable to terminate migraine pain or reverse the exaggerated skin sensitivity in migraine patients already associated with allodynia (Burstein et al., *Ann. Neurol.* DOI: 10.1002/ana.10785, 2003; Burstein and Jakubowski, *Ann. Neurol.*, 55:27-36, 2004). The development of peripheral and central sensitization correlates with the clinical manifestations of migraine. In migraine patients, throbbing occurs 5-20 minutes after the onset of headache, whereas cutaneous allodynia starts between 20-120 minutes (Burstein et al., *Brain*, 123:1703-1709, 2000). In the rat, experimentally induced peripheral sensitization of meningeal nociceptors occurs within 5-20 minutes after applying an inflammatory soup (I.S.) to the dura (Levy and Strassman, *J. Physiol.*, 538:483-493, 2002), whereas central sensitization of trigeminovascular neurons develops between 20-120 minutes (Burstein et al., *J. Neurophysiol.* 79:964-982, 1998) after I.S. administration. Parallel effects on the early or late administration of antimigraine triptans like sumatriptan on the development of central sensitization have been demonstrated in the rat (Burstein and Jakubowski, vide supra). Thus, early but not late sumatriptan prevents the long-term increase in I.S.-induced spontaneous activity seen in central trigeminovascular neurons (a clinical correlate of migraine pain intensity). In addition, late sumatriptan intervention in rats did not prevent I.S.-induced neuronal sensitivity to mechanical stimulation at the periorbital skin, nor decreased the threshold to heat (a clinical correlate of patients with mechanical and thermal allodynia in the periorbital area). In contrast, early sumatriptan prevented I.S. from inducing both thermal and mechanical hypersensitivity. After the development of central sensitization, late sumatriptan intervention reverses the enlargement of dural receptive fields and increases in sensitivity to dural indentation (a clinical correlate of pain throbbing exacerbated by bending over) while early intervention prevents its development.

Previous studies on migraine compounds such as sumatriptan (Kaube et al., *Br. J. Pharmacol.* 109:788-792, 1993), zolmitriptan (Goadsby et al., *Pain* 67:355-359, 1996), naratriptan (Goadsby et al., *Br. J. Pharmacol.*, 328:37-40, 1997), rizatriptan (Cumberbatch et al., *Eur. J. Pharmacol.*, 362:43-46, 1998), or L-471-604 (Cumberbatch et al., *Br. J. Pharmacol.* 126:1478-1486, 1999) examined their effects on nonsensitized central trigeminovascular neurons (under normal conditions) and thus do not reflect on their effects under the pathophysiolocal conditions of migraine. While triptans are effective in terminating the throbbing of migraine whether administered early or late, the peripheral action of sumatriptan is unable to terminate migraine pain with allodynia following late intervention via the effects of central sensitization of trigeminovascular neurons. The limitations of triptans suggest that improvement in the treatment of migraine pain can be achieved by utilizing drugs that can abort ongoing central sensitization, such as the compounds of the present invention.

It has been shown that systemic nitroglycerin increases nNOS levels and c-Fos-immunoreactive neurons (a marker neuronal activation) in rat trigeminal nucleus caudalis after 4 hours, suggesting NO likely mediates central sensitization of trigeminal neurons (Pardutz et al., *Neuroreport* 11(14):3071-3075, 2000). In addition, L-NAME can attenuate Fos expression in the trigeminal nucleus caudalis after prolonged (2 hrs) electrical stimulation of the superior sagittal sinus (Hoskin et al. *Neurosci. Lett.* 266(3):173-6, 1999). Taken together with ability of NOS inhibitors to abort acute migraine attack (Lassen et al., *Cephalalgia* 18(1):27-32, 1998), the compounds of the invention, alone or in combination with other antinociceptive agents, represent excellent candidate therapeutics for aborting migraine in patients after the development of allodynia.

Chronic Headache (CTTH)

NO contributes to the sensory transmission in the peripheral (Aley et al., *J. Neurosci.* 1:7008-7014, 1998) and central nervous system (Meller and Gebhart, *Pain* 52:127-136, 1993). Substantial experimental evidence indicates that central sensitization, generated by prolonged nociceptive input from the periphery, increases excitability of neurons in the CNS and is caused by, or associated with, an increase in NOS activation and NO synthesis (Bendtsen, *Cephalagia* 20:486-508, 2000; Woolf and Salter, *Science* 288:1765-1769, 2000). It has been shown that experimental infusion of the NO donor, glyceryl trinitrate, induces headache in patients. In a double-blinded study, patients with chronic tension-type headache receiving L-NMMA (an NOS inhibitor) had a significant reduction in headache intensity (Ashina and Bendtsen, *J. Headache Pain* 2:21-24, 2001; Ashina et al., *Lancet* 243 (9149):287-9, 1999). Thus the NOS inhibitors of the present invention may be useful for the treatment of chronic tension-type headache.

Acute Spinal Cord Injury, Chronic or Neuropathic Pain

In humans, NO evokes pain on intracutaneous injection (Holthusen and Arndt, *Neurosci. Lett.* 165:71-74, 1994), thus showing a direct involvement of NO in pain. Furthermore, NOS inhibitors have little or no effect on nociceptive transmission under normal conditions (Meller and Gebhart, *Pain* 52:127-136, 1993). NO is involved in the transmission and modulation of nociceptive information at the periphery, spinal cord and supraspinal level (Duarte et al., *Eur. J. Pharmacol.* 217:225-227, 1992; Haley et al., *Neuroscience* 31:251-258, 1992). Lesions or dysfunctions in the CNS may lead to the development of chronic pain symptoms, known as central pain, and includes spontaneous pain, hyperalgesia, and mechanical and cold allodynia (Pagni, *Textbook of Pain*, Churchill Livingstone, Edinburgh, 1989, pp. 634-655; Tasker In: *The Management of Pain*, pp. 264-283, J. J. Bonica (Ed.), Lea and Febiger, Philadelphia, Pa., 1990; Casey, Pain and Central Nervous System Disease: The Central Pain Syndromes, pp. 1-11 K. L. Casey (Ed.), Raven Press, New York, 1991). It has been demonstrated that systemic administration (i.p.) of the NOS inhibitors 7-NI and L-NAME relieve chronic allodynia-like symptoms in rats with spinal cord injury (Hao and Xu, *Pain* 66:313-319, 1996). The effects of 7-NI were not associated with a significant sedative effect and were reversed by L-arginine (NO precursor). The maintenance of thermal hyperalgesia is believed to be mediated by nitric oxide in the lumbar spinal cord and can be blocked by intrathecal administration of a nitric oxide synthase inhibitor like L-NAME or soluble guanylate cyclase inhibitor methylene blue (*Neuroscience* 50(1):7-10, 1992). Thus the NOS inhibitors of the present invention may be useful for the treatment of chronic or neuropathic pain.

Diabetic Neuropathy

The endogenous polyamine metabolite agmatine is a metabolite of arginine that is both an NOS inhibitor and N-methyl-D-aspartate (NMDA) channel antagonist. Agmatine is effective in both the spinal nerve ligation (SNL) model of neuropathic pain as well as the streptozotocin model of diabetic neuropathy (Karadag et al., *Neurosci. Lett.* 339(1): 88-90, 2003). Thus compounds possessing NOS inhibitory activity, such as, for example, a compound of formula I, a combination of an NOS inhibitor and an NMDA antagonist should be effective in treating diabetic neuropathy and other neuropathic pain conditions.

Inflammatory Diseases and Neuroinflammation

LPS, a well-known pharmacological tool, induces inflammation in many tissues and activates NFκB in all brain regions when administered intravenously. It also activates pro-inflammatory genes when injected locally into the striaitum (Stern et al., *J. Neuroimmunology*, 109:245-260, 2000). Recently it has been shown that both the NMDA receptor antagonist MK801 and the brain selective nNOS inhibitor 7-NI both reduce NFκB activation in the brain and thus reveal a clear role for glutamate and NO pathway in neuroinflammation (Glezer et al., *Neuropharmacology* 45(8):1120-1129, 2003). Thus, the administration of a compound of the invention, either alone or in combination with an NMDA antagonist, should be effective in treating diseases arising from neuroinflammation.

Stroke and Reperfusion Injury

The role of NO in cerebral ischemia can be protective or destructive depending on the stage of evolution of the ischemic process and on the cellular compartment producing NO (Dalkara et al., *Brain Pathology* 4:49, 1994). While the NO produced by eNOS is likely beneficial by acting as a vasodilator to improve blood flow to the affected area (Huang et al., *J. Cereb. Blood Flow Metab.* 16:981, 1996), NO produced by nNOS contributes to the initial metabolic deterioration of the ischemic penumbra, resulting in larger infarcts (Hara et al., *J. Cereb. Blood Flow Metab.* 16:605, 1996). The metabolic derangement that occurs during ischemia and subsequent reperfusion results in the expression and release of several cytokines that activate iNOS in several cell types including some of the central nervous system. NO can be produced at cytotoxic levels by iNOS, and increased levels of iNOS contribute to progressive tissue damage in the penumbra, leading to larger infarcts (Parmentier et al., *Br. J. Pharmacol.* 127:546, 1999). Inhibition of i-NOS has been shown to ameliorate cerebral ischemic damage in rats (*Am. J. Physiol.* 268:R286, 1995).

It has been shown that a synergistic neuroprotective effect is observed upon the combined administration of an NMDA antagonist (eg MK-801 or LY293558) with nNOS selective inhibitors (7-NI or ARL17477) in global cerebral ischemia (Hicks et al., *Eur. J. Pharmacol.* 381:113-119, 1999). Thus the compounds of the invention, administered either alone or in combination with NMDA antagonists, or compounds possessing mixed nNOS/NMDA activity, may be effective in treating conditions of stroke and other neurodegenerative disorders.

Complications Resulting from Coronary Artery Bypass Surgery

Cerebral damage and cognitive dysfunction still remains as a major complication of patients undergoing coronary artery bypass surgery (CABG) (Roch et al., *N. Eng. J. Med.* 335: 1857-1864, 1996; Shaw et al., *Q. J. Med.* 58:59-68, 1986). This cerebral impairment following surgery is a result of ischemia from preoperative cerebral microembolism. In a randomized trial of the NMDA antagonist remacemide, patients showed a significant overall postoperative improvement in learning ability in addition to reduced deficits (Arrowsmith et al., *Stroke* 29:2357-2362, 1998). Given the involvement of excitotoxicity produced by excessive release of glutamate and calcium influx, it is expected that a neuroprotective agent, such as a compound of the invention or an NMDA antagonist, either alone or in combination, may have a beneficial effect improving neurological outcomes after CABG.

AIDS-associated Dementia

HIV-1 infection can give rise to dementia. The HIV-1 coat protein gp-120 kills neurons in primary cortical cultures at low picomolar levels and requires external glutamate and calcium (Dawson et al., 90(8):3256-3259, 1993). This toxicity can be attenuated by administration of a compound of the invention, either alone or in combination with another therapeutic agent, such as, for example, an NMDA antagonist.

Examples of NMDA antagonist useful for any of the combinations of the invention include aptiganel; besonprodil; budipine; conantokin G; delucemine; dexanabinol; felbamate; fluorofelbamate; gacyclidine; glycine; ipenoxazone; kaitocephalin; lanicemine; licostinel; midafotel; milnacipran; neramexane; orphenadrine; remacemide; topiramate; (αR)-α-amino-5-chloro-1-(phosphonomethyl)-1H-benzimidazole-2-propanoic acid; 1-aminocyclopentane-carboxylic acid; [5-(aminomethyl)-2-[[[(5S)-9-chloro-2,3,6,7-tetrahydro-2,3-dioxo-1H-,5H-pyrido[1,2,3-de]quinoxalin-5-yl] acetyl]amino]phenoxy]-acetic acid; α-amino-2-(2-phosphonoethyl)-cyclohexanepropanoic acid; α-amino-4-(phosphonomethyl)-benzeneacetic acid; (3E)-2-amino-4-(phosphonomethyl)-3-heptenoic acid; 3-[(1E)-2-carboxy-2-phenylethenyl]-4,6-dichloro-1H-indole-2-carboxylic acid; 8-chloro-2,3-dihydropyridazino[4,5-b]quinoline-1,4-dione 5-oxide salt with 2-hydroxy-N,N,N-trimethyl-ethanaminium; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfinyl]phenyl]-guanidine; 6-chloro-2,3,4,9-tetrahydro-9-methyl-2,3-dioxo-1H-indeno[1,2-b]pyrazine-9-acetic acid; 7-chlorothiokynurenic acid; (3S,4aR,6S,8aR)-decahydro-6-(phosphonomethyl)-3-isoquinolinecarboxylic acid; (−)-6,7-dichloro-1,4-dihydro-5-[3-(methoxymethyl)-5-(3-pyridinyl)-4-H-1,2,4-triazol-4-yl]-2,3-quinoxalinedione; 4,6-dichloro-3-[(E)-(2-oxo-1-phenyl-3-pyrrolidinylidene) methyl]-1H-indole-2-carboxylic acid; (2R,4S)-rel-5,7-dichloro-1,2,3,4-tetrahydro-4-[[(phenylamino)carbonyl] amino]-2-quinolinecarboxylic acid; (3R,4S)-rel-3,4-dihydro-3-[4-hydroxy-4-(phenylmethyl)-1-piperidinyl-]-2H-1-benzopyran-4,7-diol; 2-[(2,3-dihydro-1H-inden-2-yl) amino]-acetamide; 1,4-dihydro-6-methyl-5-[(methylamino) methyl]-7-nitro-2,3-quinoxalinedione; [2-(8,9-dioxo-2,6-diazabicyclo[5.2.0]non-1(7)-en-2-yl)ethyl]-phosphonic acid; (2R,6S)-1,2,3,4,5,6-hexahydro-3-[(2S)-2-methoxypropyl]-6,11,11-trimethyl-2,6-methano-3-benzazocin-9-ol; 2-hydroxy-5-[[(pentafluorophenyl)methyl]amino]-benzoic acid; 1-[2-(4-hydroxyphenoxy)ethyl]-4-[(4-methylphenyl) methyl]-4-piperidinol; 1-[4-(1H-imidazol-4-yl)-3-butynyl]-4-(phenylmethyl)-piperidine; 2-methyl-6-(phenylethynyl)-pyridine; 3-(phosphonomethyl)-L-phenylalanine; and 3,6,7-tetrahydro-2,3-dioxo-N-phenyl-1H,5H-pyrido[1,2,3-de] quinoxaline-5-acetamide or those described in U.S. Pat. Nos. 6,071,966; 6,034,134; and 5,061,703.

Cardiogenic Shock

Cardiogenic shock (CS) is the leading cause of death for patients with acute myocardial infarction that is consistent with increased levels of NO and inflammatory cytokines. High levels of NO and peroxynitrite have many effects, including a direct inhibition on myocardial contractability, suppression of mitochondrial respiration in myocardium, alteration in glucose metabolism, reduced catacholamine responsivity, and induction of systemic vasodilation (Hochman, *Circulation* 107:2998, 2003). In a clinical study in 11 patients with persistent shock, administration of the NOS inhibitor L-NMMA resulted in increases in urine output and blood pressure and survival rate of 72% up to 30 days (Cotter et al., *Circulation* 101:1258-1361, 2000). In a randomized trial of 30 patients, it was reported that L-NAME reduced patient mortality from 67% to 27% (Cotter et al., *Eur. Heart. J.* 24(14):1287-95, 2003). Similarly, administration of a compound of the invention, either alone or in combination with another therapeutic agent, may be useful for the treatment of cardiogenic shock.

Anxiety and Depression

Recent studies of rats and mice in the forced swimming test (FST) indicate that NOS inhibitors have antidepressant activity in mice (Harkin et al. *Eur. J. Pharm.* 372:207-213, 1999) and that their effect is mediated by a serotonin dependent mechanism (Harkin et al., *Neuropharmacology* 44(5):616-623, 1993). 7-NI demonstrates anxiolytic activity in the rat plus-maze test (Yildiz et al., *Pharmacology, Biochemistry and Behavior* 65:199-202, 2000), whereas the selective nNOS inhibitor TRIM is effective in both the FST model of depression and anxiety in the light-dark compartment test (Volke et al., *Behavioral Brain Research* 140(1-2):141-7, 2003). Administration of a compound of the invention to an afflicted individual, either alone or in combination with another therapeutic agent, such as, for example, an antidepressant, may be useful for the treatment of anxiety or depression.

Attention Deficit Hyperactivity Disorder

Non-selective attention (NSA) to environmental stimuli in Spontaneously Hypertensive (SHR) and Naples Low-Excitability (NHE) rats has been used as an animal model of Attention-Deficit Hyperactivity Disorder (ADHD) (Aspide et al., *Behav. Brain Res.* 95(1):23-33, 1998). These genetically altered animals show increased episodes of rearing that have a shorter duration than observed in normal animals. A single injection of L-NAME at 10 mg/kg produced an increase in rearing duration. Similarly, using the more neuronally selective 7-NINA, an increase in the rearing duration was observed after rapid administration (i.p.), while a slow release single release dose or a slow multiple release dose (s.c. in DMSO) resulted in the opposite effect. Thus, administration of a compound of the invention may be useful for the treatment of ADHD.

Psychosis

Phencyclidine (PCP) is a non-competitive NMDA channel blocker that produces behavioral side effects in human and mammals consistent with those observed in patients with psychosis. In two animal models of psychosis, the nNOS selective inhibitor AR-R17477 antagonized PCP-induced hyperlocomotion and PCP-induced deficit in prepulse inhibition of the acoustic response startle (Johansson et al., *Pharmacol. Toxicol.* 84(5):226-33, 1999). These results suggest the involvement of nNOS in psychosis. Therefore, administration of a compound of the invention to an afflicted individual may be useful for the treatment of this or related diseases or disorders.

Head Trauma

The mechanism of neurological damage in patients with head trauma parallels that of stroke and is related to excitotoxic calcium influx from excessive glutamate release, oxidative stress and free radical production from mitochondrial dysfunction and inflammation (*Drug & Market Development* 9(3):60-63, 1998). Animals treated with nitric oxide synthase inhibitors, such as 7-NI and 3-bromo-7-nitroindazole, have shown an improvement in neurological deficits after experimental traumatic brain injury (TBI) (Mesenge et al., *J. Neurotrauma* 13:209-14, 1996). Administration of a compound of the invention to an afflicted individual may also be useful for the treatment of neurological damage in head trauma injuries.

Hypothermic Cardiac Arrest

Hypothermic cardiac arrest (HCA) is a technique used to protect from ischemic damage during cardiac surgery when the brain is sensitive to damage during the period of blood flow interruption. Various neuroprotective agents have been used as adjunct agents during HCA and reducing nitric oxide production during HCA is predicted to result in improvements in neurological function. This is based on previous studies that showed glutamate excitotoxicity plays a role in HCA-induced neurologic damage (Redmond et al., *J. Thorac. Cardiovasc. Surg.* 107:776-87, 1994; Redmond et al., *Ann. Thorac. Surg.* 59:579-84, 1995) and that NO mediates glutamate excitotoxicity (Dawson and Snyder, *J. Neurosci.* 14:5147-59, 1994). In a study of 32 dogs undergoing 2 hours of HCA at 18° C., a neuronal NOS inhibitor was shown to reduce cerebral NO production, significantly reduce neuronal necrosis, and resulted in superior neurologic function relative to controls (Tseng et al., *Ann. Thorac. Surg.* 67:65-71, 1999). Administration of a compound of the invention may also be useful for protecting patients from ischemic damage during cardiac surgery.

Neurotoxicity and Neurodegenerative Diseases

Mitochondrial dysfunction, glutamate excitotoxicity, and free radical induced oxidative damage appear to be the underlying pathogenesis of many neurodegenerative diseases, including amyotrophic lateral sclerosis (ALS), Parkinson's disease (PD), Alzheimer's disease (AD), and Huntington's disease (HD) (Schulz et al., *Mol. Cell. Biochem.* 174(1-2): 193-197, 1997; Beal, *Ann. Neurol.* 38:357-366, 1995), and NO is a primary mediator in these mechanisms. For example, it was shown by Dawson et al., in *PNAS* 88(14):6368-6371, 1991, that NOS inhibitors like 7-NI and L-NAME prevent neurotoxicity elicited by N-methyl-D-aspartate and related excitatory amino acids.

(a) Parkinson's Disease

Studies have also shown that NO plays an important role in 1-methyl-4-phenyl-1,2,3,6-tetrahydropyridine (MPTP) neurotoxicity, a commonly used animal model of Parkinson's disease (Matthews et al., *Neurobiology of Disease* 4:114-121, 1997). MPTP is converted to MPP+ by MAO-B and is rapidly taken up by the dopamine transporter into the mitochondria of dopamine containing neurons with subsequent activation of nNOS resulting in neuronal death. Mutant mice lacking the nNOS gene, but not the eNOS gene, have reduced lesions in the substantia nigra after MPP+ injection into the striatum. In primate studies, 7-NI exerts a profound neuroprotective and antiparkinsonium effect after MPTP challenge (Hantraye et al., *Nature Med* 2:1017-1021, 1996) as did the non-specific inhibitor L-NAME (T. S. Smith et. al. Neuroreport 1994, 5, 2598-2600).

(b) Alzheimer's Disease (AD)

The pathology of AD is associated with β-amyloid plaques infiltrated with activated microglia and astrocytes. When cultured rat microglia are exposed to beta-amyloid, there is a prominent microglial release of nitric oxide, especially in the presence of gamma-interferon (Goodwin et al., *Brain Research* 692(1-2):207-14, 1995). In cortical neuronal cultures, treatment with nitric oxide synthase inhibitors provides neuroprotection against toxicity elicited by human beta-amyloid (Resink et al., *Neurosci. Abstr.* 21:1010, 1995). Consistent with the glutamate hypothesis of excitoxicity in neurodegerative disorders, the weak NMDA antagonist amantadine increases the life expectancy of PD patients (Uitti et al., *Neurology* 46(6): 1551-6, 1996). In a preliminary, placebo-controlled study of patients with vascular- or Alzheimer's-type dementia, the NMDA antagonist memantine was associated with improved Clinical Global Impression of Change and Behavioral Rating Scale for Geriatric Patients scores (Winblad and Poritis, *Int. J. Geriatr. Psychiatry* 14:135-46, 1999).

(c) Amyotrophic Lateral Sclerosis

Amyotrophic lateral sclerosis (ALS) is a fatal neurodegenerative disease characterized by selective motor neuronal death. Accumulating evidence suggests that the pathogenesis of ALS is the insufficient clearance of glutamate through the glutamate transporter, and the specific distribution of $Ca^{2+}$-permeable AMPA receptors in spinal motor neurons, indicates a glutamate-induced neurotoxicity. Increased nNOS immunoreactivity is found in the spinal cords (Sasaki et al., *Acta Neuropathol.* (*Berl*) 101(4):351-7, 2001) and glial cells (Anneser et al., *Exp. Neurol.* 171(2):418-21, 2001) of ALS patients, implicating NO as an important factor in the pathogenesis of ALS.

(d) Huntington's Disease

The pathogenesis of Huntington's disease (HD) arising from a mutation in the Htt protein is linked to excitotoxicity, oxidative stress and apoptosis, in all of which excessive NO has a clear role (Peterson et al., *Exp. Neurol.* 157:1-18, 1999). Oxidative damage is one of the major consequences of defects in energy metabolism and is present in HD models after injection of excitotoxins and mitochondrial inhibitors (A. Petersen et. al., *Exp. Neurol.* 157:1-18, 1999). This mitochrondrial dysfunction is associated with the selective and progressive neuronal loss in HD (Brown et al., *Ann. Neurol.* 41:646-653, 1997). NO can directly impair the mitochondrial respiratory chain complex IV (Calabrese et al., *Neurochem. Res.* 25:1215-41, 2000). Striatal medium spiny neurons appear to be the primary target for the generation of motor dysfunction in HD. Hyperphosphorylation and activation of NMDA receptors on these neurons likely participates in the generation of motor dysfunction. It has been shown clinically that the NMDA antagonist amantadine improves choreiform dyskinesias in HD (Verhagen Metman et al., *Neurology* 59:694-699, 2002). Given the role of nNOS in NMDA mediated neurotoxicity, it is expected that nNOS inhibitors, especially those with mixed nNOS/NMDA, or combinations of drugs with nNOS and NMDA activity will also be useful in ameliorating the effects and or progression of HD. For example, pretreatment of rats with 7-nitroindazole attenuates the striatal lesions elicited by stereotaxic injections of malonate, an injury that leads to a condition resembling Huntington's disease (Hobbs et. al., *Ann. Rev. Pharm. Tox.* 39:191-220, 1999). In a R6/1 transgenic mouse model of HD expressing a human mutated htt exon1, a 116 CAG repeat, mice at 11, 19 and 35 weeks show a progressive increase in lipid peroxidation with normal levels of superoxide dismutase (SOD) at 11 weeks similar to wild type (WT) mice; a maximum level at 19 weeks, above that observed in WT mice and corresponding to the early phase of disease progression; and finally, decreasing levels at 35 weeks below that observed in WT mice (Pérez-Sevriano et al., *Brain Res.* 951:36-42, 2002). The increase in SOD activity is attributable to a compensatory neuroprotective mechanism, with decreased levels at 35 weeks corresponding to a failed protective mechanism. Concomitant with the levels of SOD, levels of calcium dependent NOS was the same for 11 week mice in both WT and R6/1 mice, but increased significantly at 19 weeks and decreased at 35 weeks relative to WT control mice. Levels of nNOS expression also increased dramatically relative to controls at 19 weeks but were decreased significantly relative to controls at 35 weeks. No significant differences were observed in levels of eNOS expression, nor could iNOS protein be detected during progression of the disease. The progressive phenotypic expression of the disease, as measured by increased weight loss, feet clasping behavior, and horizontal and vertical movements, are consistent with changes in NOS activity and nNOS expression. Finally, the effects of L-NAME administration to both R6/2 transgenic HD mice and WT mice showed improved levels of clasping behavior at a 10 mg/kg dose similar to controls, which worsened at the highest dose of 500 mg/kg (Deckel et al., *Brain Res.* 919 (1):70-81, 2001). An improvement in weight increase in HD mice was also significant at the 10 mg/kg dose, but decreased relative to controls at high dose levels of L-NAME. These results demonstrate that administration of an appropriate dose of an NOS inhibitor, such as, for example, a compound of the invention, can be beneficial in the treatment of HD.

(e) Multiple Sclerosis (MS)

MS is in an inflammatory demyelinating disease of the CNS involving cytokines and other inflammatory mediators. Many studies suggest that NO and its reactive derivative peroxynitrite are implicated in the pathogenesis of MS (Acar et al. *J. Neurol.* 250(5):588-92, 2003; Calabrese et al., *Neurochem. Res.* 28(9):1321-8, 2003). In experimental autoimmune encephalomyelitis (EAE), a model of MS, nNOS levels are slightly increased in the spinal cord of EAE rats and treatment with 7-nitroindazole results in a significant delay in the onset of EAE paralysis (Shin, *J. Vet. Sci.* 2(3):195-9, 2001).

(f) Methamphetamine-Induced Neurotoxicity

Methamphetamine is neurotoxic by destroying dopamine nerve terminals in vivo. It has been shown that methamphetamine-induced neurotoxicity can be attenuated by treatment with NOS inhibitors in vitro (Sheng et al., *Ann. N.Y. Acad. Sci.* 801:174-186, 1996) and in in vivo animal models (Itzhak et al., *Neuroreport* 11(13):2943-6, 2000). Similary, the nNOS selective inhibitor AR-17477AR, at 5 mg/kg s.c in mice, was able to prevent the methamphetamine-induced loss of the neurofilament protein NF68 in mouse brain and prevent the loss of striaital dopamine and homovanillic acid (HVA) (Sanchez et al., *J. Neurochem.* 85(2):515-524, 2003).

Administration of a compound of the invention, either alone or in combination with another therapeutic agent, such as, for example, an NMDA antagonist, may be useful for the protection or treatment of any of the neurodegenerative diseases described herein. Further, the compounds of the invention may be tested in standard assays used to assess neuroprotection (see for example, *Am. J. Physiol.* 268:R286, 1995). Chemical Dependencies and Drug Addictions (e.g., Dependencies on Drugs Alcohol and Nicotine)

A key step in the process of drug-induced reward and dependence is the regulation of dopamine release from mesolimbic dopaminergic neurons. Chronic application of cocaine alters the expression of the key protein controlling the synaptic level of dopamine—the dopamine transporter (DAT).

(a) Cocaine Addiction

Studies have shown that animals reliably self-administer stimulants intravenously and that dopamine is critical in their reinforcing effects. Recently NO containing neurons have been shown to co-localize with dopamine in areas of the striatum and ventral tegmental area and that NO can modulate stimulant-evoked dopamine (DA) release. Administration of dopamine D1 receptor antagonists decrease the levels of straital NADPH-diaphorase staining, a marker for NOS activity, while D2 antagonists produce the opposite effect. L-Arginine, the substrate of NOS, is also a potent modulator of DA release. Also, multiple NO-generating agents increase DA efflux or inhibit reuptake both in vitro and in vivo. L-NAME has been shown to significantly alter cocaine reinforcement by decreasing the amount of self-administration and by increasing the inter-response time between successive cocaine injections (Pudiak and Bozarth, Soc. Neurosci. Abs. 22:703, 1996). This indicates that NOS inhibition may be useful in the treatment of cocaine addiction.

(b) Morphine/Opioid Induced Tolerance and Withdrawal Symptoms

There is much evidence supporting the role of both the NMDA and NO pathways in opioid dependence in adult and infant animals. Adult or neonatal rodents injected with morphine sulfate develop behavioral withdrawal after precipitation with naltrexone. The withdrawal symptoms after naltrexone initiation can be reduced by administration of NOS inhibitors, such as 7-NI or L-NAME (Zhu and Barr, Psychopharmacology 150(3):325-336, 2000). In a related study, it was shown that the more nNOS selective inhibitor 7-NI attenuated more of the morphine induced withdrawal symptoms including mastication, salivation and genital effects than the less selective compounds (Vaupel et al., Psychopharmacology (Berl.) 118(4):361-8, 1995).

(c) Ethanol Tolerance and Dependence

Among the factors that influence alcohol dependence, tolerance to the effects of ethanol is an important component because it favors the exaggerated drinking of alcoholic beverages (Lêand Kiianmaa, Psychopharmacology (Berl.) 94:479-483, 1988). In a study with rats, ethanol tolerance to motor incoordination and hypothermia develop rapidly and can be blocked by i.c.v administration of 7-NI without altering cerebral ethanol concentrations (Wazlawik and Morato, Brain Res. Bull. 57(2): 165-70, 2002). In other studies, NOS inhibition with L-NAME (Rezvani et al., Pharmacol. Biochem. Behav. 50:265-270, 1995) or by i.c.v. injection of nNOS antisense (Naassila et. al., Pharmacol. Biochem. Behav. 67:629-36, 2000) reduced ethanol consumption in these animals.

Administration of a compound of the invention, either alone or in combination with another therapeutic agent, such as, for example, an NMDA antagonist, may be useful for the treatment of chemical dependencies and drug addictions.

Epilepsy

Co-administration of 7-NI with certain anticonvulsants, such as carbamazepine, shows a synergistic protective effect against amygdala-kindled seizures in rats at concentrations that do not alter roto-rod performance (Borowicz et al., Epilepsia 41(9:112-8, 2000). Thus, an NOS inhibitor, such as, for example, a compound of the invention, either alone or in combination with another therapeutic agent, such as, for example, an antiepileptic agent, may be useful for the treatment of epilepsy or a similar disorder. Examples of antiepileptic agents useful in a combination of the invention include carbamazepine, gabapentin, lamotrigine, oxcarbazepine, phenyloin, topiramate, and valproate.

Diabetic Nephropathy

Urinary excretion of NO byproducts is increased in diabetic rats after streptozotocin treatment and increased NO synthesis has been suggested to be involved in diabetic glomerular hyperfiltration. The neuronal isoform nNOS is expressed in the loop of Henle and mucula densa of the kidney and inhibition of this isoform using 7-NI reduces glomerular filtration without affecting renal arteriole pressure or renal blood flow (Sigmon et al., Gen. Pharmacol. 34(2):95-100, 2000). Both the non-selective NOS inhibitor L-NAME and the nNOS selective 7-NI normalize renal hyperfiltration in diabetic animals (Ito et al., J. Lab Clin. Med. 138(3):177-185, 2001). Therefore, administration of a compound of the invention may be useful for the treatment of diabetic nephropathy.

Combination Formulations, and Uses Thereof

In addition to the formulations described above, one or more compounds of the invention can be used in combination with other therapeutic agents. For example, one or more compounds of the invention can be combined with another NOS inhibitor. Exemplary inhibitors useful for this purpose include, without limitation, those described in U.S. Pat. No. 6,235,747; U.S. patent application Ser. Nos. 09/127,158, 09/325,480, 09/403,177, 09/802,086, 09/826,132, 09/740, 385, 09/381,887, 10/476,958, 10/483,140, 10/484,960, 10/678,369, 10/819,853, 10/938,891; International Publication Nos. WO 97/36871, WO 98/24766, WO 98/34919, WO 99/10339, WO 99/11620, and WO 99/62883.

In another example, one or more compounds of the invention can be combined with an antiarrhythmic agent. Exemplary antiarrhythmic agents include, without limitation, lidocaine and mixiletine.

GABA-B agonists, alpha-2-adrenergic receptor agonists, cholecystokinin antagonists, $5HT_{1B/1D}$ agonists, or CGRP antagonists can also be used in combination with one or more compounds of the invention. Non-limiting examples of alpha-2-adrenergic receptor agonists include clonidine, lofexidine, and propanolol. Non-limiting examples of cholecystokinin antagonists include L-365, 260; CI-988; LY262691; S0509, or those described in U.S. Pat. No. 5,618,811. Non-limiting examples of $5HT_{1B/1D}$ agonists that may be used in combination with a compound of the invention include dihydroergotamine, eletriptan, frovatriptan, naratriptan, rizatriptan, sumatriptan, donitriptan, or zolmitriptan. Non-limiting examples of CGRP antagonists that may be used in combination with a compound of the invention include quinine analogues as described in International Publication No. WO9709046, non-peptide antagonists as described in International Publication Nos. WO0132648, WO0132649, WO9811128, WO9809630, WO9856779, WO0018764, or other antagonists such as SB-(+)-273779 or BIBN-4096BS.

Substance P antagonists, also known as $NK_1$ receptor antagonists, are also useful in combination with one or more compounds of the invention. Exemplary inhibitors useful for this purpose include, without limitation, those compounds disclosed in U.S. Pat. Nos. 3,862,114, 3,912,711, 4,472,305, 4,481,139, 4,680,283, 4,839,465, 5,102,667, 5,162,339, 5,164,372, 5,166,136, 5,232,929, 5,242,944, 5,300,648, 5,310,743, 5,338,845, 5,340,822, 5,378,803, 5,410,019, 5,411,971, 5,420,297, 5,422,354, 5,446,052, 5,451,586, 5,525,712, 5,527,811, 5,536,737, 5,541,195, 5,594,022, 5,561,113, 5,576,317, 5,604,247, 5,624,950, and 5,635,510; International Publication Nos. WO 90/05525, WO 91/09844, WO 91/12266, WO 92/06079, WO 92/12151, WO 92/15585, WO 92/20661, WO 92/20676, WO 92/21677, WO 92/22569, WO 93/00330, WO 93/00331, WO 93/01159, WO 93/01160, WO 93/01165, WO 93/01169, WO 93/01170, WO 93/06099, WO 93/10073, WO 93/14084, WO 93/19064, WO 93/21155, WO 94/04496, WO 94/08997, WO 94/29309, WO 95/11895, WO 95/14017, WO 97/19942, WO 97/24356, WO 97/38692, WO 98/02158, and WO 98/07694; European Patent Publication Nos. 284942, 327009, 333174, 336230, 360390, 394989, 428434, 429366, 443132, 446706, 484719, 499313, 512901, 512902, 514273, 514275, 515240, 520555, 522808, 528495, 532456, and 591040.

Suitable classes of antidepressant agents that may be used in combination with a compound of the invention include, without limitation, norepinephrine re-uptake inhibitors, selective serotonin re-uptake inhibitors (SSRIs), selective noradrenaline/norepinephrine reuptake inhibitors (NARIs), monoamine oxidase inhibitors (MAOs), reversible inhibitors of monoamine oxidase (RIMAs), dual serotonin/noradrenaline re-uptake inhibitors (SNRIs), α-adrenoreceptor antagonists, noradrenergic and specific serotonergic antidepressants (NaSSAs), and atypical antidepressants.

Non-limiting examples of norepinephrine re-uptake inhibitors include tertiary amine tricyclics and secondary amine tricyclics, such as, for example, adinazolam, amineptine, amoxapine, butriptyline, demexiptiline, desmethylamitriptyline, desmethylclomipramine, demexiptiline, desipramine, doxepin, dothiepin, fluacizine, imipramine, imipramine oxide, iprindole, lofepramine, maprotiline, melitracen, metapramine, norclolipramine, nortriptyline, noxiptilin, opipramol, perlapine, pizotifen, pizotyline, propizepine, protriptyline, quinupramine, tianeptine, trimipramine, trimipramineamiltriptylinoxide, and pharmaceutically acceptable salts thereof.

Non-limiting examples of selective serotonin re-uptake inhibitors include, for example, clomipramine, femoxetine, fluoxetine, fluvoxamine, paroxetine, and sertraline, and pharmaceutically acceptable salts thereof.

Non-limiting examples of selective noradrenaline/norepinephrine reuptake inhibitors include, for example, atomoxetine, bupropion; reboxetine, tomoxetine and viloxazine and pharmaceutically acceptable salts thereof.

Non-limiting examples of selective monoamine oxidase inhibitors include, for example, isocarboxazid, phenezine, tranylcypromine and selegiline, and pharmaceutically acceptable salts thereof. Other monoamine oxidase inhibitors useful in a combination of the invention include clorgyline, cimoxatone, befloxatone, brofaromine, bazinaprine, BW-616U (Burroughs Wellcome), BW-1370U87 (Burroughs Wellcome), CS-722 (RS-722) (Sankyo), E-2011 (Eisai), harmine, harmaline, moclobemide, PharmaProjects 3975 (Hoechst), RO 41-1049 (Roche), RS-8359 (Sankyo), T-794 (Tanabe Seiyaku), toloxatone, K-Y 1349 (Kalir and Youdim), LY-51641 (Lilly), LY-121768 (Lilly), M&B 9303 (May & Baker), MDL 72394 (Marion Merrell), MDL 72392 (Marion Merrell), sercloremine, and MO 1671, and pharmaceutically acceptable salts thereof. Suitable reversible inhibitors of monoamine oxidase that may be used in the present invention include, for example, moclobemide, and pharmaceutically acceptable salts thereof.

Non-limiting examples of dual serotonin/norepinephrine reuptake blockers include, for example, duloxetine, milnacipran, mirtazapine, nefazodone, and venlafaxine.

Non-limiting examples of other antidepressants that may be used in a method of the present invention include adinazolam, alaproclate, amineptine, amitriptyline amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone, citalopram, clemeprol, clovoxamine, dazepinil, deanol, demexiptiline, dibenzepin, dimetacrine, dothiepin, droxidopa, enefexine, estazolam, etoperidone, fengabine, fezolamine, fluotracen, idazoxan, indalpine, indeloxazine, levoprotiline, litoxetine; medifoxamine, metralindole, mianserin, minaprine, montirelin, nebracetam, nefopam, nialamide, nomifensine, norfluoxetine, orotirelin, oxaflozane, pinazepam, pirlindone, ritanserin, rolipram, sercloremine, setiptiline, sibutramine, sulbutiamine, sulpiride, tenilox-azine, thozalinone, thymoliberin, tiflucarbine, tofenacin, tofisopam, toloxatone, veralipride, viqualine, zimelidine, and zometrapine, and pharmaceutically acceptable salts thereof, and St. John's wort herb, or *Hypencuin perforatum*, or extracts thereof.

In another example, opioids can be used in combination with one or more compounds of the invention. Exemplary opioids useful for this purpose include, without limitation, alfentanil, butorphanol, buprenorphine, dextromoramide, dezocine, dextropropoxyphene, codeine, dihydrocodeine, diphenoxylate, etorphine, fentanyl, hydrocodone, hydromorphone, ketobemidone, loperamide, levorphanol, levomethadone, meperidine, meptazinol, methadone, morphine, morphine-6-glucuronide, nalbuphine, naloxone, oxycodone, oxymorphone, pentazocine, pethidine, piritramide, propoxylphene, remifentanil, sulfentanyl, tilidine, and tramadol.

In yet another example, anti-inflammatory compounds, such as steroidal agents or non-steroidal anti-inflammatory drugs (NSAIDs), can be used in combination with one or more compounds of the invention. Non-limiting examples of steroidal agents include prednisolone and cortisone. Non-limiting examples of NSAIDs include acemetacin, aspirin, celecoxib, deracoxib, diclofenac, diflunisal, ethenzamide, etofenamate, etoricoxib, fenoprofen, flufenamic acid, flurbiprofen, lonazolac, lomoxicam, ibuprofen, indomethacin, isoxicam, kebuzone, ketoprofen, ketorolac, naproxen, nabumetone, niflumic acid, sulindac, tolmetin, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, suprofen, tiaprofenic acid, tenoxicam, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, and 2-(3,5-difluorophenyl)-3-[4-(methylsulfonyl)phenyl]-2-cyclopenten-1-one). Compounds of the invention may also be use in combination with acetaminophen.

Any of the above combinations can be used to treat any appropriate disease, disorder, or condition. Exemplary uses for combinations of a compound of the invention and another therapeutic agent are described below.

Opioid-NOS Inhibitor Combinations in Chronic, Neuropathic Pain

Nerve injury can lead to abnormal pain states known as neuropathic pain. Some of the clinical symptoms include tactile allodynia (nociceptive responses to normally innocuous mechanical stimuli), hyperalgesia (augmented pain intensity in response to normally painful stimuli), and spontaneous pain. Spinal nerve ligation (SNL) in rats is an animal model of neuropathic pain that produces spontaneous pain, allodynia, and hyperalgesia, analogous to the clinical symptoms observed in human patients (Kim and Chung, *Pain* 50:355-363, 1992; Seltzer, *Neurosciences* 7:211-219, 1995).

Neuropathic pain can be particularly insensitive to opioid treatment (Benedetti et al., *Pain* 74:205-211, 1998) and is still considered to be relatively refractory to opioid analgesics (MacFarlane et al., *Pharmacol. Ther.* 75:1-19, 1997; Watson, *Clin. J Pain* 16:S49-S55, 2000). While dose escalation can overcome reduced opioid effectiveness, it is limited by increased side effects and tolerance. Morphine administration is known to activate the NOS system, which limits the analgesic action of this drug (Machelska et al., *NeuroReport* 8:2743-2747, 1997; Wong et al., *Br. J. Anaesth.* 85:587, 2000; Xiangqi and Clark, *Mol. Brain. Res.* 95:96-102, 2001). However, it has been shown that the combined systemic administration of morphine and L-NAME can attenuate mechanical and cold allodynia at subthreshold doses at which neither drug administered alone was effective (Ulugol et al., *Neurosci. Res. Com.* 30(3): 143-153, 2002). The effect of L-NAME co-administration on morphine analgesia appears to be mediated by nNOS, as L-NAME loses its ability to potentiate morphine analgesia in nNOS null-mutant mice (Clark and Xiangqi, *Mol. Brain. Res.* 95:96-102, 2001). Enhanced analgesia has been demonstrated in the tail-flick or paw pressure models using coadministration of L-NAME or 7-NI with either a mu-, delta-, or kappa-selective opioid agonist (Machelska et al., *J. Pharmacol. Exp. Ther.* 282:977-984, 1997).

While opioids are an important therapy for the treatment of moderate to severe pain, in addition to the usual side effects that limit their utility, the somewhat paradoxical appearance of opioid-induced hyperalgesia may actually render patients more sensitive to pain and potentially aggravate their pain (Angst and Clark, Anesthesiology, 2006, 104(3), 570-587; Chu et. al. J. Pain 2006, 7(1) 43-48). The development of tolerance and opioid induced hyperalgesia is consistent with increased levels of NO production in the brain. The reduced analgesic response to opioids is due to an NO-induced upregulated hyperalgesic response (Heinzen and Pollack, Brain Res. 2004, 1023, 175-184).

Thus, the combination of an nNOS inhibitor with an opioid (for example, those combinations described above) can enhance opioid analgesia in neuropathic pain and prevent the development of opioid tolerance and opioid-induced hyperalgesia.

Antidepressant-NOS Inhibitor Combinations for Chronic Pain, Neuropathic Pain, Chronic Headache or Migraine Many antidepressants are used for the treatment of neuropathic pain (McQuay et al., Pain 68:217-227, 1996) and migraine (Tomkins et al., Am. J. Med. 111:54-63, 2001), and act via the serotonergic or noradrenergic system. NO serves as a neuromodulator of these systems (Garthwaite and Boulton, Annu. Rev. Physiol. 57:683, 1995). 7-NI has been shown to potentiate the release of noradrenaline (NA) by the nicotinic acetylcholine receptor agonist DMPP via the NA transporter (Kiss et al., Neuroscience Lett. 215:115-118, 1996). It has been shown that local administration of antidepressants, such as paroxetine, tianeptine, and imipramine decrease levels of hippocampal NO (Wegener et al., Brain Res. 959:128-134, 2003). It is likely that NO is important in the mechanism by which antidepressants are effective for treating pain and depression, and that a combination of an nNOS inhibitor with an antidepressant, such as, for example, those combinations described above, will produce better treatments.

Serotonin $5HT_{1B,1D,1F}$ Agonist or CGRP Antagonist and NOS Inhibitor Combinations in Migraine Administration of Glyceryl trinitrate (GTN), an NO donor, induces immediate headaches in normal individuals and results in delayed migraine attacks in migraineurs with a 4-6 hour latency period (Iversen et al., Pain 38:17-24, 1989). In patients with migraine attack, levels of CGRP (Calcitonin Gene Related Peptide), a potent vasodialator, in the carotid artery correlate with the onset and ablation of migraine attack (Durham, Curr Opin Investig Drugs 5(7):731-5, 2004). Sumatriptan, an antimigraine drug having affinity at $5HT_{1B}$, $5HT_{1D}$, and $5HT_{1F}$ receptors, reduces GTN-induced immediate headache and in parallel contracts cerebral and extracerebral arteries (Iversen and Olesen, Cephalagia 13(Suppl 13):186, 1993). The antimigraine drug rizatriptan also reduces plasma levels of CGRP following migraine pain reduction (Stepien et al., Neurol. Neurochir. Pol. 37(5):1013-23, 2003). Both NO and CGRP have therefore been implicated as a cause for migraine. Serotonin $5HT_{1B/1D}$ agonists have been shown to block NMDA receptor-evoked NO signaling in brain cortex slices (Strosznajder et al., Cephalalgia 19(10):859, 1999). These results suggest that a combination of a compound of the invention and a selective or non-selective $5HT_{1B/1D/1F}$ agonist or a CGRP antagonist, such as those combinations described above, would be useful for the treatment of migraine.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent or carrier.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003—20th edition) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal alone or in combination with pharmaceutically acceptable carriers, as noted above, the proportion of which is determined by the solubility and chemical nature of the compound, chosen route of administration, and standard pharmaceutical practice.

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of between 0.05 mg and 3000 mg (measured as the solid form). A preferred dose ranges between 0.05-500 mg/kg, more preferably between 0.5-50 mg/kg.

A compound of the invention can be used alone or in combination with other agents that have NOS activity, or in combination with other types of treatment (which may or may not inhibit NOS) to treat, prevent, and/or reduce the risk of stroke, neuropathic or migraine pain, or other disorders that benefit from NOS inhibition. In combination treatments, the dosages of one or more of the therapeutic compounds may be reduced from standard dosages when administered alone. In this case, dosages of the compounds when combined should provide a therapeutic effect.

In addition to the above-mentioned therapeutic uses, a compound of the invention can also be used in diagnostic assays, screening assays, and as a research tool.

In diagnostic assays, a compound of the invention may be useful in identifying or detecting NOS activity. For such a use, the compound may be radiolabelled (as described elsewhere herein) and contacted with a population of cells of an organism. The presence of the radiolabel on the cells may indicate NOS activity.

In screening assays, a compound of the invention may be used to identify other compounds that inhibit NOS, for example, as first generation drugs. As research tools, the compounds of the invention may be used in enzyme assays and assays to study the localization of NOS activity. Such information may be useful, for example, for diagnosing or monitoring disease states or progression. In such assays, a compound of the invention may also be radiolabeled.

The following non-limiting examples are illustrative of the present invention:

EXAMPLE 1

Preparation of N-(2-benzyl-1-(2-(1-methylpyrrolidin-2-yl)ethyl)-1H-indol-5-yl)thiophene-2-carboximidamide (6)

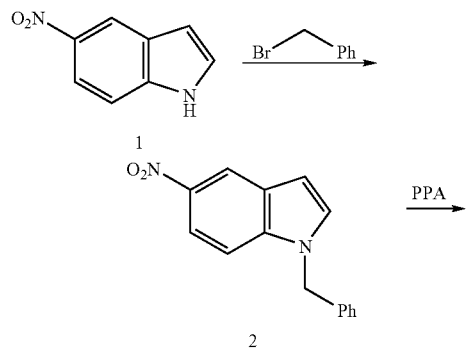

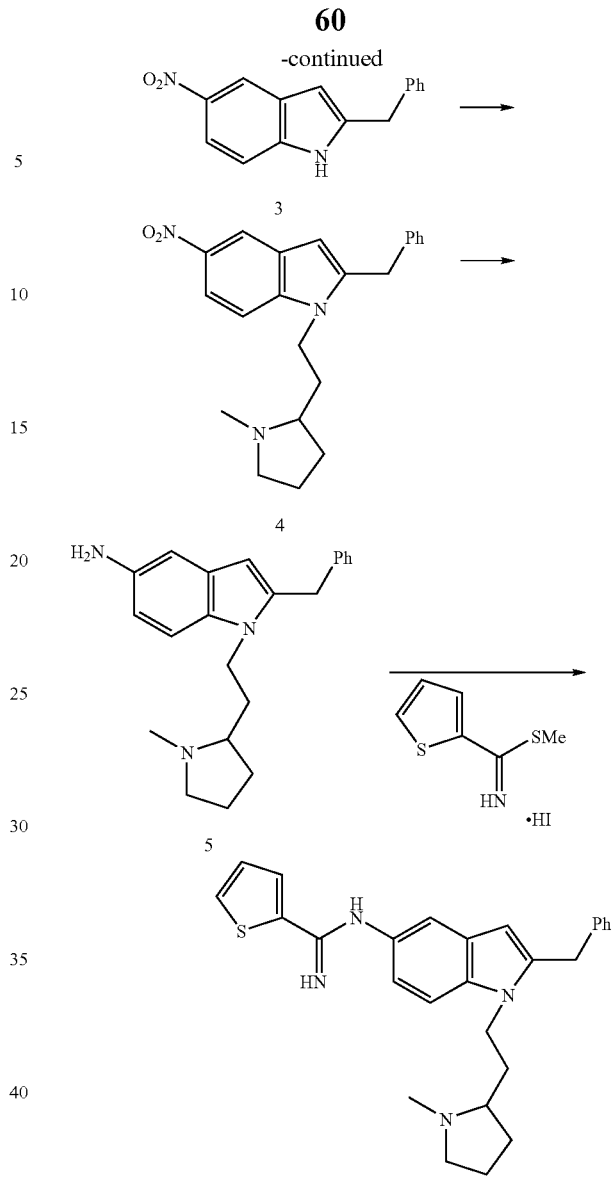

1-Benzyl-5-nitro-1H-indole (2): Compound 1 (1.0 g, 6.167 mmol) was subjected to conditions as per *Organic Syntheses*, Coll. Vol. 6, p 104. The crude product slurried in boiling Hexanes, filtered and dried to yield compound 2. $^1$H NMR (CDCl$_3$) δ 8.61 (d, 1H, J=2.1 Hz), 8.09 (dd, 1H, J=2.2, 9.0 Hz), 7.37-7.27 (m, 5H), 7.14-7.09 (m, 2H), 6.74 (d, 1H, J=3.2 Hz), 5.37 (s, 2H); ESI-MS (m/z, %): 253 (M+1, 100%).

2-Benzyl-5-nitro-1H-indole (3): A solution of compound 2 (0.5 g, 1.982 mmol) was treated with polyphosphoric acid as per *Synthetic Communications* 1997, 27 (12), 2033-2039. The crude product purified via silica gel column chromatography (EtOAc: Hexanes, 1:4) to provide compound 3 (173 mg, 34.6%); $^1$H NMR (CDCl$_3$) δ 8.50 (d, 1H, J=2.1 Hz), 8.13 (brs, 1H), 8.05 (dd, 1H, J=2.2, 9.0 Hz), 7.40-7.25 (2×m, 6H), 6.51 (d, 1H, J=1.4 Hz), 4.17 (s, 2H); ESI-MS (m/z, %): 253 (M+1, 100%).

2-Benzyl-1-(2-(1-methylpyrrolidin-2-yl)ethyl)-5-nitro-1H-indole (4): Compound 3 (165 mg, 0.654 mmol), 2-(2-chloroethyl)-1-methylpyrrolidine hydrochloride (132.4 mg, 0.719 mmol), and powdered potassium carbonate (271.2 mg, 1.962 mmol) were placed in an argon-purged flask. DMF (5 mL, Aldrich sure seal™) was added and the mixture heated to 65° C. in an oil bath for 20 hours. The solution was cooled to room temperature and diluted with water (10 mL) and ethyl acetate (25 mL). The layers were separated and the aqueous phase extracted with ethyl acetate (2×25 mL). The organic extracts were combined, washed with brine (2×10 mL) and dried over magnesium sulfate. The sample was filtered, concentrated, and the resultant crude product purified using dry silica gel column chromatography eluting with 15-20 mL portions of solvent system (2M $NH_3$ in methanol:$CH_2Cl_2$, 5:95) to afford a yellow solid 4 (152 mg, 63.9%); $^1$H NMR ($CDCl_3$) δ 8.50 (d, 1H, J=2.2 Hz), 8.07 (dd, 1H, J=2.2, 9.0 Hz), 7.36-7.17 (m, 6H), 6.44 (s, 1H), 4.16 (d, 2H, J=3.0 Hz), 4.10-3.97 (m, 2H), 3.06 (t, 1H, J=7.1 Hz), 2.21 (s, 3H), 2.15-2.00 (2×m, 2H), 1.97-1.55 (m, 5H), 1.53-1.40 (m, 1H); ESI-MS (m/z, %): 364 (M+1, 100%).

N-(2-Benzyl-1-(2-(1-methylpyrrolidin-2-yl)ethyl)-1H-indol-5-yl)thiophene-2-carboximidamide (6): Compound 4 (125 mg, 0.344 mmol) was dissolved in anhydrous ethanol (7 mL) in a dry argon purged flask. Palladium, 10 wt % on activated carbon (36.2 mg, 0.034 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of 2M $NH_3$ in methanol:$CH_2Cl_2$, 5:95 shows complete conversion to compound 5, which is utilized without isolation. The mixture is filtered through a pad of celite to remove insolubles, the pad washed with anhydrous ethanol (7 mL) and the ethanolic solution of the amine 5 is charged to a small, argon purged flask fitted with a magnetic stirbar. Thiophene-2-carboximidothioic acid methyl ester hydroiodide (127.5 mg, 0.447 mmol) is added to the flask and the reaction was stirred under Ar at ambient temperature for 48 hours, at which time the solution was diluted with diethyl ether (100 ml) resulting in the formation of a off-white precipitate that was collected on a sintered glass funnel and washed with ether. The solid was partitioned between $H_2O$ and ethyl acetate and 3M sodium hydroxide solution added to adjust pH to 8-9. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (2M $NH_3$ in methanol:$CH_2Cl_2$, 5:95) to afford beige foam 6 (75 mg, 49.3%); $^1$H NMR (DMSO-$d_6$) δ 7.71 (d, 1H, J=3.7 Hz), 7.58 (d, 1H, J=5.2 Hz), 7.35-7.20 (m, 6H), 7.09 (m, 1H), 6.92 (s, 1H), 6.64 (d, 1H, J=8.5 Hz), 6.23 (brs, 2H), 6.10 (s, 1H), 4.14 (s, 2H), 3.99 (t, 2H, J=8.0 Hz), 2.90 (quintet, 1H, J=4.6 Hz), 2.10 (s, 3H), 2.05-1.97 (m, 2H), 1.91-1.80 (m, 1H), 1.69-1.56 (m, 3H), 1.49-1.35 (m, 2H); ESI-MS (m/z, %): 443 (M+1, 70%), 219 (100%).

EXAMPLE 2

Preparation of N-(1-(2-(diethylamino)ethyl)-2-(4-(trifluoro methoxy)benzyl)-1H-indol-5-yl)thiophene-2-carboximidamide (11)

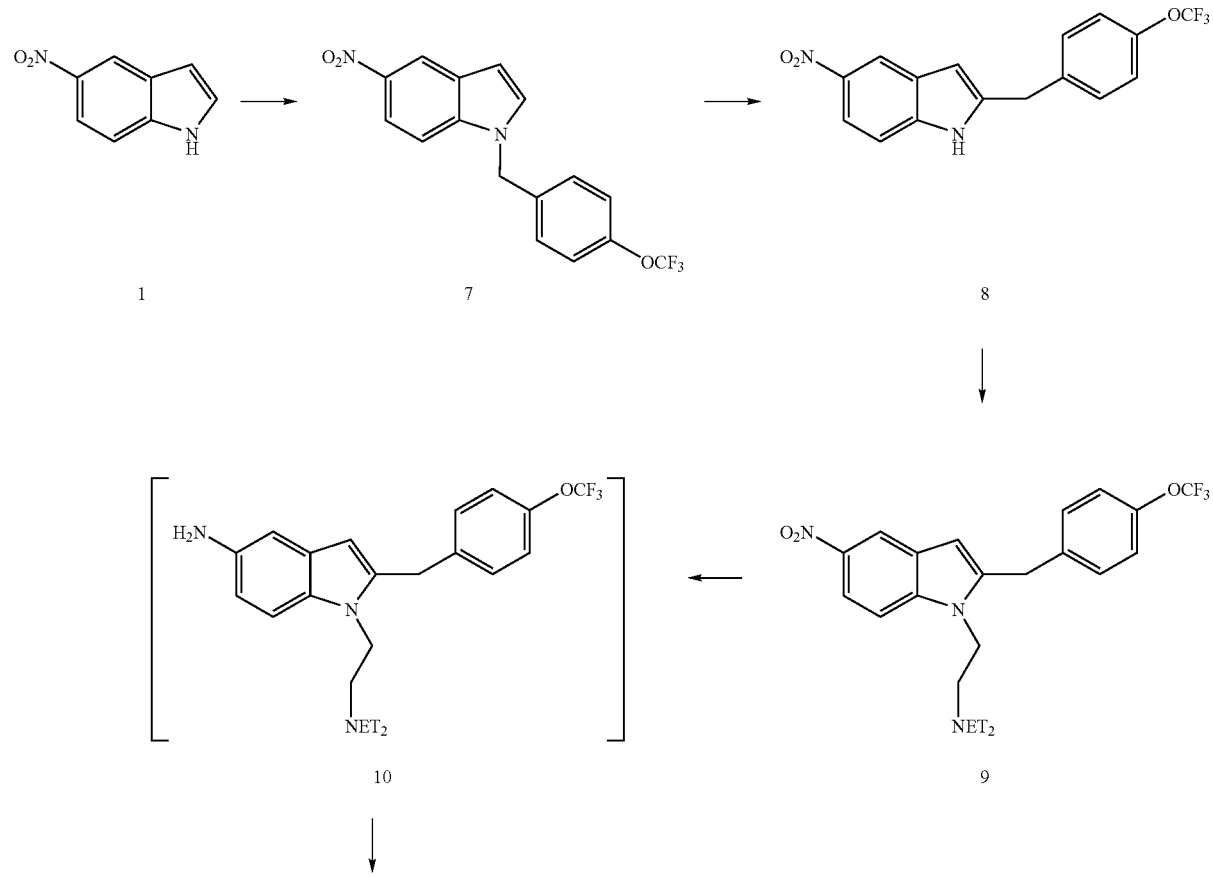

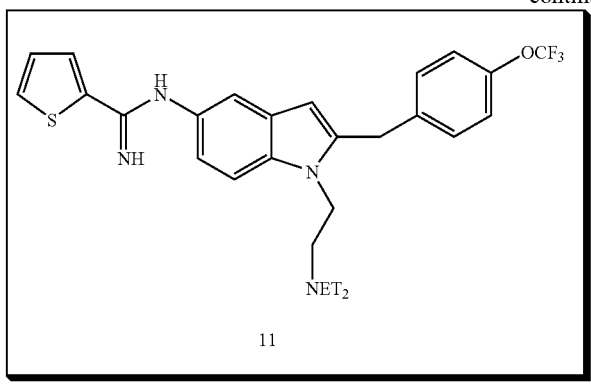

11

5-Nitro-1-(4-(trifluoromethoxy)benzyl)-1H-indole (7): Freshly crushed potassium hydroxide (0.692 g, 12.332 mmol) was charged to a small argon purged flask fitted with magnetic stirbar and dimethylsulfoxide (10 mL) and mixture stirred vigorously for 5 minutes. Compound 1 (500 mg, 3.083 mmol) was added in one portion and the resulting mixture stirred at room temperature for 45 minutes then cooled briefly to 0° C. 1-(bromomethyl)-4-(trifluoromethoxy)benzene (1.572 g, 6.167 mmol) is added drop wise, the mixture stirred for 15 minutes then diluted with H$_2$O. The solution was diluted with diethyl ether and transferred to a separatory funnel and the organic layer collected. The aqueous layer was further extracted with diethyl ether and the combined organic layers were washed with H$_2$O (twice), brine, dried over magnesium sulphate, filtered and concentrated to afford crude. The crude product was slurried in boiling hexanes and the solid was collected on a sintered glass funnel and dried to yield compound 7 (0.815 g, 78.6%) as a pale yellow solid. $^1$H NMR (DMSO-d$_6$) δ 5.58 (s, 2H), 6.82 (d, 1H, J=3.4 Hz), 7.33 (s, 4H), 7.71 (d, 1H, J=9.1 Hz), 7.80 (d, 1H, J=3.4 Hz), 8.01 (dd, 1H, J=9.0, 2.2 Hz), 8.60 (d, 1H, J=2.2 Hz); APCI-MS (m/z, %): 337 (MH$^+$, 100%).

5-Nitro-2-(4-(trifluoromethoxy)benzyl)-1H-indole (8): Compound 7 (0.80 g, 2.379 mmol) was treated with polyphosphoric acid as outlined in *Synthetic Communications*, 1997, 27(12), 2033-2039. The crude product was purified using silica gel column chromatography (EtOAc: Hexanes, 1:4) to afford compound 8 (280 mg, 35%) as a yellow solid. $^1$H NMR (DMSO-d$_6$) δ 4.17 (s, 2H), 6.47 (s, 1H), 7.28-7.38 (m, 2H), 7.41-7.50 (m, 3H), 7.93 (dd, 1H, J=8.9, 2.3 Hz), 8.46 (d, 1H, J=2.2 Hz), 11.78 (brs, 1H); APCI-MS (m/z, %): 337 (MH$^+$, 100%)

N,N-Diethyl-2-(5-nitro-2-(4-(trifluoromethoxy)benzyl)-1H-indol-1-yl)ethanamine (9): Compound 8 (77 mg, 0.229 mmol), 2-chloro-N,N-diethylethanamine hydrochloride (43.3 mg, 0.252 mmol), potassium carbonate (95 mg, 0.687 mmol) and anhydrous dimethylformamide (5 mL) were charged to a small, argon purged flask fitted with a magnetic stirbar and resulting solution heated in an oil bath at 65° C. for 2 hours. After cooling to room temperature the mixture was diluted with H$_2$O and ethyl acetate, transferred to a separatory funnel and the organic layer collected. The aqueous layer was further extracted with ethyl acetate and the combined organic layers were washed with brine (twice), dried over magnesium sulphate, filtered and concentrated to afford crude solid. The crude product was purified via chromatography on silica gel (2M NH$_3$ in MeOH:CH$_2$Cl$_2$, 2.5:97.5) to yield compound 9 (79 mg, 79.2%) as a yellow solid. $^1$H NMR (DMSO-d$_6$) δ 0.77 (t, 6H, J=7.1 Hz), 2.39 (q, 4H, J=7.2 Hz), 2.50 (m, 2H), 4.19 (t, 2H, J=6.5 Hz), 4.31 (s, 2H), 6.40 (s, 1H), 7.33-7.41 (m, 4H), 7.58 (d, 1H, J=9.1 Hz), 7.99 (dd, 1H, J=9.0, 2.2 Hz), 8.48 (d, 1H, J=2.3 Hz).

N-(1-(2-(Diethylamino)ethyl)-2-(4-(trifluoro methoxy) benzyl)-1H-indol-5-yl)thiophene-2-carboximidamide (11): Compound 9 (75 mg, 0.172 mmol) was dissolved in anhydrous ethanol (5 mL) in a dry argon purged flask. Palladium, 10wt % on activated carbon (18.3 mg, 0.0172 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography (2M NH$_3$ in MeOH:CH$_2$Cl$_2$, 2.5:97.5) shows complete conversion to 10, which is utilized without isolation. The mixture is filtered through a pad of celite to remove insolubles, the pad washed with anhydrous ethanol (5 mL) and the ethanolic solution of the amine 10 is charged to a small, argon purged flask fitted with a magnetic stirbar. Thiophene-2-carboximidothioic acid methyl ester hydroiodide (63.8 mg, 0.224 mmol) is added to the flask and the reaction was stirred under argon at ambient temperature for 45 hours. The solution was diluted with diethyl ether (100 ml) and cooled in an ice bath. No precipitate formed thus the solvent was evaporated. The residue was purified using silica gel column chromatography (2M NH$_3$ in MeOH:CH$_2$Cl$_2$, 2.5:97.5 to 5:95) to afford a pale yellow residue 11 (47 mg, 53.0%). $^1$H NMR (MeOD) δ 0.98 (t, 6H, J=7.1 Hz), 2.47-2.56 (2×m, 6H), 4.13 (t, 2H, J=7.1 Hz), 4.24 (s, 2H), 6.24 (s, 1H), 6.84 (dd, 1H, J=8.4, 1.6 Hz), 7.09-7.13 (m, 2H), 7.17-7.24 (m, 2H), 7.33-7.39 (m, 3H), 7.56 (d, 1H, J=5.2 Hz), 7.64 (d, 1H, J=3.7 Hz); ESI-MS (m/z, %): 515 (MH$^+$, 100%).

EXAMPLES 3

Preparation of N-(1-(2-(1-methylpyrrolidin-2-yl)ethyl)-2-(4-(trifluoromethoxy)benzyl)-1H-indol-5-yl)thiophene-2-carboximidamide (14)

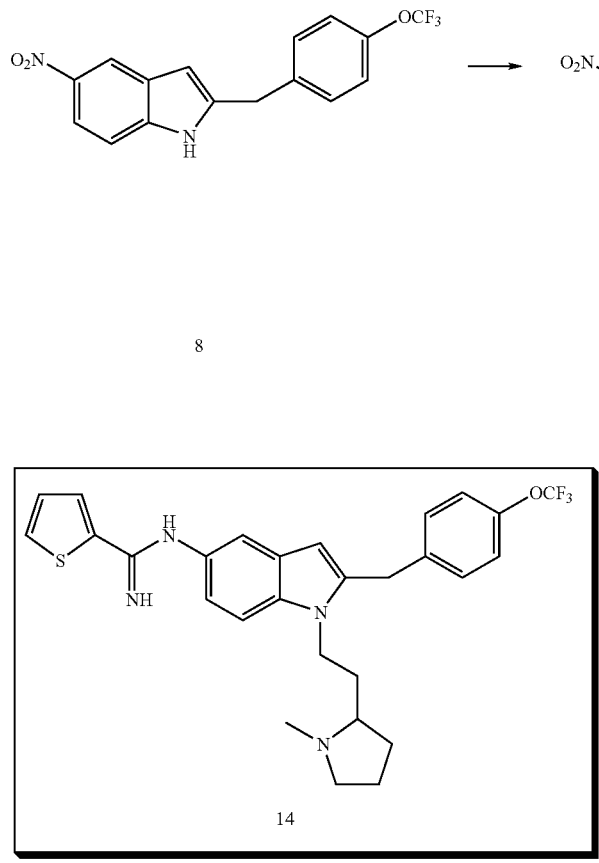

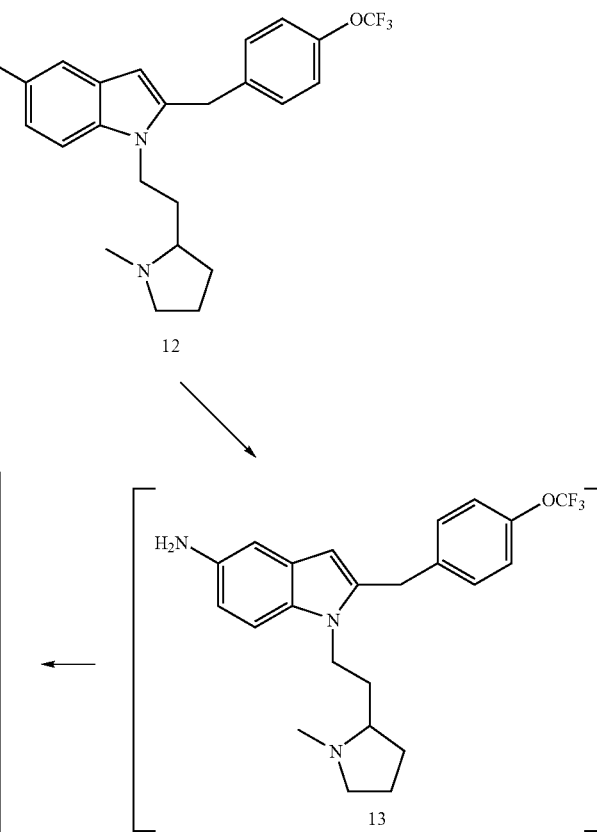

1-(2-(1-Methylpyrrolidin-2-yl)ethyl)-5-nitro-2-(4-(trifluoromethoxy)benzyl)-1H-indole (12): compound 8 (75 mg, 0.223 mmol), 2-(2-chloroethyl)-1-methylpyrrolidine hydrochloride (45.2 mg, 0.245 mmol), potassium carbonate (92.4 mg, 0.669 mmol) and anhydrous dimethylformamide (5 mL) were charged to a small, argon purged flask fitted with a magnetic stirbar and resulting solution heated in an oil bath at 65° C. for 20 hours. After cooling to room temperature the mixture was diluted with $H_2O$ and ethyl acetate, transferred to a separatory funnel and the organic layer collected. The aqueous layer was further extracted with ethyl acetate and the combined organic layers were washed with brine (twice), dried over magnesium sulphate, filtered and concentrated to afford crude solid. The crude product was purified using dry silica gel column chromatography eluting with 25 mL portions of solvent system (2M $NH_3$ in MeOH:$CH_2Cl_2$, 2.5:97.5) to yield a yellow residue, 12 (100 mg, quantitative). $^1$H NMR (DMSO-$d_6$) δ 1.35-1.45 (m, 2H), 1.58-1.64 (m, 3H), 1.72-1.88 (m, 1H), 1.97-2.05 (m, 2H), 2.08 (s, 3H), 2.86-2.95 (m, 1H), 4.15 (t, 2H, J=7.7 Hz), 4.29 (s, 2H), 6.49 (s, 1H), 7.33-7.43 (m, 4H), 7.57 (d, 1H, J=9.1 Hz), 8.00 (dd, 1H, J=9.1, 2.2 Hz), 8.50 (d, 1H, J=2.2 Hz); ESI-MS (m/z, %): 448 (MH$^+$, 100%).

N-(1-(2-(1-Methylpyrrolidin-2-yl)ethyl)-2-(4-(trifluoromethoxy)benzyl)-1H-indol-5-yl)thiophene-2-carboximidamide (14): Compound 12 (95 mg, 0.212 mmol) was dissolved in anhydrous ethanol (10 mL) in a dry argon purged flask. Palladium, 10 wt % on activated carbon (22.6 mg, 0.0212 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of 2M $NH_3$ in MeOH:$CH_2Cl_2$, 5:95 shows complete conversion to 13, which is utilized without isolation. The mixture is filtered through a pad of celite to remove insolubles, the pad washed with anhydrous ethanol (5 mL) and the ethanolic solution of the amine 13 is charged to a small, argon purged flask fitted with a magnetic stirbar. Thiophene-2-carboximidothioic acid methyl ester hydroiodide (78.6 mg, 0.276 mmol) is added to the flask and the reaction was stirred under argon at ambient temperature for 44 hours. The solution was diluted with diethyl ether (100 ml) and cooled in an ice bath. No precipitate formed thus the solvent was evaporated. The residue was partitioned between $H_2O$ and ethyl acetate and 1M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulphate, filtered, concentrated and the crude freebase purified via chromatography on silica gel (2M $NH_3$ in MeOH:$CH_2Cl_2$, 2.5:97.5 to 5:95) to yield compound 14 (60 mg, 53.7%) as a yellow solid. $^1$H NMR (DMSO-$d_6$) δ 1.36-48 (m, 2H), 1.53-1.60 (m, 3H), 1.80-1.86 (m, 1H), 1.92-2.05 (m, 2H), 2.08 (s, 3H), 2.87-2.93 (m, 1H), 4.00 (t, 2H, J=8.0 Hz), 4.19 (s, 2H), 6.12 (s, 1H), 6.23 (brs, 2H), 6.63-6.67 (m, 1H), 6.93 (s, 1H), 7.07-7.10 (m, 1H), 7.26 (d, 1H, J=8.6 Hz), 7.31-7.41 (m, 4H), 7.58 (d, 1H, J=5.3 Hz), 7.71 (d, 1H, J=3.7 Hz); ESI-MS (m/z, %): 527 (MH+, 100%).

EXAMPLE 4

Preparation of N-(2-(4-nitrophenyl)-1-(2-(piperidin-1-yl)ethyl)-1H-indol-5-yl)thiophene-2-carboximidamide (18)

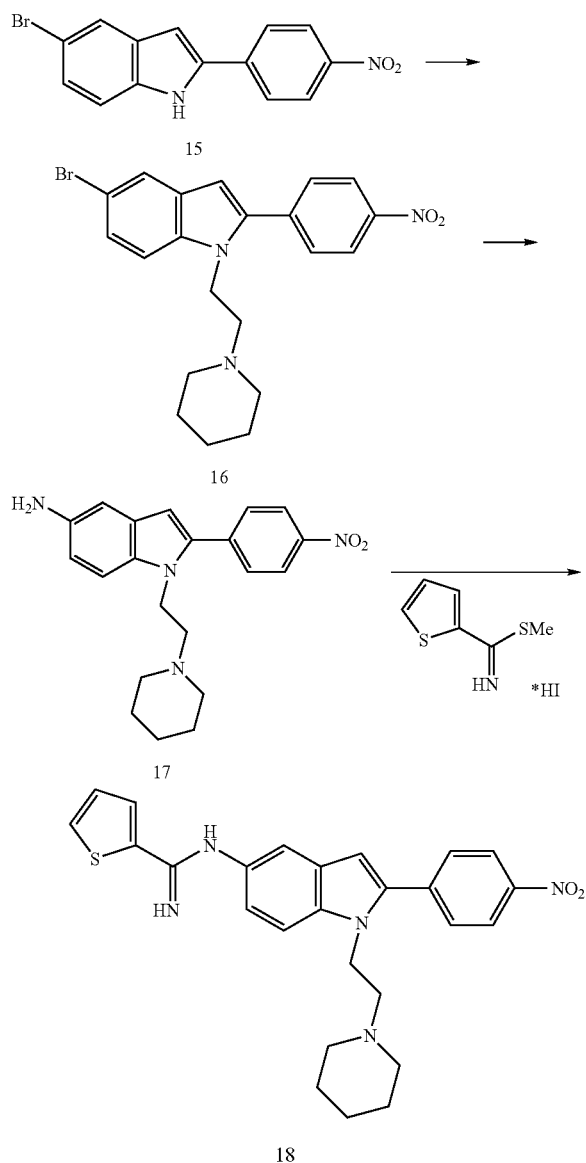

5-Bromo-2-(4-nitrophenyl)-1-(2-(piperidin-1-yl)ethyl)-1H-indole (16): Compound 15 (2.0 g, 6.306 mmol), 1-(2-chloroethyl)piperidine hydrochloride (1.277 g, 6.937 mmol), and powdered potassium carbonate (2.615 g, 18.918 mmol) were placed in an argon-purged flask. DMF (30 mL, Aldrich sure seal™) was added and the mixture stirred at 60° C. in an oil bath for 18 hours. The solution was cooled to room temperature and diluted with water (50 mL) and ethyl acetate (50 mL). The layers were separated and the aqueous phase extracted with ethyl acetate (2×50 mL). The organic extracts were combined, washed with water, brine (twice) and dried over magnesium sulfate. The sample was filtered, concentrated to afford a brown oil. The crude was taken up in ethyl acetate and treated with 1M HCl resulting in the formation of a yellow solid that was collected on a sintered glass funnel and washed with cold $H_2O$. The wet solid was treated with ethanol and concentrated to remove last traces of $H_2O$. The semi-purified solid was slurried in boiling ethanol/methanol, filtered and dried to yield golden solid 16 (1.73 g, 64.1%); $^1$H NMR (MeOD) δ 8.42 (d, 2H, J=8.5 Hz), 7.88-7.80 (2×m, 3H), 7.58 (d, 1H, J=8.7 Hz), 7.43 (m, 1H), 6.77 (s, 1H), 4.72 (t, 2H, J=8.0 Hz), 3.40 (m, 1H), 3.29 (m, 2H), 2.90-2.77 (m, 2H), 1.94-1.54 (2×m, 5H), 1.47-1.25 (m, 1H); ESI-MS (m/z, %): 428/430 (M+1, 100%).

2-(4-Nitrophenyl)-1-(2-(piperidin-1-yl)ethyl)-1H-indol-5-amine (17): Compound 16 (0.5 g, 1.167 mmol) and tris(dibenzylideneacetone)dipalladium (0) (53.4 mg, 0.058 mmol) were charged to an argon-purged flask fitted with a magnetic stirbar and condenser. Anhydrous tetrahydrofuran (15 mL) was added and stirring begun. Tri-tert-butylphosphine, 10 wt % in hexanes (0.358 mL, 0.1167 mmol) and lithium bis(trimethylsilyl)amide solution (3.501 mL, 3.501 mmol, 1.0 M in THF) were added and the mixture heated to reflux for 2 hours. The solution was cooled to room temperature overnight, diluted with water (15 mL) and 3M sodium hydroxide solution added to adjust pH to 9. Ethyl acetate added and the mixture was transferred to a separatory funnel and the organic layer collected. The aqueous layer was further extracted with ethyl acetate and the combined organic layers were washed with $H_2O$, brine, dried over magnesium sulphate, filtered, concentrated and the crude residue purified twice via chromatography on silica gel (2M $NH_3$ in methanol:$CH_2Cl_2$, 2.5:97.5) to afford orange solid 17 (265 mg, 62.4%); $^1$H NMR (DMSO-$d_6$) δ 8.31 (d, 2H, J=8.9 Hz), 7.89 (d, 2H, J=8.9 Hz), 7.25 (d, 1H, J=8.6 Hz), 6.71 (d, 1H, J=1.9 Hz), 6.63 (dd, 1H, J=2.0, 8.5 Hz), 6.47 (s, 1H), 4.64 (brs, 2H), 4.22 (t, 2H, J=6.6 Hz), 2.43 (t, 2H, J=6.5 Hz), 2.17 (m, 4H), 1.30 (m, 6H); ESI-MS (m/z, %): 365 (M+1, 100%).

N-(2-(4-Nitrophenyl)-1-(2-(piperidin-1-yl)ethyl)-1H-indol-5-yl)thiophene-2-carboximidamide (18): Compound 17 (250 mg, 0.686 mmol) and anhydrous ethanol (15 mL) were charged to a dry argon purged flask fitted with magnetic stirbar. Thiophene-2-carboximidothioic acid methyl ester hydroiodide (254.3 mg, 0.891 mmol) is added to the flask and the reaction was stirred under argon at ambient temperature for 48 hours at which time, thin layer chromatography in a solvent system of 2M $NH_3$ in methanol:$CH_2Cl_2$, 5:95 (developed twice) shows incomplete consumption of 17. A condenser was added and the mixture heated to reflux for 5 hours. An additional amount of the thiophene-2-carboximidothioic acid methyl ester hydroiodide (0.2 eq) was added and stirring continued at 65° C. for an additional 24 hours. A further portion of thiophene-2-carboximidothioic acid methyl ester hydroiodide (0.2 eq) was added and stirring continued for an additional 18 hours at reflux. After cooling to room temperature, the solution was diluted with diethyl ether (150 ml) resulting in the formation of off-white precipitate that was collected on a sintered glass funnel and washed with ether. The solid was partitioned between $H_2O$ and ethyl acetate and 3M sodium hydroxide solution added to adjust pH to 9-10. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (2M NH₃ in methanol:CH₂Cl₂, 2.5:97.5) to afford orange-yellow solid 18 (69 mg, 21.2%); ¹H NMR (DMSO-d₆) δ 8.35 (d, 2H, J=8.7 Hz), 7.93 (d, 2H, J=8.7 Hz), 7.73 (d, 1H, J=3.7 Hz), 7.60 (d, 1H, J=5.3 Hz), 7.51 (d, 1H, J=8.6 Hz), 7.10 (m, 1H), 7.07 (s, 1H), 6.80 (d, 1H, J=8.5 Hz), 6.66 (s, 1H), 6.32 (brs, 2H), 4.32 (t, 2H, J=6.5 Hz), 2.49 (m, 2H), 2.21 (m, 4H), 1.31 (m, 6H); ESI-MS (m/z, %): 474 (M+1, 100%).

EXAMPLE 5

Preparation of N-(1-(2-(1-methylpyrrolidin-2-yl)ethyl)-2-(4-nitrophenyl)-1H-indol-5-yl)thiophene-2-carboximidamide (21)

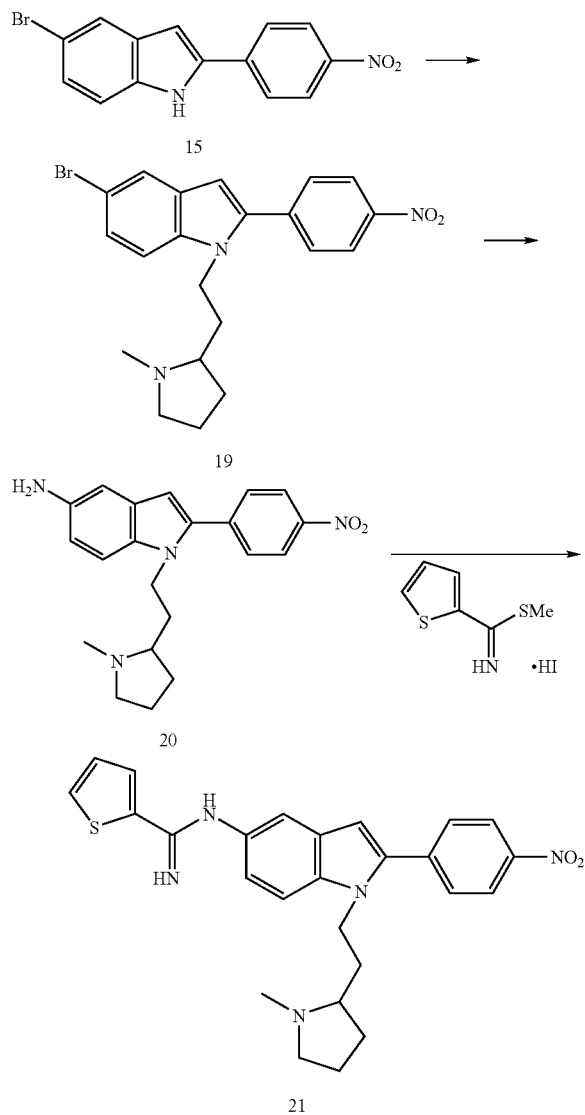

5-Bromo-1-(2-(1-methylpyrrolidin-2-yl)ethyl)-2-(4-nitrophenyl)-1H-indole (19): Compound 15 (2.0 g, 6.306 mmol), 2-(2-chloroethyl)-1-methylpyrrolidine hydrochloride (1.277 g, 6.937 mmol), and powdered potassium carbonate (2.615 g, 18.918 mmol) were placed in an argon-purged flask. DMF (30 mL, Aldrich sure seal™) was added and the mixture stirred at 60° C. in an oil bath for 18 hours. The solution was cooled to room temperature and diluted with water (50 mL) and ethyl acetate (50 mL). The layers were separated and the aqueous phase extracted with ethyl acetate (2×50 mL). The organic extracts were combined, washed with water, brine (twice) and the ethyl acetate solution treated with 1M hydrochloric acid resulting in the formation of a yellow solid that was collected on a sintered glass funnel and washed with cold H₂O. The wet solid was treated with ethanol and concentrated to remove last traces of H₂O. The semi-purified solid was recrystallized from ethanol to yield golden solid 19 (1.52 g, 56.3%); ¹H NMR (MeOD) δ 8.42 (d, 2H, J=8.7 Hz), 7.85 (d, 2H, J=8.7 Hz), 7.78 (d, 1H, J=1.9 Hz), 7.54 (d, 1H, J=8.8 Hz), 7.39 (m, 1H), 6.74 (s, 1H), 4.47 (t, 2H, J=7.3 Hz), 3.57-3.45 (m, 1H), 3.07-2.90 (m, 2H), 2.70 (s, 3H), 2.31-2.15 (m, 1H), 2.04-1.84 (m, 3H), 1.80-1.69 (m, 1H), 1.51-1.37 (m, 1H); ESI-MS (m/z, %): 428/430 (M+1, 100%).

1-(2-(1-Methylpyrrolidin-2-yl)ethyl)-2-(4-nitrophenyl)-1H-indol-5-amine (20): Compound 19 (0.5 g, 1.167 mmol) and tris(dibenzylideneacetone) dipalladium (0) (53.4 mg, 0.058 mmol) were charged to an argon-purged flask fitted with a magnetic stirbar and condenser. Anhydrous tetrahydrofuran (15 mL) was added and stirring begun. Tri-tert-butylphosphine (0.358 mL, 0.1167 mmol, 10 wt % in hexanes) and lithium bis(trimethylsilyl)amide solution (3.501 mL, 3.501 mmol, 1.0 M in THF) were added and the mixture heated to reflux for 2 hours. The solution was cooled to room temperature overnight, diluted with water (15 mL) and 3M sodium hydroxide solution added to adjust pH to 9. Ethyl acetate added and the mixture was transferred to a separatory funnel and the organic layer collected. The aqueous layer was further extracted with ethyl acetate and the combined organic layers were washed with H₂O, brine, dried over magnesium sulphate, filtered, concentrated and the crude residue purified twice via chromatography on silica gel (2M NH₃ in methanol:CH₂Cl₂, 5:95) to afford dark red solid 20 (102 mg, 24.0%); ¹H NMR (DMSO-d₆) δ 8.33 (d, 2H, J=8.7 Hz), 7.82 (d, 2H, J=8.8 Hz), 7.25 (d, 1H, J=8.8 Hz), 6.72 (d, 1H, J=1.8 Hz), 6.63 (m, 1H), 6.49 (s, 1H), 4.64 (brs, 2H), 4.25-4.12 (m, 2H), 2.88-2.78 (m, 1H), 1.99 (s, 3H), 1.91 (q, 1H, J=8.8 Hz), 1.84-1.72 (m, 2H), 1.64-1.55 (m, 1H), 1.52-1.35 (m, 3H), 1.30-1.16 (m, 1H); ESI-MS (m/z, %): 365 (M+1, 100%).

N-(1-(2-(1-Methylpyrrolidin-2-y)ethyl)-2-(4-nitrophenyl)-1H-indol-5-yl)thiophene-2-carboximidamide (21): Compound 20 (97 mg, 0.266 mmol) and anhydrous ethanol (10 mL) were charged to a dry argon purged flask fitted with magnetic stirbar. Thiophene-2-carboximidothioic acid methyl ester hydroiodide (98.7 mg, 0.346 mmol) is added to the flask and the reaction was stirred under argon at ambient temperature for 46 hours at which time, thin layer chromatography in a solvent system of 2M NH₃ in methanol:CH₂Cl₂, 5:95 (developed twice) shows incomplete consumption of 20. A condenser was added and the mixture heated to reflux for 5 hours. An additional amount of the thiophene-2-carboximidothioic acid methyl ester hydroiodide (0.2 eq) was added and stirring continued at 65° C. for an additional 24 hours. A further portion of thiophene-2-carboximidothioic acid methyl ester hydroiodide (0.2 eq) and ethanol (10 mL) were added and stirring continued for an additional 72 hours at reflux. Thin layer chromatography in a solvent system of 2M NH₃ in methanol:CH₂Cl₂, 5:95 (developed twice) shows incomplete consumption of 20. A further portion of thiophene-2-carboximidothioic acid methyl ester hydroiodide (1.0 eq) was added and the mixture heated to reflux for 6 hours then stirred at ambient temperature for 48 hours. The mixture was filtered through a sintered glass funnel to remove insolubles, the filtrate concentrated and the residue purified using dry silica gel column chromatography eluting with 30 mL portions of solvent system (2M NH$_3$ in methanol:CH$_2$Cl$_2$, 5:95) to afford an orange oil 21 (35 mg, 27.8%); $^1$H NMR (DMSO-d$_6$) δ 8.36 (d, 2H, J=8.6 Hz), 8.18 (s, 1H), 7.86 (d, 2H, J=8.8 Hz), 7.75 (d, 1H, J=3.2 Hz), 7.61 (d, 1H, J=5.3 Hz), 7.52 (d, 1H, J=8.8 Hz), 7.14-7.05 (2×m, 2H), 6.85-6.80 (m, 1H), 6.69 (s, 1H), 4.29 (m, 2H), 2.91-2.84 (m, 1H), 2.08 and 2.06 (2×s, 3H), 2.03-1.93 (m, 1H), 1.90-1.78 (m, 1H), 1.72-1.63 (m, 1H), 1.61-1.43 (m, 3H), 1.37-1.20 (m, 2H); ESI-MS (m/z, %): 474 (M+1, 100%).

EXAMPLE 6

Preparation of N-(1-(2-(dimethylamino)ethyl)-2-methyl-1H-indol-5-yl)thiophene-2-carboximidamide (25)

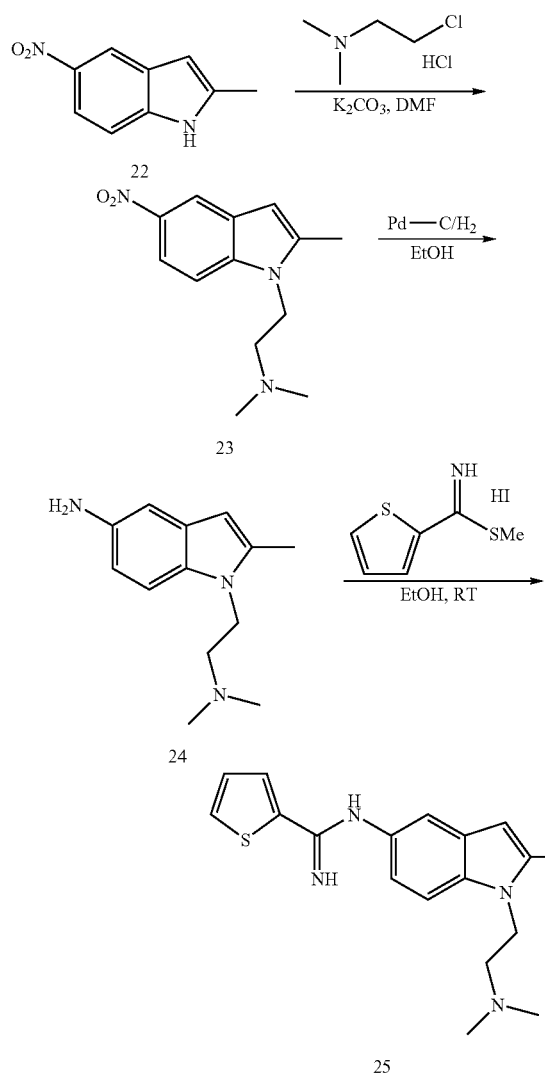

N,N-Dimethyl-2-(2-methyl-5-nitro-1H-indol-1-yl)ethanamine (23): A mixture of compound 22 (0.3 g, 1.702 mmol), 2-chloro-N,N-dimethylethanamine hydrochloride (0.26 g, 1.873 mmol) and K$_2$CO$_3$ (0.7 g, 5.108 mmol) in dry DMF (3 mL) was stirred at 65-70° C. for 18 h. The reaction was brought to room temperature, diluted with water (25 mL) and CH$_2$Cl$_2$ (25 mL). The CH$_2$Cl$_2$ layer was separated and aqueous layer was extracted in to CH$_2$Cl$_2$ (25 mL). The combined organic layer washed with brine (15 mL) and dried (Na$_2$SO$_4$). Solvent was evaporated and crude was purified by column chromatography (2 M NH$_3$ in MeOH:CH$_2$Cl$_2$, 3:97) to obtain compound 23 (0.38 g, 90%) as a solid. $^1$H NMR (DMSO-d$_6$) δ 2.18 (s, 6H), 2.47 (s, 3H), 2.51 (t, 2H, J=7.2 Hz), 4.27 (t, 2H, J=6.9 Hz), 6.50 (s, 1H), 7.58 (d, 1H, J=9.3 Hz), 7.95 (dd, 1H, J=2.1, 9.0 Hz), 8.42 (d, 1H, J=2.1 Hz); ESI-MS (m/z, %) 248 (MH$^+$, 100).

1-(2-(Dimethylamino)ethyl)-2-methyl-1H-indol-5-amine (24): A solution of compound 23 (0.35 g, 1.415 mmol) in dry ethanol (3 mL) was treated with Pd—C (~0.05 g) and flushed with hydrogen gas. The reaction was stirred under hydrogen atm. for overnight. The reaction was filtered through celite bed, washed with methanol (3×10 mL) and dried to obtain crude compound 24 (0.29 g, 94%) as a syrup. $^1$H NMR (DMSO-d$_6$) δ 2.18 (s, 6H), 2.32 (s, 3H), 2.42 (t, 2H, J=7.2 Hz), 4.03 (t, 2H, J=7.2 Hz), 4.37 (s, 2H), 5.88 (s, 1H), 6.42 (dd, 1H, J=2.1, 8.4 Hz), 6.56 (d, 1H, J=2.1 Hz), 7.00 (d, 1H, J=8.7 Hz); ESI-MS (m/z, %) 218 (MH$^+$, 100).

N-(1-(2-(Dimethylamino)ethyl)-2-methyl-1H-indol-5-yl)thiophene-2-carboximidamide (25): A solution of compound 24 (0.275 g, 1.266 mmol) in dry ethanol (5 mL) was treated with thiophene-2-carboximidothioic acid methyl ester hydroiodide (0.72 g, 2.532 mmol) at room temperature and stirred for overnight (16 h). The reaction was diluted with sat. NaHCO$_3$ solution (25 mL) and product was extracted into CH$_2$Cl$_2$ (2×25 mL). The combined CH$_2$Cl$_2$ layer was washed with brine (15 mL) and dried (Na$_2$SO$_4$). Solvent was evaporated and crude was purified by column chromatography (2 M NH$_3$ in MeOH:CH$_2$Cl$_2$, 5:95) to obtain compound 25 (0.32 g, 78%) as a foam. $^1$H NMR (DMSO-d$_6$) δ 2.22 (s, 6H), 2.39 (s, 3H), 2.46-2.51 (m, 2H, merged with DMSO peak), 4.14 (t, 2H, J=6.9 Hz), 6.09 (s, 1H), 6.20 (brs, 2H), 6.61 (dd, 1H, J=1.2, 8.4 Hz), 6.87 (s, 1H), 7.09 (t, 1H, J=4.2 Hz), 7.27 (d, 1H, J=8.7 Hz), 7.57 (d, 1H, J=5.1 Hz), 7.70 (d, 1H, J=3.3 Hz); ESI-MS (m/z, %) 327 (MH$^+$, 100); ESI-HRMS calculated for C$_{18}$H$_{23}$N$_4$S (MH$^+$), calculated: 327.1637; observed: 327.1653; HPLC purity: 98% by area.

EXAMPLE 7

Preparation of N-(2-methyl-1-(2-(pyrrolidin-1-yl)ethyl)-1H-indol-5-yl)thiophene-2-carboximidamide (28)

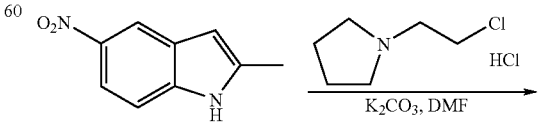

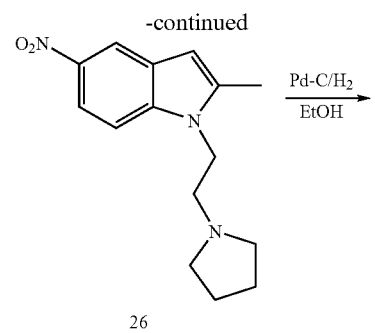

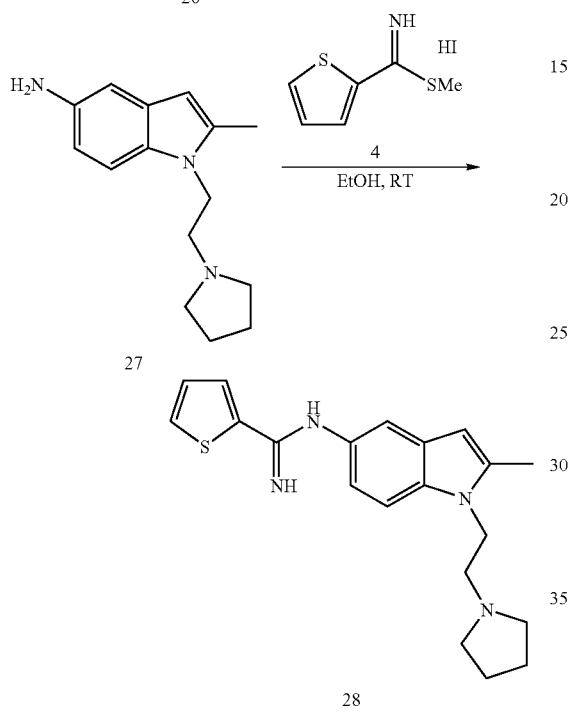

2-Methyl-5-nitro-1-(2-(pyrrolidin-1-yl)ethyl)-1H-indole (26): A mixture of compound 22 (0.3 g, 1.702 mmol), 1-(2-chloroethyl)pyrrolidine hydrochloride (0.31 g, 1.873 mmol) and $K_2CO_3$ (0.7 g, 5.108 mmol) in dry DMF (3 mL) was stirred at 65-70° C. for 18 h. The reaction was brought to room temperature, diluted with water (25 mL) and $CH_2Cl_2$ (25 mL). The $CH_2Cl_2$ layer was separated and aqueous layer was extracted in to $CH_2Cl_2$ (25 mL). The combined organic layer washed with brine (15 mL) and dried ($Na_2SO_4$). Solvent was evaporated and crude was purified by column chromatography (2 M $NH_3$ in MeOH:$CH_2Cl_2$, 3:97) to obtain compound 26 (0.46 g, quantitative) as a solid. $^1$H NMR (DMSO-$d_6$) δ 1.56-1.68 (m, 4H), 2.44-2.48 (m, 7H), 2.70 (t, 2H, J=6.9 Hz), 4.29 (t, 2H, J=6.9 Hz), 6.51 (s, 1H), 7.57 (d, 1H, J=9.0 Hz), 7.95 (dd, 1H, J=2.4, 9.1 Hz), 8.42 (d, 1H, J=2.1 Hz); ESI-MS (m/z, %) 274 (MH$^+$, 100).

2-Methyl-1-(2-(pyrrolidin-1-yl)ethyl)-1H-indol-5-amine (27): A solution of compound 26 (0.44 g, 1.609 mmol) in dry ethanol (5 mL) was treated with Pd—C (~0.05 g) and flushed with hydrogen gas. The reaction was stirred under hydrogen atm. for overnight. The reaction was filtered through celite bed, washed with methanol (3×10 mL) and dried to obtain crude compound 27 (0.39 g, quantitative) as a syrup. $^1$H NMR (DMSO-$d_6$) δ 1.60-1.70 (m, 4H), 2.32 (s, 3H), 2.40-2.48 (m, 4H), 2.60 (t, 2H, J=7.2 Hz), 4.06 (t, 2H, J=7.2 Hz), 4.37 (s, 2H), 5.88 (s, 1H), 6.42 (dd, 1H, J=2.1, 8.7 Hz), 6.56 (d, 1H, J=1.8 Hz), 7.00 (d, 1H, J=8.4 Hz); ESI-MS (m/z, %) 244 (MH$^+$, 100).

N-(2-Methyl-1-(2-(pyrrolidin-1-yl)ethyl)-1H-indol-5-yl)thiophene-2-carboximidamide (28): A solution of compound 27 (0.37 g, 1.520 mmol) in dry ethanol (5 mL) was treated with thiophene-2-carboximidothioic acid methyl ester hydroiodide (0.86 g, 3.040 mmol) at room temperature and stirred for overnight (16 h). The reaction was diluted with sat. $NaHCO_3$ solution (25 mL) and product was extracted into $CH_2Cl_2$ (2×25 mL). The combined $CH_2Cl_2$ layer was washed with brine (15 mL) and dried ($Na_2SO_4$). Solvent was evaporated and crude was purified by column chromatography (2 M $NH_3$ in MeOH:$CH_2Cl_2$, 5:95) to obtain compound 28 (0.43 g, 81%) as a foam. $^1$H NMR (DMSO-$d_6$) δ 1.64-1.76 (m, 4H), 2.39 (s, 3H), 2.46-2.58 (m, 4H), 2.66 (t, 2H, J=7.2 Hz), 4.16 (t, 2H, J=7.2 Hz), 6.09 (s, 1H), 6.20 (brs, 2H), 6.61 (dd, 1H, J=1.8, 8.5 Hz), 6.87 (d, 1H, J=1.2 Hz), 7.08 (dd, 1H, J=3.9, 4.9 Hz), 7.27 (d, 1H, J=8.7 Hz), 7.57 (d, 1H, J=5.4 Hz), 7.70 (d, 1H, J=3.6 Hz); ESI-MS (m/z, %) 253 (MH$^+$, 100), 177 (56); ESI-HRMS calculated for $C_{20}H_{25}N_4S$ (MH$^+$), calculated: 353.1794; observed: 353.1804; HPLC purity: 97% by area.

EXAMPLE 8

Preparation of N-(2-methyl-1-(2-(1-methylpyrrolidin-2-yl)ethyl)-1H-indol-5-yl)thiophene-2-carboximidamide (32)

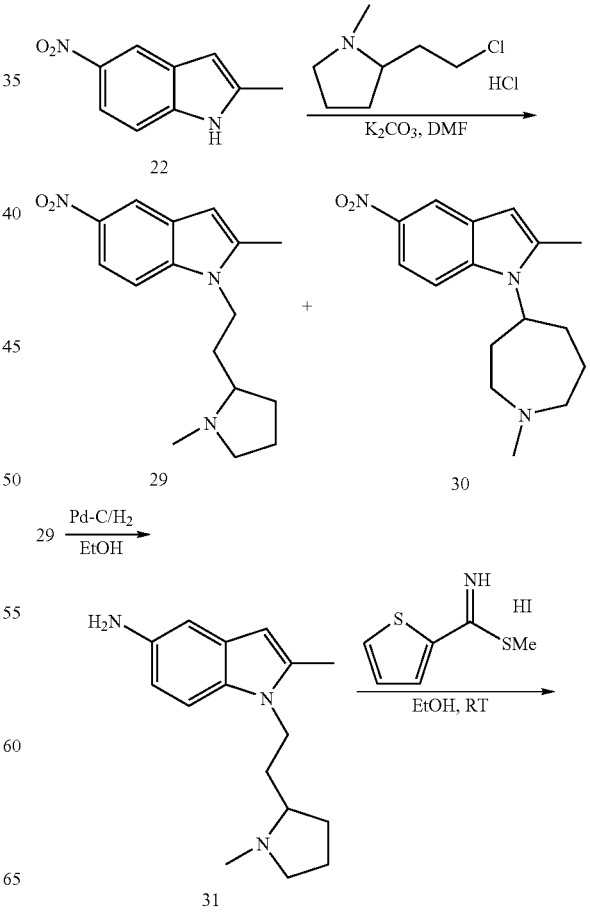

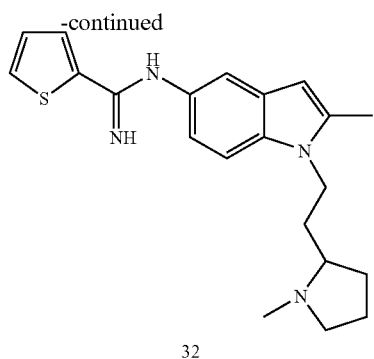

32

2-Methyl-1-(2-(1-methylpyrrolidin-2-yl)ethyl)-5-nitro-1H-indole (29): A mixture of compound 22 (0.5 g, 2.838 mmol), 2-(2-chloroethyl)-1-methylpyrrolidine hydrochloride (0.57 g, 3.121 mmol) and K$_2$CO$_3$ (1.17 g, 8.514 mmol) in dry DMF (3 mL) was stirred at 65-70° C. for 18 h. The reaction was brought to room temperature, diluted with water (25 mL) and CH$_2$Cl$_2$ (25 mL). The CH$_2$Cl$_2$ layer was separated and aqueous layer was extracted in to CH$_2$Cl$_2$ (25 mL). The combined organic layer washed with brine (15 mL) and dried (Na$_2$SO$_4$). Solvent was evaporated and crude was purified by column chromatography (2 M NH$_3$ in MeOH:CH$_2$Cl$_2$, 3:97) to obtain compound 29 (0.53 g) and a mixture of compound 29 and 30 (0.2 g) in 91% yield. $^1$H NMR (DMSO-d$_6$) δ 1.42-1.68 (m, 4H), 1.81-2.16 (m, 4H), 2.19 (s, 3H), 2.46 (s, 3H), 2.90-2.96 (m, 1H), 4.20 (t, 2H, J=8.1 Hz), 6.52 (s, 1H), 7.56 (d, 1H, J=9.3 Hz), 7.96 (dd, 1H, J=2.4, 9.0 Hz), 8.43 (d, 1H, J=2.1 Hz); ESI-MS (m/z, %) 288 (MH$^+$, 100), 191 (35).

2-Methyl-1-(2-(1-methylpyrrolidin-2-yl)ethyl)-1H-indol-5-amine (31): A solution of compound 29 (0.5 g, 1.739 mmol) in dry ethanol (3 mL) was treated with Pd—C (~0.05 g) and flushed with hydrogen gas. The reaction was stirred under hydrogen atm. for overnight. The reaction was filtered through celite bed, washed with methanol (3×15 mL) and dried to obtain crude compound 31 (0.34 g, 77%) as a syrup. $^1$H NMR (DMSO-d$_6$) δ 1.40-1.67 (m, 4H), 1.82-1.93 (m, 2H), 1.98-2.10 (m, 2H), 2.18 (s, 3H), 2.31 (s, 3H), 2.90-2.96 (m, 1H), 3.97 (t, 2H, J=7.5 Hz), 4.39 (s, 2H), 5.88 (s, 1H), 6.43 (dd, 1H, J=2.1, 8.4 Hz), 6.57 (d, 1H, J=1.8 Hz), 7.00 (d, 1H, J=8.7 Hz); ESI-MS (m/z, %) 258 (MH$^+$, 28), 161 (100).

N-(2-Methyl-1-(2-(1-methylpyrrolidin-2-yl)ethyl)-1H-indol-5-yl)thiophene-2-carboximidamide (32): A solution of compound 31 (0.32 g, 1.243 mmol) in dry ethanol (10 mL) was treated with thiophene-2-carboximidothioic acid methyl ester hydroiodide (0.7 g, 2.486 mmol) at room temperature and stirred for 4 h. The reaction was diluted with sat. NaHCO$_3$ solution (25 mL) and product was extracted into CH$_2$Cl$_2$ (2 25 mL). The combined CH$_2$Cl$_2$ layer washed with brine (15 mL) and dried (Na$_2$SO$_4$). Solvent was evaporated and crude was purified by column chromatography (2 M NH$_3$ in MeOH:CH$_2$Cl$_2$, 5:95) to obtain compound 32 (0.45 g, 99%) as a foam. $^1$H NMR (DMSO-d$_6$) δ 1.48-1.68 (m, 4H), 1.87-1.98 (m, 2H), 2.01-2.18 (m, 2H), 2.22 (s, 3H), 2.39 (s, 3H), 2.92-2.98 (m, 1H), 4.07 (t, 2H, J=7.8 Hz), 6.09 (s, 1H), 6.19 (brs, 2H), 6.62 (dd, 1H, J=1.5, 8.5 Hz), 6.87 (s, 1H), 7.08 (dd, 1H, J=3.6, 4.9 Hz), 7.26 (d, 1H, J=8.4 Hz), 7.57 (d, 1H, J=5.4 Hz), 7.70 (d, 1H, J=3.6 Hz); ESI-MS (m/z, %) 367 (MH$^+$, 62), 184 (100), 126 (37); ESI-HRMS calculated for C$_{21}$H$_{27}$N$_4$S (MH$^+$), calculated: 367.1950, observed: 367.1965; HPLC purity: 96.2% by area.

EXAMPLE 9

Preparation of N-((1-(2-(1-methylpyrrolidin-2-yl)ethyl)-1H-indol-5-yl)methyl)thiophene-2-carboximidamide (37)

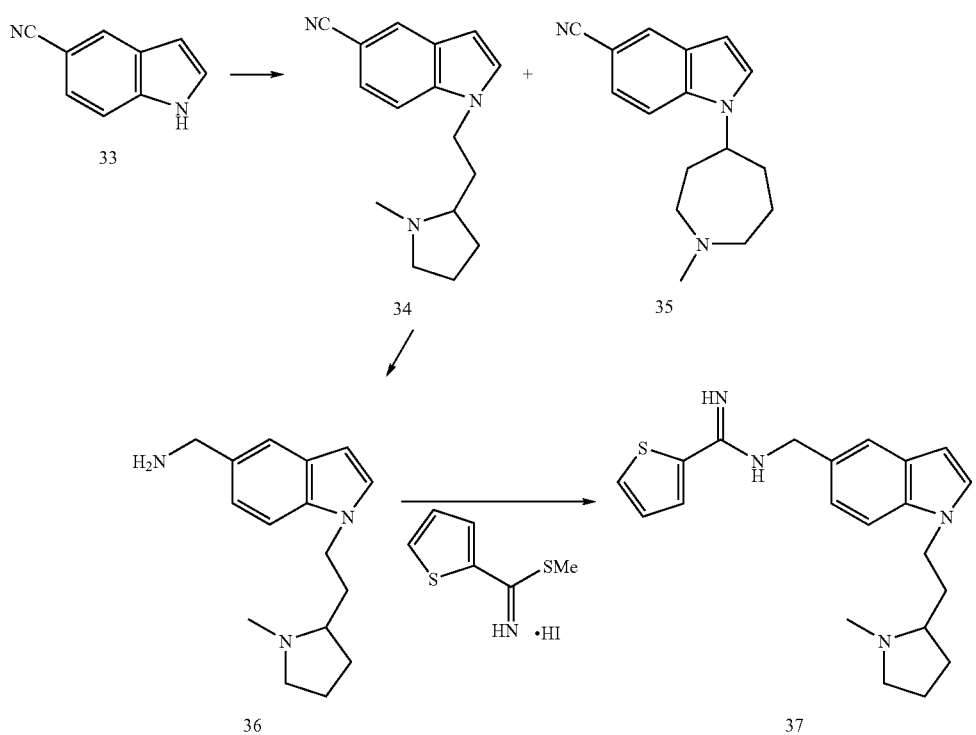

1-(2-(1-Methylpyrrolidin-2-yl)ethyl)-1H-indole-5-carbonitrile (34): Compound 33 (0.5 g, 3.517 mmol), 2-(2-chloroethyl)-1-methylpyrrolidine hydrochloride (0.712 g, 3.869 mmol), and powdered potassium carbonate (1.458 g, 10.551 mmol) were placed in an argon-purged flask.

DMF (15 mL, Aldrich sure seal™) was added and the mixture heated to 65° C. in an oil bath for 48 hours. The solution was cooled to room temperature and diluted with water (15 mL) and ethyl acetate (25 mL). The layers were separated and the aqueous phase extracted with ethyl acetate (2×25 mL). The organic extracts were combined, washed with brine (2×10 mL) and dried over magnesium sulfate. The sample was filtered, concentrated, and the resultant crude product purified using dry silica gel column chromatography eluting with 50 mL portions of solvent system (2M $NH_3$ in methanol:$CH_2Cl_2$, 2.5:97.5 to 5:95) to afford two compounds, pale yellow oil 34 (0.36 g, 40.4%); $^1$H NMR ($CDCl_3$) δ 7.97 (s, 1H), 7.45-7.37 (2×m, 2H), 7.23 (d, 1H, J=3.1 Hz), 6.58 (d, 1H, J=3.4 Hz), 4.28-4.11 (m, 2H), 3.10-3.04 (m, 1H), 2.28 (s, 3H), 2.22-2.04 (m, 3H), 1.99-1.66 (2×m, 4H), 1.55-1.43 (m, 1H); ESI-MS (m/z, %): 254 (M+1, 100%) and a rearranged product, colorless oil 35; $^1$H NMR ($CDCl_3$) δ 7.96 (s, 1H), 7.41 (s, 2H), 7.36 (d, 1H, J=3.4 Hz), 6.59 (d, 1H, J=3.4 Hz), 4.60 (quintet, 1H), 2.81-2.64 (m, 4H), 2.44 (s, 3H), 2.22-2.07 (m, 4H), 2.00-1.92 (m, 1H), 1.85-1.72 (m, 1H); ESI-MS (m/z, %): 254 (M+1, 100%).

(1-(2-(1-Methylpyrrolidin-2-yl)ethyl)-1H-indol-5-yl)methanamine (36): To a dry argon purged flask fitted with a magnetic stirbar, condenser and dropping funnel is charged lithium aluminum hydride (80.9 mg, 2.131 mmol), anhydrous diethyl ether (10 mL) and stirring begun. A solution of compound 34 (360 mg, 1.421 mmol) in anhydrous diethyl ether (10 mL) is charged to the dropping funnel and added drop wise to the $LiAlH_4$ suspension and mixture stirred at ambient temperature for 30 minutes. The reaction was quenched by the sequential addition of 100 ul $H_2O$, 125 ul 3M sodium hydroxide and 300 ul $H_2O$. After filtration to remove insolubles, the solution was concentrated and the residue purified twice via chromatography on silica gel (2M $NH_3$ in methanol:$CH_2Cl_2$, 5:95 to 1:9) to afford pale yellow oil 36 (149 mg, 40.7%); $^1$H NMR (DMSO-$d_6$) δ 7.45 (s, 1H), 7.37-7.33 (2×m, 2H), 7.10 (d, 1H, J=8.2 Hz), 6.35 (d, 1H, J=3.1 Hz), 4.15 (t, 2H, J=7.4 Hz), 3.76 (s, 2H), 2.93-2.87 (m, 1H), 2.15 (s, 3H), 2.12-2.03 (m, 1H), 2.00-1.93 (m, 2H), 1.88-1.79 (m, 1H), 1.68-1.52 (m, 3H), 1.44-1.35 (m, 1H); ESI-MS (m/z, %): 258 (M+1, 100%).

N-((1-(2-(1-Methylpyrrolidin-2-yl)ethyl)-1H-indol-5-yl)methyl)thiophene-2-carboximidamide (37): Compound 36 (124 mg, 0.482 mmol) and anhydrous ethanol (10 mL) were charged to a dry argon purged flask fitted with magnetic stirbar. Thiophene-2-carboximidothioic acid methyl ester hydroiodide (178.5 mg, 0.626 mmol) is added to the flask and the reaction was stirred under argon at ambient temperature for 96 hours. The solution was diluted with diethyl ether (50 mL) resulting in the formation of an off-white precipitate which was collected on a sintered glass funnel and washed with ether. The solid was partitioned between $H_2O$ and ethyl acetate and 3M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (2M $NH_3$ in methanol:$CH_2Cl_2$, 1:9) to afford a pale yellow residue 37 (100 mg, 56.6%); $^1$H NMR (DMSO-$d_6$) δ 7.60 (d, 1H, J=3.8 Hz), 7.51 (m, 2H), 7.39-7.34 (2×m, 2H), 7.16-7.13 (m, 1H), 7.06 (dd, 1H, J=3.8, 5.1 Hz), 6.86-6.54 (brs, 2H), 6.37 (d, 1H, J=3.0 Hz), 4.38 (s, 2H), 4.16 (t, 2H, J=7.3 Hz), 2.94-2.87 (m, 1H), 2.16 (s, 3H), 2.11-1.92 (2×m, 3H), 1.89-1.80 (m, 1H), 1.69-1.55 (m, 3H), 1.48-1.36 (m, 1H); ESI-MS (m/z, %): 367 (M+1, 100%).

EXAMPLE 10

Preparation of N-(1-(3-morpholinopropyl)-1H-indol-5-yl)thiophene-2-carboximidamide dihydrochloride (40)

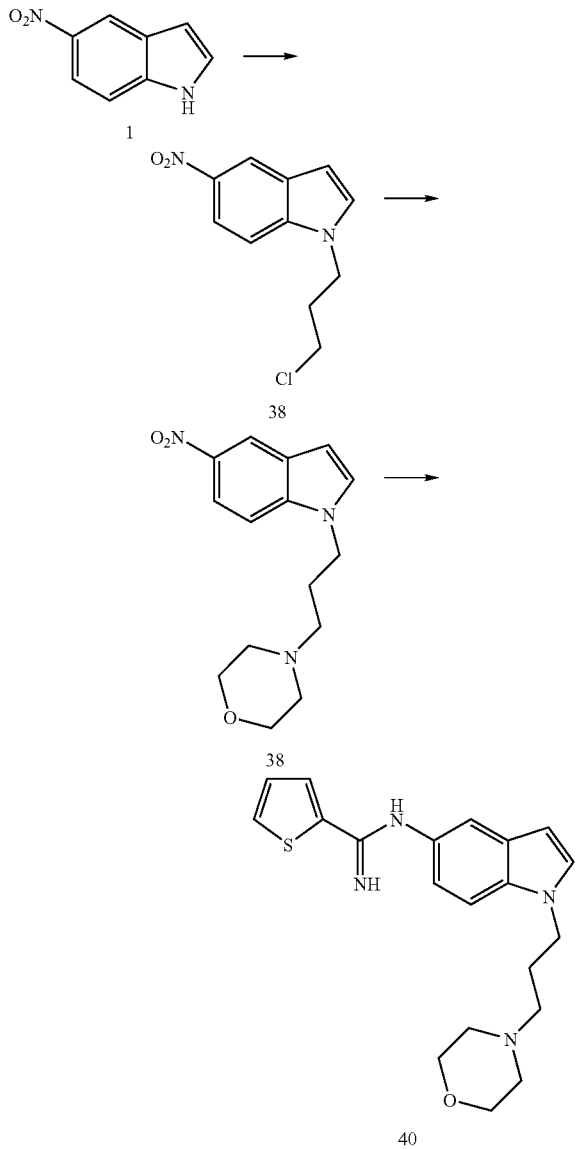

1-(3-Chloropropyl)-5-nitro-1H-indole (38): To a flask (2 neck, 250 mL) containing sodium hydride (0.98 g, 24.5 mmol, 60% in mineral oil) was added dry DMF (30 mL) while cooling in an ice bath. A solution of compound 1 (1.0 g, 617 mmol) in DMF (20 mL) was added to the ice-cold solution resulting in the formation of a wine coloured solution. This solution was stirred followed by the addition of 1-chloro-3-iodopropane (1.95 mL, 3 eq) neat. The mixture was removed from the ice bath and stirred for 2 hours and quenched with water (80 mL) and brine (20 mL). A yellow precipitate slowly formed which was collected by filtration and washed with water. The sample was air dried overnight. The sample was recrystallized from toluene to obtain compound 38 (1.0886 g, 74%) as a solid. mp 74-76° C.

4-(3-(5-Nitro-1H-indol-1-yl)propyl)morpholine (39): To a small reaction vial containing a magnetic stirbar was added compound 38 (155 mg, 0.649 mmol), potassium iodide (1.078 g, 6.49 mmol) and potassium carbonate (898.0 mg, 6.49 mmol). The vial was sealed and purged with argon. Anhydrous acetonitrile (4 mL) was added through the septum, followed by morpholine (0.57 mL, 6.54 mmol). The vial was placed in the heating block and stirred at 81° C. for 68 hours. The reaction was cooled to room temperature. The non-homogenous reaction was diluted with dichloromethane (5 mL) and filtered through celite. Additional dichloromethane (10 mL) followed by methanol (5 mL) was used to wash the celite plug. The filtrate was concentrated on the rotary evaporator and dried further under high vacuum. The product was purified using silica gel column chromatography (2M $NH_3$ in methanol:$CH_2Cl_2$, 5:95) to obtain compound 39 (190 mg, 100%) as a yellow oil. $^1$H NMR ($CDCl_3$) δ 8.59 (d, J=2.1 Hz, 1H), 8.11 (dd, J=2.7, 9.0 Hz, 1H), 7.42 (d, J=9.0 Hz, 1H), 7.28 (d, J=3.3 Hz, 1H), 6.69 (d, J=3.0 Hz, 1H), 4.30 (t, J=6.3 Hz, 2H), 3.75 (brs, 4H), 2.41 (brs, 4H), 2.27 (brs, 2H), 2.04 (brs, 2H); ESI-MS (m/z, %): 290 (M+1, 100).

N-(1-(3-Morpholinopropyl)-1H-indol-5-yl)thiophene-2-carboximidamide (40): To an argon purged round bottom flask containing compound 39 (153 mg, 0.529 mmol) was added 10% by weight palladium on carbon (56 mg, 0.053 mmol) and a magnetic stirbar, followed by the addition of absolute ethanol (10 mL). The system was fitted with a hydrogen filled balloon. The argon atmosphere was removed using a water aspirator and replaced with hydrogen. The atmosphere was removed twice more and replaced with hydrogen a total of 3 times and was stirred for 17.5 hours. TLC (2M $NH_3$ in methanol:$CH_2Cl_2$, 5:95) revealed the reaction was complete. The reaction was filtered through a 5 um PTFE frit. The frit washed with absolute ethanol (5 mL). The filtrate was transferred to a reaction vial fitted with a magnetic stirbar, and was purged with argon. Methyl thiophene-2-carbimidothioate hydroiodide (226 mg, 0.793 mmol) was added as a solid and the reaction was stirred at room temperature for 18 hours. The reaction was complete by TLC and was diluted with ether (40 mL) and the reaction was filtered to collect the precipitate. The precipitate washed with ether. The precipitate was dissolved in ethanol and stirred at room temperature with DOWES-66 resin (3.00 g). The mixture was stirred at room temperature for 2 hours. The reaction was filtered and the filtrate concentrated. The material was purified by silica gel column chromatography (2M $NH_3$ in methanol:$CH_2Cl_2$, 2.5:97.5 to 5:95) to obtain compound 40 (122 mg) as a brown oil. $^1$H NMR (DMSO-$d_6$) δ 7.72 (d, J=3.6 Hz, 1H), 7.58 (d, J=3.6 Hz, 1H), 7.41 (d, J=8.7 Hz, 1H), 7.29 (d, J=3.0 Hz, 1H), 7.09 (t, J=4.5 Hz, 1H), 6.97 (s, 1H), 6.69 (d, J=9.0 Hz, 1H), 6.32 (d, J=3.0 Hz, 1H), 6.22 (brs, 2H), 4.17 (t, J=6.6 Hz, 2H), 3.58 (t, J=4.5 Hz, 4H), 2.31 (m, 4H), 2.21 (t, J=6.9 Hz, 2H), 1.90 (m, 2H); ESI-MS (m/z, %): 369 (M+1); ESI-HRMS calculated for $C_{20}H_{25}N_4OS$ ($MH^+$): 369.1743, Observed: 369.1754.

EXAMPLE 11

Preparation of N-(1-(3-adamantanaminopropyl)-1H-indol-5-yl)thiophene-2-carboximidamide (42)

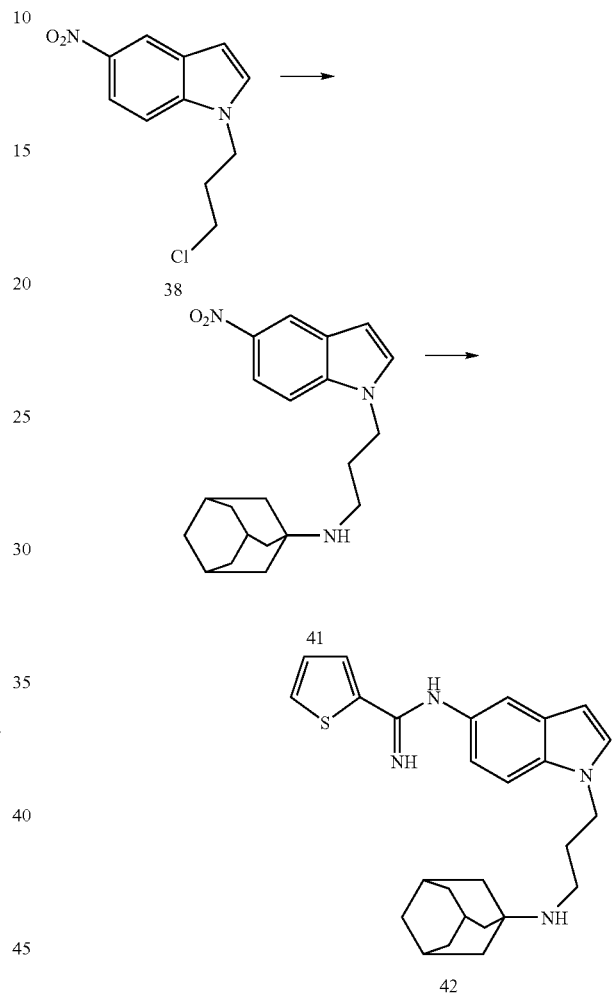

1-N-(3-(5-Nitro-1H-indol-1-yl)propyl)adamantanamine (41): Reaction performed as described for compound 39. Concentration of filtrate from celite afforded a pale brown solid. The product was purified using silica gel column chromatography (2M $NH_3$ in methanol: $CH_2Cl_2$, 5:95) to obtain compound 41 (221 mg, 96.5%) as a thick yellow oil. $^1$H NMR ($CDCl_3$) δ 8.59 (d, J=2.1 Hz, 1H), 8.11 (dd, J=2.1, 9.0 Hz, 1H), 7.40 (d, J=9.0 Hz, 1H), 7.29 (d, J=3.0 Hz, 1H), 6.67 (d, J=3.0 Hz, 1H), 4.29 (t, J=6.9 Hz, 2H), 2.60 (t, J=6.6 Hz, 2H), 2.00 (m, 5H), 1.64 (m, 12H); ESI-MS (m/z, %): 354 (M+1, 100).

N-(1-(3-Adamantanaminopropyl)-1H-indol-5-yl)thiophene-2-carboximidamide (42): Reaction performed as described for compound 40. The material was purified by silica gel column chromatography (2M $NH_3$ in methanol: $CH_2Cl_2$, 2.5:97.5 to 5:95) to obtain compound 42 (235 mg) as a brown oil. $^1$H NMR (methanol-$d_4$) δ 7.71 (dd, J=1.2, 3.9 Hz, 1H), 7.67 (d, J=4.5 Hz, 1H), 7.60 (d, J=5.7 Hz, 1H), 7.48 (d, J=8.7 Hz, 1H), 7.26 (d, J=2.7 Hz, 1H), 7.22 (d, J=1.8 Hz, 1H), 7.14 (m, 2H), 6.90 (dd, J=1.8, 8.7 Hz, 1H), 6.45 (d, J=3.0 Hz, 1H), 4.28 (t, J=6.9 Hz, 2H), 2.65 (m, 2H), 2.04 (m, 5H), 1.70 (m, 12H); ESI-MS (m/z, %): 433 (M+1); ESI-HRMS calculated for $C_{26}H_{33}N_4S$ ($MH^+$): 433.242, Observed: 433.2399.

EXAMPLE 12

Preparation of N-(1-(3-((1-ethylpyrrolidin-2-yl)methylamino)propyl)-1H-indol-5-yl)thiophene-2-carboximidamide (44)

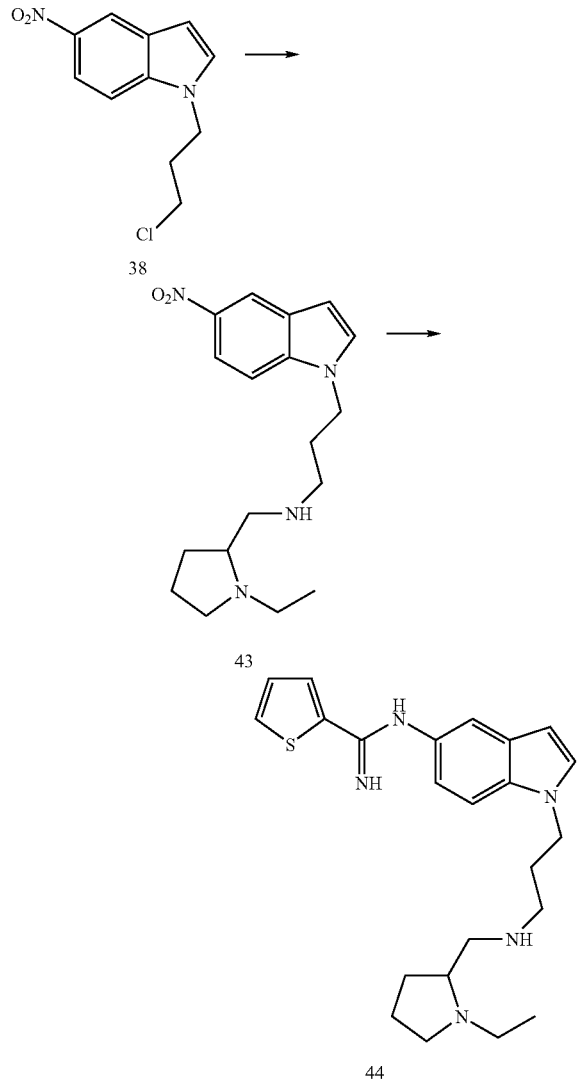

N-((1-Ethylpyrrolidin-2-yl)methyl)-3-(5-nitro-1H-indol-1-yl)propan-1-amine (43): Reaction performed as described for compound 39. Concentration of filtrate from celite afforded brown oil. The crude product was purified using silica gel column chromatography (2M $NH_3$ in methanol:$CH_2Cl_2$, 2.5:97.5 to 5:95) to obtain compound 43 (212 mg, 99%) as a yellow-orange oil. $^1$H NMR ($CDCl_3$) δ 8.59 (d, J=2.1 Hz, 1H), 8.10 (dd, J=2.7, 9.0 Hz, 1H), 7.42 (d, J=9.0 Hz, 1H), 7.29 (d, J=3.3 Hz, 1H), 6.67 (d, J=3 Hz, 1H), 4.30 (dt, J=2.4, 6.6 Hz, 2H), 3.24 (m, 1H), 2.90 (m, 1H), 2.48 (m, 5H), 2.28 (m, 2H), 2.01 (m, 5H), 1.75 (m, 3H); ESI-MS (m/z, %): 331 ($MH^+$, 100).

N-(1-(3-((1-Ethylpyrrolidin-2-yl)methylamino)propyl)-1H-indol-5-yl)thiophene-2-carboximidamide (44): Reaction performed as described for compound 40. The material was purified by silica gel column chromatography (2M $NH_3$ in methanol:$CH_2Cl_2$, 2.5:97.5 to 5:95) to obtain compound 44 (170 mg) as brown oil. $^1$H NMR (DMSO-$d_6$) δ 7.72 (d, J=3.6 Hz, 1H), 7.58 (d, J=3.6 Hz, 1H), 7.40 (d, J=8.4 Hz, 1H), 7.27 (d, J=3.0 Hz, 1H), 7.09 (s, 1H), 6.98 (s, 1H), 6.69 (d, J=9.0 Hz, 1H), 6.51 (J=6.6 Hz, 1H), 6.32 (brs, 2H), 4.18 (t, J=6.6 Hz, 2H), 4.04 (m, 1H), 3.02 (m, 1H), 2.78 (m, 2H), 2.38 (m, 3H), 2.07 (m, 3H), 1.85 (m, 4H), 1.60 (m, 4H); ESI-MS (m/z, %): 410 ($MH^+$, 100).

EXAMPLE 13

Preparation of N-(1-(3-(cyclopropylamino)propyl)-1H-indol-5-yl)thiophene-2-carboximidamide (46)

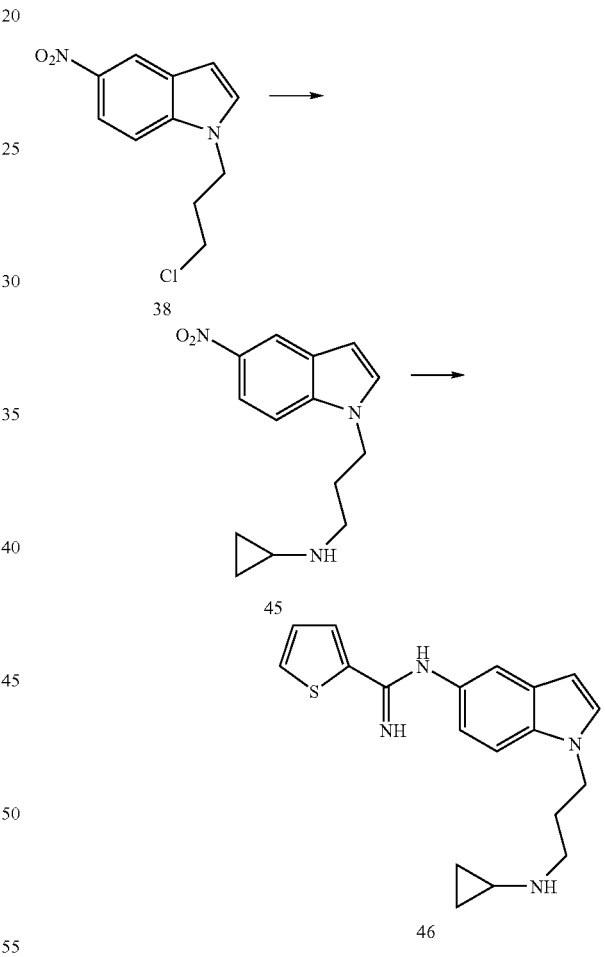

N-(3-(5-Nitro-1H-indol-1-yl)propyl)cyclopropanamine (45): Reaction performed as described for compound 39. Concentration of filtrate from celite afforded a pale yellow solid. The crude product was purified using silica gel column chromatography (2M $NH_3$ in methanol: $CH_2Cl_2$, 5:95) to obtain compound 45 (144 mg, 87%) as a yellow oil. $^1$H NMR ($CDCl_3$) δ 8.59 (d, J=2.1 Hz, 1H), 8.11 (dd, J=2.7, 9.0 Hz, 1H), 7.40 (d, J=9.0 Hz, 1H), 7.28 (d, J=3.3 Hz, 1H), 6.68 (d, J=3.0 Hz, 1H), 4.27 (t, J=6.9 Hz, 2H), 2.73 (t, J=6.9 Hz, 2H), 2.10 (m, 3H), 0.48 (m, 3H); ESI-MS (m/z, %): 259 (M+1, 100).

N-(1-(3-(Cyclopropylamino)propyl)-1H-indol-5-yl)thiophene-2-carboximidamide (46): Reaction performed as described for compound 40. The material was purified by silica gel column chromatography (2M NH$_3$ in methanol: CH$_2$Cl$_2$, 2.5:97.5 to 5:95) to obtain compound 46 (173 mg) as a brown oil. $^1$H NMR (methanol-d$_4$) δ 7.72 (d, J=3.6 Hz, 1H), 7.58 (d, J=3.6 Hz, 1H), 7.40 (d, J=8.7 Hz, 1H), 7.29 (d, J=3.0 Hz, 1H), 7.09 (t, J=4.5 Hz, 1H), 6.97 (s, 1H), 6.69 (d, J=9.0 Hz, 1H), 6.32 (d, J=3.0 Hz, 1H), 6.22 (brs, 2H), 4.17 (t, J=6.6 Hz, 2H), 3.59 (t, J=4.5 Hz, 4H), 2.32 (m, 4H), 2.22 (t, J=6.9 Hz, 2H), 1.91 (m, 2H); ESI-MS (m/z, %) 339 (M+1); ESI-HRMS calculated for C$_{19}$H$_{23}$N$_4$S (MH$^+$): 339.1637, observed: 339.1644.

EXAMPLE 14

Preparation of N-(1-(3-(dimethylamino)propyl)-1H-indol-5-yl)thiophene-2-carboximidamide (48)

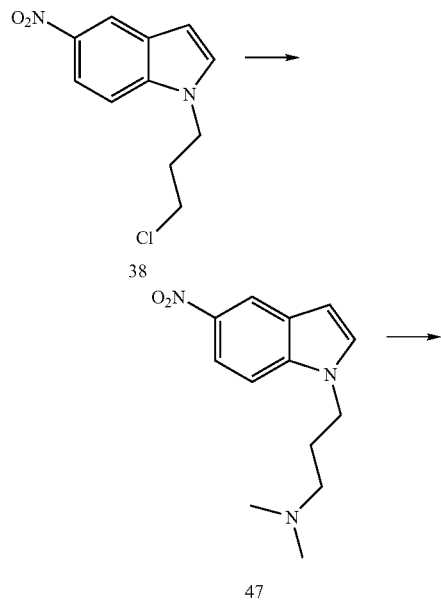

-continued

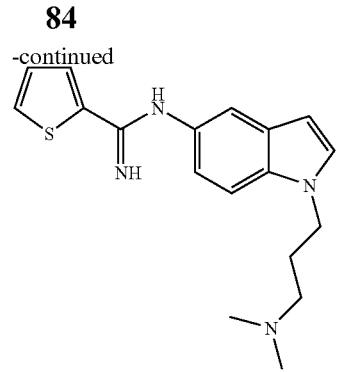

N,N-Dimethyl-3-(5-nitro-1H-indol-1-yl)propan-1-amine (47): Reaction performed as described for compound 39. Concentration of filtrate from celite afforded a pale yellow solid. The crude product was purified using silica gel column chromatography (2M NH$_3$ in methanol: CH$_2$Cl$_2$, 5:95) to obtain compound 47 (152 mg, 95%) as a yellow oil. $^1$H NMR (CDCl$_3$) δ 8.59 (d, J=2.1 Hz, 1H), 8.11 (dd, J=2.7, 9.0 Hz, 1H), 7.42 (d, J=9.0 Hz, 1H), 7.29 (d, J=3.3 Hz, 1H), 6.68 (d, J=3.0 Hz, 1H), 4.28 (t, J=6.9 Hz, 2H), 2.24 (m, 8H), 2.03 (m, 2H); ESI-MS (m/z, %): 248 (M+1, 100).

N-(1-(3-(Dimethylamino)propyl)-1H-indol-5-yl)thiophene-2-carboximidamide (48): Reaction performed as described for compound 40. The material was purified by silica gel column chromatography (2M NH$_3$ in methanol: CH$_2$Cl$_2$, 2.5:97.5 to 5:95) to obtain compound 48 (48 mg) as a brown solid. $^1$H NMR (methanol-d$_4$) δ 7.63 (dd, J=1.8, 3.6 Hz, 1H), 7.56 (d, J=4.2 Hz, 1H), 7.45 (d, J=8.7 Hz, 1H), 7.22 (d, J=3.0 Hz, 1H), 7.18 (d, J=1.8 Hz, 1H), 7.13 (t, J=4.5 Hz, 1H), 6.87 (dd, J=2.1, 8.7 Hz, 1H), 6.41 (d, J=3.3 Hz, 1H), 4.23 (t, J=6.9 Hz, 2H), 2.27 (m, 2H), 2.23 (s, 6H), 2.03 (m, 2H); ESI-MS 327 (M+1); ESI-HRMS calculated for C$_{18}$H$_{23}$N$_4$S (MH$^+$): 327.1637, Observed: 327.1640.

EXAMPLE 15

Preparation of N-(1-(2-(1-methylpyrrolidin-2-yl)ethyl)-1H-indol-5-yl)furan-2-carboximidamide (53) and N-(1-(1-methylazepan-4-yl)-1H-indol-5-yl)furan-2-carboximidamide (54)

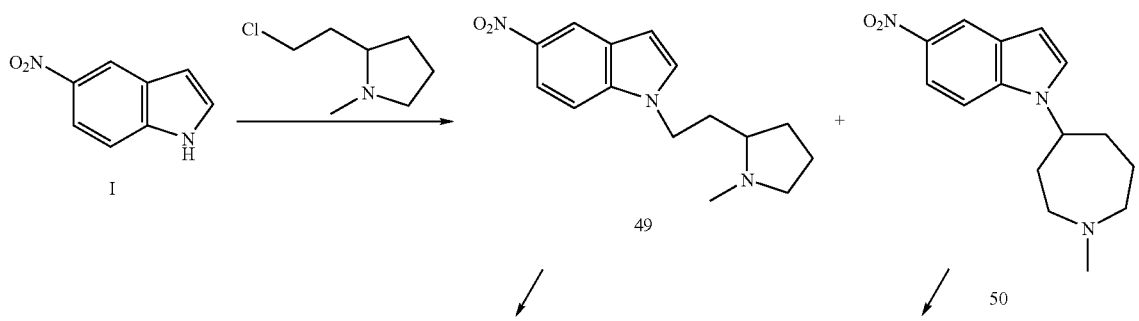

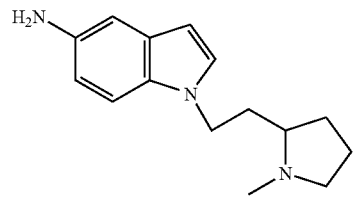

51

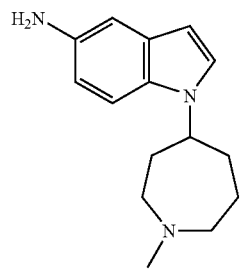

52

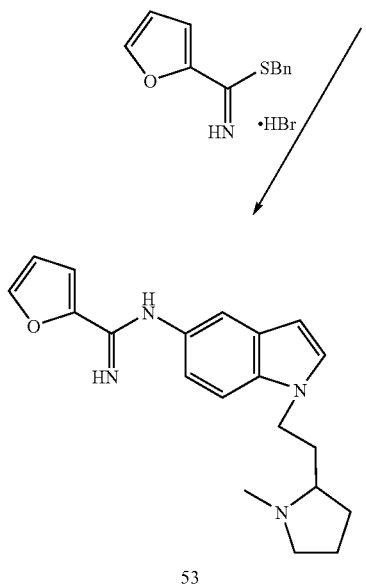

53

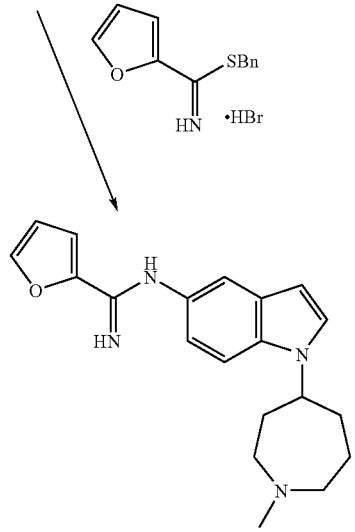

54

1-(2-(1-Methylpyrrolidin-2-yl)ethyl)-5-nitro-1H-indole (49) and 1-(1-methylazepan-4-yl)-5-nitro-1H-indole (50): Compound 1 (1.0 g, 6.167 mmol), 2-(2-chloroethyl)-1-methylpyrrolidine hydrochloride (1.249 g, 6.784 mmol) and powdered potassium carbonate (2.557 g, 18.501 mmol) were placed in an oven dried, argon-purged flask. DMF (20 mL, Aldrich sure seal™) was added and the mixture heated to 65° C. in an oil bath for 22 hours. The solution was cooled to room temperature and diluted with water (20 mL) and ethyl acetate (50 mL). The mixture was transferred to a separatory funnel and the organic layer collected. The aqueous phase further extracted with ethyl acetate (2×50 mL). The organic extracts were combined, washed with brine (2×10 mL) and dried over magnesium sulfate. The sample was filtered, concentrated, and the resultant crude product purified using dry silica gel column chromatography eluting with 50 mL portions of solvent system (2M $NH_3$ in methanol:$CH_2Cl_2$, 5:95) to afford two compounds, compound 49: yellow oil (0.829 g, 49.2%); $^1$H NMR (CDCl$_3$) δ 8.58 (d, 1H, J=2.0 Hz), 8.12 (dd, 1H, J=9.1, 2.2 Hz), 7.38-7.35 (m, 1H), 7.27 (s, 1H), 6.69 (d, 1H, J=3.1 Hz), 4.32-4.14 (m, 2H), 3.15-3.08 (m, 1H), 2.31 (s, 3H), 2.28-2.08 (m, 3H), 2.01-1.66 (2×m, 4H), 1.59-1.47 (m, 1H); ESI-MS: 274 (M+1, 100%) and compound 50 (a rearranged product): yellow oil (0.259 g, 15.4%); $^1$H NMR (CDCl$_3$) δ 8.58 (d, 1H, J=2.2 Hz), 8.11 (dd, 1H, J=9.3, 2.2 Hz), 7.43-7.38 (2×m, 2H), 6.69 (d, 1H, J=3.3 Hz), 4.64 (quintet, 1H, J=7.2 Hz), 2.85-2.69 (m, 4H), 2.48 (s, 3H), 2.28-2.13 (2×m, 4H), 2.06-1.92 (m, 1H), 1.87-1.77 (m, 1H); ESI-MS (m/z, %): 274 (M+1, 100%).

N-(1-(2-(1-Methylpyrrolidin-2-yl)ethyl)-1H-indol-5-yl)furan-2-carboximidamide (53): Compound 49 (103.6 mg, 0.379 mmol) was dissolved in anhydrous ethanol (5 mL) in a dry argon purged flask. Palladium, 10 wt % on activated carbon (40.3 mg, 0.0379 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of 2M $NH_3$ in methanol:$CH_2Cl_2$, 5:95 shows complete conversion to 51, which is utilized without isolation. The mixture is filtered through a pad of celite to remove insolubles, the pad washed with anhydrous ethanol (5 mL) and the ethanolic solution of the amine 51 is charged to a small, argon purged flask fitted with a magnetic stirbar. Benzyl furan-2-carbimidothioate hydrobromide (168.5 mg, 0.565 mmol) is added to the flask and the reaction was stirred under argon at ambient temperature for 18 hours, at which time the solvent was evaporated and the residue partitioned between $H_2O$ and ethyl acetate and 1M sodium hydroxide solution added to adjust pH to 8-9. The mixture was transferred to a separatory funnel and the organic layer collected. The aqueous layer was further extracted with ethyl acetate and the combined organic layers were washed with brine, dried over magnesium sulphate, filtered, concentrated and the crude purified via chromatography on silica gel (2M $NH_3$ in methanol:$CH_2Cl_2$, 5:95) to afford colorless residue 53 (125 mg, 98%); $^1$H NMR (DMSO-d$_6$) δ 7.77 (s, 1H), 7.37 (d, 1H, J=8.5 Hz), 7.31 (d, 1H, J=3.0 Hz), 7.07 (d, 1H, J=3.2 Hz), 6.97 (s, 1H), 6.69 (d, 1H, J=8.3 Hz), 6.60-6.57 (m, 1H), 6.31 (d, 1H, J=3.2 Hz), 6.01 (brs, 2H), 4.14 (t, 2H, J=7.3 Hz), 2.96-2.90 (m, 1H), 2.19 (s, 3H), 2.10-1.98, (m, 3H), 1.90-1.84 (m, 1H), 1.71-1.66 (m, 3H), 1.63-1.53 (m, 1H); ESI-MS (m/z, %): 337 (M+1, 100%).

N-(1-(1-Methylazepan-4-yl)-1H-indol-5-yl)furan-2-carboximidamide (54): Compound 50 (103.6 mg, 0.379 mmol) was dissolved in anhydrous ethanol (5 mL) in dry argon purged flask. Palladium, 10 wt % on activated carbon (40.3 mg, 0.0379 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of 2M $NH_3$ in methanol:$CH_2Cl_2$, 5:95 shows complete conversion to 52, which is utilized without isolation. The mixture is filtered through a pad of celite to remove insolubles, the pad washed with anhydrous ethanol (5 mL) and the ethanolic solution of the amine 52 is charged to a small, argon purged flask fitted with a magnetic stirbar. Benzyl furan-2-carbimidothioate hydrobromide (169.5 mg, 0.569 mmol) is added to the flask and the reaction was stirred under argon at ambient temperature for 96 hours, at which time the solvent was evaporated and the residue partitioned between $H_2O$ and ethyl acetate and 1M sodium hydroxide solution added to adjust pH to 8-9. The mixture was transferred to a separatory funnel and the organic layer collected. The aqueous layer was further extracted with ethyl acetate and the combined organic layers were washed with brine, dried over magnesium sulphate, filtered, concentrated and the crude purified via chromatography on silica gel (2M $NH_3$ in methanol:$CH_2Cl_2$, 5:95) to afford pale yellow solid 54 (87 mg, 68.2%); $^1$H NMR (DMSO-$d_6$) δ 7.77 (s, 1H), 7.42-7.39 (2×m, 2H), 7.08 (d, 1H, J=3.1 Hz), 6.96 (s, 1H), 6.68 (d, 1H, J=8.6 Hz), 6.61-6.58 (m, 1H), 6.32 (d, 1H, J=3.2 Hz), 6.02 (brs, 2H), 4.57 (quintet, 1H, J=4.8 Hz), 2.73-2.55 (m, 4H), 2.31 (s, 3H), 2.15-1.99, (m, 4H), 1.87-1.64 (m, 2H); ESI-MS (m/z, %): 337 (M+1, 100%).

EXAMPLE 16

Preparation of (+)-55 and (−)-55

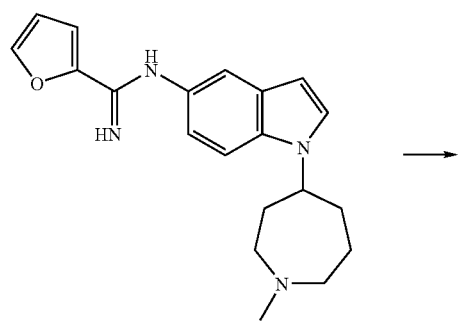

54

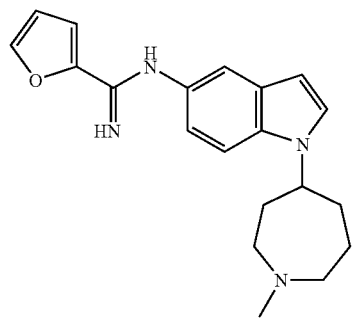

(+)-55

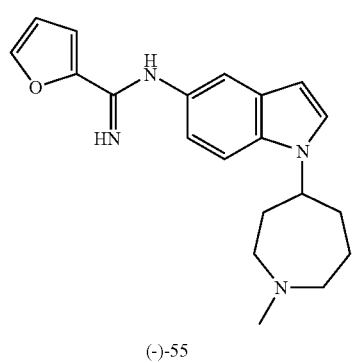

(−)-55

Preparation of compounds (+)-55 and (−)-55: Separation of enantiomers was achieved by chiral HPLC.

Column: Chiralpak AD-H

Eluent: 100% Acetonitrile (0.1% Diethylamine)

Flow Rate: 300 m/min Isocratic

Wavelength: 300 nm

Compound (+)-55: $1^{st}$ eluting isomer, Rt=9.2 min., $^1$H NMR (DMSO-$d_6$) δ 7.78 (s, 1H), 7.43-7.40 (2×m, 2H), 7.10 (brs, 1H), 7.03 (s, 1H), 6.71 (d, 1H, J=8.4 Hz), 6.61 (s, 1H), 6.33 (d, 1H, J=3.1 Hz), 6.40-6.20 (brs, 1H), 4.59 (quintet, 1H, J=4.8 Hz), 2.73-2.55 (m, 4H), 2.32 (s, 3H), 2.18-1.98 (m, 4H), 1.88-1.65 (m, 2H); ESI-MS (m/z, %): 337 (M+1, 60%), 169 (M+ doubly charged, 100%); ESI-HRMS calculated for $C_{20}H_{25}N_4O$ (MH$^+$): 337.2039; observed: 337.2022.

Compound (−)-55: $2^{nd}$ eluting isomer, Rt=14.6 mins, $^1$H NMR (DMSO-$d_6$) δ 7.80 (s, 1H), 7.44-7.40 (2×m, 2H), 7.12 (brs, 1H), 7.04 (s, 1H), 6.73 (d, 1H, J=8.5 Hz), 6.61 (s, 1H), 6.34 (d, 1H, J=3.0 Hz), 4.59 (quintet, 1H, J=4.8 Hz), 2.74-2.56 (m, 4H), 2.33 (s, 3H), 2.18-1.92 (m, 4H), 1.87-1.65 (m, 2H); ESI-MS (m/z, %): 337 (M+1, 80%), 169 (M+ doubly charged, 100%); ESI-HRMS calculated for $C_{20}H_{25}N_4O$ (MH$^+$): 337.2036; observed: 337.2022.

EXAMPLE 17

Preparation of N-(1-(2-(1-methylpyrrolidin-2-yl)ethyl)-1H-indol-5-yl)thiophene-2-carboximidamide (56)

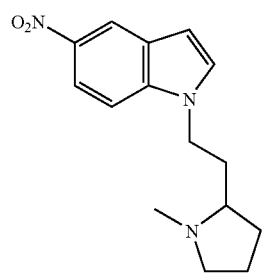

49

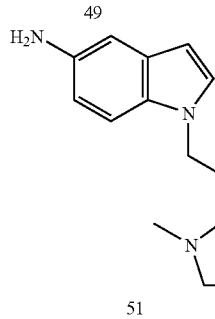

51

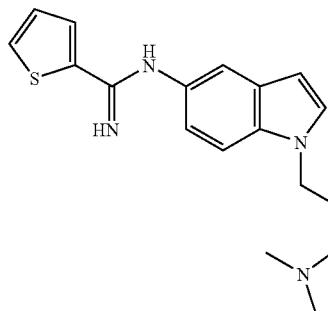

56

N-(1-(2-(1-Methylpyrrolidin-2-yl)ethyl)-1H-indol-5-yl)thiophene-2-carboximidamide (56): compound 49 (103.6 mg, 0.379 mmol) was dissolved in anhydrous ethanol (5 mL) in a dry argon purged flask. Palladium, 10 wt % on activated carbon (40.3 mg, 0.0379 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of (2M NH$_3$ in methanol:CH$_2$Cl$_2$, 1:9) shows complete conversion to 51, which is utilized without isolation. The mixture is filtered through a pad of celite to remove insolubles, the pad washed with anhydrous ethanol (5 mL) and the ethanolic solution of the amine 51 is charged to a small, argon purged flask fitted with a magnetic stir bar. Thiophene-2-carboximidothioic acid methyl ester hydroiodide (161.2 mg, 0.565 mmol) is added to the flask and the reaction was stirred under argon at ambient temperature for 90 hours, at which time the solvent was evaporated and the residue was partitioned between H$_2$O and ethyl acetate and 1M sodium hydroxide solution added to adjust pH to 8-9. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (2M NH$_3$ in methanol:CH$_2$Cl$_2$, 2.5:97.5 to 5:95) to yield pale yellow oil 56 (30 mg, 23.5%); $^1$H NMR (DMSO-d$_6$) δ 7.71 (d, 1H, J=3.7 Hz), 7.60-7.55 (m, 1H), 7.37 (d, 1H, J=8.7 Hz), 7.32 (d, 1H, J=3.0 Hz), 7.10-7.07 (m, 1H), 6.98 (s, 1H), 6.70 (d, 1H, J=8.5 Hz), 6.32 (d, 1H, J=3.0 Hz), 6.24 (brs, 2H), 4.14 (t, 2H, J=7.5 Hz), 2.96-2.90 (m, 1H), 2.19 (s, 3H), 2.11-1.95 (m, 3H), 1.93-1.75 (m, 1H), 1.71-1.55 (m, 3H), 1.48-1.40 (m, 1H); ESI-MS (m/z, %): 353 (M+1, 80%).

EXAMPLE 18

Preparation of (+)-57 and (−)-57

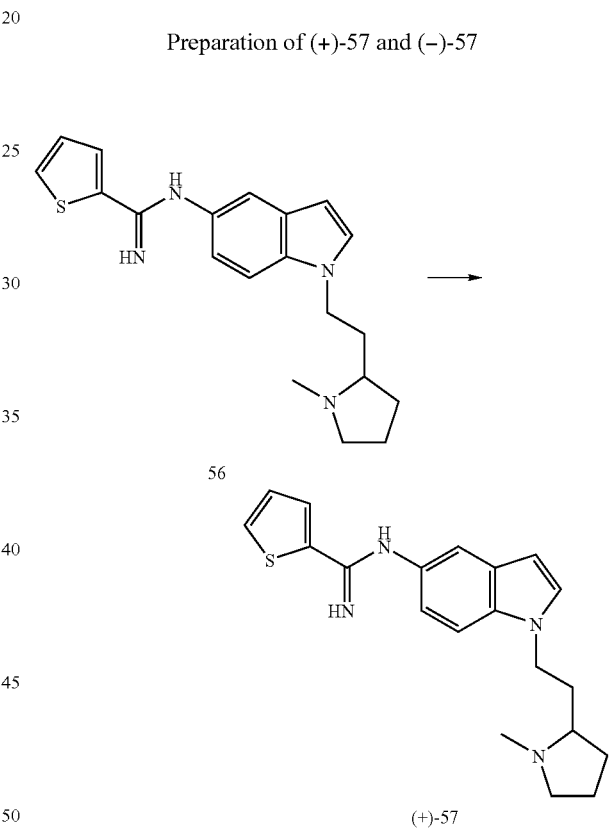

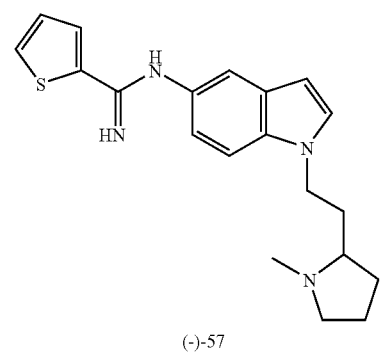

(−)-57

Preparation of compounds (+)-57 and (−)-57: Separation of enantiomers was achieved by chiral HPLC.

Column: Chiracel OD-H 20×250 mm

Eluent: 8% Ethanol/92% Hexane (0.1% Diethylamine)

Flow Rate: 5.6 mL/min Isocratic

Wavelength: 230 nm (+)-57: $1^{st}$ eluting isomer, Rt=28.6 mins, $^1$H NMR (DMSO-$d_6$) δ 7.72 (d, 1H, J=3.2 Hz), 7.59 (d, 1H, J=4.6 Hz), 7.38 (d, 1H, J=8.6 Hz), 7.32 (d, 1H, J=3.0 Hz), 7.11-7.08 (m, 1H), 6.99 (s, 1H), 6.71 (dd, 1H, J=8.4, 1.3 Hz), 6.32 (d, 1H, J=3.0 Hz), 6.40-6.20 (brs, 2H), 4.14 (t, 2H, J=7.4 Hz), 2.99-2.90 (m, 1H), 2.21 (s, 3H), 2.14-2.01 (m, 3H), 1.96-1.85 (m, 1H), 1.72-1.58 (m, 3H), 1.53-1.41 (m, 1H); ESI-MS (m/z, %): 353 (M+1, 50%), 177 (M+ doubly charged, 100%); ESI-HRMS calculated for $C_{20}H_{25}N_4S$ (MH$^+$): 353.1807; observed: 353.1794.

(−)-57: $2^{nd}$ eluting isomer, Rt=30.3 mins, $^1$H NMR (DMSO-$d_6$) δ 7.73 (d, 1H, J=3.4 Hz), 7.60 (d, 1H, J=5.2 Hz), 7.39 (d, 1H, J=8.6 Hz), 7.33 (d, 1H, J=3.0 Hz), 7.12-7.09 (m, 1H), 7.01 (s, 1H), 6.72 (m, 1H), 6.33 (d, 1H, J=3.0 Hz), 6.45-6.20 (brs, 2H), 4.15 (t, 2H, J=7.4 Hz), 3.02-2.92 (m, 1H), 2.23 (s, 3H), 2.17-2.03 (m, 3H), 1.98-1.86 (m, 1H), 1.74-1.60 (m, 3H), 1.54-1.42 (m, 1H); ESI-MS (m/z, %): 353 (M+1, 50%), 177 (M+ doubly charged, 100%); ESI-HRMS calculated for $C_{20}H_{25}N_4S$ (MH$^+$): 353.1805; observed: 353.1794.

EXAMPLE 19

Preparation of N-(1-(1-methylazepan-4-yl)-1H-indol-5-yl)thiophene-2-carboximidamide (58)

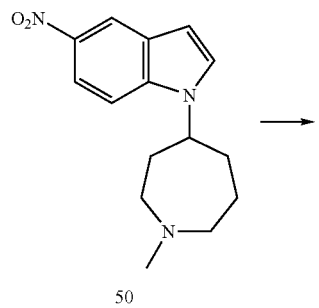

50

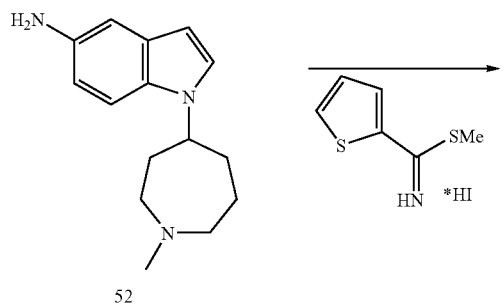

52

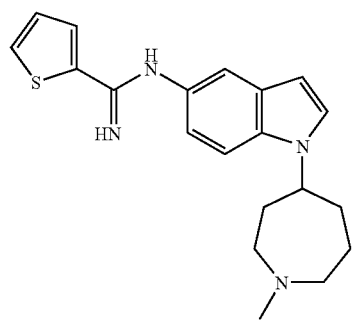

58

N-(1-(1-Methylazepan-4-yl)-1H-indol-5-yl)thiophene-2-carboximidamide (58): Compound 50 (103.6 mg, 0.379 mmol) was dissolved in anhydrous ethanol (5 mL) in a dry argon purged flask. Palladium, 10 wt % on activated carbon (40.3 mg, 0.0379 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of 2M $NH_3$ in methanol:$CH_2Cl_2$, 5:95 shows complete conversion to 52, which is utilized without isolation. The mixture is filtered through a pad of celite to remove insolubles, the pad washed with anhydrous ethanol (5 mL) and the ethanolic solution of the amine 52 is charged to a small, argon purged flask fitted with a magnetic stirbar. Thiophene-2-carboximidothioic acid methyl ester hydroiodide (216.2 mg, 0.758 mmol) is added to the flask and the reaction was stirred under argon at ambient temperature for 96 hours, at which time the solvent was evaporated and the residue partitioned between $H_2O$ and ethyl acetate and 1M sodium hydroxide solution added to adjust pH to 8-9. The mixture was transferred to a separatory funnel and the organic layer collected. The aqueous layer was further extracted with ethyl acetate and the combined organic layers were washed with brine, dried over magnesium sulphate, filtered, concentrated and the crude purified via chromatography on silica gel (2M $NH_3$ in methanol:$CH_2Cl_2$, 3.25:96.75 to 5:95) to afford pale yellow-off white residue 58 (70 mg, 52.4%); $^1$H NMR (DMSO-$d_6$) δ 7.71 (d, 1H, J=2.8 Hz), 7.58 (d, 1H, J=4.4 Hz), 7.43-7.39 (2×m, 2H), 7.10-7.07 (m, 1H), 6.97 (d, 1H, J=1.1 Hz), 6.69-6.66 (m, 1H), 6.33 (d, 1H, J=3.0 Hz), 6.25 (brs, 2H), 4.58 (m, 1H), 2.73-2.55 (m, 4H), 2.31 (s, 3H), 2.15-1.94 (m, 4H), 1.84-1.65 (m, 3H); ESI-MS (m/z, %): 353 (M+1, 100%).

EXAMPLE 20

Preparation of 1-(1-(2-(1-methylpyrrolidin-2-yl)ethyl)-1H-indol-5-yl)-3-nitroguanidine (59)

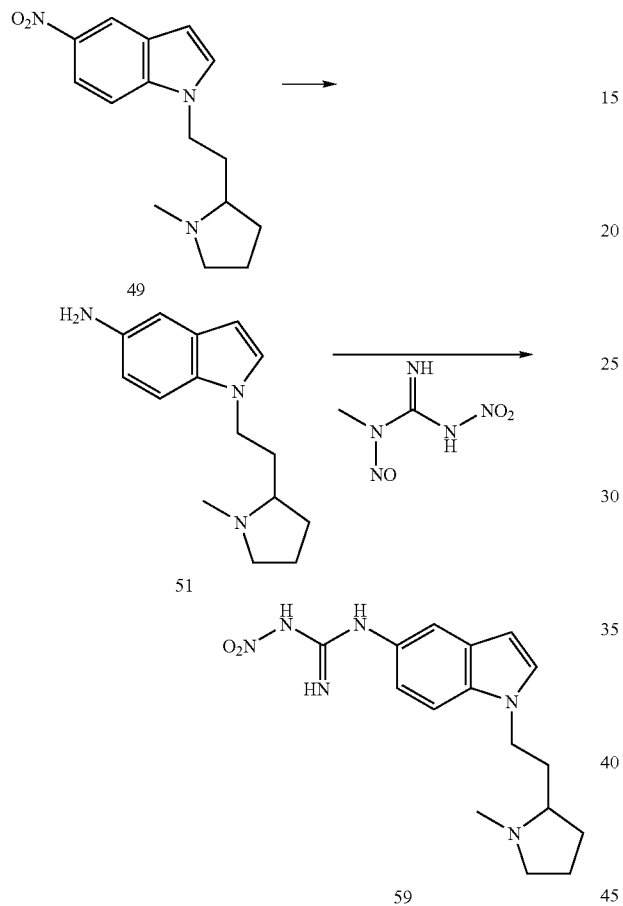

1-(1-(2-(1-Methylpyrrolidin-2-yl)ethyl)-1H-indol-5-yl)-3-nitroguanidine (59): Compound 49 (200 mg, 0.732 mmol) was dissolved in anhydrous ethanol (7 mL) in a dry argon purged flask. Palladium, 10 wt % on activated carbon (77.9 mg, 0.0732 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of 2M $NH_3$ in methanol:$CH_2Cl_2$, 5:95 shows complete conversion to 51, which is utilized without isolation. The mixture is filtered through a pad of celite to remove insolubles, the pad washed with anhydrous ethanol (7 mL) and the ethanolic solution of the amine 51 is charged to a small, argon purged flask fitted with a magnetic stir bar and condenser. $H_2O$ (7 mL) and 1-methyl-3-nitro-1-nitrosoguanidine (118 mg, 0.805 mmol; McKay, A. F., *J. Am. Chem. Soc.* 71, 1968-1970, 1949) is added to the flask and the reaction heated to reflux for 2 hours then cooled to room temperature and stirred under Ar at ambient temperature for 7 days, at which time the ethanol was evaporated and the red gum that formed partitioned between $H_2O$ and ethyl acetate The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (methanol:$CH_2Cl_2$, 1:4) to yield after trituration with diethyl ether, a beige solid 59 (52 mg, 21.5%); $^1$H NMR (DMSO-$d_6$) δ 9.69 (brs, 1H), 8.00 (brs, 2H), 7.50-7.44 (2×m, 3H), 7.01 (dd, 1H, J=9.4, 1.9 Hz), 6.46 (d, 1H, J=3.0 Hz), 4.19 (t, 2H, J=7.4 Hz), 2.96-2.90 (m, 1H), 2.18 (s, 3H), 2.11-1.98 (m, 3H), 1.93-1.81 (m, 1H), 1.71-1.59 (m, 3H), 1.50-1.37 (m, 1H); ESI-MS (m/z, %): 331 (M+1, 100%); ESI-HRMS calculated for $C_{16}H_{23}N_6O_2$ (MH$^+$): 331.1890; observed: 331.1877.

EXAMPLE 21

Preparation of N-(1-(2-(1-methylpiperidin-2-yl)ethyl)-1H-indol-5-yl)thiophene-2-carboximidamide (62)

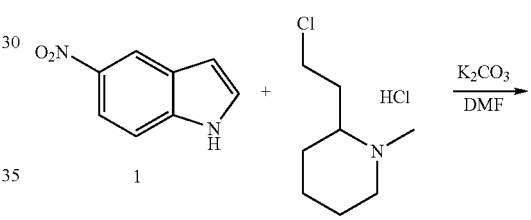

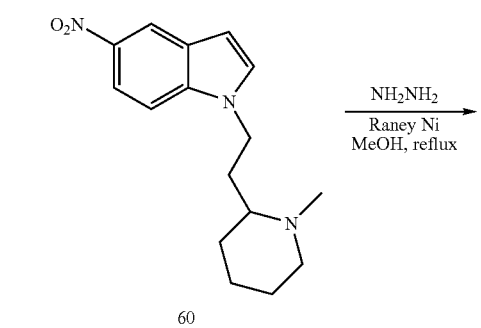

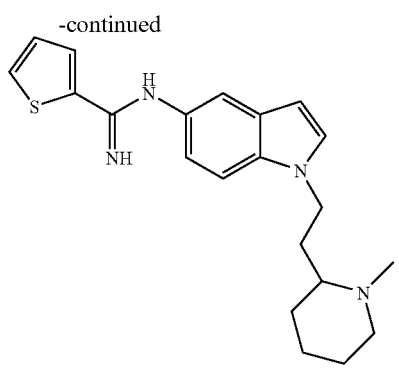

1-(2-(1-Methylpiperidin-2-yl)ethyl)-5-nitro-1H-indole (60): A suspension of compound 1 (400 mg, 2.50 mmol), 2-(2-chloroethyl)-1-methylpiperidine hydrochloride (537 mg, 2.71 mmol) and potassium carbonate (1.0 g, 7.41 mmol) in DMF (7.5 mL) was heated at 60° C. overnight. After cooling, the mixture was poured into $H_2O$ (50 mL) then extracted with $CH_2Cl_2$ (100 mL). The organic layer was separated, washed with brine and concentrated to give a yellow brown solid which was subjected to flash chromatography on silica gel (2M $NH_3$ in MeOH:$CH_2Cl_2$, 5:95) to give compound 60 (450 mg, 62.5%) as a yellow oil. $^1H$ NMR (DMSO-$d_6$) δ 8.57 (d, J=2.2 Hz, 1H), 8.03 (dd, J=2.4, 9.0 Hz, 1H), 7.70 (m, 2H), 6.75 (d, J=3.1 Hz, 1H), 4.28 (t, 2H, J=7.3 Hz), 2.77-2.73 (m, 1H), 2.14 (s, 3H), 1.92-1.84 (m, 4H), 1.67-1.35 (m, 6H); ESI-MS (m/z, %): 288 (M+1, 100%).

1-(2-(1-Methylpiperidin-2-yl)ethyl)-1H-indol-5-amine (61): A solution of compound 60 (400 mg, 1.4 mmol) in methanol (10 mL) was added to Raney Nickel (slurry in $H_2O$, 50 mg) in a round bottom flask. The suspension was treated with hydrazine hydrate (435 µL, 14.0 mmol) and heated at reflux for 10 minutes then filtered through a pad of celite. The celite pad washed with methanol (10 mL). The filtrate was concentrated to give a dark brown residue which was subjected to flash silica gel chromatography (2M $NH_3$ in MeOH: $CH_2Cl_2$, 5:95) to give compound 61 (260 mg, 72.2%) as a viscous oil. $^1H$ NMR (DMSO-$d_6$) δ 7.14 (d, J=3.0 Hz, 1H), 7.09 (d, J=8.4 Hz, 1H), 6.67 (d, J=1.8 Hz, 1H), 6.52 (dd, J=1.8, 8.7 Hz, 1H), 6.09 (d, J=1.8 Hz, 1H), 4.45 (brs, 2H), 4.04 (t, J=7.2 Hz, 2H), 2.76-2.72 (m, 1H), 2.15 (s, 3H), 2.02-1.17 (m, 10H); ESI-MS (m/z, %): 258 (M+1).

N-(1-(2-(1-Methylpiperidin-2-yl)ethyl)-1H-indol-5-yl)thiophene-2-carboximidamide (62): A solution of compound 61 (235 mg, 0.91 mmol) in EtOH (10 mL) was treated with methyl thiophene-2-carbimidothioate hydroiodide (520 mg, 1.83 mmol) and stirred overnight at room temperature. Argon was bubbled through the mixture for 20 minutes then it was concentrated to give brownish oil. This residue was partitioned between $CH_2Cl_2$ (50 mL) with 10% MeOH and saturated sodium bicarbonate (20 mL). The aqueous layer was extracted with an additional $CH_2Cl_2$ (50 mL). The combined organic layers were washed with brine, dried over sodium sulfate and concentrated to give a brown residue which was subjected to flash chromatography on silica gel (MeOH: $CH_2Cl_2$, 5:95 to 2M $NH_3$ in MeOH:$CH_2Cl_2$, 1:9) to give compound 62 (154 mg, 46.1%) as a yellow solid. $^1H$ NMR (DMSO-$d_6$) δ 7.71 (d, J=2.9 Hz, 1H), 7.58 (d, J=5.1 Hz, 1H), 7.37-7.30 (m, 2H), 7.10-7.08 (m, 1H), 6.98 (s, 1H), 6.70 (dd, J=1.5, 6.9 Hz, 1H), 6.31 (d, J=3.0 Hz, 1H), 6.25 (brs, 2H), 4.15 (t, J=7.5 Hz, 2H), 2.79-2.75 (m, 1H), 2.19 (s, 3H), 2.05-1.15 (m, 10H); ESI-MS (m/z, %): 367 (M+1,50), 184 (M+2, 100); ESI-HRMS calculated for $C_{21}H_{27}N_4S$ (MH$^+$): 367.1966, observed: 367.1937.

This compound 62 (121 mg, 0.33 mmol) was converted to the dihydrochloride salt by dissolving in 10% MeOH/$CH_2Cl_2$ (10 mL) solution, cooled to 0° C. and treated with 1 mL of a 1M HCl in $Et_2O$ solution. The solution was stirred for 20 minutes then concentrated to give yellow-brown oil. A yellow solid was obtained after drying under high vacuum overnight. Yield: 120 mg. HPLC analysis indicated that product is >99% pure.

EXAMPLE 22

Preparation of N-(1-(Quinuclidin-3-yl)-1H-indol-5-yl)thiophene-2-carboximidamide (71)

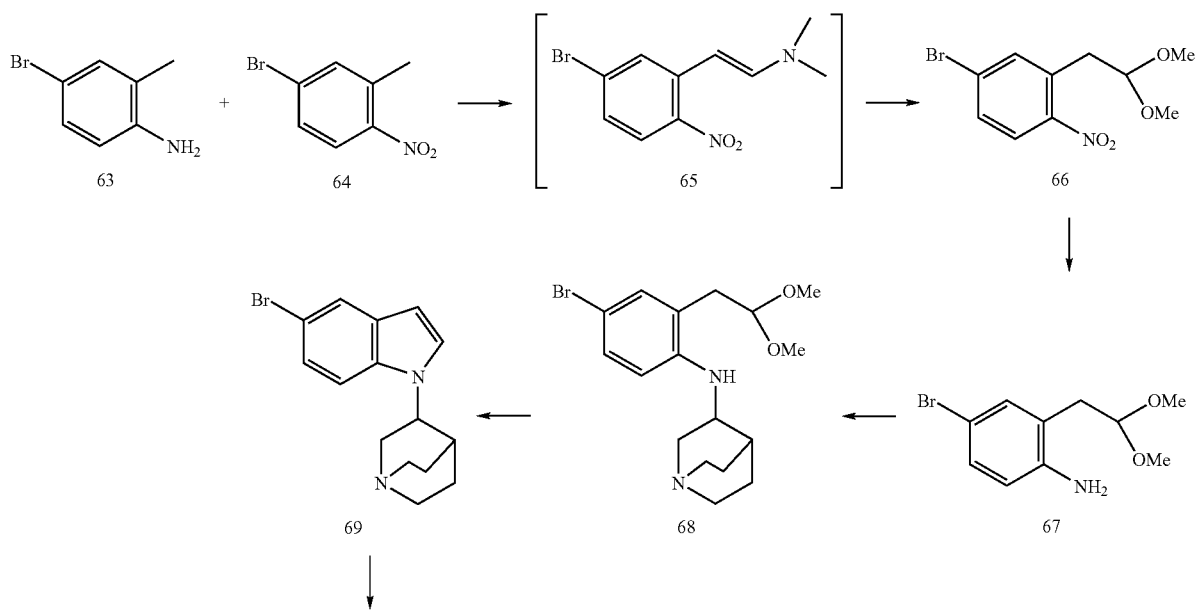

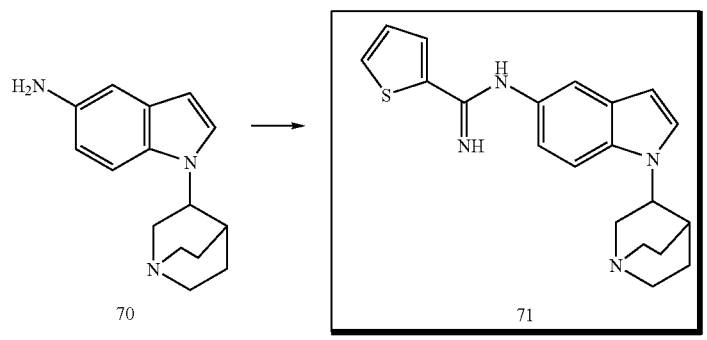

4-Bromo-2-(2,2-dimethoxyethyl)-1-nitrobenzene (66): Compound 64 (500 mg, 2.315 mmol) (Olsen et al., U.S. Pat. No. 4,287,201) was dissolved in anhydrous dimethylformamide (10 mL) in a dry argon purged flask fitted with a magnetic stir bar and condenser. Dimethylformamide dimethylacetal (828 mg, 6.945 mmol) and pyrrolidine (165 mg, 2.315 mmol) are added to the flask and mixture heated 110° C. for 90 minutes. After cooling to room temperature, the reaction mixture was diluted with diethyl ether and $H_2O$, transferred to a separatory funnel and the organic layer collected. The organic layer washed with $H_2O$ (twice) and the combined aqueous layers back extracted with diethyl ether (twice). The combined organic layers were dried over anhydrous sodium sulphate, filtered, concentrated to yield a dark red oil, 65, which is utilized without purification. The crude enamine is dissolved in anhydrous methanol, treated with chlorotrimethylsilane (3 equivalents) and refluxed for 20 hours. The reaction was concentrated under reduced pressure and the residue was partitioned between a saturated sodium bicarbonate solution and ethyl acetate. The mixture was transferred to a separatory funnel and the organic layer collected. The aqueous layer was further extracted with ethyl acetate and the combined organic layers were washed with brine, dried over sodium sulphate, filtered, concentrated and the residue purified via chromatography on silica gel (EtOAc:Hexanes, 1:9) to yield a pale brown solid, 66 (330 mg, 49.2%). $^1$H NMR ($CDCl_3$) δ 3.20 (d, 2H, J=5.2 Hz), 3.35 (s, 6H), 4.55 (t, 1H, J=5.2 Hz), 7.51 (dd, 1H, J=8.5, 2.1 Hz), 7.58 (d, 1H, J=1.9 Hz), 7.78 (d, 1H, J=8.6 Hz); ESI-MS (m/z, %): 312/314 (M+Na$^+$, 90%), 198/200 (100%); ESI-HRMS calculated for $C_{10}H_{12}NO_4NaBr$ (M+Na$^+$), calculated: 311.9841; observed: 311.9826.

4-Bromo-2-(2,2-dimethoxyethyl)aniline (67): Compound 66 (75 mg, 0.259 mmol) was dissolved in anhydrous ethanol (10 mL) in a dry argon purged flask fitted with a magnetic stir bar and condenser. Sodium dithionite (158.8 mg, 0.776 mmol) and sodium bicarbonate (130.6 mg, 1.554 mmol) are added to the flask and mixture heated to reflux for 24 hours. After cooling to room temperature, the reaction was quenched by the addition of $H_2O$ (10 mL) and the ethanol removed under reduced pressure. The resulting aqueous layer was transferred to a separatory funnel and extracted with ethyl acetate (three times). The combined organic layers were washed with brine, dried over sodium sulphate, filtered, concentrated and the residue purified via chromatography on silica gel (methanol:$CH_2Cl_2$, 2:98) to yield a brown oil, 67 (32 mg, 47.5%). $^1$H NMR ($CDCl_3$) δ 2.83 (d, 2H, J=5.3 Hz), 3.38 (s, 6H), 4.48 (t, 1H, J=5.3 Hz), 6.61 (d, 1H, J=8.2 Hz), 7.13 (d, 1H, J=2.2 Hz), 7.15-7.17 (m, 1H); ESI-MS (m/z, %): 198/200 (M$^+$–2MeO, 100%).

N-(4-Bromo-2-(2,2-dimethoxyethyl)phenyl)-quinuclidin-3-amine (68): Compound 67 (160 mg, 0.615 mmol) and quinuclidin-3-one (115.5 mg, 0923 mmol) were stirred in acetic acid (5 mL) under argon in the presence of anhydrous sodium sulfate (874 mg, 6.150 mmol) at room temperature for 30 minutes. Sodium triacetoxyborohydride (391 mg, 1.845 mmol) was then added and the mixture stirred for 24 hours at room temperature. Thin layer chromatography in a solvent system of 2M $NH_3$ in methanol:$CH_2Cl_2$, 5:95 shows incomplete consumption of 67, thus a second portion of quinuclidin-3-one (38.4 mg, 0.307 mmol) is added and the mixture stirred for a further 20 hours. After dilution with a mixture of 8:1 ethyl acetate:hexanes, the reaction is quenched with saturated sodium bicarbonate. The mixture was transferred to a separatory funnel and the organic layer separated. The organic layer was dried over sodium sulfate and concentrated under reduced pressure and the residue purified via chromatography on silica gel (2M $NH_3$ in methanol:$CH_2Cl_2$, 2.5: 97.5 to 5:95) to yield a colorless residue, 68 (137 mg, 60.3%). $^1$H NMR (DMSO-$d_6$) δ 1.25-1.39 (m, 1H), 1.53-1.80 (2×m, 3H), 1.86-1.94 (m, 1H), 2.64-2.77 (m, 4H), 2.80 (d, 2H, J=5.2 Hz), 3.14-3.24 (m, 1H), 3.27 and 3.29 (2×s, 6H), 3.34-3.40 (m, 1H), 4.54 (t, 1H, J=5.2 Hz), 5.04 (d, 1H, J=5.8 Hz), 6.43 (d, 1H, J=8.3 Hz), 7.13-7.15 (m, 1H), 7.17 (s, 1H); ESI-MS (m/z, %): 369/371 (MH$^+$, 100%).

3-(5-Bromo-1H-indol-1-yl)quinuclidine (69): Compound 68 (137 mg, 0.371 mmol) was dissolved in anhydrous 1M HCl/methanol (10 mL) in a dry argon purged flask, refluxed for 1 hour, concentrated under reduced pressure to yield HCl salt of 69 as an off-white solid (129 mg, 100%). $^1$H NMR (MeOD) δ 1.89-2.00 (m, 2H), 2.10-2.20 (m, 1H), 2.25-2.34 (m, 1H), 2.39-2.44 (m, 1H), 3.43-3.53 (m, 3H), 3.64-3.77 (m, 1H), 3.86-3.93 (m, 1H), 4.00-4.09 (m, 1H), 5.17-5.22 (m, 1H), 6.58 (d, 1H, J=3.4 Hz), 7.31 (dd, 1H, J=8.5, 1.8 Hz), 7.42 (d, 1H, J=8.8 Hz), 7.70 (d, 1H, J=3.5 Hz), 7.73 (d, 1H, J=1.8 Hz); ESI-MS (m/z, %): 305/307 (MH$^+$, 100%).

1-(Quinuclidin-3-yl)-1H-indol-5-amine (70): Compound 69 (95 mg, 0.311 mmol), Tris(dibenzylideneacetone)dipalladium (0) (28.5 mg, 0.031 mmol) and anhydrous tetrahydrofuran (10 mL) were charged to a dry argon purged flask fitted with magnetic stir bar and condenser. A solution of tri-tert-butylphosphine (10 wt % in hexane, 125.9 mg, 0.062 mmol) is added followed by dropwise addition of a 1M tetrahydrofuran solution of Lithium bis(trimethylsilyl)amide (0.993 ml, 0.993 mmol) and mixture refluxed for a period of 45 minutes. The mixture was cooled to room temperature then to 0° C., quenched with 1M HCl (10 mL) and stirred for 15 minutes. The solution was diluted with ethyl acetate and conc. $NH_4OH$ added to adjust pH to 9. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (2M NH$_3$ in methanol:CH$_2$Cl$_2$, 5:95) to yield a yellow residue 70 (60 mg, 79.9%). $^1$H NMR (DMSO-d$_6$) δ 1.22-1.47 (m, 2H), 1.57-1.70 (m, 1H), 1.73-1.90 (2×m, 2H), 2.66-2.84 (2×m, 3H), 2.97-3.04 (m, 1H), 3.09-3.20 (m, 2H), 4.41-4.54 (2×m, 3H), 6.17 (d, 1H, J=3.1 Hz), 6.51 (dd, 1H, J=8.8, 2.0 Hz), 6.68 (d, 1H, J=2.0 Hz), 7.12 (d, 1H, J=8.7 Hz), 7.50 (d, 1H, J=3.2 Hz); ESI-MS (m/z, %): 242 (MH$^+$, 100%).

N-(1-(Quinuclidin-3-yl)-1H-indol-5-yl)thiophene-2-carboximidamide (71): Compound 70 (60 mg, 0.249 mmol) is charged to a small, argon purged flask fitted with a magnetic stir bar. Anhydrous ethanol (5 mL) and thiophene-2-carboximidothioic acid methyl ester hydroiodide (124 mg, 0.435 mmol) are added to the flask and the reaction was stirred under argon at ambient temperature for 18 hours, at which time the solvent was evaporated and the residue was partitioned between H$_2$O and ethyl acetate and 1M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (2M NH$_3$ in methanol:CH$_2$Cl$_2$, 5:95 to 7.5:92.5) then a second time on silica gel (methanol:CH$_2$Cl$_2$, 1:9 to 2 M NH$_3$ in methanol:CH$_2$Cl$_2$, 1:9) to yield a yellow solid, 71 (30 mg, 34.4%). $^1$H NMR (DMSO-d$_6$) δ 1.27-1.53 (2×m, 2H), 1.60-1.69 (m, 1H), 1.79-1.96 (2×m, 2H), 2.69-2.87 (m, 3H), 3.03-3.13 (m, 1H), 3.19-3.30 (m, 1H), 3.34-3.44 (m, 1H), 4.57-4.68 (m, 1H), 6.28 (brs, 2H), 6.39 (d, 1H, J=3.1 Hz), 6.70 (dd, 1H, J=8.4, 1.6 Hz), 7.00 (d, 1H, J=1.2 Hz), 7.09 (dd, 1H, J=4.9, 3.9 Hz), 7.39 (d, 1H, J=8.6 Hz), 7.59 (d, 1H, J=5.1 Hz), 7.67 (d, 1H, J=3.2 Hz), 7.71 (d, 1H, J=3.5 Hz); ESI-MS (m/z, %): 351 (M+1, 60%), 176 (M++doubly charged, 100%); ESI-HRMS calculated for C$_{20}$H$_{23}$N$_4$S (MH$^+$): 351.1637, observed: 351.1639.

EXAMPLE 23

Preparation of N-(1-(pyridin-3-yl)-1H-indol-5-yl)thiophene-2-carboximidamide (74)

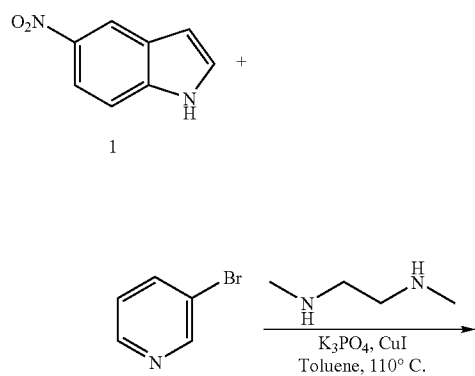

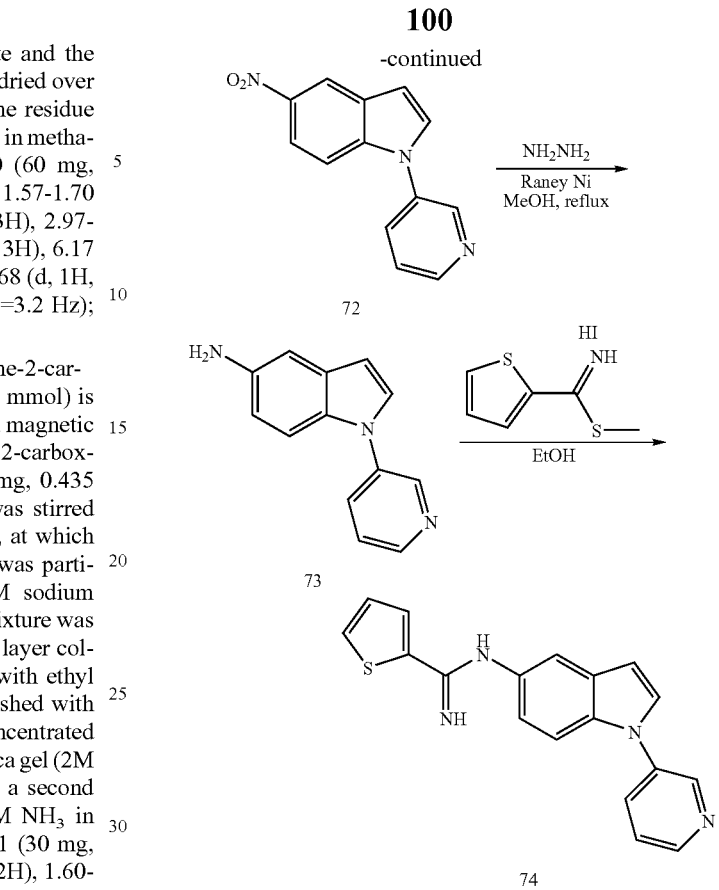

5-Nitro-1-(pyridin-3-yl)-1H-indole (72): A suspension of compound 1 (195 mg, 1.20 mmol), 3-Bromopyridine (98 μL, 1.00 mmol), copper iodide (9.5 mg, 0.05 mmol) and K$_3$PO$_4$ (400 mg, 2.10 mmol) in toluene (6 mL) was treated with N,N'-dimethylethylenediamine (21.5 μL, 0.20 mmol) then heated at 110° C. overnight. A TLC analysis indicated mostly starting indole and 3-bromopyridine and a new more polar spot. The reaction mixture was treated with additional copper iodide ((9.5 mg, 0.05 mmol) and N,N'-dimethylethylenediamine (21.5 μL, 0.20 mmol). The mixture was heated at 110° C. for 7 hours. After cooling, the mixture was poured into H$_2$O (20 mL) then extracted with CH$_2$Cl$_2$ (100 mL). The organic layer was separated, washed with brine and concentrated to give a yellow solid which was subjected to flash chromatography on silica gel (CH$_2$Cl$_2$ to MeOH:CH$_2$Cl$_2$, 5:95) to give compound 72 (195 mg, 67.9%) as a yellow solid. $^1$H NMR (DMSO-d$_6$) δ 8.90 (d, J=2.4 Hz, 1H), 8.70-8.69 (m, 2H), 8.16-8.07 (m, 2H), 7.99 (d, J=3.2 Hz, 1H), 7.71-7.65 (m, 2H), 7.05 (d, J=3.3 Hz); ESI-MS (m/z, %): 240 (M+1, 100%).

1-(Pyridin-3-yl)-1H-indol-5-amine (73): A solution of compound 72 (350 mg, 1.46 mmol) in methanol (10 mL) was added to Raney Nickel (slurry in H$_2$O, 50 mg) in a round bottom flask. The suspension was heated at reflux for 10 minutes then filtered through a pad of celite. The celite pad washed with methanol (20 mL). The filtrate was concentrated and the residue was subjected to silica gel chromatography (CH$_2$Cl$_2$ to MeOH:CH$_2$Cl$_2$, 5:95) to give compound 73 (300 mg, 98.4%) as a viscous oil. $^1$H NMR (DMSO-d$_6$) δ 8.81 (d, J=2.6 Hz, 1H), 8.53-8.51 (m, 1H), 8.02-7.99 (m, 1H), 7.56-7.54 (m, 2H), 7.32 (d, J=8.7 Hz, 1H), 6.77 (d, J=1.9 Hz, 1H), 6.59 (dd, J=2.1, 6.7 Hz, 1H), 6.47 (d, J=3.4 Hz, 1H), 4.72 (brs, 2H); ESI-MS (m/z, %): 210 (M+1, 100%).

N-(1-(Pyridin-3-yl)-1H-indol-5-yl)thiophene-2-carboximidamide (74): A solution of compound 73 (275 mg, 1.32 mmol) in 15 mL EtOH was treated with methyl thiophene-2-carbimidothioate hydroiodide (750 mg, 2.63 mmol) and stirred overnight at room temperature. Argon was bubbled through the mixture for 20 minutes then it was diluted with $CH_2Cl_2$ (50 mL) and treated with saturated sodium bicarbonate (20 mL). The organic layer was separated and the aqueous layer was extracted with an additional 50 mL $CH_2Cl_2$. The combined organic layers were dried over sodium sulfate and concentrated to give a yellow solid which was subjected to flash chromatography on silica gel using 5% MeOH/$CH_2Cl_2$ to 5% 2M $NH_3$ in MeOH/$CH_2Cl_2$ to give an off-white residue, compound 74 (210 mg, 50%). HPLC analysis indicated that the product is >98% pure. $^1$H NMR (DMSO-$d_6$) δ 8.85 (d, J=2.5 Hz, 1H), 8.58 (d, J=4.0 Hz, 1H), 8.08-8.05 (m, 1H), 7.75-7.53 (m, 5H), 7.12-7.09 (m, 2H), 6.78 (dd, J=1.5, 7.0 Hz, 1H), 6.67 (d, J=3.1 Hz, 1H), 6.35 (brs, 2H); ESI-MS (m/z, %): 319 (M+1, 100%); ESI-HRMS calculated for $C_{18}H_{15}N_4S$ (MH$^+$): 319.1011, observed: 319.1015.

This compound 74 (170 mg, 0.53 mmol) was converted to the dihydrochloride salt by dissolving in 10% MeOH/$CH_2Cl_2$ solution (10 mL), cooled to 0° C. and treated with 1M HCl in $Et_2O$ solution (2 mL). The solution was stirred for 20 minutes then concentrated to give a yellow solid after drying under high vacuum overnight. Yield: 190 mg. HPLC analysis indicated that the product is >98% pure.

EXAMPLE 24

Preparation of N-(1-(6-aminopyridin-3-yl)-1H-indol-5-yl)thiophene-2-carboximidamide (77)

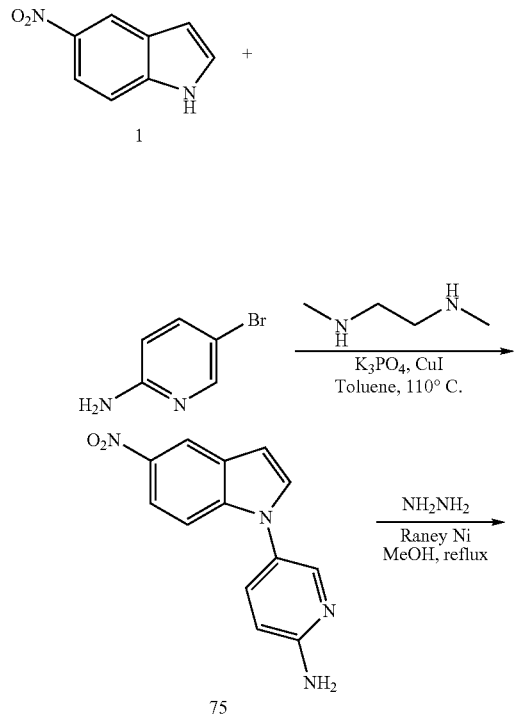

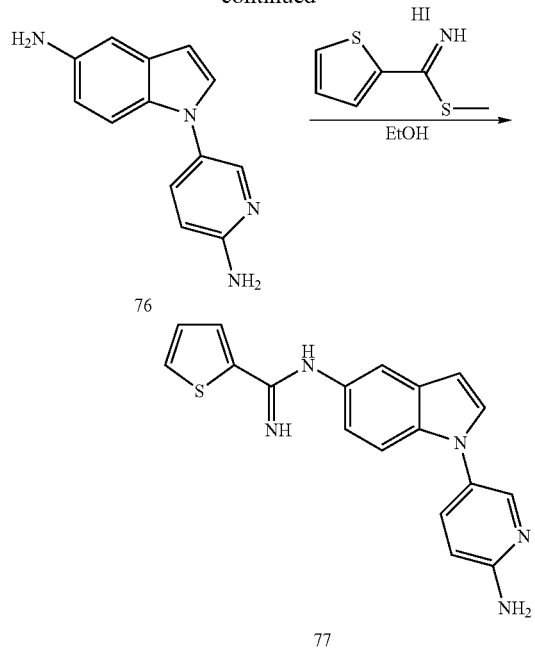

5-(5-Nitro-1H-indol-1-yl)pyridin-2-amine (75): A suspension of compound 1 (195 mg, 1.20 mmol), 5-bromopyridin-2-amine (173 mg, 1.00 mmol), copper iodide (9.5 mg, 0.05 mmol) and $K_3PO_4$ (400 mg, 2.10 mmol) in toluene (6 mL) was treated with N,N'-dimethylethylenediamine (21.5 μL, 0.20 mmol) then heated at 110° C. overnight. A TLC analysis indicated mostly starting indole and 3-bromopyridine and a new more polar spot. The reaction mixture was treated with additional copper iodide ((9.5 mg, 0.05 mmol) and N,N'-dimethylethylenediamine (21.5 μL, 0.20 mmol). The mixture was heated at 110° C. for 7 hours. After cooling, the mixture was poured into $H_2O$ (20 mL) then extracted with $CH_2Cl_2$ (100 mL). The organic layer was separated, washed with brine and concentrated to give a yellow solid which was subjected to flash chromatography on silica gel ($CH_2Cl_2$ to MeOH:$CH_2Cl_2$, 5:95) to give the desired compound 75 (110 mg, 36.1%). $^1$H NMR (DMSO-$d_6$) δ 8.65 (d, J=2.2 Hz, 1H), 8.10 (d, J=2.7 Hz, 1H), 8.05 (dd, J=2.7, 6.9 Hz, 1H), 7.76 (d, J=3.2 Hz, 1H), 7.60 (dd, J=2.9, 6.0 Hz, 1H), 7.47 (d, J=9.2 Hz, 1H), 6.94 (d, J=3.2 Hz, 1H), 6.61 (d, J=8.8 Hz, 1H); ESI-MS (m/z, %): 255 (M+1, 100%).

1-(6-Aminopyridin-3-yl)-1H-indol-5-amine (76): A solution of compound 75 (200 mg, 0.79 mmol) in methanol (10 mL) was added to Raney Nickel (slurry in $H_2O$, 50 mg) in a round bottom flask. The suspension was heated at reflux for 10 minutes then filtered through a pad of celite. The celite pad washed with methanol (20 mL). The filtrate was concentrated and the residue was subjected to silica gel chromatography ($CH_2Cl_2$ to MeOH:$CH_2Cl_2$, 1:9) to give compound 76 (140 mg, 79.1%) as an off-white solid. $^1$H NMR (DMSO-$d_6$) δ 8.01 (d, J=2.7 Hz, 1H), 7.51 (dd, J=2.9, 6.1 Hz, 1H), 7.27 (d, J=3.0 Hz, 1H), 7.04 (d, J=8.6 Hz, 1H), 6.73 (d, J=2.1 Hz, 1H), 6.59 (s, 1H), 6.56 (s, 1H), 6.55 (dd, J=2.1, 6.8 Hz, 1H), 6.33 (d, J=3.0 Hz, 1H), 6.10 (brs, 2H), 4.61 (brs, 2H); ESI-MS (m/z, %): 225 (M+1, 100%).

N-(1-(6-Aminopyridin-3-yl)-1H-indol-5-yl)thiophene-2-carboximidamide (77): A solution of compound 76 (120 mg, 0.53 mmol) in EtOH (5 mL) was treated with methyl thiophene-2-carbimidothioate hydroiodide (183 mg, 0.64 mmol) and stirred overnight at room temperature. Argon was bubbled through the mixture for 20 minutes then the suspension was diluted with $CH_2Cl_2$ (50 mL) and treated with saturated sodium bicarbonate (20 mL). The organic layer was separated and the aqueous layer was extracted with an additional $CH_2Cl_2$ (50 mL). The combined organic layers were dried over sodium sulfate and concentrated to give a yellow solid which was subjected to flash chromatography on silica gel (MeOH:$CH_2Cl_2$, 5:95 to 2M $NH_3$ in MeOH:$CH_2Cl_2$, 5:95) to give compound 77 (86 mg, 48.9%) as a yellow solid. HPLC analysis indicated that the product is >99% pure. $^1$H NMR (DMSO-$d_6$) δ 8.06 (d, J=2.5 Hz, 1H), 7.72 (d, J=3.4 Hz, 1H), 7.60-7.50 (m, 2H), 7.42 (d, J=3.0 Hz, 1H), 7.11-7.06 (m, 2H), 6.71 (d, J=8.9 Hz, 1H), 6.61 (d, J=8.8 Hz, 1H), 6.53 (d, J=3.0, 1H), 6.30 (brs, 2H), 6.16 (brs, 2H); ESI-MS (m/z, %): 334 (M+1, 100%); ESI-HRMS calculated for $C_{18}H_{16}N_5S$ ($MH^+$): 334.1120, observed: 334.1135.

This compound 77 (65 mg, 0.20 mmol) was converted to the dihydrochloride salt by dissolving in 10% MeOH/$CH_2Cl_2$ solution (10 mL), cooled to 0° C. and treated with 1M HCl in $Et_2O$ solution (2 mL). The solution was stirred for 20 minutes then concentrated to give a yellow solid after drying under high vacuum overnight. Yield: 70 mg. HPLC analysis indicated that the product is >99% pure.

EXAMPLE 25

Preparation of N-(1-(1-methylpiperidin-4-yl)-1H-indol-5-yl)thiophene-2-carboximidamide (82)

N-(4-Bromophenyl)-1-methylpiperidin-4-amine (78): 4-bromoaniline (1.0 g, 5.813 mmol) was dissolved in anhydrous dichloroethane (30 mL) in a dry argon purged flask fitted with a magnetic stir bar. 1-methylpiperidin-4-one (671 ul, 5.813 mmol), acetic acid (329 ul, 5.813 mmol) and sodium triacetoxyborohydride (1.848 g, 8.719 mmol) are added to the flask and mixture stirred at ambient temperature for 22 hours then heated to 55° C. for 4 hours. After cooling to room temperature, the mixture was transferred to a separatory funnel and 1M sodium hydroxide solution added to adjust pH to 10. The organic layer was collected and the aqueous layer further extracted with dichloromethane. The combined organic layers were washed with brine, dried over magnesium sulphate, filtered, concentrated and the crude purified via chromatography on silica gel (methanol:$CH_2Cl_2$, 5:95 then 2M $NH_3$ in methanol:$CH_2Cl_2$, 1:9) to yield an off-white solid, 78 (1.0 g, 63.9%). $^1$H NMR ($CDCl_3$) δ 1.40-1.58 (m, 2H), 1.98-2.22 (m, 4H), 2.31 (s, 3H), 2.73-2.89 (m, 2H), 3.15-3.32 (m, 1H), 3.45-3.58 (m, 1H), 6.47 (d, 2H, J=8.8 Hz), 7.23 (d, 2H, J=8.8 Hz); ESI-MS (m/z, %): 269/271 ($MH^+$, 100%).

1-(5-Bromo-2-(1-methylpiperidin-4-ylamino)phenyl)-2-chloroethanone (79): To a stirred solution of boron trichloride (1M solution in $CH_2Cl_2$, 3.34 mL, 3.34 mmol) in anhydrous $CH_2Cl_2$ (5 mL) in a dry argon purged flask cooled in an ice-bath was added dropwise a solution of compound 78 (0.75 g, 2.786 mmol) in anhydrous $CH_2Cl_2$ (5 mL). Chloroacetonitrile (0.351 mL, 5.572 mmol) added dropwise and the mixture heated to reflux for 6 hours. After cooling to room temperature, ice-cold 1M HCl (5 mL) is added slowly and the reaction refluxed for 20 minutes. After cooling, the organic layer was separated and the acidic aqueous layer further extracted with $CH_2Cl_2$ (twice). The combined organic layers were washed with brine, and concentrated to yield the hydrochloride salt of compound 79, as a bright yellow solid (583

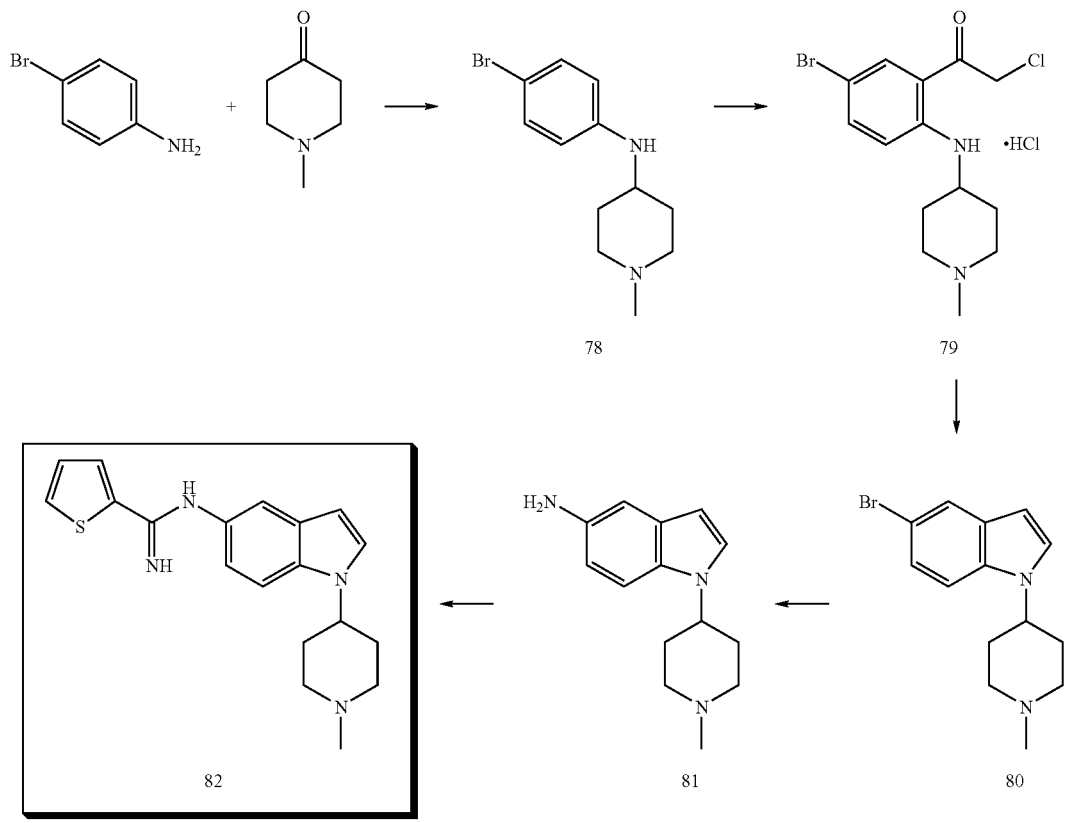

mg, 54.7%). $^1$H NMR (DMSO-$d_6$) δ 1.61-1.74 (m, 2H), 1.90-2.25 (2×m, 3H), 2.75, 2.80 (2×s, 3H), 2.96-3.16 (m, 2H), 3.40-3.53 (m, 1H), 3.66-3.80 (m, 1H), 5.13 (s, 2H), 6.97 (d, 1H, J=9.1 Hz), 7.58 (d, 1H, J=9.1 Hz), 7.97 (s, 1H), 8.57 (d, 1H, J=7.4 Hz), 10.35 (brs, 1H); ESI-MS (m/z, %): 345/347/349 (MH$^+$, 100%).

5-Bromo-1-(1-methylpiperidin-4-yl)-1H-indole (80): To an ice cold solution of compound 79 (583 mg, 1.526 mmol) in 95% ethanol (25 mL) was added 1M sodium hydroxide (1.526 mL, 1.526 mmol) followed by sodium borohydride (28.9 mg, 0.763 mmol) and the mixture stirred under ice cooling for 45 minutes. The reaction was quenched with ice cold H$_2$O (25 mL), diluted with CH$_2$Cl$_2$, transferred to a separatory funnel and the organic layer separated. The aqueous layer was further extracted with CH$_2$Cl$_2$ (twice) and the combined organic layers washed with brine, dried over sodium sulfate and concentrated to residue. The residue was taken up in anhydrous dioxane (25 mL) and heated to reflux for 3 hours. After cooling to room temperature the reaction was treated with ice-cold 2N potassium carbonate, diluted with CH$_2$Cl$_2$, transferred to a separatory funnel and the organic layer separated. The aqueous layer was further extracted with CH$_2$Cl$_2$ (twice) and the combined organic layers washed with water (twice), brine, dried over sodium sulfate concentrated under reduced pressure and the residue purified via chromatography on silica gel (2M NH$_3$ in methanol:CH$_2$Cl$_2$ 2.5:97.5 to 5:95) to yield an off white solid, 80 (265 mg, 59.3%). $^1$H NMR (DMSO-$d_6$) δ 1.83-1.93 (m, 2H), 1.95-2.04 (m, 2H), 2.13 (dt, 2H, J=11.5, 2.2 Hz), 2.23 (s, 3H), 2.89 (d, 2H, J=11.4 Hz), 4.28-4.35 (m, 1H), 6.44 (d, 1H, J=3.1 Hz), 7.22 (dd, 1H, J=8.7, 1.8 Hz), 7.51-7.56 (m, 2H), 7.72 (d, 1H, J=1.9 Hz); ESI-MS (m/z, %): 293/295 (MH$^+$, 100%).

1-(1-Methylpiperidin-4-yl)-1H-indol-5-amine (81): Compound 80 (265 mg, 0.904 mmol), Tris(dibenzylideneacetone) dipalladium (0) (82.7 mg, 0.0904 mmol) and anhydrous tetrahydrofuran (20 mL) were charged to a dry argon purged flask fitted with magnetic stir bar and condenser. A solution of tri-tert-butylphosphine (10 wt % in hexane, 365.7 mg, 538 ul, 0.1808 mmol) is added followed by dropwise addition of a 1 M tetrahydrofuran solution of lithium bis(trimethylsilyl)amide (2.71 ml, 2.710 mmol) and mixture refluxed for a period of 45 minutes. The mixture was cooled to room temperature then to 0° C., quenched with 1M HCl (10 mL) and stirred for 10 minutes. The solution was diluted with ethyl acetate and 5M NH$_4$OH added to adjust pH to 9. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (EtOAc:methanol:Et$_3$N, 8:1:1) to yield a pale yellow solid 81 (102 mg, 49.2%). $^1$H NMR (DMSO-$d_6$) δ: 1.80-1.98 (m, 4H), 2.11 (dt, 2H, J=11.2, 3.5 Hz), 2.23 (s, 3H), 2.88 (d, 2H, J=11.6 Hz), 4.08-4.19 (m, 1H), 4.46 (brs, 2H), 6.13 (d, 1H, J=3.0 Hz), 6.51 (dd, 1H, J=8.8, 2.1 Hz), 6.67 (d, 1H, J=2.0 Hz), 7.18 (d, 1H, J=8.6 Hz), 7.24 (d, 1H, J=3.1 Hz); EI-MS (m/z, %): 229 (M$^+$, 100%).

N-(1-(1-Methylpiperidin-4-yl)-1H-indol-5-yl)thiophene-2-carboximidamide (82): Compound 81 (100 mg, 0.436 mmol) is charged to a small, argon purged flask fitted with a magnetic stir bar. Anhydrous ethanol (7 mL) and thiophene-2-carboximidothioic acid methyl ester hydroiodide (217.6 mg, 0.763 mmol) are added to the flask and the reaction was stirred under argon at ambient temperature for 23 hours, at which time the solvent was evaporated and the residue was partitioned between H$_2$O and ethyl acetate and 1M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (2M NH$_3$ in methanol:CH$_2$Cl$_2$, 5:95 to 7.5:92.5) to yield a yellow solid, 82 (83 mg, 56.2%). $^1$H NMR (DMSO-$d_6$) δ 1.85-2.05 (m, 4H), 2.10-2.19 (m, 2H), 2.24 (s, 3H), 2.90 (d, 2H, J=11.4 Hz), 4.20-4.32 (m, 1H), 6.25 (br s, 2H), 6.35 (d, 1H, J=3.0 Hz), 6.69 (dd, 1H, J=9.8, 1.4 Hz), 6.98 (s, 1H), 7.07-7.10 (m, 1H), 7.41 (d, 1H, J=3.1 Hz), 7.45 (d, 1H, J=8.7 Hz), 7.59 (d, 1H, J=5.1 Hz), 7.71 (d, 1H, J=3.1 Hz); ESI-MS (m/z, %): 339 (MH$^+$, 100%); ESI-HRMS calculated for C$_{19}$H$_{23}$N$_4$S (MH$^+$): 339.1637, observed: 339.1647.

EXAMPLE 26

Preparation of N-(1-(8-methyl-8-azabicyclo[3.2.1]octan-3-yl)-1H-indol-5-yl)thiophene-2-carboximidamide (86)

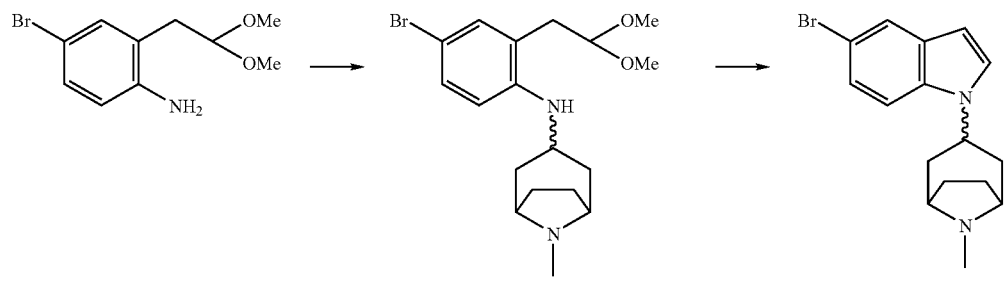

67  83  84

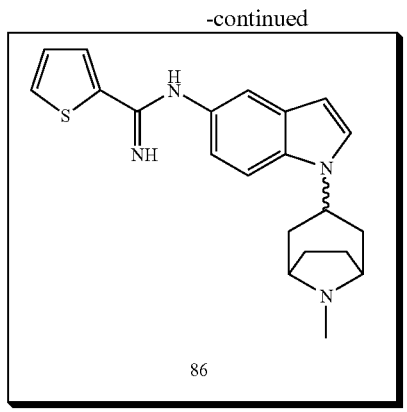

86

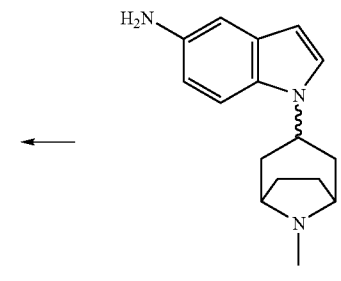

85

N-(4-Bromo-2-(2,2-dimethoxyethyl)phenyl)-8-methyl-8-azabicyclo[3.2.1]octan-3-amine (83): Crude compound 67 (225.4 mg, 0.866 mmol) and 8-methyl-8-azabicyclo[3.2.1]octan-3-one (241.1 mg, 1.732 mmol) were stirred in acetic acid (10 mL) under argon in the presence of anhydrous sodium sulfate (1.230 g, 8.660 mmol) at room temperature for 30 minutes. Sodium triacetoxyborohydride (550.6 mg, 2.598 mmol) was then added and the mixture stirred for 24 hours at room temperature. After dilution with a mixture of 8:1 ethyl acetate:Hexanes, the reaction is quenched with saturated sodium bicarbonate. The mixture was transferred to a separatory funnel and the organic layer separated. The organic layer was dried over sodium sulfate and concentrated under reduced pressure and the residue purified via chromatography on silica gel (2M $NH_3$ in methanol:$CH_2Cl_2$, 5:95%) to yield a pale yellow residue, 83 (120 mg, 36.1%) as an 5:1 or 1:5 mixture of endo/exo stereoisomers. $^1$H NMR (major isomer-DMSO-$d_6$) δ 1.56-1.70 (m, 2H), 1.87-1.99 (m, 4H), 2.04-2.09 (m, 2H), 2.21 (s, 3H), 2.79 (d, 2H, J=5.3 Hz), 3.03-3.17 (m, 2H), 3.28 (s, 6H), 3.40-3.49 (m, 1H), 4.54 (t, 1H, J=5.3 Hz), 4.98 (s, 1H), 6.36 (d, 1H, J=9.3 Hz), 7.11-7.21 (m, 2H); ESI-MS (m/z, %): 383/385 (MH$^+$, 100%).

5-Bromo-1-(8-methyl-8-azabicyclo[3.2.1]octan-3-yl)-1H-indole (84): Compound 83 (118 mg, 0.308 mmol) was dissolved in anhydrous 1M HCl/methanol (10 mL) in a dry argon purged flask, refluxed for 1 hour, concentrated under reduced pressure to yield a shiny brown solid, 84 (125 mg, 100%) as a 5:1 or 1:5 mixture of endo/exo stereoisomers. $^1$H NMR (major isomer-DMSO-$d_6$) δ 1.85-1.96 (m, 2H), 2.15-2.26 (m, 2H), 2.31-2.40 (m, 2H), 2.66 (d, 3H, J=4.9 Hz), 2.76-2.93 (m, 2H), 3.87-3.96 (m, 2H), 4.99-5.11 (m, 1H), 6.49 (d, 1H, J=3.4 Hz), 7.24-7.34 (m, 1H), 7.49 (d, 1H, J=8.8 Hz), 7.76 (d, 1H, J=1.6 Hz), 7.79 (d, 1H, J=2.9 Hz); ESI-MS (m/z, %): 319/321 (MH$^+$, 100%).

1-(8-Methyl-8-azabicyclo[3.2.1]octan-3-yl)-1H-indol-5-amine (85): Compound 84 (73 mg, 0.2287 mmol), tris(dibenzylideneacetone)dipalladium (0) (20.9 mg, 0.0229 mmol) and anhydrous tetrahydrofuran (10 mL) were charged to a dry argon purged flask fitted with magnetic stir bar and condenser. A solution of tri-tert-butylphosphine (10 wt % in hexane, 92.5 mg, 0.0457 mmol) is added followed by dropwise addition of a 1M tetrahydrofuran solution of lithium bis(trimethylsilyl)amide (0.686 ml, 0.686 mmol) and mixture refluxed for a period of 90 minutes. The mixture was cooled to room temperature then to 0° C., quenched with 1M HCl (10 mL) and stirred for 15 minutes. The solution was diluted with ethyl acetate and conc. $NH_4OH$ added to adjust pH to 9. The mixture was transferred to a separatory funnel and the organic layer collected. The aqueous layer was further extracted with ethyl acetate and the combined organic layers were washed with brine, dried over magnesium sulphate, filtered, concentrated to yield crude. The crude amine was combined with a second crude from an identical reaction and the residue purified via chromatography on silica gel (EtOAc:methanol:Et$_3$N, 8:1:1) to yield a brown solid 85 (52 mg, 37.6%) as a 5:1 or 1:5 mixture of endo/exo stereoisomers. $^1$H NMR (major isomer-DMSO-$d_6$) δ 1.53-1.70 (m, 4H), 2.00-2.09 (m, 2H), 2.18 (s, 3H), 3.17-3.32 (m, 2H), 4.54 (quintuplet, 1H, J=8.2 Hz), 6.11 (d, 1H, J=3.1 Hz), 6.49 (dd, 1H, J=8.6, 2.1 Hz), 6.65 (d, 1H, J=1.9 Hz), 7.05 (d, 1H, J=8.7 Hz), 7.26 (d, 1H, J=3.2 Hz); ESI-MS (m/z, %): 256 (MH$^+$, 100%).

N-(1-(8-Methyl-8-azabicyclo[3.2.1]octan-3-yl)-1H-indol-5-yl)thiophene-2-carboximidamide (86): Compound 85 (52 mg, 0.2036 mmol) is charged to a small, argon purged flask fitted with a magnetic stir bar. Anhydrous ethanol (5 mL) and thiophene-2-carboximidothioic acid methyl ester hydroiodide (87.1 mg, 0.3056 mmol) are added to the flask and the reaction was stirred under argon at ambient temperature for 23 hours, at which time the solvent was evaporated and the residue was purified via chromatography on silica gel (methanol:$CH_2Cl_2$, 1:9 to 2M $NH_3$ in methanol:$CH_2Cl_2$, 5:95) to yield a pale yellow residue, 86 (77 mg, 100%). $^1$H NMR (major isomer-MeOD) δ 1.81-1.89 (m, 2H), 2.07-2.14 (m, 2H), 2.23-2.31 (m, 2H), 2.48 (s, 3H), 2.69-2.79 (m, 2H), 3.49-3.59 (m, 2H), 4.51-4.61 (m, 1H), 6.58 (d, 1H, J=3.3 Hz), 7.13 (dd, 1H, J=8.7, 1.9 Hz), 7.31-7.34 (m, 1H), 7.54-7.57 (m, 2H), 7.61 (d, 1H, J=3.5 Hz), 7.94-7.97 (m, 2H); ESI-MS (m/z, %): 365 (MH$^+$, 15%), 183 (M++doubly charged, 100%); ESI-HRMS calculated for $C_{21}H_{25}N_4S$ (MH$^+$): 365.1794, observed: 365.1784.

EXAMPLE 27

Preparation of N-(1-(tetrahydro-2H-pyran-4-yl)-1H-indol-5-yl)thiophene-2-carboximidamide (90)

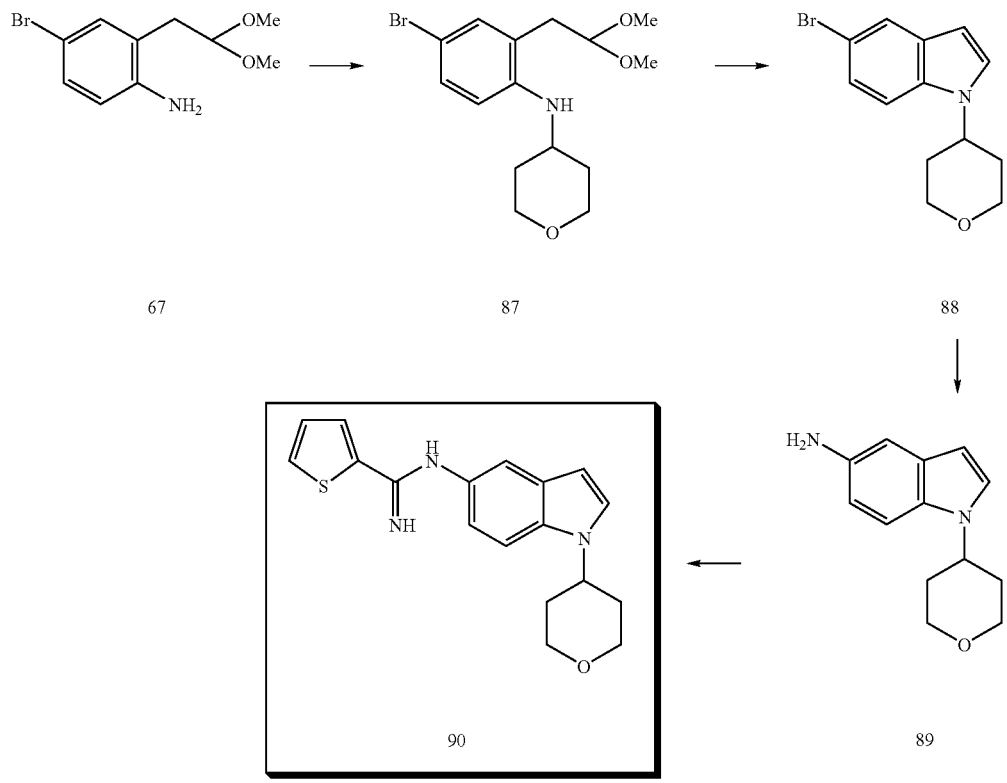

N-(4-Bromo-2-(2,2-dimethoxyethyl)phenyl)tetrahydro-2H-pyran-4-amine (87): Compound 67 (300 mg, 1.153 mmol) and dihydro-2H-pyran-4(3H)-one (231 mg, 2.306 mmol) were stirred in acetic acid (10 mL) under Argon in the presence of anhydrous sodium sulfate (1.638 g, 11.530 mmol) at room temperature for 30 minutes. Sodium triacetoxyborohydride (733 mg, 3.459 mmol) was then added and the mixture stirred for 19 hours at room temperature. After dilution with a mixture of 8:1 ethyl acetate:Hexanes, the reaction is quenched with saturated sodium bicarbonate. The mixture was transferred to a separatory funnel and the organic layer separated. The organic layer was dried over sodium sulfate and concentrated under reduced pressure and the residue purified via chromatography on silica gel (EtOAc: Hexanes, 1:4 then 2M $NH_3$ in methanol:$CH_2Cl_2$, 3:7 then 100% methanol) to yield a pale yellow oil, 87 (168 mg, 42.3%). $^1$H NMR (DMSO-$d_6$) δ 1.34-1.47 (m, 2H), 1.86 (d, 2H, J=12.3 Hz), 2.75 (d, 2H, J=5.3 Hz), 3.27 (s, 6H), 3.35-3.49 (2×m, 3H), 3.77-3.91 (2×m, 2H), 4.52 (t, 1H, J=5.3 Hz), 4.89 (d, 1H, J=7.6 Hz), 6.60 (d, 1H, J=9.4 Hz), 7.10-7.20 (m, 2H); ESI-MS (m/z, %): 344/346 (MH$^+$, 5%), 280/282 (cyclized product, 100%).

5-Bromo-1-(tetrahydro-2H-pyran-4-yl)-1H-indole (88): Compound 87 (168 mg, 0.488 mmol) was dissolved in anhydrous 1M HCl/methanol (10 mL) in a dry argon purged flask, refluxed for 1 hour, concentrated under reduced pressure to yield compound 88 as a pale brown solid (145 mg, 100%). $^1$H NMR (DMSO-$d_6$) δ 1.77-2.06 (m, 4H), 3.57 (dt, 2H, J=11.4, 2.1 Hz), 3.99 (dd, 2H, J=11.2, 4.0 Hz), 4.59-4.69 (m, 1H), 6.46 (d, 1H, J=3.2 Hz), 7.23 (dd, 1H, J=8.9, 2.1 Hz), 7.57-7.60 (m, 2H), 7.73 (d, 1H, J=1.8 Hz). ESI-MS (m/z, %): 280/282 (MH$^+$, 100%).

1-(Tetrahydro-2H-pyran-4-yl)-1H-indol-5-amine (89): Compound 88 (140 mg, 0.500 mmol), tris(dibenzylideneacetone)dipalladium (0) (45.7 mg, 0.050 mmol) and anhydrous tetrahydrofuran (15 mL) were charged to a dry argon purged flask fitted with magnetic stir bar and condenser. A solution of tri-tert-butylphosphine (10 wt % in hexane, 202.3 mg, 0.100 mmol) is added followed by dropwise addition of a 1M tetrahydrofuran solution of lithium bis(trimethylsilyl)amide (1.500 ml, 1.500 mmol) and mixture refluxed for a period of 45 minutes. The mixture was cooled to room temperature then to 0° C., quenched with 1M HCl (10 mL) and stirred for 15 minutes. The solution was diluted with ethyl acetate and conc. $NH_4OH$ added to adjust pH to 9. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (EtOAc: Hexanes, 7:3) to yield a pale brown solid 89 (96 mg, 88.8%). $^1$H NMR (DMSO-$d_6$) δ 1.80-1.99 (m, 4H), 3.53 (dt, 2H, J=11.4, 2.9 Hz), 3.95-3.99 (m, 2H), 4.39-4.50 (m, 1H), 4.55 (brs, 2H), 6.14 (d, 1H, J=4.1 Hz), 6.52 (dd, 1H, J=8.8, 2.1 Hz), 6.68 (d, 1H, J=1.9 Hz), 7.23 (d, 1H, J=8.6 Hz), 7.27 (d, 1H, J=3.2 Hz); ESI-MS (m/z, %): 217 (MH$^+$, 100%).

N-(1-(Tetrahydro-2H-pyran-4-yl)-1H-indol-5-yl)thiophene-2-carboximidamide (90): Compound 89 (95 mg, 0.439 mmol) is charged to a small, argon purged flask fitted with a magnetic stir bar. Anhydrous ethanol (5 mL) and thiophene-2-carboximidothioic acid methyl ester hydroiodide (219.2 mg, 0.769 mmol) are added to the flask and the reaction was stirred under argon at ambient temperature for 21 hours, at which time the solvent was evaporated and the residue was partitioned between H₂O and ethyl acetate and 1M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (methanol:CH₂Cl₂, 5:95 to 7.5:92.5) to yield a pale yellow residue, 90 (45 mg, 31.5%). ¹H NMR (DMSO-d₆) δ 1.82-2.11 (m, 4H), 3.57 (t, 2H, J=11.0 Hz), 3.92-4.07 (m, 2H), 4.50-4.68 (m, 1H), 6.33 (brs, 2H), 6.37 (d, 1H, J=2.5 Hz), 6.71 (d, 1H, J=8.2 Hz), 7.00 (s, 1H), 7.09-7.11 (m, 1H), 7.45 (d, 1H, J=2.7 Hz), 7.52 (d, 1H, J=8.6 Hz), 7.60 (d, 1H, J=4.8 Hz), 7.72 (d, 1H, J=2.7 Hz); ESI-MS (m/z, %): 326 (MH⁺, 100%); ESI-HRMS calculated for C₁₈H₂₀N₃OS (MH⁺): 326.1321, observed: 326.1332.

EXAMPLE 28

Preparation of N-(1-(2-(dimethylamino)ethyl)-1H-indol-5-yl)thiophene-2-carboximidamide (93)

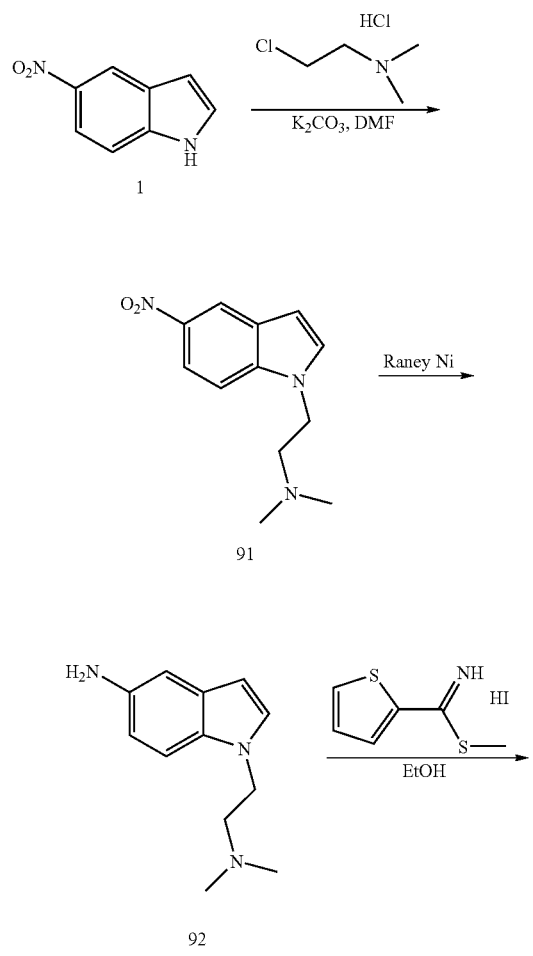

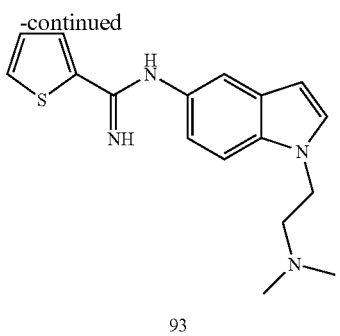

N,N-Dimethyl-2-(5-nitro-1H-indol-1-yl)ethanamine (91): A suspension of compound 1 (500 mg, 3.08 mmol), (N,N-dimethyamino)ethyl chloride hydrochloride (577 mg, 4.00 mmol) and potassium carbonate (1.28 g, 9.26 mmol) in DMF (5 mL) was stirred at 80° C. for 3 hours. Reaction was transferred to a separatory funnel and diluted with cold water and ethyl acetate. The aqueous was extracted twice more with ethyl acetate and the combined organic fractions were washed with brine, dried over Na₂SO₄, filtered and concentrated. The residue was subjected to flash chromatography on silica gel using 0-10% 2M NH₃ in MeOH/CH₂Cl₂ to give compound 91 (521 mg, 73%) as a yellow solid. ¹H NMR (CDCl₃) δ 8.59 (d, J=2.1 Hz, 1H), 8.12 (dd, J=2.4, 9.3 Hz, 1H), 7.37 (d, J=9.0 Hz, 1H), 7.32 (d, J=3.3 Hz, 1H), 6.68 (d, J=3.3 Hz, 1H), 4.26 (t, J=6.6 Hz, 2H), 2.71 (t, J=7.2 Hz, 2H), 2.29 (s, 6H); ESI-MS (m/z, %): 234 (M+1).

1-(2-(Dimethylamino)ethyl)-1H-indol-5-amine (92): A suspension of compound 91 (250 mg, 1.07 mmol) in dry methanol (10 mL) was treated with Ra—Ni (~0.05 g) followed by hydrazine hydrate (0.33 mL, 10.7 mmol) and the resulting mixture was refluxed for 20 min. The dark green reaction was cooled to room temperature, filtered through a celite pad, washed with methanol (2×10 mL). The combined methanol layer was evaporated and crude was purified by column chromatography (2 M NH₃ in MeOH:CH₂Cl₂, 5:95) to obtain compound 92(119 mg, 55%) as a yellow oil. ¹H NMR (CDCl₃) δ 7.16 (d, J=8.7 Hz, 1H), 7.05 (d, J=3.0 Hz, 1H), 6.92 (d, J=2.1 Hz, 1H), 6.67 (dd, J=2.1, 8.7 Hz, 1H), 6.30 (d, J=3.0 Hz, 1H), 4.17 (t, J=7.2 Hz, 2H), 2.68 (t, J=7.5 Hz, 2H), 2.29 (s, 6H); ESI-MS (m/z, %): 204 (M+1).

N-(1-(2-(Dimethylamino)ethyl)-1H-indol-5-yl) thiophene-2-carboximidamide (93): A solution of compound 92 (0.104 g, 0.512 mmol) in absolute ethanol (3 mL) was treated with methyl thiophene-2-carbimidothioate hydroiodide (0.290 g, 1.02 mmol) at room temperature and the resulting mixture was stirred for 3 hours. The reaction was diluted with saturated aqueous sodium bicarbonate (5 mL) followed by dichloromethane (30 mL) and transferred to a separatory funnel. The aqueous was extracted twice more with dichloromethane (2×30 mL). The combined organics were washed with brine and dried (Na₂SO₄). Solvent was evaporated and crude was purified by column chromatography (2M ammonia in methanol:dichloromethane, 5:95). Product was dried under high vacuum. HPLC revealed a 10% impurity. A second purification by column chromatography using less polar solvent conditions (2M ammonia in methanol:dichloromethane, 0:100-2.5:97.5) afforded pure product 93 (35 mg, 22%) as a yellow oil. ¹H NMR (CDCl₃) δ 7.43 (d, J=4.5 Hz, 2H), 7.33 (d, J=8.7 Hz, 1H), 7.21 (d, J=1.2 Hz, 1H), 7.13 (d, J=3.0 Hz, 1H), 7.08 (t, J=4.2 Hz, 1H), 6.67 (dd, J=1.8, 8.7 Hz, 1H), 6.43 (d, J=3.0 Hz, 1H), 4.22 (t, J=7.5 Hz, 2H), 2.72 (t, J=7.5 Hz, 2H), 2.31 (s, 6H); ES-MS (m/z, %): 313 (M+1); ESI-HRMS calculated for $C_{17}H_{21}N_4S$ (MH$^+$): 313.1481, Observed: 313.1467.

EXAMPLE 29

Preparation of N-(1-(2-(piperidin-1-yl)ethyl)-1H-indol-5-yl)thiophene-2-carboximidamide (96)

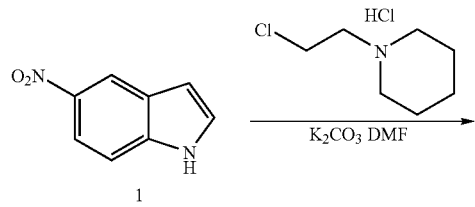

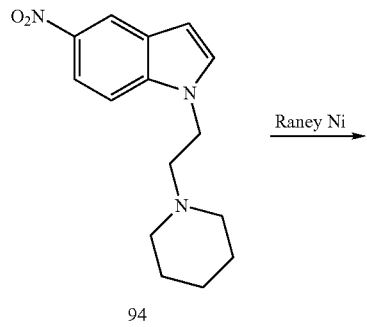

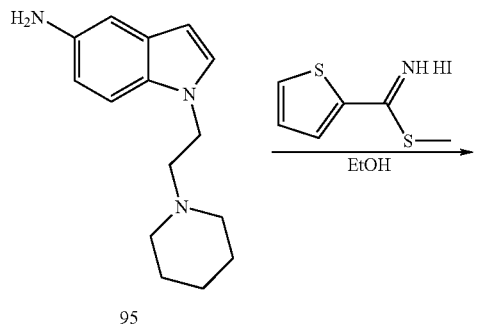

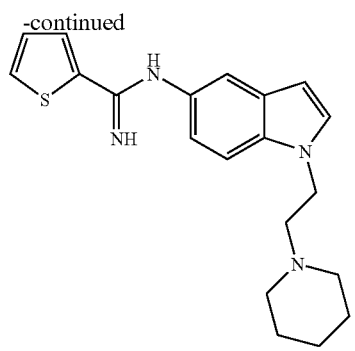

5-Nitro-1-(2-(piperidin-1-yl)ethyl)-1H-indole (94): A suspension of compound 1 (500 mg, 3.08 mmol), 1-(2-chloroethyl)piperidine hydrochloride (737 mg, 4.00 mmol) and potassium carbonate (1.28 g, 9.26 mmol) in DMF (5 mL) was stirred at 80° C. for 3 hours. Reaction was transferred to a separatory funnel and diluted with cold water and ethyl acetate. The aqueous was extracted twice more with ethyl acetate and the combined organic fractions were washed with brine, dried over $Na_2SO_4$, filtered and concentrated. The residue was subjected to flash chromatography on silica gel using 0-10% 2M $NH_3$ in MeOH/$CH_2Cl_2$ to give compound 94 (417 mg, 50%) as a yellow solid. $^1$H NMR (CDCl$_3$) δ 8.58 (d, J=2.1 Hz, 1H), 8.11 (dd, J=2.4, 9 Hz, 1H), 7.38 (d, J=9.3 Hz, 1H), 7.32 (d, J=3.3 Hz, 1H), 6.66 (d, J=3.3 Hz, 1H), 4.27 (t, J=6.6 Hz, 2H), 2.70 (t, J=7.2 Hz, 2H), 2.43 (m, 4H), 1.58 (m, 4H); ESI-MS (m/z, %): 274 (M+1).

1-(2-(Piperidin-1-yl)ethyl)-1H-indol-5-amine (95): A suspension of compound 94 (250 mg, 0.915 mmol) in dry methanol (10 mL) was treated with Ra—Ni (~0.05 g) followed by hydrazine hydrate (0.33 mL, 10.7 mmol) and the resulting mixture was refluxed for 20 min. The dark green reaction was cooled to room temperature, filtered through a celite pad, washed with methanol (2×10 mL). The combined methanol layer was evaporated and crude was purified by column chromatography (2 M $NH_3$ in MeOH:$CH_2Cl_2$, 5:95) to obtain compound 95 (215 mg, 97%) as a yellow oil. $^1$H NMR (CDCl$_3$) δ 7.16 (d, J=8.7 Hz, 1H), 7.05 (d, J=3.0 Hz, 1H), 6.92 (d, J=2.1 Hz, 1H), 6.67 (dd, J=2.1, 8.7 Hz, 1H), 6.29 (d, J=3.0 Hz, 1H), 4.18 (t, J=7.2 Hz, 2H), 2.67 (t, J=7.5 Hz, 2H), 2.45 (m, 4H), 1.59 (m, 4H); ESI-MS (m/z, %): 244 (M+1).

N-(1-(2-(piperidin-1-yl)ethyl)-1H-indol-5-yl)thiophene-2-carboximidamide (96): A solution of compound 95 (0.200 mg, 0.822 mmol) in absolute ethanol (3 mL) was treated with methyl thiophene-2-carbimidothioate hydroiodide (0.350 g, 1.23 mmol) at room temperature and the resulting mixture was stirred for 3 hours. The reaction was diluted with saturated aqueous sodium bicarbonate (5 mL) followed by dichloromethane (30 mL) and transferred to a separatory funnel. The aqueous was extracted twice more with dichloromethane (2×30 mL). The combined organics were washed with brine and dried ($Na_2SO_4$). Solvent was evaporated and crude was purified by column chromatography (2M ammonia in methanol:dichloromethane, 5:95) to obtain compound 96 (130 mg, 45%) as a yellow oil. $^1$H NMR (CDCl$_3$) δ 7.43 (d, J=2.7 Hz, 1H), 7.41 (s, 1H), 7.34 (d, J=8.7 Hz, 1H), 7.21 (d, J=1.2 Hz, 1H), 7.14 (d, J=3.0 Hz, 1H), 7.08 (t, J=4.2 Hz, 1H), 6.67 (dd, J=1.8, 8.7 Hz, 1H), 6.42 (d, J=3.0 Hz, 1H), 4.24 (t, J=7.5 Hz, 2H), 2.73 (t, J=7.5 Hz, 2H), 2.47 (m, 4H), 1.61 (m, 4H); ESI-MS (m/z, %): 353 (M+1); ESI-HRMS calculated for $C_{20}H_{25}N_4S$ (MH$^+$): 353.1794, Observed: 353.1796.

EXAMPLE 30

Preparation of (S)—N-(1-((1-methylpyrrolidin-2-yl)methyl)-1H-indol-5-yl)thiophene-2-carboximidamide (104)

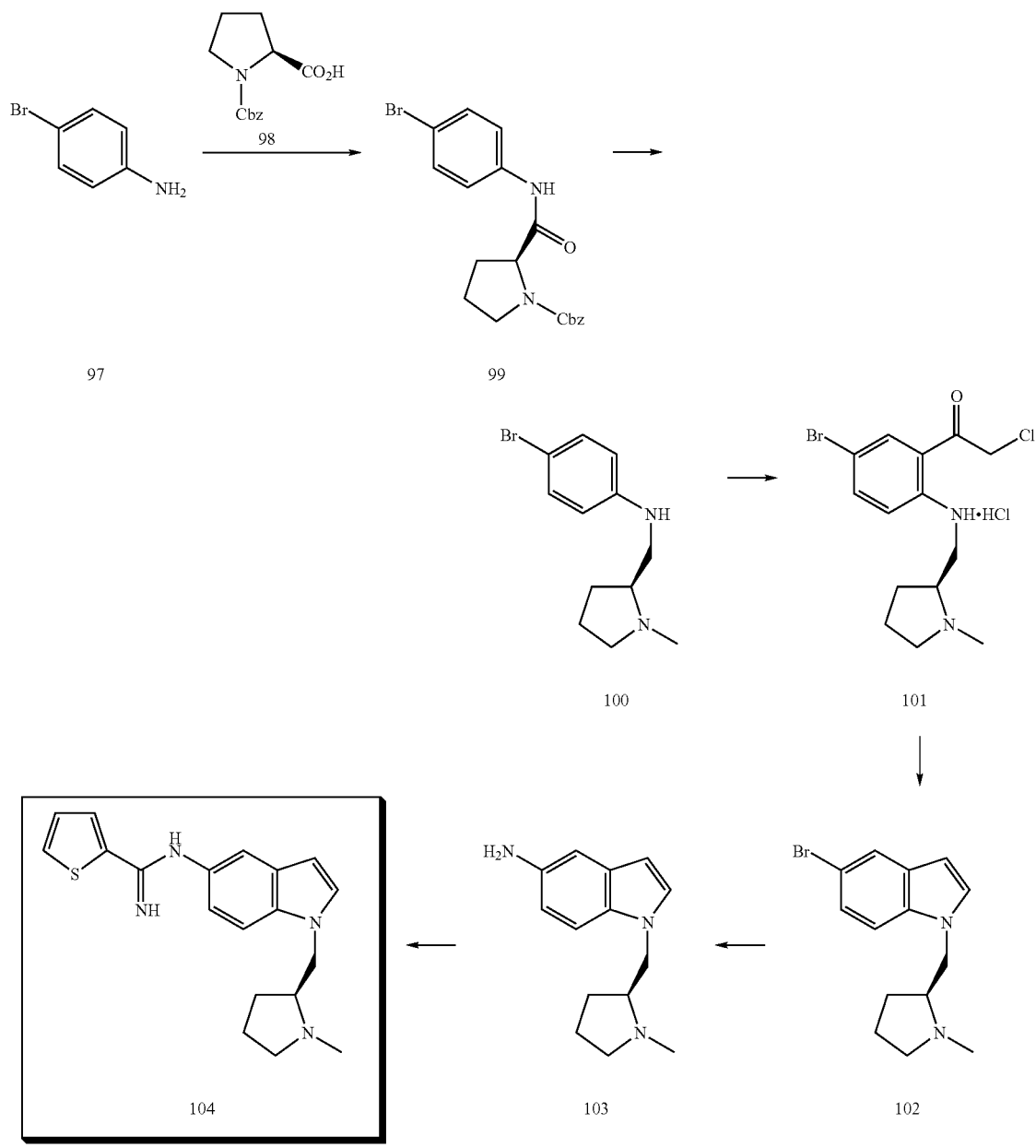

(S)-Benzyl-2-(4-bromophenylcarbamoyl)pyrrolidine-1-carboxylate (99): Compound 98 (1.0 g, 4.012 mmol) and triethylamine (0.56 mL, 4.012 mmol) were dissolved in anhydrous tetrahydrofuran (20 mL) and the solution cooled to 0° C. Ethyl chloroformate (0.384 mL, 4.012 mmol) was added dropwise over 10 minutes and the resulting solution stirred for 30 minutes at 0° C. To this solution was added a solution of compound 97 (0.690 g, 4.012 mmol) in anhydrous tetrahydrofuran (5 mL) over 10 minutes. After 1 hour at 0° C. the mixture was allowed to slowly warm to room temperature and stirred at room temperature for 45 hours at which time the mixture was diluted with ethyl acetate and filtered through a pad of celite. The organic layer was concentrated and the crude purified via chromatography on silica gel (EtOAc: Hexanes, 1:4 to 1:1) to yield compound 99 (1.56 g, 96.5%) as a white solid. $^1$H NMR (CDCl$_3$) δ 1.81-2.08 (m, 3H), 2.43-2.63 (m, 1H), 3.37-3.62 (m, 2H), 4.39-4.57 (br, 1H), 5.10-5.32 (brs, 2H), 7.18-7.50 (m, 9H), 9.29 (brs, 1H). ESI-MS (m/z, %): 425/427 (MNa$^+$, 100%), 403/405 (MH$^+$, 10%).

(S)-4-Bromo-N-((1-methylpyrrolidin-2-yl)methyl)aniline (100): Lithium aluminum hydride (0.263 g, 6.943 mmol) and anhydrous tetrahydrofuran (10 mL) were charged to a dry argon purged flask fitted with magnetic stir bar, condenser and dropping funnel and the mixture cooled to 0° C. A solution of compound 99 (0.70 g, 1.736 mmol) in anhydrous tetrahydrofuran (15 mL) is charged to the dropping funnel and added dropwise to the cold solution over 20 minutes. The resulting mixture was allowed to warm to room temperature over 90 minutes then heated to reflux for 45 minutes. After cooling to room temperature, then to 0° C., the reaction was quenched by the portionwise addition of sodium sulfate decahydrate (approximately 4.0 g). Water (5 mL) and ethylacetate (50 mL) were added and mixture stirred overnight, transferred to a separatory funnel (washing with a small amount of water and ethyl acetate) and the organic layer separated. The aqueous layer was further extracted with ethyl acetate and the combined organic layers washed with brine, dried over sodium sulfate, concentrated and the residue purified via chromatography on silica gel (MeOH:$CH_2Cl_2$, 3:97 to 1:9) to yield compound 100 (308 mg, 66.0%) as a pale yellow oil. $^1$H NMR (DMSO-$d_6$) δ 1.48-1.67 (2×m, 3H), 1.83-1.95 (m, 1H), 2.14 (q, 1H, J=8.6 Hz), 2.28 (s, 3H), 2.32-2.38 (m, 1H), 2.81-2.89 (m, 1H), 2.93-2.99 (m, 1H), 3.10-3.17 (m, 1H), 5.54-5.66 (m, 1H), 6.55 (d, 2H, J=8.9 Hz), 7.17 (d, 2H, J=8.9 Hz); ESI-MS (m/z, %): 269/271 (MH$^+$, 100%).

(S)-1-(5-Bromo-2-((1-methylpyrrolidin-2-yl)methylamino)phenyl)-2-chloroethanone (101): To a stirred solution of boron trichloride (1.56 mL, 1.56 mmol, 1M solution in $CH_2Cl_2$) in anhydrous dichloroethane (15 mL) in a dry argon purged flask cooled in an ice-bath was added dropwise a solution of compound 100 (0.30 g, 1.115 mmol) in anhydrous dichloroethane (5 mL). Chloroacetonitile (0.141 mL, 2.229 mmol) was added dropwise and the mixture heated to reflux for 20 hours. After cooling to room temperature, ice-cold 1M HCl (5 mL) is added slowly and the reaction refluxed for 20 minutes. After cooling, the organic layer was separated and the acidic aqueous layer further extracted with dichloromethane (twice). The combined organic layers were washed with brine, and concentrated to yield the crude hydrochloride salt of compound 101 (352 mg, 82.6%) as a bright yellow residue. $^1$H NMR (DMSO-$d_6$) δ 1.49-1.60 (m, 1H), 1.60-1.77 (m. 1H), 1.82-1.93 (m, 1H), 2.02-2.20 (m, 2H), 2.28 (s, 3H), 2.97-3.10 (m, 1H), 3.12-3.22 (m, 1H), 3.62-3.84 (m, 1H), 3.99-4.11 (m, 1H), 5.09 (s, 2H), 6.82 (d, 1H, J=9.0 Hz), 7.52 (dd, 1H, J=9.0, 2.3 Hz), 7.91 (d, 1H, J=2.3 Hz), 10.35 (brs, 1H); ESI-MS (m/z, %): 345/347/349 (MH$^+$, 100%).

(S)-5-Bromo-1-((1-methylpyrrolidin-2-yl)methyl)-1H-indole (102): To an ice cold solution of compound 101 (402 mg, 1.052 mmol) in 95% ethanol (20 mL) was added 1M sodium hydroxide (1.052 mL, 1.052 mmol) followed by sodium borohydride (19.9 mg, 0.526 mmol) and the mixture stirred under ice cooling for 45 minutes. The reaction was quenched with ice cold $H_2O$ (5 mL), diluted with dichloromethane, transferred to a separatory funnel and the organic layer separated. The aqueous layer was further extracted with dichloromethane (twice) and the combined organic layers washed with brine, dried over sodium sulfate and concentrated to residue. The residue was taken up in anhydrous dioxane (20 mL) and heated to reflux for 2.5 hours. After cooling to room temperature the reaction was treated with ice-cold 2N potassium carbonate, diluted with dichloromethane, transferred to a separatory funnel and the organic layer separated. The aqueous layer was further extracted with dichloromethane (twice) and the combined organic layers washed with water (twice), brine, dried over sodium sulfate concentrated under reduced pressure and the residue purified via chromatography on silica gel (MeOH:$CH_2Cl_2$, 3:97) to yield compound 102 (110 mg, 35.7%) as a yellow oil. $^1$H NMR (DMSO-$d_6$) δ 1.42-1.50 (m, 1H), 1.50-1.60 (m, 2H), 1.62-1.71 (m, 1H), 2.09-2.14 (m, 1H), 2.17 (s, 3H), 2.50-2.57 (m, 1H), 2.90-2.96 (m, 1H), 4.05 (dd, 1H, J=14.1, 6.3 Hz), 4.23 (dd, 1H, J=14.0, 5.1 Hz), 6.41 (d, 1H, J=3.0 Hz), 7.22 (dd, 1H, J=8.9, 1.9 Hz), 7.42-7.49 (m, 2H), 7.71 (d, 1H, J=2.0 Hz); ESI-MS (m/z, %): 293/295 (MH$^+$, 100%).

(S)-1-((1-Methylpyrrolidin-2-yl)methyl)-1H-indol-5-amine (103): compound 102 (106 mg, 0.362 mmol), tris(dibenzylideneacetone)dipalladium (0) (33.1 mg, 0.0362 mmol) and anhydrous tetrahydrofuran (10 mL) were charged to a dry argon purged flask fitted with magnetic stir bar and condenser. A solution of tri-tert-butylphosphine (146.3 mg, 222 ul, 0.0723 mmol, 10 wt % in hexane) is added followed by dropwise addition of a 1M tetrahydrofuran solution of lithium bis(trimethylsilyl)amide (1.084 ml, 1.084 mmol) and mixture refluxed for a period of 90 minutes. The mixture was cooled to room temperature then to 0° C., quenched with 1M HCl (10 mL) and stirred for 10 minutes. The solution was diluted with ethyl acetate and 5M $NH_4OH$ added to adjust pH to 9. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (MeOH:$CH_2Cl_2$, 1:9) to yield compound 103 (67 mg, 80.8%)as a pale yellow solid. $^1$H NMR (DMSO-$d_6$) δ 1.40-1.70 (2×m, 4H), 2.08-2.20 (m, 1H), 2.18 (s, 3H), 2.89-2.99 (m, 1H), 3.89 (dd, 1H, J=14.1, 6.9 Hz), 4.12 (dd, 1H, J=14.2, 5.1 Hz), 4.46 (brs, 2H), 6.10 (d, 1H, J=3.0 Hz), 6.51 (dd, 1H, J=8.7, 2.0 Hz), 6.66 (d, 1H, J=2.0 Hz), 7.12-7.15 (m, 2H); ESI-MS (m/z, %): 230 (MH$^+$, 100%).

(S)—N-(1-((1-Methylpyrrolidin-2-yl)methyl)-1H-indol-5-yl)thiophene-2-carboximidamide (104): compound 103 (65 mg, 0.283 mmol) is charged to a small, argon purged flask fitted with a magnetic stir bar. Anhydrous ethanol (7 mL) and thiophene-2-carboximidothioic acid methyl ester hydroiodide (121.2 mg, 0.425 mmol) are added to the flask and the reaction was stirred under argon at ambient temperature for 17 hours, at which time the solvent was evaporated and the residue was partitioned between $H_2O$ and ethyl acetate and 1M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulphate, filtered, concentrated and the residue purified via chromatography on silica gel (MeOH:$CH_2Cl_2$, 1:9 then 2M $NH_3$ in MeOH:$CH_2Cl_2$, 5:95 to 1:9) to yield compound 104 (30 mg, 31.3%) as a yellow solid. $^1$H NMR (DMSO-$d_6$) δ 1.47-1.76 (m, 4H), 2.16 (q, 1H, J=8.5 Hz), 2.25 (s, 3H), 2.50-2.59 (m, 1H), 2.92-3.02 (m, 1H), 3.97 (dd, 1H, J=14.1, 7.1 Hz), 4.23 (dd, 1H, J=14.0, 4.8 Hz), 6.23 (brs, 2H), 6.31 (d, 1H, J=3.0 Hz), 6.69 (d, 1H, J=8.3 Hz), 6.98 (s, 1H), 7.08-7.11 (m, 1H), 7.31 (d, 1H, J=3.0 Hz), 7.39 (d, 1H, J=8.6 Hz), 7.58 (d, 1H, J=5.2 Hz), 7.71 (d, 1H, J=3.7 Hz); ESI-MS (m/z, %): 339 (MH+, 100%); ESI-HRMS calculated for C₁₉H₂₃N₄S (MH+): 339.1637, observed: 339.1653.

EXAMPLE 31

Preparation of N-[3-(1-methyl-1,2,3,6-tetrahydro-pyridin-4-yl)-1H-indol-6-yl]-thiophene-2-carboxamidine (107) and N-[3-(1-methyl-piperidin-4-yl)-1H-indol-6-yl]-thiophene-2-carboxamidine (108)

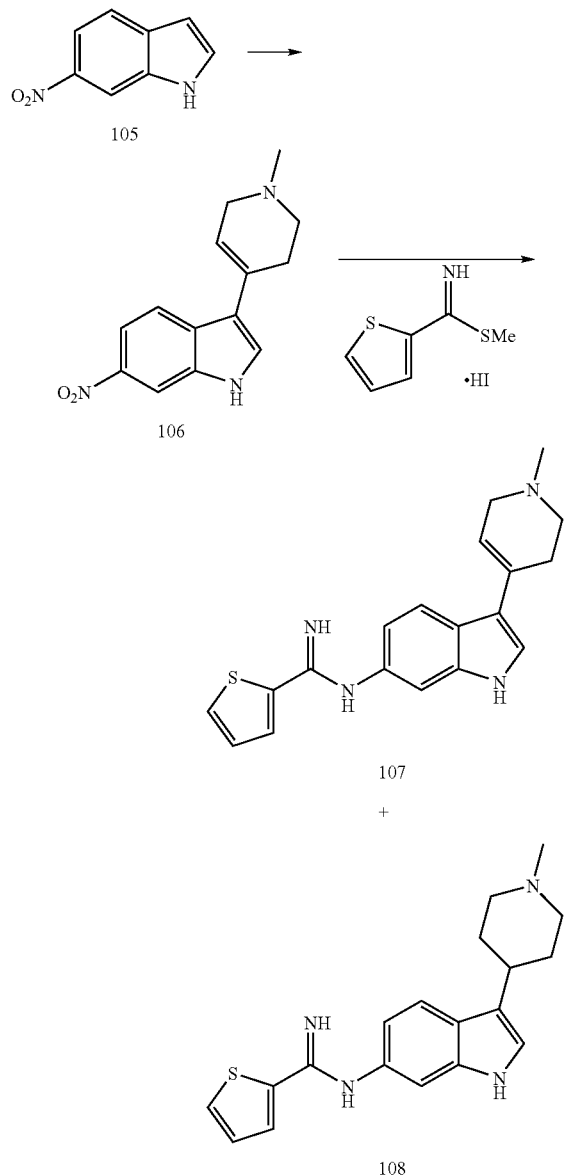

3-(1-Methyl-1,2,3,6-tetrahydro-pyridin-4-yl)-6-nitro-1H-indole (106): A solution of compound 105 (0.5 g, 3.083 mmol) in dry EtOH (5 mL) was treated with pyrrolidine (0.77 mL, 9.250 mmol), N-methyl-4-piperidone (0.75 mL, 6.167 mmol) at room temperature. The resulting solution was refluxed for 2 days. The reaction was brought to room temperature, further cooled to 0° C. and the solid was filtered off. The solid washed with ethanol (2×5 mL) and dried to obtain compound 106 (0.567 g, 72%) as a solid. Decomposed at 220° C.; ¹H NMR (DMSO-d₆) δ 2.28 (s, 3H), 2.50-2.58 (m, 4H), 3.00-3.05 (m, 2H), 6.18 (s, 1H), 7.83 (s, 1H), 7.89 (dd, 1H, J=2.1, 9.0 Hz), 7.97 (d, 1H, J=9.0 Hz), 8.31 (d, 1H, J=2.1 Hz), 11.88 (brs, 1H); ESI-MS (m/z, %): 258 (MH+, 100).

N-[3-(1-Methyl-1,2,3,6-tetrahydro-pyridin-4-yl)-1H-indol-6-yl]-thiophene-2-carboxamidine (107) and N-[3-(1-methyl-piperidin-4-yl)-1H-indol-6-yl]-thiophene-2-carboxamidine (108): A solution of compound 106 (0.15 g, 0.582 mmol) in dry MeOH (5 mL) was treated with Raney-Ni (~0.05 g) and hydrazine hydrate (0.18 mL, 5.829 mmol) at room temperature and resulting mixture was refluxed for 3 h. The reaction was brought to room temperature, solid was filtered off through celite bed and washed with MeOH:CH₂Cl₂ (1:1, 2×10 mL). The combined organic layer was evaporated and crude was purified by column chromatography (2 M NH₃ in MeOH:CH₂Cl₂, 1:9) to obtain the free amine.

A solution of the above amine in dry EtOH (10 mL) was treated with thiophene-2-carboximidothioic acid methyl ester hydroiodide (0.33 g, 1.165 mmol) at room temperature and stirred for 24 h. The solvent was evaporated and product was precipitated with ether (100 mL). The solid was dissolved into sat. NaHCO₃ sol.: CH₂Cl₂ (40 mL, 1:1). The organic layer was separated and aqueous layer was extracted with CH₂Cl₂ (2×20 mL). The combined CH₂Cl₂ layer washed with brine (15 mL) and dried (Na₂SO₄). The solvent was evaporated and crude was purified by column chromatography (2M NH₃ in MeOH:CH₂Cl₂, 5:95 to 1:9) to obtain compounds 107 (0.085 g, 50%, over two steps) and 108 (0.04 g, 20%, over two steps). Compound 107: Foam; ¹H NMR (DMSO-d₆) δ 2.28 (s, 3H), 2.50-2.57 (m, 4H), 3.00-3.04 (m, 2H), 6.09 (s, 1H), 6.31 (brs, 1H), 6.59 (dd, 1H, J=1.2, 8.4 Hz), 6.82 (s, 1H), 7.09 (dd, 1H, J=3.6, 4.9 Hz), 7.24 (d, 1H, J=2.1 Hz), 7.59 (d, 1H, J=5.1 Hz), 7.70-7.73 (m, 2H), 10.85 (s, 1H); ESI-MS (m/z, %): 337 (MH+, 100). Compound 108: Foam; ¹H NMR (DMSO-d₆) δ 1.62-1.75 (m, 2H), 1.90-1.94 (m, 2H), 2.02-2.09 (m, 2H), 2.22 (s, 3H), 2.64-2.72 (m, 1H), 2.85-2.89 (m, 2H), 6.31 (brs, 1H), 6.53 (dd, 1H, J=1.2, 8.2 Hz), 6.79 (s, 1H), 6.94 (d, 1H, J=1.8 Hz), 7.09 (dd, 1H, J=3.6, 4.9 Hz), 7.45 (d, 1H, J=8.4 Hz), 7.59 (d, 1H, J=4.2 Hz), 7.72 (d, 1H, J=3.6 Hz), 10.53 (brs, 1H); ESI-MS (m/z, %): 339 (MH+, 100).

EXAMPLE 32

Preparation of N-(3-(1-azabicyclo[2.2.2]oct-2-en-3-yl)-1H-indol-6-yl)thiophene-2-carboximidamide (111)

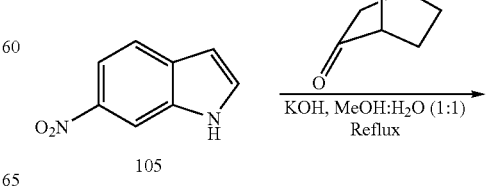

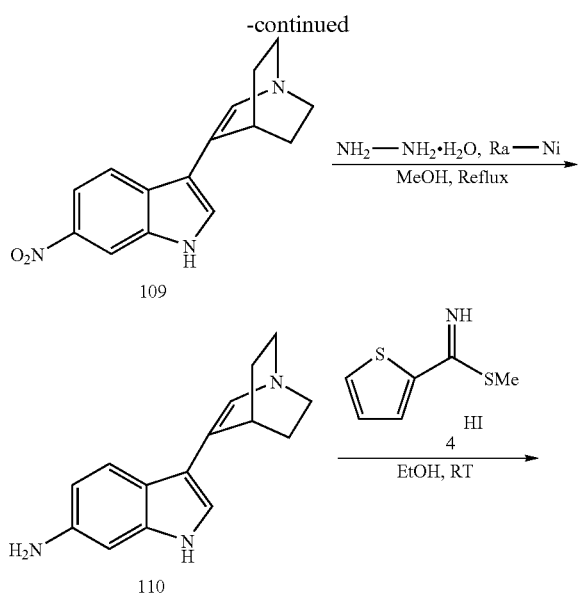

N-(3-(1-Azabicyclo[2.2.2]oct-2-en-3-yl)-1H-indol-6-yl)thiophene-2-carboximidamide (111): A solution of compound 110 (0.33 g, 1.378 mmol) in dry ethanol (15 mL) was treated with thiophene-2-carboximidothioic acid methyl ester hydroiodide (0.78 g, 2.757 mmol) at room temperature and the resulting brown mixture was stirred for over night (16 h). Solvent was evaporated, crude was diluted with sat. NaHCO$_3$ solution (25 mL) and product was extracted into CH$_2$Cl$_2$ (2×25 mL). The combined CH$_2$Cl$_2$ layer washed with brine (20 mL) and dried (Na$_2$SO$_4$). Solvent was evaporated, crude was purified by column chromatography (2M NH$_3$ in MeOH:CH$_2$Cl$_2$, 1:9) to obtain compound III (0.42 g, 81%) as a solid. mp 148-150° C.; $^1$H NMR (DMSO-d$_6$) δ 1.44-1.56 (m, 2H), 1.66-1.78 (m, 2H), 2.52-2.58 (m, 2H), 2.89-2.98 (m, 2H), 3.04-3.10 (m, 1H), 6.29 (s, 2H), 6.61 (dd, 1H, J=1.8, 8.7 Hz), 6.78 (s, 1H), 6.83 (s, 1H), 7.09 (t, 1H, J=4.2 Hz), 7.39 (d, 1H, J=2.4 Hz), 7.59 (d, 1H, J=4.8 Hz), 7.63 (d, 1H, J=8.4 Hz), 7.72 (d, 1H, J=3.3 Hz), 10.97 (s, 1H); ESI-MS (m/z %): 349 (MH$^+$, 95), 161 (100); ESI-HRMS calculated for C$_{20}$H$_{21}$N$_4$S (MH$^+$), calculated: 349.1481; observed: 349.1494.

EXAMPLE 33

Preparation of N-(3-(quinuclidin-3-yl)-1H-indol-6-yl)thiophene-2-carboximidamide (112)

3-(6-Nitro-1H-indol-3-yl)-1-azabicyclo[2.2.2]oct-2-ene (109): A solution of compound 105 (1.0 g, 6.167 mmol) in methanol:H$_2$O (20 mL, 1:1) was treated with KOH (1.73 g, 30.835 mmol), followed by 3-quinuclidone hydrochloride (1.99 g, 12.334 mmol) at room temperature and the resulting dark brown mixture was refluxed for 36 h. The reaction was brought to room temperature, filtered and washed with methanol:H$_2$O (3×5 mL, 1:1), followed by methanol (5 mL). The yellow solid was dried under vacuum to obtain compound 109 (1.4 g, 84%). mp 274-276° C.; $^1$H NMR (DMSO-d$_6$) δ 1.46-1.58 (m, 2H), 1.68-1.76 (m, 2H), 2.52-2.58 (m, 2H), 2.89-2.97 (m, 2H), 3.08-3.12 (m, 1H), 6.89 (d, 1H, J=1.2 Hz), 7.91-7.97 (m, 3H), 8.32 (d, 1H, J=1.2 Hz), 11.98 (s, 1H); ESI-MS (m/z, %): 270 (MH$^+$, 100).

3-(1-Azabicyclo[2.2.2]oct-2-en-3-yl)-1H-indol-6-amine (110): Compound 109 (0.4 g, 1.485 mmol) in dry methanol (10 mL) was treated with Ra—Ni (~0.05 g) and hydrazine hydrate (0.46 mL, 1.029 mmol). The resulting mixture was placed in a pre-heated oil bath and refluxed for 2 min (until yellow colour disappears). The reaction was brought to room temperature, filtered through celite bed and washed with methanol (3×10 mL). The combined methanol layer was evaporated and crude was purified by column chromatography (2M NH$_3$ in MeOH:CH$_2$Cl$_2$, 1:9) to obtain compound 110 (0.35 g, quantitative) as a foam. mp 65-67° C.; $^1$H NMR (DMSO-d$_6$) δ 1.42-1.54 (m, 2H), 1.62-1.74 (m, 2H), 2.52-2.56 (m, 2H), 2.86-2.94 (m, 2H), 2.98-3.02 (m, 1H), 4.75 (s, 2H), 6.41 (dd, 1H, J=2.1, 8.4 Hz), 6.53 (d, 1H, J=1.8 Hz), 6.69 (s, 1H), 7.16 (d, 1H, J=2.4 Hz), 7.35 (d, 1H, J=8.4 Hz), 10.57 (s, 1H); ESI-MS (m/z, %): 240 (MH$^+$, 100).

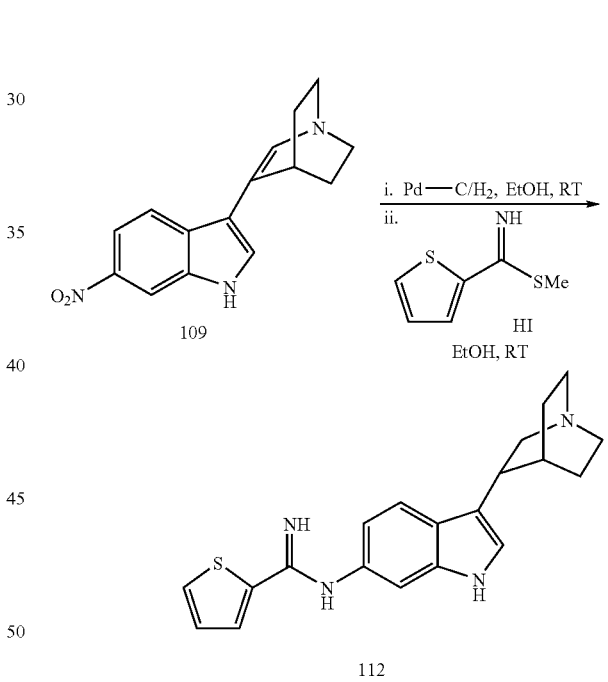

N-(3-(Quinuclidin-3-yl)-1H-indol-6-yl)thiophene-2-carboximidamide (112): Compound 109 (0.4 g, 1.485 mmol) in dry ethanol (10 mL) was treated with Pd—C (~0.05 g), purged with hydrogen gas and stirred for 36 h at room temperature under hydrogen atm (balloon pressure). The reaction was filtered through celite bed and washed with ethanol (2×5 mL). The combined ethanol layer was treated with thiophene-2-carboximidothioic acid methyl ester hydroiodide (0.84 g, 2.970 mmol) at room temperature and stirred for over night (14 h). The solvent was evaporated, crude was diluted with sat. NaHCO$_3$ solution (25 mL) and product was extracted into CH$_2$Cl$_2$ (2×25 mL). The combined CH$_2$Cl$_2$ layer washed with brine (20 mL) and dried (Na$_2$SO$_4$). The solvent was evaporated and crude was purified by column chromatography (2M NH$_3$ in MeOH:CH$_2$Cl$_2$, 1:9) to obtain compound 112 (0.4 g, 77%) as a solid. mp 144-146° C.; $^1$H NMR (DMSO-d$_6$) δ 1.20-1.28 (m, 1H), 1.56-1.74 (m, 3H), 2.62-2.72 (m, 1H), 2.79-2.92 (m, 3H), 3.09-3.34 (m, 4H), 6.30 (s, 2H), 6.53 (d, 1H, J=8.4 Hz), 6.79 (s, 1H), 7.07-7.10 (m, 2H), 7.38 (d, 1H, J=8.4 Hz), 7.58 (d, 1H, J=4.5 Hz), 7.72 (d, 1H, J=3.0 Hz), 10.61 (s, 1H); ESI-MS (m/z, %): 351 (MH$^+$, 38), 176 (100); ESI-HRMS calculated for C$_{20}$H$_{23}$N$_4$S (MH$^+$), calculated: 351.1637; observed: 351.1637.

EXAMPLE 34

Preparation of N-(3-(1-methylpyrrolidin-3-yl)-1H-indol-6-yl) thiophene-2-carboximidamide (117)

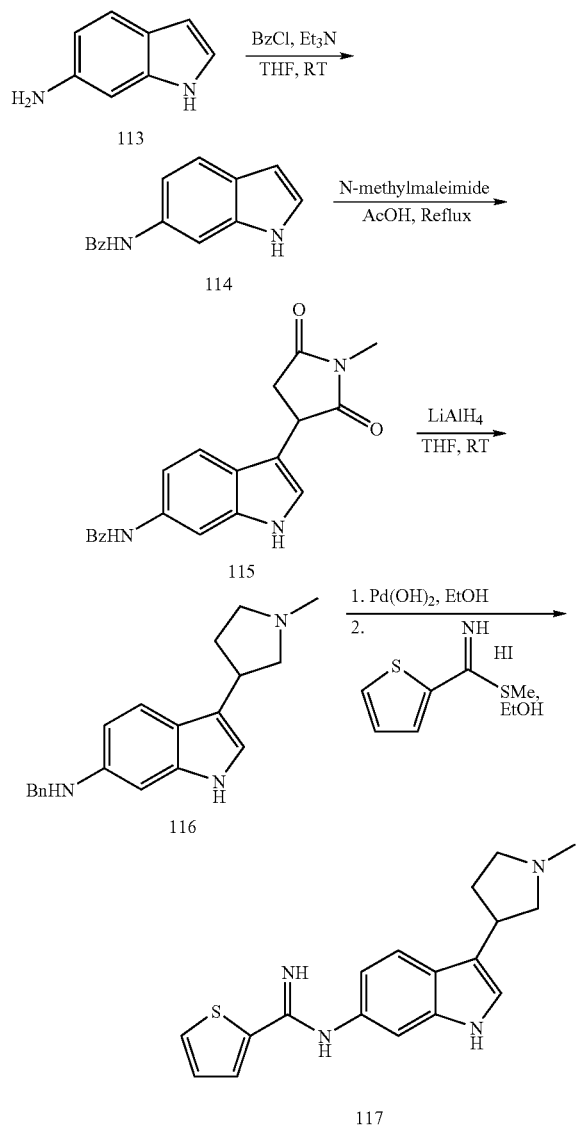

N-(1H-Indol-6-yl)benzamide (114): A solution of compound 113 (2.0 g, 15.133 mmol) in dry THF (30 mL) was treated with Et$_3$N (6.32 mL, 45.399 mmol) followed by benzoyl chloride (1.84 mL, 15.889 mmol) at 0° C. The reaction was brought to room temperature over a period of 30 min. and stirred for 1 h. The reaction was diluted with water (25 mL) and product was extracted into ethyl acetate (2×30 mL). The combined ethyl acetate layer washed with brine (20 mL), dried (Na$_2$SO$_4$) and solvent was evaporated to obtain crude product. The crude was diluted with ethyl acetate (25 mL) followed by hexanes (150 mL) and the precipitate was filtered to obtain compound 114 (3.55 g, 99%) as a solid. $^1$H NMR (CDCl$_3$) δ 6.53 (t, 1H, J=2.4 Hz), 6.95 (dd, 1H, J=2.1, 8.4 Hz), 7.21 (t, 1H, J=2.7 Hz), 7.48-7.60 (m, 4H), 7.88-7.92 (m, 3H), 8.27 (brs, 2H); ESI-MS (m/z, %): 259 (M+Na, 80), 237 (MH$^+$, 100).

N-(3-(1-Methyl-2,5-dioxopyrrolidin-3-yl)-1H-indol-6-yl) benzamide (115): Compound 114 (3.5 g, 14.813 mmol) and N-methylmaleimide (4.07 g, 37.033 mmol) in glacial acetic acid (100 mL) was refluxed for 56 h. The reaction was brought to room temperature and acetic acid was evaporated. The crude solid was taken into ethyl acetate (100 mL), washed with sat. NaHCO$_3$ solution (3×20 mL), brine (20 mL) and dried (Na$_2$SO$_4$). Solvent was evaporated and crude was purified by column chromatography (EtOAc: Hexanes, 1:3 to 1:1) to obtain compound 115 (2.32 g, 45%) as a foam. $^1$H NMR (DMSO-d$_6$) δ 2.80 (dd, 1H, J=5.1, 18.0 Hz), 2.92 (s, 3H), 3.23 (dd, 1H, J=9.3, 18.0 Hz), 4.34 (dd, 1H, J=5.1, 9.3 Hz), 7.26-7.36 (m, 2H), 7.45-7.60 (m, 4H), 7.95-7.98 (m, 2H), 8.07 (s, 1H), 10.17 (s, 1H), 11.02 (s, 1H); ESI-MS (m/z, %) 370 (M+Na, 100), 348 (MH$^+$, 58).

N-Benzyl-3-(1-methylpyrrolidin-3-yl)-1H-indol-6-amine (116): A solution of compound 115 (2.28 g, 6.563 mmol) in dry THF (30 mL) was treated with LiAlH$_4$ (2.49 g, 65.636 mmol) portion wise over a period of 45 min. at 0° C. The reaction was brought to room temperature and stirred for 48 h. The reaction was quenched with sodium sulfate decahydrate (8.0 g) followed by careful addition of water (9 mL) at 0° C. and stirred for 30 min. at room temperature. The reaction was diluted with ethyl acetate (50 mL), filtered and washed with ethyl acetate (2×50 mL). The combined ethyl acetate layer was evaporated and crude was purified by column chromatography (2M NH$_3$ in MeOH:CH$_2$Cl$_2$, 5:95 to 1:9) to obtain compound 116 (0.44 g, 22%) as a foam. $^1$H NMR (DMSO-d$_6$) δ 1.76-1.87 (m, 1H), 2.11-2.23 (m, 1H), 2.27 (s, 3H), 2.36 (t, 1H, J=8.4 Hz), 2.42-2.48 (m, 1H), 2.64-2.71 (m, 1H), 2.90 (t, 1H, J=8.1 Hz), 3.37-3.45 (m, 1H), 4.26 (d, 2H, J=5.7 Hz), 5.88 (t, 1H, J=6.0 Hz), 6.34 (d, 1H, J=0.9 Hz), 6.45 (dd, 1H, J=1.8, 8.4 Hz), 6.72 (d, 1H, J=1.2 Hz), 7.17-7.38 (m, 6H), 10.11 (s, 1H); ESI-MS (m/z, %) 306 (MH$^+$, 100); ESI-HRMS calculated for C$_{20}$H$_{24}$N$_3$ (MH$^+$), calculated: 306.1964, observed: 306.1967.

N-(3-(1-Methylpyrrolidin-3-yl)-1H-indol-6-yl) thiophene-2-carboximidamide (117): A solution of compound 116 (0.42 g, 1.375 mmol) in absolute ethanol (5 mL) was treated with 20% Pd(OH)$_2$ on carbon (0.5 g) at room temperature, then purged with hydrogen gas and stirred under hydrogen atm. (balloon pressure) for 48 h. The reaction was filtered through celite bed and washed with ethanol (2×5 mL). The combined ethanol layer was treated with thiophene-2-carboximidothioic acid methyl ester hydroiodide (0.78 g, 2.750 mmol) at room temperature and stirred for 48 h. The reaction was basified with sat. NaHCO$_3$ solution (30 mL) and product was extracted into CH$_2$Cl$_2$ (2×25 mL). The combined CH$_2$Cl$_2$ layer washed with brine (15 mL) and dried (Na$_2$SO$_4$). Solvent was evaporated and crude was purified by column chromatography (2M NH$_3$ in MeOH:CH$_2$Cl$_2$, 1:9) to obtain compound 117 (0.285 g, 64%) as a solid. mp 89-91° C.; $^1$H NMR (DMSO-d$_6$) δ 1.86-1.95 (m, 1H), 2.18-2.27 (m, 1H), 2.45-2.59 (m, 2H), 2.68-2.76 (m, 1H), 2.96 (t, 1H, J=8.1 Hz), 3.45-3.56 (m, 1H), 6.29 (brs, 2H), 6.54 (dd, 1H, J=1.2, 8.1 Hz), 6.78 (s, 1H), 6.99 (d, 1H, J=1.8 Hz), 7.09 (t, 1H, J=4.2 Hz), 7.49 (d, 1H, J=8.1 Hz), 7.58 (d, 1H, J=4.8 Hz), 7.71 (d, 1H, J=3.6 Hz), 10.51 (s, 1H); ESI-MS (m/z, %) 325 (MH+, 38), 282 (31), 163 (100); ESI-HRMS calculated for $C_{18}H_{21}N_4S$ (MH+), calculated: 325.1481; observed: 325.1495.

EXAMPLE 35

Preparation of N-(3-(4-(methylamino)cyclohexyl)-1H-indol-6-yl)thiophene-2-carboximidamide (123)

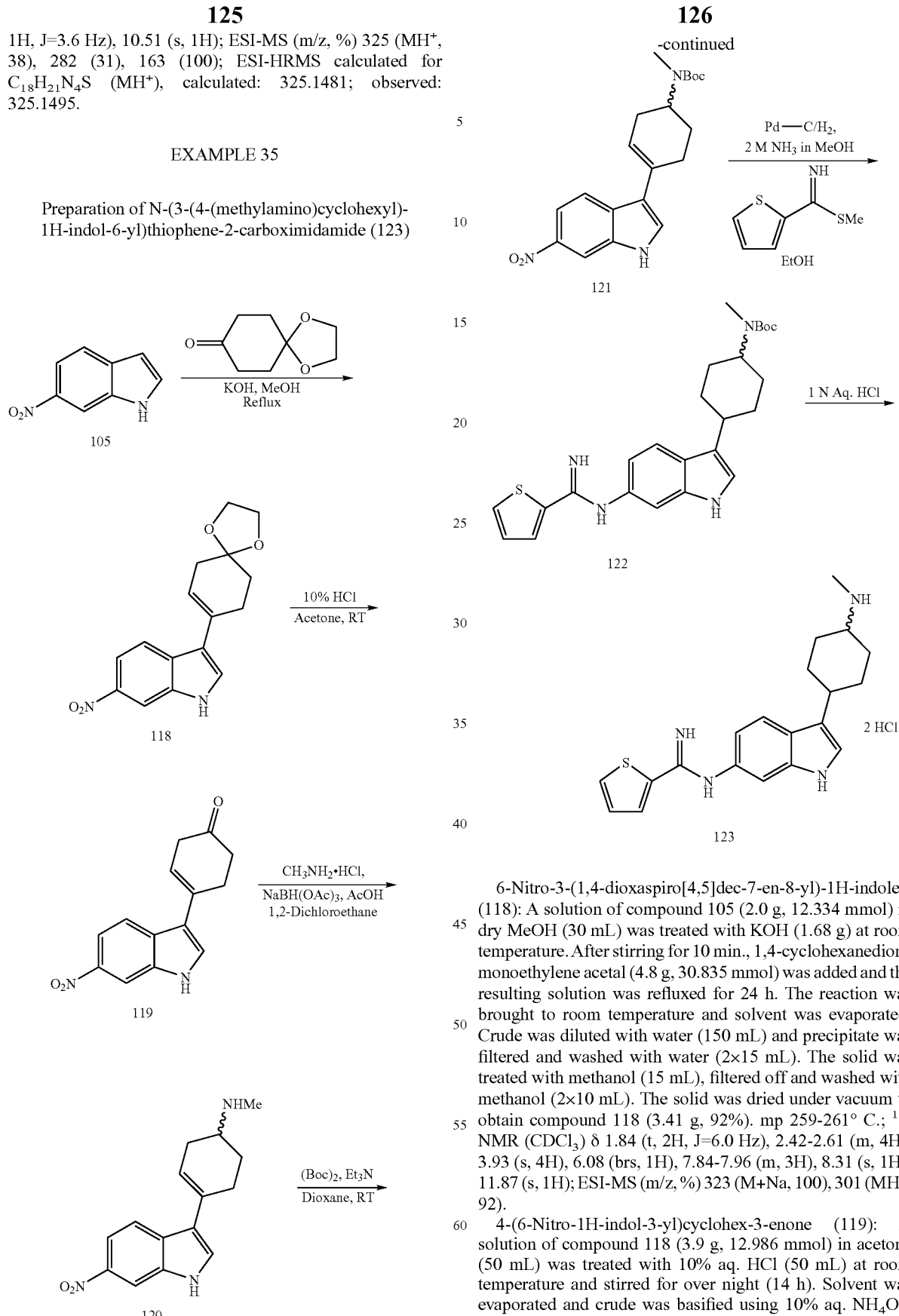

6-Nitro-3-(1,4-dioxaspiro[4,5]dec-7-en-8-yl)-1H-indole (118): A solution of compound 105 (2.0 g, 12.334 mmol) in dry MeOH (30 mL) was treated with KOH (1.68 g) at room temperature. After stirring for 10 min., 1,4-cyclohexanedione monoethylene acetal (4.8 g, 30.835 mmol) was added and the resulting solution was refluxed for 24 h. The reaction was brought to room temperature and solvent was evaporated. Crude was diluted with water (150 mL) and precipitate was filtered and washed with water (2×15 mL). The solid was treated with methanol (15 mL), filtered off and washed with methanol (2×10 mL). The solid was dried under vacuum to obtain compound 118 (3.41 g, 92%). mp 259-261° C.; $^1$H NMR (CDCl$_3$) δ 1.84 (t, 2H, J=6.0 Hz), 2.42-2.61 (m, 4H), 3.93 (s, 4H), 6.08 (brs, 1H), 7.84-7.96 (m, 3H), 8.31 (s, 1H), 11.87 (s, 1H); ESI-MS (m/z, %) 323 (M+Na, 100), 301 (MH+, 92).

4-(6-Nitro-1H-indol-3-yl)cyclohex-3-enone (119): A solution of compound 118 (3.9 g, 12.986 mmol) in acetone (50 mL) was treated with 10% aq. HCl (50 mL) at room temperature and stirred for over night (14 h). Solvent was evaporated and crude was basified using 10% aq. NH$_4$OH solution (100 mL). The solid was filtered off, washed with 10% NH$_4$OH solution (20 mL), water (2×15 mL) and dried under vacuum to obtain compound 119 (2.81 g, 85%) as a yellow solid. mp 175-177° C.; $^1$H NMR (DMSO-d$_6$) δ 2.58 (t, 2H, J=6.9 Hz), 2.90 (t, 2H, J=6.9 Hz), 3.04-3.10 (m, 2H), 6.24 (t, 1H, J=3.9 Hz), 7.90-8.01 (m, 3H), 8.33 (d, 1H, J=2.1 Hz), 11.95 (s, 1H); ESI-MS (m/z, %): 279 (M+Na, 100), 257 (MH$^+$, 33).

N-Methyl-4-(6-nitro-1H-indol-3-yl)cyclohex-3-enamine (120): A solution of compound 119 (0.5 g, 1.951 mmol) in 1,2-dichloroethane (10 mL) was treated with AcOH (0.11 mL, 1.951 mmol), methylamine hydrochloride (0.13 g, 1.951 mmol), NaBH(OAC)$_3$ (0.62 g, 2.926 mmol) at room temperature and stirred for over night (16 h). The reaction was basified with 2 N NaOH (25 mL) and product was extracted into ethyl acetate (2×25 mL). The combined ethyl acetate layer washed with brine (15 mL) and dried (Na$_2$SO$_4$). Solvent was evaporated and crude was purified by column chromatography (2M NH$_3$ in MeOH:CH$_2$Cl$_2$, 1:9) to obtain compound 120 (0.47 g, 89%) as a solid. mp 170-172° C.; $^1$H NMR (DMSO-d$_6$) δ 1.37-1.50 (m, 1H), 1.90-1.99 (m, 2H), 2.33 (s, 3H), 2.43-2.64 (m, 4H), 6.14 (brs, 1H), 7.80 (s, 1H), 7.86-7.96 (m, 2H), 8.30 (d, 1H, J=2.1 Hz); ESI-MS (m/z, %): 272 (MH$^+$, 100), 241 (43).

tert-Butyl methyl(4-(6-nitro-1H-indol-3-yl)cyclohex-3-enyl)carbamate (121): A solution of compound 120 (0.45 g, 1.658 mmol) in dry 1,4-dioxane (10 mL) was treated with Et$_3$N (0.46 mL, 3.317 mmol) followed by (Boc)$_2$O (0.38 g, 1.741 mmol) at room temperature and the resulting solution was stirred for over night (16 h). Solvent was evaporated and crude was purified by column chromatography (EtOAc:Hexanes, 1:1) to obtain compound 121 (0.44 g, 71%) as a solid. mp 229-231° C.; $^1$H NMR (DMSO-d$_6$) δ 1.41 (s, 9H), 1.78-1.90 (m, 2H), 2.22-2.42 (m, 2H), 2.56-2.62 (m, 2H), 2.73 (s, 3H), 4.08-4.16 (m, 1H), 6.18 (brs, 1H), 7.83 (s, 1H), 7.88-7.98 (m, 2H), 8.31 (d, 1H, J=2.1 Hz), 11.87 (s, 1H); ESI-MS (m/z, %): 394 (M+Na, 57), 372 (MH$^+$, 12), 316 (87), 272 (54), 241 (100), 163 (64).

tert-Butyl methyl(4-(6-(thiophene-2-carboximidamido)-1H-indol-3-yl)cyclohexyl)carbamate (122): A solution of compound 121 (0.2 g, 0.538 mmol) in 2M NH$_3$ in MeOH (5 mL) was treated with Pd—C (0.02 g) and flushed with hydrogen gas. The reaction was stirred at room temperature for over night (16 h) under hydrogen atm. (balloon pressure). The solution was filtered using celite bed and washed with methanol (2×15 mL). The solvent was evaporated to obtain crude amine (0.18 g, 98%) as foam.

A solution of above crude amine dry ethanol (5 mL) was treated with thiophene-2-carboximidothioic acid methyl ester hydroiodide (0.30 g, 1.076 mmol) at room temperature and stirred for 24 h. The solvent was evaporated, crude was diluted with sat. NaHCO$_3$ sol. (25 mL) and product was extracted into CH$_2$Cl$_2$ (2×20 mL). The combined CH$_2$Cl$_2$ layer washed with brine (15 mL) and dried (Na$_2$SO$_4$). The solvent was evaporated and crude was purified by column chromatography (2M NH$_3$ in MeOH:CH$_2$Cl$_2$, 5:95) to obtain compound 122 (0.185 g, 76%) as a solid in 1:2 ration of diastereomers. $^1$H NMR (DMSO-d$_6$) δ 1.39, 1.41 (2s, 9H), 1.52-1.84 (m, 6H), 2.06-2.19 (m, 2H), 2.62, 2.72 (2s, 3H), 3.25-3.29 (m, 1H), 3.80-3.90 (m, 1H), 6.35 (brs, 2H), 6.55 (d, 1H, J=8.4 Hz), 6.80, 6.82 (2s, 1H), 6.94-7.14 (m, 2H), 7.45 (t, 1H, J=10.2 Hz), 7.60 (d, 1H, J=5.1 Hz), 7.72 (d, 1H, J=3.6 Hz), 10.52, 10.57 (2s, 1H); ESI-MS (m/z, %): 453 (MH$^+$, 100).

Dihydrochloride salt of N-(3-(4-(methylamino)cyclohexyl)-1H-indol-6-yl)thiophene-2-carboximidamide (123): Compound 122 (0.155 g, 0.342 mmol) was treated with 1N HCl solution (20 mL) at room temperature and the resulting solution was refluxed for 2 h. The reaction was brought to room temperature, filtered and washed with water (2×5 mL). The solvent was evaporated and crude was recrystallised from ethanol/ether to obtain compound 123 (0.12 g, 83%) as a solid in 1:2 ration of diastereomers. $^1$H NMR (DMSO-d$_6$) δ 1.53-1.65 (m, 2H), 1.76-2.20 (m, 6H), 2.54, 2.55 (2s, 3H), 2.70-2.86 (m, 1H), 3.02-3.20 (m, 1H), 7.00 (d, 1H, J=8.1 Hz), 7.25-7.43 (m, 3H), 7.76 (d, 1H, J=8.4 Hz), 8.17 (s, 2H), 8.69 (s, 1H), 9.10-9.20 (m, 2H), 9.69 (s, 1H), 11.22, 11.26 (2s, 1H), 11.49 (s, 1H); ESI-MS (m/z, %): 353 (MH$^+$, 12), 322 (100), 119 (38); ESI-HRMS calculated for C$_{20}$H$_{25}$N$_4$S (MH$^+$ for free base), calculated: 353.1806; observed: 353.1794.

EXAMPLE 36

Preparation of N-(3-(4-(methylamino)cyclohex-1-enyl)-1H-indol-6-yl)thiophene-2-carboximidamide (125)

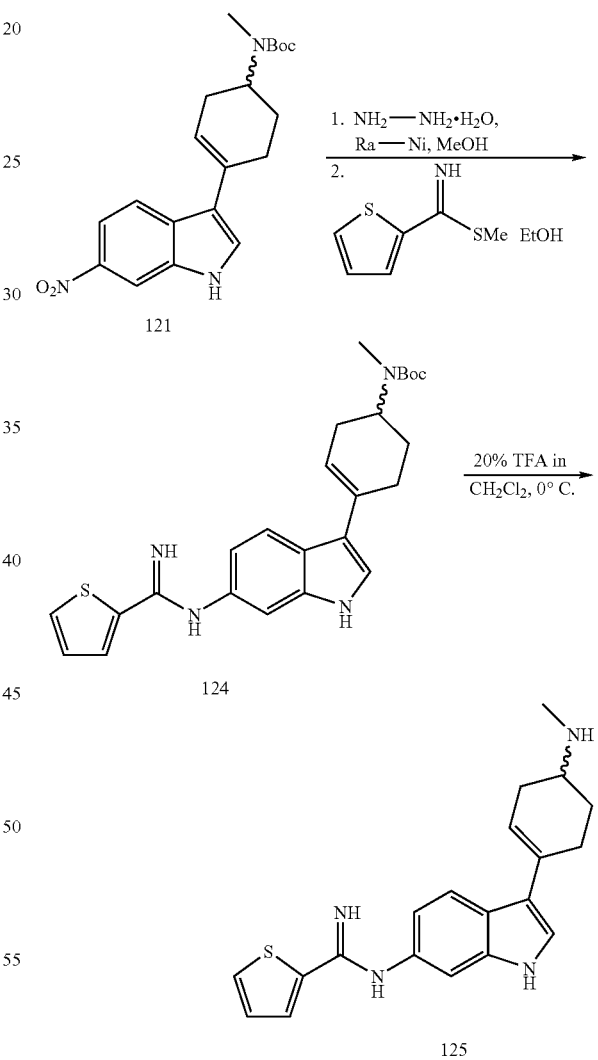

tert-Butyl methyl(4-(6-(thiophene-2-carboximidamido)-1H-indol-3-yl)cyclohex-3-enyl)carbamate (124): A solution of compound 121 (0.2 g, 0.538 mmol) in dry MeOH (3 mL) was treated with hydrazine hydrate (0.16 mL, 5.384 mmol), Ra—Ni (~0.02 g) and the resulting solution was refluxed for 2 min. in a pre-heated oil bath. The reaction was brought to room temperature, filtered using celite bed and washed with MeOH:CH$_2$Cl$_2$ (2×15 mL, 1:1). The solvent was evaporated and crude was purified by column chromatography (2 M NH$_3$ in MeOH:CH$_2$Cl$_2$, 5:95) to obtain free amine (0.18 g, 98%) as a solid. $^1$H NMR (DMSO-d$_6$) δ 1.41 (s, 9H), 1.72-1.84 (m, 2H), 2.16-2.34 (m, 2H), 2.54-2.59 (m, 2H), 2.72 (s, 3H), 4.00-4.16 (m, 1H), 4.82 (s, 2H), 6.03 (brs, 1H), 6.40 (dd, 1H, J=1.8, 8.5 Hz), 6.53 (d, 1H, J=1.8 Hz), 7.01 (d, 1H, J=2.1 Hz), 7.44 (d, 1H, J=8.4 Hz), 10.46 (s, 1H); ESI-MS (m/z, %) 364 (M+Na, 11), 342 (MH$^+$, 6), 286 (100), 211 (32).

A solution of above free amine (0.17 g, 0.497 mmol) in dry ethanol (5 mL) was treated with thiophene-2-carboximidothioic acid methyl ester hydroiodide (0.28 g, 0.995 mmol) at room temperature and stirred for 24 h. The solvent was evaporated, crude was diluted with sat. NaHCO$_3$ sol. (20 mL) and product was extracted into CH$_2$Cl$_2$ (2×20 mL). The combined CH$_2$Cl$_2$ layer washed with brine (20 mL) and dried (Na$_2$SO$_4$). The solvent was evaporated and crude was purified by column chromatography (2M NH$_3$ in MeOH:CH$_2$Cl$_2$, 5:95) to obtain compound 124 (0.17 g, 70%) as a solid. $^1$H NMR (DMSO-d$_6$) δ 1.42 (s, 9H), 1.74-1.90 (m, 2H), 2.18-2.40 (m, 2H), 2.52-2.60 (m, 2H), 2.73 (s, 3H), 4.05-4.20 (m, 1H), 6.11 (s, 1H), 6.31 (s, 2H), 6.60 (d, 1H, J=8.1 Hz), 6.82 (s, 1H), 7.09 (dd, 1H, J=3.9, 4.9 Hz), 7.23 (d, 1H, J=2.1 Hz), 7.59 (d, 1H, J=5.4 Hz), 7.69-7.74 (m, 2H), 10.84 (s, 1H); ESI-MS (m/z, %) 451 (MH$^+$, 100).

N-(3-(4-(Methylamino)cyclohex-1-enyl)-1H-indol-6-yl)thiophene-2-carboximidamide (125): A solution of compound 124 (0.14 g, 0.310 mmol) in CH$_2$Cl$_2$ (5 mL) was treated with 40% TFA in CH$_2$Cl$_2$ (5 mL) at 0° C. and the resulting solution was stirred at same temperature for 3 h. The solvent was evaporated, crude was diluted with 10% cold NH$_4$OH solution (25 mL) and precipitated solid was filtered off. Crude product was dried and purified by column chromatography (2 M NH$_3$ in MeOH:CH$_2$Cl$_2$, 1:9) to obtain compound 125 (0.095 g, 88%) as a solid. $^1$H NMR (DMSO-d$_6$) δ 1.36-1.48 (m, 1H), 1.90-1.98 (m, 2H), 2.34 (s, 3H), 2.38-2.64 (m, 4H), 6.07 (brs, 1H), 6.30 (brs, 2H), 6.58 (dd, 1H, J=1.2, 8.4 Hz), 6.81 (s, 1H), 7.09 (t, 1H, J=4.2 Hz), 7.20 (d, 1H, J=2.1 Hz), 7.59 (d, 1H, J=5.1 Hz), 7.68-7.72 (m, 2H), 10.79 (s, 1H); ESI-MS (m/z, %) 351 (MH$^+$, 100), 119(91); ESI-HRMS calculated for C$_{20}$H$_{23}$N$_4$S (MH$^+$); calculated: 351.1637; observed: 351.1638.

EXAMPLE 37

Preparation of N-(3-(4-(methylamino)cyclohexyl)-1H-indol-6-yl)thiophene-2-carboximidamide (129)

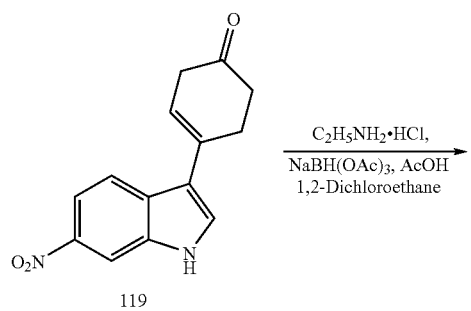

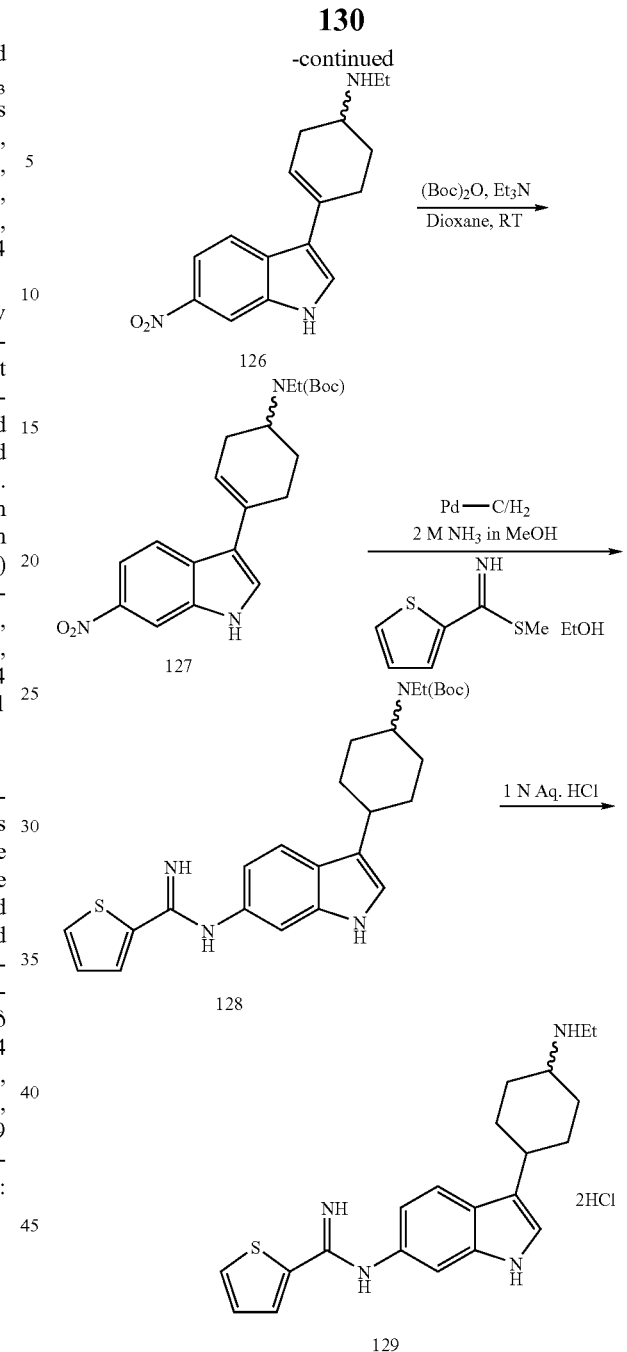

N-Methyl-4-(6-nitro-1H-indol-3-yl)cyclohex-3-enamine (126): A solution of compound 119 (0.5 g, 1.951 mmol) in 1,2-dichloroethane (10 mL) was treated with AcOH (0.11 mL, 1.951 mmol), ethylamine hydrochloride (0.159 g, 1.951 mmol), NaBH(OAC)$_3$ (0.62 g, 2.926 mmol) at room temperature and stirred for overnight (16 h). The reaction was basified with 2N NaOH (25 mL) and product was extracted into ethyl acetate (2×25 mL). The combined ethyl acetate layer washed with brine (15 mL) and dried (Na$_2$SO$_4$). Solvent was evaporated and crude was purified by column chromatography (2M NH$_3$ in MeOH:CH$_2$Cl$_2$, 1:9) to obtain compound 126 (0.55 g, 99%) as a semi-solid. $^1$H NMR (DMSO-d$_6$) δ 1.07 (t, 3H, J=7.2 Hz), 1.47-1.58 (m, 1H), 1.99-2.08 (m, 2H), 2.42-2.59 (m, 3H), 2.67-2.73 (m, 2H), 2.82-2.90 (m, 2H), 6.14 (brs, 1H), 7.81 (s, 1H), 7.86-7.97 (m, 2H), 8.31 (d, 1H, J=2.1 Hz); ESI-MS (m/z, %): 286 (MH$^+$, 100), 241 (33).

tert-Butyl methyl(4-(6-nitro-1H-indol-3-yl)cyclohex-3-enyl)carbamate (127): A solution of compound 126 (0.53 g, 1.857 mmol) in dry 1,4-dioxane (10 mL) was treated with Et$_3$N (0.51 mL, 3.714 mmol) followed by (Boc)$_2$O (0.42 g, 1.950 mmol) at room temperature and the resulting solution was stirred for over night (16 h). Solvent was evaporated and crude was purified by column chromatography (EtOAc: Hexanes, 1:1) to obtain compound 127 (0.6 g, 84%) as a solid. mp 208-210° C.; $^1$H NMR (DMSO-d$_6$) δ 1.09 (t, 3H, J=6.9 Hz), 1.42 (s, 9H), 1.80-1.96 (m, 2H), 2.26-2.40 (m, 2H), 2.56-2.64 (m, 2H), 3.12-3.20 (m, 2H), 4.00-4.10 (m, 1H), 6.17 (brs, 1H), 7.82 (s, 1H), 7.90-7.97 (m, 2H), 8.31 (d, 1H, J=1.8 Hz), 11.87 (s, 1H); ESI-MS (m/z, %): 408 (M+Na, 88), 330 (100), 328 (39), 286 (73).

tert-Butyl methyl(4-(6-(thiophene-2-carboximidamido)-1H-indol-3-yl)cyclohexyl)carbamate (128): A solution of compound 127 (0.2 g, 0.518 mmol) in 2 M NH$_3$ in MeOH (5 mL) was treated with Pd—C (0.02 g) and flushed with hydrogen gas. The reaction was stirred at room temperature for over night (16 h) under hydrogen atm. (balloon pressure). The solution was filtered using celite bed and washed with methanol (2×15 mL). The solvent was evaporated to obtain crude amine (0.18 g, 97%) as foam.

A solution of above crude amine in dry ethanol (5 mL) was treated with thiophene-2-carboximidothioic acid methyl ester hydroiodide (0.29 g, 1.037 mmol) at room temperature and stirred for 24 h. The solvent was evaporated, crude was diluted with sat. NaHCO$_3$ sol. (25 mL) and product was extracted into (2×20 mL). The combined CH$_2$Cl$_2$ layer washed with brine (15 mL) and dried (Na$_2$SO$_4$). The solvent was evaporated and crude was purified by column chromatography (2M NH$_3$ in MeOH:CH$_2$Cl$_2$, 5:95) to obtain compound 128 (0.16 g, 66%) as a solid in 1:1 ration of diastereomers. $^1$H NMR (DMSO-d$_6$) δ 1.00, 1.08 (2t, 3H, J=6.9 Hz), 1.38-1.59 (m, 11H), 1.70-1.87 (m, 4H), 2.07 (d, 1H, J=11.1 Hz), 2.17 (d, 1H, J=10.8 Hz), 2.66-2.76 (m, 1H), 3.00-3.17 (m, 2H), 3.70-3.80 (m, 1H), 6.34 (brs, 2H), 6.55 (d, 1H, J=8.4 Hz), 6.81 (d, 1H, J=6.6 Hz), 6.93, 7.14 (2s, 1H), 7.09 (t, 1H, J=4.2 Hz), 7.44 (dd, 1H, J=8.4, 11.5 Hz), 7.60 (d, 1H, J=5.1 Hz), 7.72 (d, 1H, J=3.3 Hz), 10.52, 10.56 (2s, 1H); ESI-MS (m/z, %): 467 (MH$^+$, 100).

Dihydrochloride salt of N-(3-(4-(methylamino)cyclohexyl)-1H-indol-6-yl)thiophene-2-carboximidamide (129): Compound 128 (0.115 g, 0.246 mmol) was treated with 1N HCl solution (20 mL) at room temperature and the resulting solution was refluxed for 2 h. The reaction was brought to room temperature, filtered and washed with water (2×5 mL). The solvent was evaporated and crude was recrystallised from ethanol/ether to obtain compound 129 (0.08 g, 74%) as a solid in 1:1 ration of diastereomers. $^1$H NMR (DMSO-d$_6$) δ 1.23-1.29 (m, 3H), 1.52-1.66 (m, 2H), 1.80-1.92 (m, 4H), 2.00-2.20 (m, 2H), 2.79-3.24 (m, 4H), 7.00 (d, 1H, J=8.1 Hz), 7.25-7.43 (m, 3H), 7.76 (t, 1H, J=7.5 Hz), 8.17 (d, 2H, J=4.2 Hz), 8.70 (s, 1H), 8.91 (s, 1H), 9.01 (s, 1H), 9.68 (s, 1H), 11.21, 11.27 (2s, 1H), 11.47 (s, 1H); ESI-MS (m/z, %): 367 (MH$^+$, 12), 322 (100), 119 (38); ESI-HRMS calculated for C$_{21}$H$_{27}$N$_4$S (MH$^+$ for free base), calculated: 367.1968; observed: 367.1950.

EXAMPLE 38

Preparation of -(3-(4-(ethylamino)cyclohex-1-enyl)-1H-indol-6-yl)thiophene-2-carboximidamide (132)

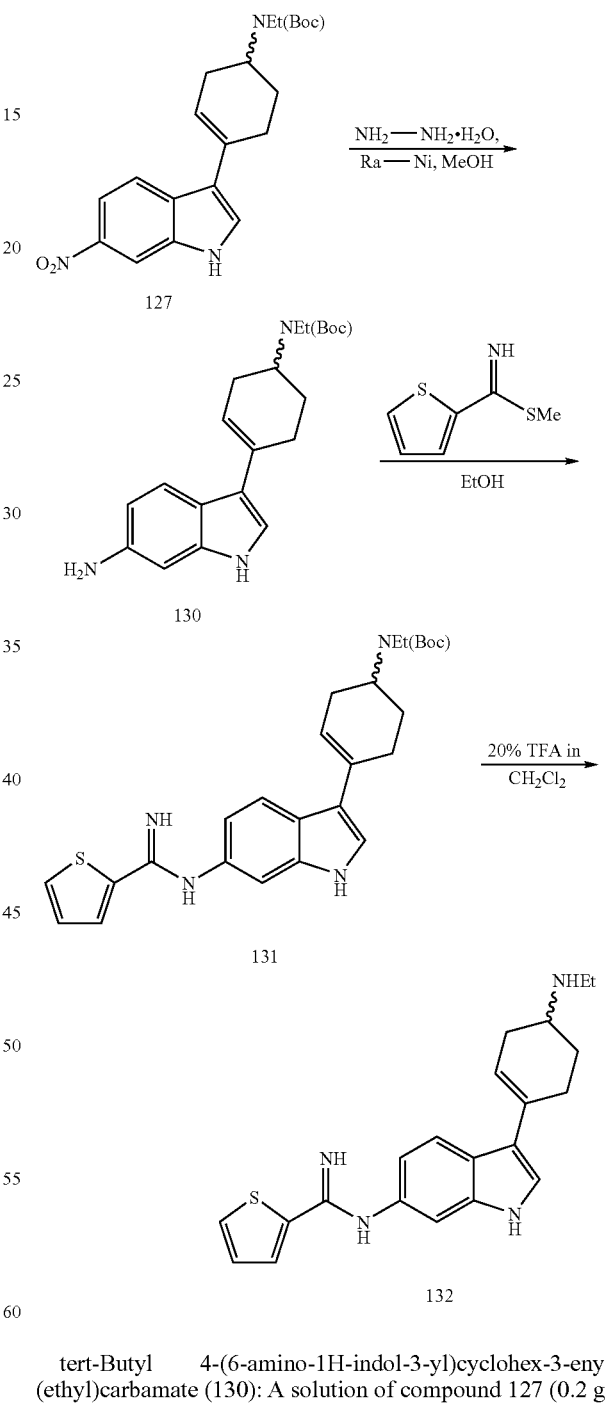

tert-Butyl 4-(6-amino-1H-indol-3-yl)cyclohex-3-enyl (ethyl)carbamate (130): A solution of compound 127 (0.2 g, 0.518 mmol) in dry MeOH (3 mL) was treated with Ra—Ni (0.02 g) followed by hydrazine hydrate (0.16 mL, 5.188 mmol) at room temperature. The reaction was placed in a pre-heated oil bath and refluxed for 2 min. The reaction brought to room temperature, filtered through celite bed and washed with methanol (2×15 mL). The solvent was evaporated and crude was purified by column chromatography (2M NH₃ in MeOH:CH₂Cl₂, 2.5:97.5) to obtain compound 130 as a foam. ¹H NMR (DMSO-d₆) δ 1.08 (t, 3H, J=6.9 Hz), 1.41 (s, 9H), 1.72-1.89 (m, 2H), 2.18-2.60 (m, 4H), 3.10-3.20 (m, 2H), 4.01 (brs, 1H), 4.71 (s, 2H), 6.02 (brs, 1H), 6.39 (dd, 1H, J=1.5, 8.5 Hz), 6.51 (d, 1H, J=1.8 Hz), 6.99 (d, 1H, J=2.1 Hz), 7.43 (d, 1H, J=8.4 Hz), 10.44 (s, 1H); ESI-MS (m/z, %): 378 (M+Na, 8), 356 (MH⁺, 4), 300 (100).

tert-Butyl ethyl(4-(6-(thiophene-2-carboximidamido)-1H-indol-3-yl)cyclohex-3-enyl)carbamate (131): A solution of above compound 130 in dry EtOH (5 mL) was treated with thiophene-2-carboximidothioic acid methyl ester hydroiodide (0.29 g, 1.037 mmol) at room temperature and stirred for 24 h. Solvent was evaporated and crude was diluted with sat. NaHCO₃ solution (20 mL) and product was extracted into CH₂Cl₂ (2×20 mL). The combined CH₂Cl₂ layer washed with brine (15 mL) and dried (Na₂SO₄). Solvent was evaporated and crude was purified by column chromatography (2M NH₃ in MeOH:CH₂Cl₂, 5:95) to obtain compound 131 (0.18 g, 75%, over two steps) as a yellow solid. mp 110-112° C.; ¹H NMR (DMSO-d₆) δ 1.09 (t, 3H, J=6.6 Hz), 1.42 (s, 9H), 1.82-1.93 (m, 2H), 2.22-2.64 (m, 4H), 3.12-3.18 (m, 2H), 4.06 (brs, 1H), 6.10 (s, 1H), 6.32 (s, 2H), 6.60 (d, 1H, J=8.4 Hz), 6.82 (s, 1H), 7.09 (t, 1H, J=4.5 Hz), 7.23 (s, 1H), 7.59 (d, 1H, J=4.8 Hz), 7.68-7.73 (m, 2H), 10.84 (s, 1H); ESI-MS (m/z, %) 465 (MH⁺, 100).

N-(3-(4-(Ethylamino)cyclohex-1-enyl)-1H-indol-6-yl)thiophene-2-carboximidamide (132): A solution of compound 131 (0.08 g, 0.172 mmol) was treated with 20% TFA in CH₂Cl₂ (10 mL) at 0° C. and stirring was continued for 2 h at same temperature. Solvent was evaporated and crude was diluted with 10% aq. NH₄OH (25 mL) and product was extracted into CH₂Cl₂ (2 20 mL). The combined CH₂Cl₂ layer washed with brine (15 mL) and dried (Na₂SO₄). Solvent was evaporated and crude was purified by column chromatography (2M NH₃ in MeOH: CH₂Cl₂, 1:9) to obtain compound 132 (0.055 g, 89%) as a solid. Compound was repurified using reverse phase column chromatography (CH₃CN: pH 10.6 buffer, 20:80 to 55:45) on biotage to obtain pure product. mp 95-97° C.; ¹H NMR (DMSO-d₆) δ 1.04 (t, 3H, J=7.2 Hz), 1.38-1.49 (m, 1H), 1.91-1.99 (m, 2H), 2.40-2.48 (m, 2H), 2.56-2.80 (m, 4H), 6.07 (s, 1H), 6.30 (s, 2H), 6.59 (d, 1H, J=8.4 Hz), 6.81 (s, 1H), 7.09 (t, 1H, J=4.5 Hz), 7.20 (d, 1H, J=2.1 Hz), 7.59 (d, 1H, J=5.1 Hz), 7.68-7.72 (m, 2H), 10.80 (s, 1H); ESI-MS (m/z, %) 365 (MH⁺, 7), 160 (50), 119 (100); ESI-HRMS calculated for C₂₁H₂₅N₄S (MH⁺), calculated: 365.1794; observed: 365.1801.

EXAMPLE 39

Preparation of N-(3-((1s,4s)-4-(propylamino)cyclohexyl)-1H-indol-6-yl)thiophene-2-carboximidamide (137) and N-(3-((1r,4r)-4-(propylamino)cyclohexyl)-1H-indol-6-yl)thiophene-2-carboximidamide (138)

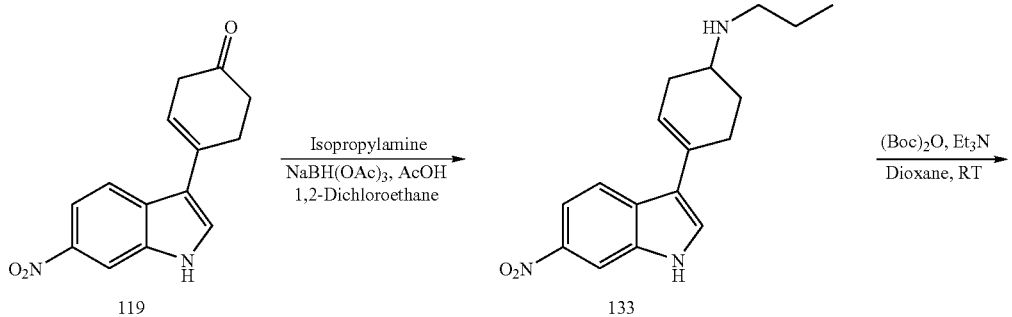

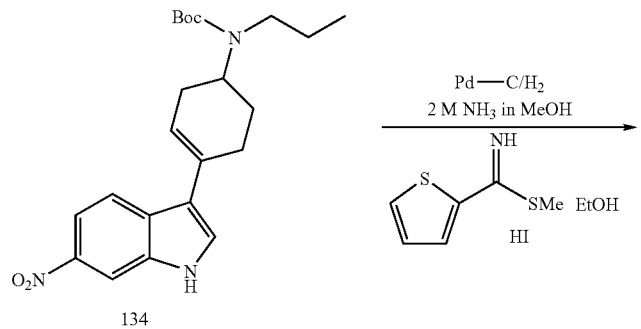

-continued

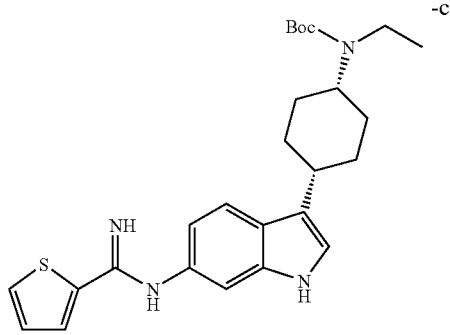

135

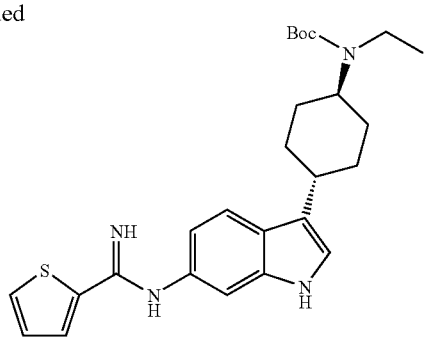

136

↓ 1 N Aq. HCl

↓ 25% TFA in CH₂Cl₂, 0° C.

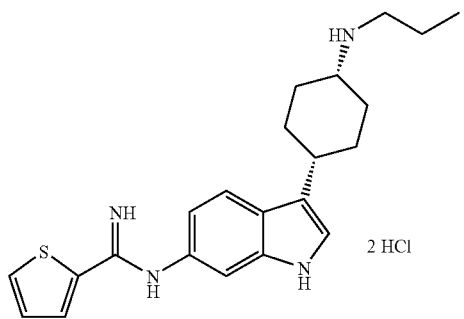

2 HCl

137

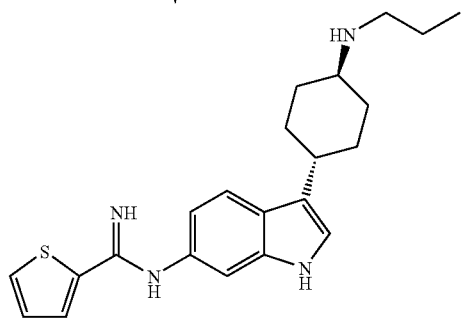

138

4-(6-Nitro-1H-indol-3-yl)-N-propylcyclohex-3-enamine (133): A solution of compound 119 (0.75 g, 2.926 mmol) in 1,2-dichloroethane (20 mL) was treated with AcOH (0.16 mL, 2.926 mmol), n-propylamine (0.24 g, 2.926 mmol), NaBH(OAc)₃ (0.93 g, 4.390 mmol) at room temperature and stirred for over night (16 h). The reaction was basified with 2 N NaOH (25 mL) and product was extracted into ethyl acetate (3×50 mL). The combined ethyl acetate layer was washed with brine (20 mL) and dried (Na₂SO₄). Solvent was evaporated and crude was purified by column chromatography (2 M NH₃ in MeOH:CH₂Cl₂, 1:9) to obtain compound 133 (0.58 g, 66%) as a brown semi-solid. $^1$H NMR (DMSO-d₆) δ 0.89 (t, 3H, J=7.2 Hz), 1.37-1.51 (m, 4H), 1.91-2.00 (m, 2H), 2.44-2.57 (m, 4H), 2.68-2.76 (m, 1H), 6.14 (s, 1H), 7.80 (s, 1H), 7.86-7.97 (m, 2H), 8.30 (d, 1H, J=2.1 Hz), 11.82 (brs, 1H); ESI-MS (m/z, %) 300 (MH⁺, 100).

tert-Butyl 4-(6-nitro-1H-indol-3-yl)cyclohex-3-enyl(propyl)carbamate (134): A solution of compound 133 (0.56 g, 1.870 mmol) in dry 1,4-dioxane (20 mL) was treated with Et₃N (0.52 mL, 3.741 mmol) followed by (Boc)₂O (0.42 g, 1.964 mmol) at room temperature and the resulting solution was stirred for over night (16 h). Solvent was evaporated and crude was purified by column chromatography (EtOAc: Hexanes, 1:1) to obtain compound 134 (0.67 g, 90%) as a solid. mp 214-216° C.; $^1$H NMR (DMSO-d₆) δ 0.84 (t, 3H, J=7.2 Hz), 1.41 (s, 9H), 1.47-1.54 (m, 2H), 1.76-2.01 (m, 2H), 2.25-2.64 (m, 4H), 3.06 (t, 2H, J=6.9 Hz), 3.89-4.06 (m, 1H), 6.17 (brs, 1H), 7.82 (d, 1H, J=2.7 Hz), 7.89 (dd, 1H, J=2.4, 9.0 Hz), 7.96 (d, 1H, J=9.0 Hz), 8.31 (d, 1H, J=2.1 Hz), 11.86 (s, 1H); ESI-MS (m/z, %) 422 (M+Na, 23), 359 (100), 352 (48).

tert-Butyl propyl ((1s,4s)-4-(6-(thiophene-2-carboximidamido)-1H-indol-3-yl)cyclohexyl)carbamate (135) and tert-butyl propyl((1r,4r)-4-(6-(thiophene-2-carboximidamido)-1H-indol-3-yl)cyclohexyl)carbamate (136): A solution of compound 134 (0.2 g, 0.500 mmol) in 2 M NH₃ in MeOH (5 mL) was treated with Pd—C (0.02 g) and flushed with hydrogen gas. The reaction was stirred at room temperature for over night (14 h) under hydrogen atm. (balloon pressure). The solution was filtered using celite bed and washed with methanol:CH₂Cl₂, (2×15 mL, 1:1). The combined solvent was evaporated to obtain crude amine as a mixture of diastereomers.

A solution of above crude amine in dry ethanol (10 mL) was treated with thiophene-2-carboximidothioic acid methyl ester hydroiodide (0.28 g, 0.995 mmol) at room temperature and stirred for over night (16 h). The solvent was evaporated, crude was diluted with sat. NaHCO₃ sol. (20 mL) and product was extracted into CH₂Cl₂ (2×20 mL). The combined CH₂Cl₂ layer washed with brine (20 mL) and dried (Na₂SO₄). The solvent was evaporated and crude was purified by column chromatography (2M NH₃ in MeOH:CH₂Cl₂, 5:95) to obtain compound 135 and 136 (0.19 g, 79% over two steps) as a partially separable mixture of diastereomers. Faster isomer (135): 0.05 g, solid, mp 127-129° C.; $^1$H NMR (DMSO-d₆) δ 0.78 (t, 3H, J=7.2 Hz), 1.37 (s, 9H), 1.41-1.43 (m, 4H), 1.71-1.87 (m, 4H), 2.12-2.22 (m, 2H), 2.96 (t, 2H, J=7.5 Hz), 3.20-3.28 (m, 1H), 3.62-3.72 (m, 1H), 6.56 (brs, 1H), 6.59 (d, 1H, J=8.1 Hz), 6.86 (s, 1H), 7.12 (t, 1H, J=4.2 Hz), 7.17 (s, 1H), 7.44 (d, 1H, J=8.4 Hz), 7.64 (d, 1H, J=4.8 Hz), 7.75 (d, 1H, J=3.3 Hz), 10.61 (s, 1H); ESI-MS (m/z, %) 481 (MH⁺, 100); Slower isomer (136): 0.04 g, solid, mp 78-80° C.; $^1$H NMR (DMSO-d₆) δ 0.85 (t, 3H, J=7.5 Hz), 1.41 (s, 9H), 1.46-1.59 (m, 4H), 1.70-1.76 (m, 4H), 2.06 (d, 2H, J=12.0 Hz), 2.67-2.74 (m, 1H), 3.05 (brs, 2H), 3.62-3.78 (m, 1H), 6.32 (brs, 2H), 6.54 (dd, 1H, J=0.9, 8.2 Hz), 6.79 (s, 1H), 6.93 (d, 1H, J=1.5 Hz), 7.09 (t, 1H, J=4.5 Hz), 7.46 (d, 1H, J=8.4 Hz), 7.59 (d, 1H, J=5.1 Hz), 7.72 (d, 1H, J=3.3 Hz), 10.51 (s, 1H); ESI-MS (m/z, %) 481 (MH$^+$, 100).

Dihydrochloride salt of N-(3-((1s,4s)-4-(propylamino)cyclohexyl)-1H-indol-6-yl)thiophene-2-carboximidamide (137): Compound 135 (0.033 g, 0.068 mmol) was treated with 1 N HCl solution (20 mL) at room temperature and the resulting solution was refluxed for 2 h. The reaction was brought to room temperature, filtered and washed with water (2×5 mL). The solvent was evaporated and crude was recrystallised from ethanol/ether to obtain compound 137 (0.027 g, 87%) as a solid. $^1$H NMR (DMSO-d$_6$) δ 0.93 (t, 3H, J=7.5 Hz), 1.67-1.75 (m, 2H), 1.80-1.92 (m, 6H), 2.00-2.08 (m, 2H), 2.80-2.90 (m, 2H), 3.08-3.14 (m, 1H), 3.22-3.26 (m, 1H), 7.00 (d, 1H, J=8.1 Hz), 7.37-7.43 (m, 3H), 7.74 (d, 1H, J=8.4 Hz), 8.15 (s, 2H), 8.70 (s, 1H), 8.83 (brs, 2H), 9.68 (s, 1H), 11.26 (s, 1H), 11.45 (s, 1H); EI-MS (m/z, %) 380 (M$^+$, free base, 100), 267 (47), 158 (52); EI-HRMS calculated for C$_{22}$H$_{28}$N$_4$S (M$^+$, free base), calculated: 380.203469; observed: 380.203595.

N-(3-((1r,4r)-4-(Propylamino)cyclohexyl)-1H-indol-6-yl)thiophene-2-carboximidamide (138): Compound 136 (0.03 g, 0.062 mmol) was treated with 25% TFA in CH$_2$Cl$_2$ (5 mL) at 0° C. and the resulting solution was stirred at same temperature for 2 h. The solvent was evaporated, crude was diluted with 2N NaOH solution (20 mL) and product was extracted into CH$_2$Cl$_2$ (2×20 mL). The combined CH$_2$Cl$_2$ layer washed with brine (10 mL) and dried (Na$_2$SO$_4$). The solvent was evaporated and crude was purified by column chromatography (2M NH$_3$ in MeOH: CH$_2$Cl$_2$, 5:95) to obtain compound 138 (0.021 g, 91%) as a solid. $^1$H NMR (DMSO-d$_6$) δ 0.88 (t, 3H, J=7.5 Hz), 1.12-1.24 (m, 3H), 1.33-1.54 (m, 5H), 1.96-2.10 (m, 4H), 2.38-2.46 (m, 2H), 2.62-2.72 (m, 1H), 6.26 (s, 2H), 6.52 (dd, 1H, J=1.8, 8.2 Hz), 6.77 (s, 1H), 6.91 (d, 1H, J=1.5 Hz), 7.09 (dd, 1H, J=3.9, 4.9 Hz), 7.45 (d, 1H, J=8.1 Hz), 7.58 (d, 1H, J=5.1 Hz), 7.71 (d, 1H, J=3.6 Hz), 10.47 (s, 1H); ESI-MS (m/z, %): 381 (MH$^+$, 74), 322 (100), 191 (35), 119 (44); ESI-HRMS calculated for C$_{22}$H$_{29}$N$_4$S (MH$^+$), calculated: 381.2107; observed: 381.2105.

EXAMPLE 40

Preparation of N-(3-(4-(isopropylamino)cyclohex-1-enyl)-1H-indol-6-yl)thiophene-2-carboximidamide (142)

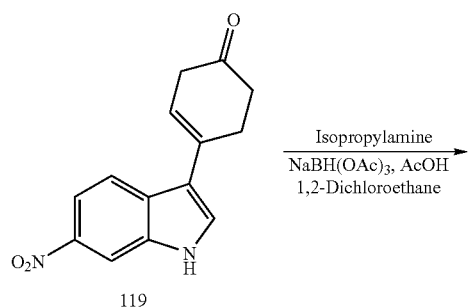

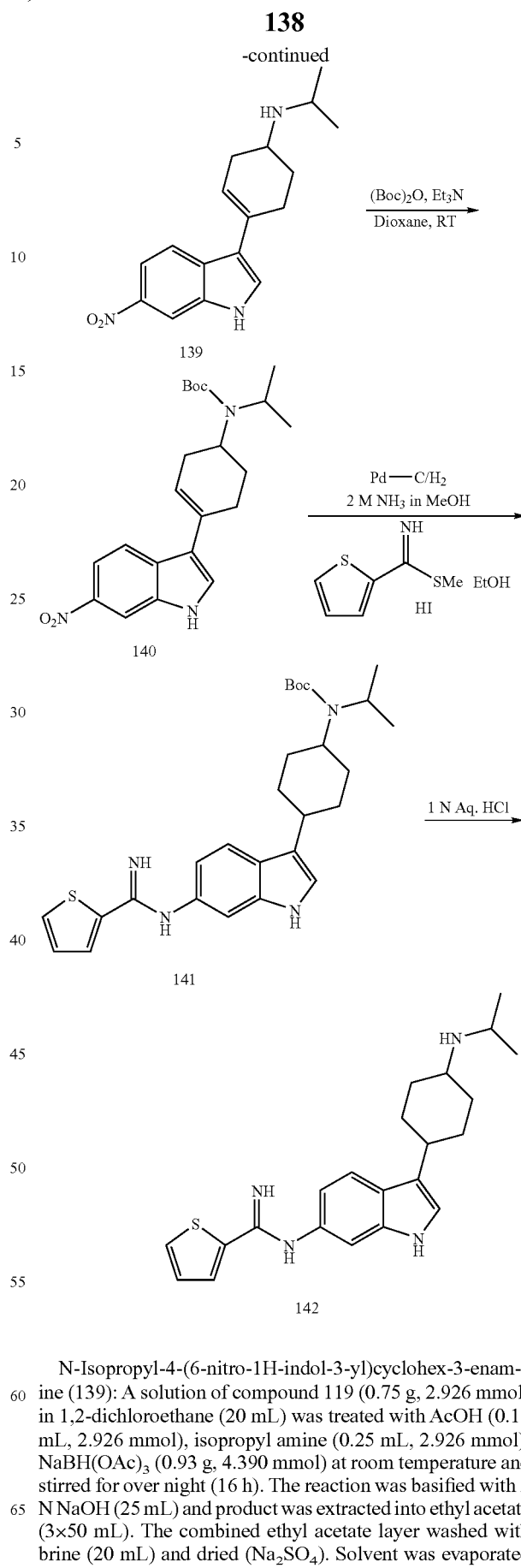

N-Isopropyl-4-(6-nitro-1H-indol-3-yl)cyclohex-3-enamine (139): A solution of compound 119 (0.75 g, 2.926 mmol) in 1,2-dichloroethane (20 mL) was treated with AcOH (0.16 mL, 2.926 mmol), isopropyl amine (0.25 mL, 2.926 mmol), NaBH(OAc)$_3$ (0.93 g, 4.390 mmol) at room temperature and stirred for over night (16 h). The reaction was basified with 2 N NaOH (25 mL) and product was extracted into ethyl acetate (3×50 mL). The combined ethyl acetate layer washed with brine (20 mL) and dried (Na$_2$SO$_4$). Solvent was evaporated and crude was purified by column chromatography (2 M NH$_3$ in MeOH:CH$_2$Cl$_2$, 1:9) to obtain compound 139 (0.636 g, 73%) as a semi-solid. $^1$H NMR (DMSO-d$_6$) δ 0.99 (d, 6H, J=6.0 Hz), 1.36-1.47 (m, 1H), 1.89-1.97 (m, 2H), 2.45-2.56 (m, 2H), 2.81-2.89 (m, 1H), 2.91-2.99 (m, 1H), 3.16 (brs, 1H), 6.14 (brs, 1H), 7.80 (s, 1H), 7.88 (dd, 1H, J=2.1, 9.0 Hz), 7.95 (d, 1H, J=9.0 Hz), 8.30 (d, 1H, J=2.1 Hz), 11.83 (brs, 1H); ESI-MS (m/z, %) 300 (MH$^+$, 100), 241 (35).

tert-Butyl isopropyl(4-(6-nitro-1H-indol-3-yl)cyclohex-3-enyl)carbamate (140): A solution of compound 139 (0.615 g, 2.054 mmol) in dry 1,4-dioxane (20 mL) was treated with Et$_3$N (0.57 mL, 4.108 mmol) followed by (Boc)$_2$O (0.47 g, 2.157 mmol) at room temperature and the resulting solution was stirred for 4 days. Solvent was evaporated and crude was purified by column chromatography (EtOAc: Hexanes, 1:1) to obtain compound 140 (0.55 g, 67%) as a solid with minor amount of di-Boc protected compound.

tert-Butyl isopropyl(4-(6-(thiophene-2-carboximida-mido)-1H-indol-3-yl)cyclohex-3-enyl)carbamate (141): A solution of compound 140 (0.34 g, 0.851 mmol) in 2M NH$_3$ in MeOH (15 mL) was treated with Pd—C (0.05 g) and flushed with hydrogen gas. The reaction was stirred at room temperature for over night (16 h) under hydrogen atm. (balloon pressure). The solution was filtered using celite bed and washed with methanol (2×15 mL). The solvent was evaporated to obtain crude amine as foam.

A solution of above crude amine in dry ethanol (15 mL) was treated with thiophene-2-carboximidothioic acid methyl ester hydroiodide (0.48 g, 1.702 mmol) at room temperature and stirred for 24 h. The solvent was evaporated, crude was diluted with sat. NaHCO$_3$ sol. (25 mL) and product was extracted into CH$_2$Cl$_2$ (2×20 mL). The combined CH$_2$Cl$_2$ layer washed with brine (15 mL) and dried (Na$_2$SO$_4$). The solvent was evaporated and crude was purified by column chromatography (2M NH$_3$ in MeOH:CH$_2$Cl$_2$, 5:95) to obtain compound 141 (0.22 g, 55%) as a solid, including minor amount of di-Boc protected compound as a mixture of diastereomers.

N-(3-(4-(Isopropylamino)cyclohex-1-enyl)-1H-indol-6-yl)thiophene-2-carboximidamide (142): Compound 141 (0.2 g, 0.416 mmol) was treated with 1N HCl solution (20 mL) at room temperature and the resulting solution was refluxed for 2 h. The reaction was brought to room temperature, filtered and washed with water (2×5 mL). The solvent was evaporated to obtain dihydrochloride salt of compound 142 (0.13 g, 69%) as a foam. The product was further purified by reverse phase column chromatography (CH$_3$CN: pH 10.6 Buffer, 1:4 to 1:1) to obtain compound 142 as a mixture of diastereomers in 2:3 ratio. $^1$H NMR (DMSO-d$_6$) δ 0.91-1.00 (m, 6H), 1.05-1.23 (m, 2H), 1.44-1.70 (m, 4H), 1.81-2.00 (m, 3H), 2.62-2.72 (m, 1H), 2.78-2.95 (m, 2H), 6.26 (s, 2H), 6.52 (d, 1H, J=8.1 Hz), 6.77 (s, 1H), 6.93 (d, 1H, J=12.9 Hz), 7.09 (t, 1H, J=4.5 Hz), 7.45 (d, 1H, J=8.4 Hz), 7.58 (d, 1H, J=5.1 Hz), 7.71 (d, 1H, J=3.0 Hz), 10.47 (s, 1H); ESI-MS (m/z, %) 381 (MH$^+$, 46), 339 (36), 322 (100), 119 (56); ESI-HRMS calculated for C$_{22}$H$_{29}$N$_4$S (MH$^+$), calculated: 381.2107; observed: 381.2105.

NOS In Vitro Inhibition Assays

The compounds of the present invention have been found to exhibit selective inhibition of the neuronal isoform of NOS (nNOS). Compounds may be examined for their efficacy in preferentially inhibiting nNOS over iNOS and/or eNOS by a person skilled in the art, for example, by using the methods described in Examples 18 and herein below.

EXAMPLE 18 nNOS (Human), eNOS (Human) and iNOS (Human) Enzyme Assay

Recombinant human inducible NOS (iNOS), human endothelial constitutive NOS (eNOS) or human neuronal constitutive NOS(nNOS) were produced in Baculovirus-infected Sf9 cells (ALEXIS). In a radiometric method, NO synthase activity was determined by measuring the conversion of [$^3$H]L-arginine to [$^3$H]L-citrulline. To measure iNOS, 10 μL of enzyme was added to 100 μL of 100 mM HEPES, pH=7.4, containing 1 mM CaCl$_2$, 1 mM EDTA, 1 mM dithiotheitol, 1 μM FMN, 1 μM FAD, 10 μM tetrahydrobiopterin, 120 μM NADPH, and 100 nM CaM. To measure eNOS or nNOS, 10 μL of enzyme was added to 100 μL of 40 mM HEPES, pH=7.4, containing 2.4 mM CaCl$_2$, 1 mM MgCl$_2$, 1 mg/mL BSA, 1 mM EDTA, 1 mM dithiothreitol, 1 μM FMN, 1 μM FAD, 10 μM tetrahydrobiopterin, 1 mM NADPH, and 1.2 μM CaM.

To measure enzyme inhibition, a 15 μL solution of a test substance was added to the enzyme assay solution, followed by a pre-incubation time of 15 min at RT. The reaction was initiated by addition of 20 μL L-arginine containing 0.25 μCi of [$^3$H]arginine/mL and 24 μM L-arginine. The total volume of the reaction mixture was 150 μL in every well. The reactions were carried out at 37° C. for 45 min. The reaction was stopped by adding 20 μL of ice-cold buffer containing 100 mM HEPES, 3 mM EGTA, 3 mM EDTA, pH=5.5. [$^3$H]L-citrulline was separated by DOWEX (ion-exchange resin DOWEX 50 W X 8-400, SIGMA) and the DOWEX was removed by spinning at 12,000 g for 10 min in the centrifuge. An 70 μL aliquot of the supernatant was added to 100 μL of scintillation fluid and the samples were counted in a liquid scintillation counter (1450 Microbeta Jet, Wallac). Specific NOS activity was reported as the difference between the activity recovered from the test solution and that observed in a control sample containing 240 mM of the inhibitor L-NMMA. All assays were performed at least in duplicate. Standard deviations were 10% or less. Results for exemplary compounds of the invention are shown in Table 3. These results again show the selectivity of the compounds of the invention for nNOS inhibition.

TABLE 3

Selective inhibition of human NOS by compounds of the Invention

| Ex No. | Compound No | Structure | Human nNOS (μM) | Human eNOS (μM) | Human iNOS (μM) | Ratio e/n |
|---|---|---|---|---|---|---|
| 1 | 6 | 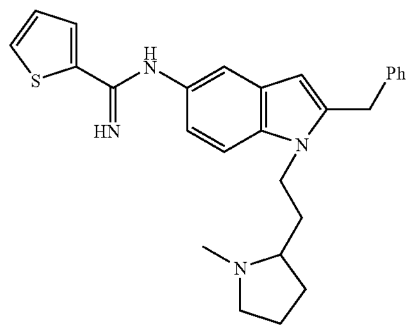 | 0.19 | 7.9 | | 41.57 |
| 2 | 11 | 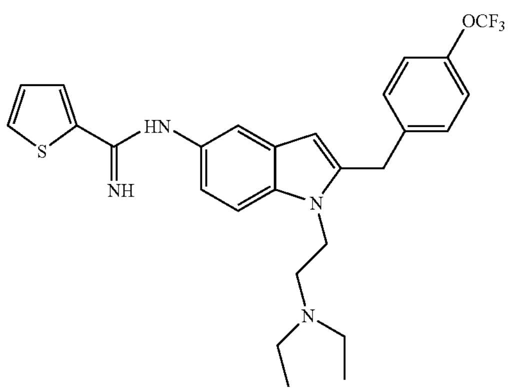 | 0.8 | 4.5 | 17 | 5.62 |
| 3 | 14 | 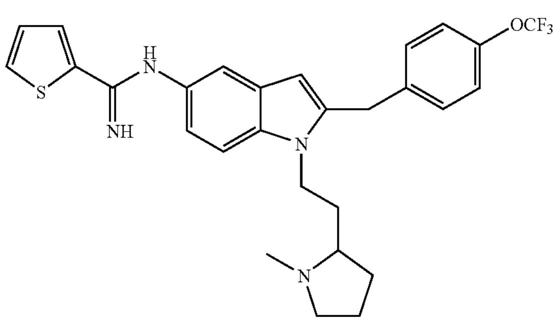 | 0.31 | 1.52 | 93 | 4.90 |
| 4 | 18 | 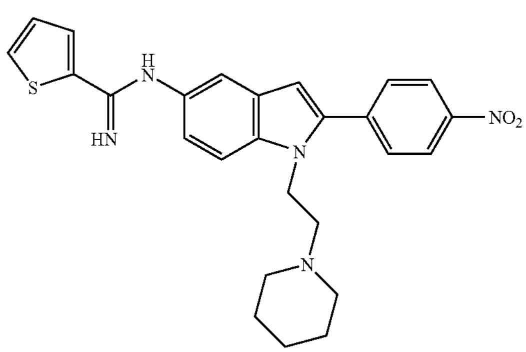 | 0.41 | 19 | | 46.34 |

TABLE 3-continued

Selective inhibition of human NOS by compounds of the Invention

| Ex No. | Compound No | Structure | Human nNOS (μM) | Human eNOS (μM) | Human iNOS (μM) | Ratio e/n |
|---|---|---|---|---|---|---|
| 5 | 21 | 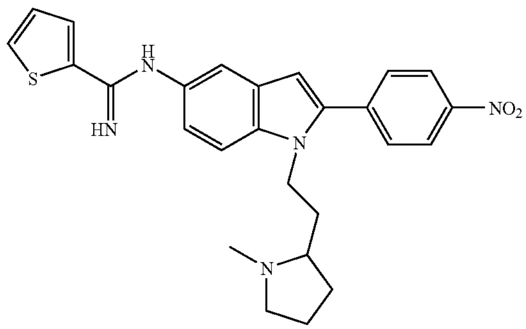 | 1.28 | 13.2 | 52 | 10.31 |
| 6 | 25 | 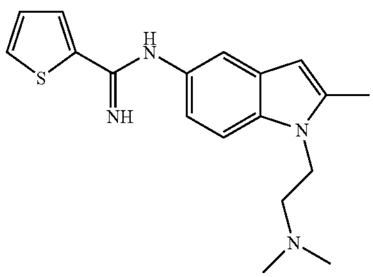 | 0.82 | 3.18 | | 3.88 |
| 7 | 28 | 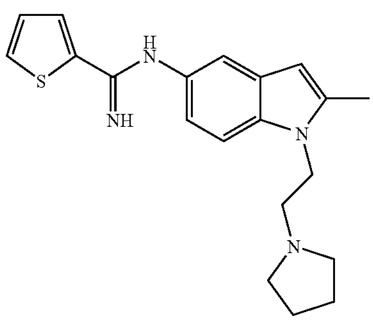 | 0.20 | 1.49 | | 7.41 |
| 8 | 32 | 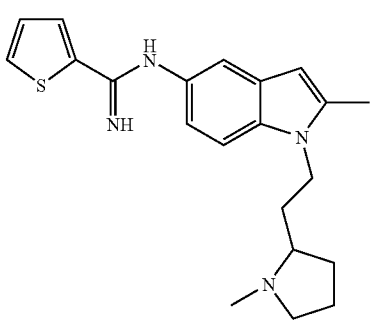 | 0.14 | 2.87 | | 20.2 |

TABLE 3-continued
Selective inhibition of human NOS by compounds of the Invention
| Ex No. | Compound No | Structure | Human nNOS (μM) | Human eNOS (μM) | Human iNOS (μM) | Ratio e/n |
|---|---|---|---|---|---|---|
| 9 | 37 | 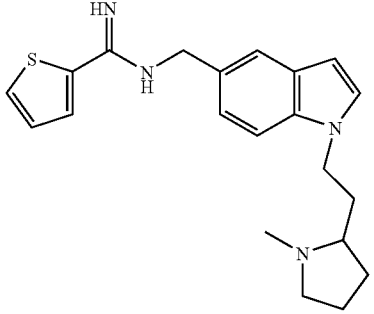 | 73 | 91 | Not determined | 1.24 |
| 10 | 40 | 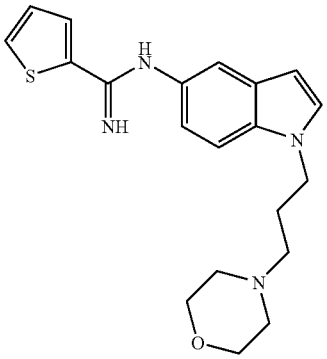 | 0.66 | 6 | | 9.09 |
| 11 | 42 | 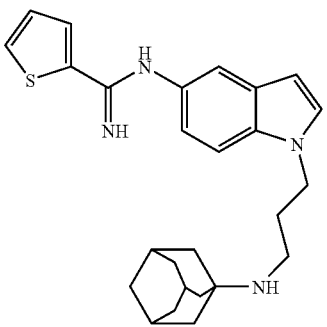 | 0.36 | 3.15 | | 8.67 |
| 12 | 44 | 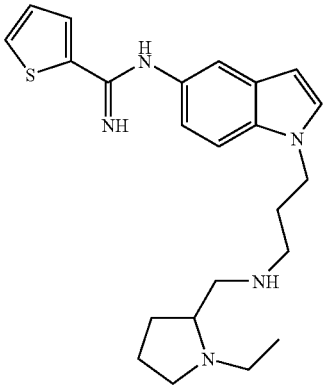 | 0.13 | 6.33 | Not determined | 47.95 |

TABLE 3-continued
Selective inhibition of human NOS by compounds of the Invention
| Ex No. | Compound No | Structure | Human nNOS (μM) | Human eNOS (μM) | Human iNOS (μM) | Ratio e/n |
|---|---|---|---|---|---|---|
| 13 | 46 | 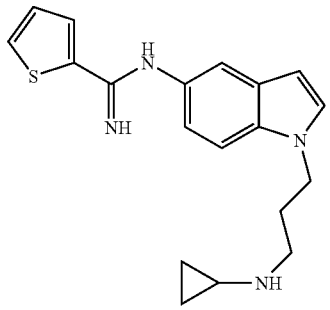 | 0.26 | 8.72 | | 32.53 |
| 14 | 48 | 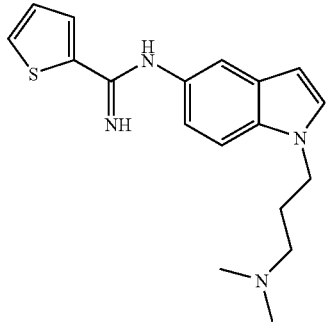 | 0.47 | 12.4 | | 25.88 |
| 15 | 53 | 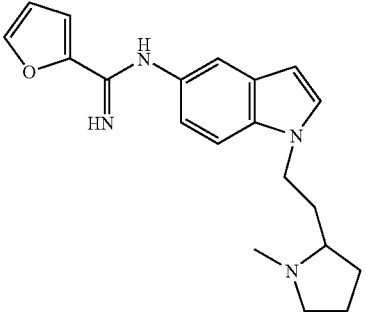 | 0.25 | 13.9 | | 54.94 |
| 15 | 54 | 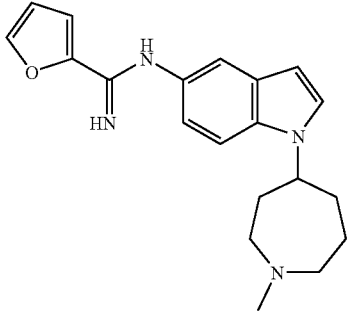 | 0.43 | 38.5 | 49 | 88.70 |

TABLE 3-continued

Selective inhibition of human NOS by compounds of the Invention

| Ex No. | Compound No | Structure | Human nNOS (μM) | Human eNOS (μM) | Human iNOS (μM) | Ratio e/n |
|---|---|---|---|---|---|---|
| 16 | (+)-55 | (+)-55 | 0.40 | 24.5 | 10 | 60.49 |
| 16 | (−)-55 | (−)-isomer | 0.56 | 28.5 | 46 | 50.08 |
| 17 | 56 | 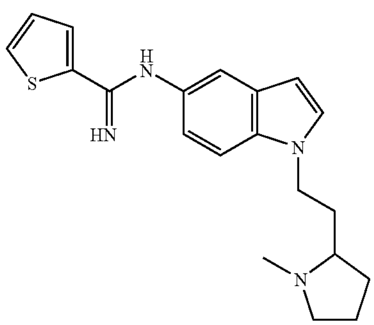 | 0.07 | 4.49 |  | 63.23 |
| 18 | (+)-57 | (+)-isomer | 0.06 | 3.37 | 22 | 55.79 |

TABLE 3-continued
Selective inhibition of human NOS by compounds of the Invention
| Ex No. | Compound No | Structure | Human nNOS (μM) | Human eNOS (μM) | Human iNOS (μM) | Ratio e/n |
|---|---|---|---|---|---|---|
| 18 | (−)-57 | 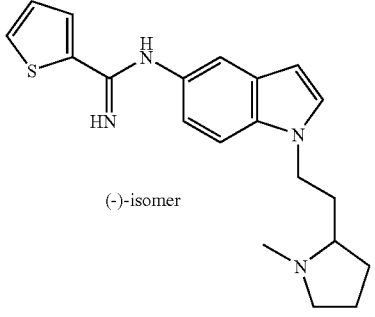 (−)-isomer | 0.02 | 1.92 | 1.7 | 83.84 |
| 19 | 58 | 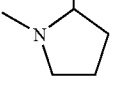 | 0.12 | 11.5 | 7.6 | 93.49 |
| 20 | 59 | 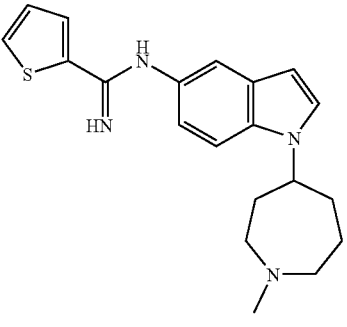 | 1.44 | 8.65 | Not Active | 6.00 |
| 21 | 62 | 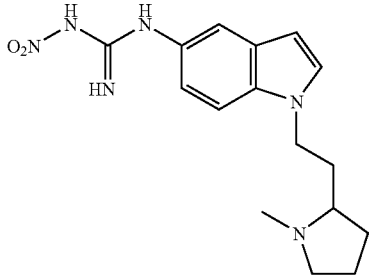 | 0.09 | 6.4 | | 68.01 |

TABLE 3-continued

Selective inhibition of human NOS by compounds of the Invention

| Ex No. | Compound No | Structure | Human nNOS (μM) | Human eNOS (μM) | Human iNOS (μM) | Ratio e/n |
|---|---|---|---|---|---|---|
| 22 | 71 | | 0.36 | 12.1 | 29 | 32.79 |
| 23 | 74 | | 0.38 | 2.57 | | 6.74 |
| 24 | 77 | | 0.55 | 3.08 | | 5.54 |
| 25 | 82 | | 0.41 | 15.8 | 15 | 38.07 |
| 26 | 86 | | 0.76 | 18.9 | 11.0 | 24.70 |

TABLE 3-continued

Selective inhibition of human NOS by compounds of the Invention

| Ex No. | Compound No | Structure | Human nNOS (μM) | Human eNOS (μM) | Human iNOS (μM) | Ratio e/n |
|---|---|---|---|---|---|---|
| 27 | 90 | 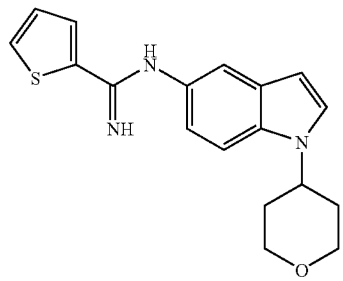 | 1.04 | 9.72 | | 9.34 |
| 28 | 93 | 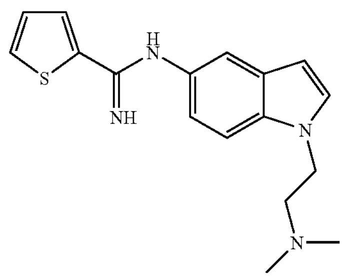 | 0.17 | 3.70 | | 21.3 |
| 29 | 96 | 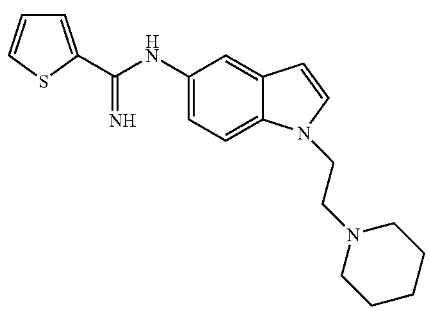 | 0.17 | 9.2 | | 53.80 |
| 30 | 104 | 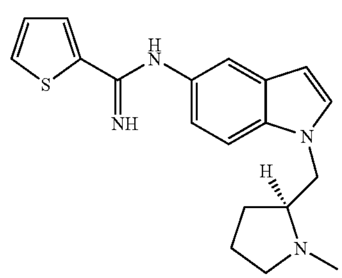 | 0.11 | 3.35 | | 30.2 |
| 31 | 107 | 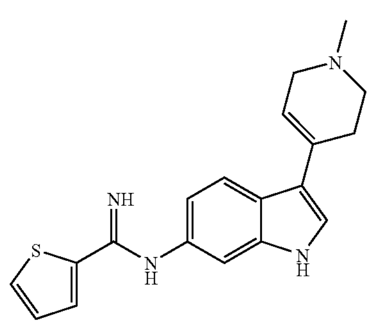 | 1.1 | 29 | 12 | 26.36 |

TABLE 3-continued

Selective inhibition of human NOS by compounds of the Invention

| Ex No. | Compound No | Structure | Human nNOS (μM) | Human eNOS (μM) | Human iNOS (μM) | Ratio e/n |
|---|---|---|---|---|---|---|
| 31 | 108 | 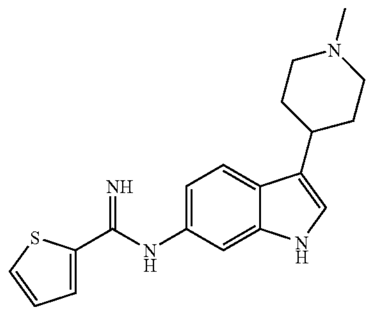 | 0.71 | 17 | 9.3 | 23.94 |
| 32 | 111 | 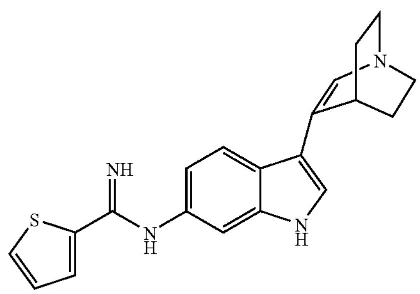 | 1.53 | 46.2 | | 30.19 |
| 33 | 112 | 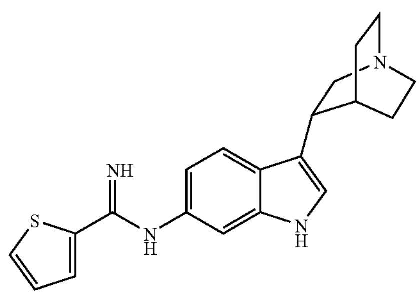 | 1.13 | 31.4 | 0.4 | 27.78 |
| 34 | 117 | 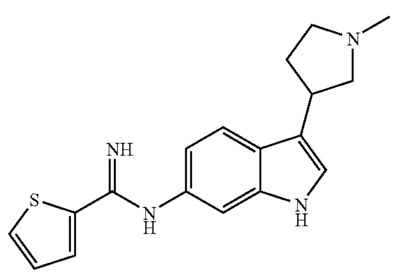 | 0.2 | 7.09 | | 35.45 |
| 35 | 123 | 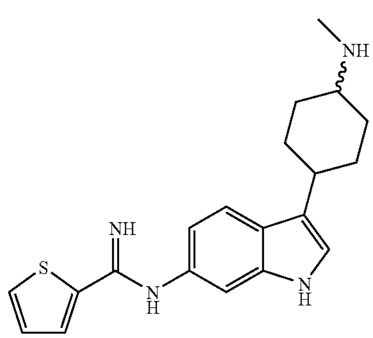 | 0.32 | 9.47 | | 28.96 |

TABLE 3-continued

Selective inhibition of human NOS by compounds of the Invention

| Ex No. | Compound No | Structure | Human nNOS (μM) | Human eNOS (μM) | Human iNOS (μM) | Ratio e/n |
|---|---|---|---|---|---|---|
| 36 | 125 | 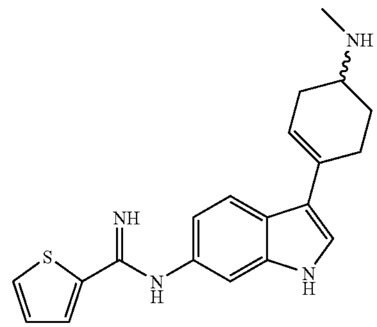 | 0.45 | 21.0 | | 46.4 |
| 37 | 129 | 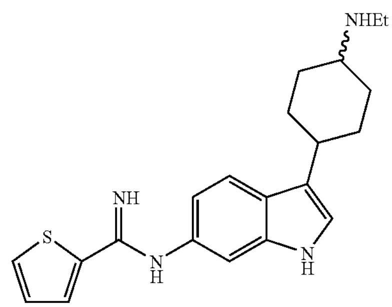 | 0.26 | 14.9 | 4.2 | 57.08 |
| 38 | 132 | 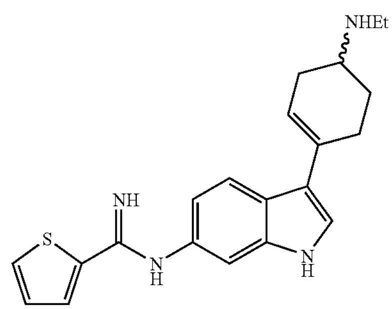 | 0.73 | 17.4 | 1.93 | 23.83 |
| 39 | 137 | 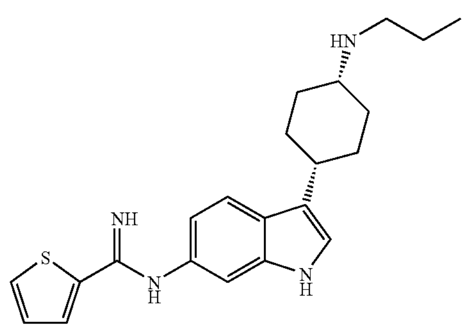 | 0.20 | 5.54 | 8.26 | 27.02 |

TABLE 3-continued

Selective inhibition of human NOS by compounds of the Invention

| Ex No. | Compound No | Structure | Human nNOS (μM) | Human eNOS (μM) | Human iNOS (μM) | Ratio e/n |
|---|---|---|---|---|---|---|
| 39 | 138 | 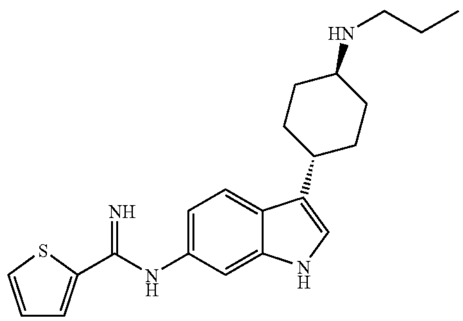 | 0.72 | 11.40 | | 15.83 |
| 40 | 142 | 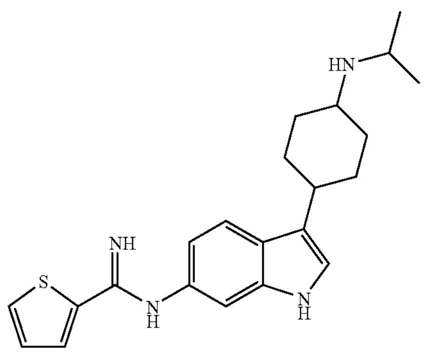 | 0.29 | 6.99 | | 23.6 |

EXAMPLE 19

Efficacy in Models Predictive of Neuropathic-like Pain States

The efficacy of compound 107 for the treatment of neuropathic pain was assessed using standard animal models predictive of anti-hyperalgesic and anti-allodynic activity induced by a variety of methods.

The Chung Model of Injury-Induced Neuropathic-Like Pain:

The experimental designs for the Chung Spinal Nerve Ligation SNL Model assay for neuropathic pain are depicted in FIG. 1. Nerve ligation injury was performed according to the method described by Kim and Chung (Kim and Chung, Pain 50:355-363, 1992). This technique produces signs of neuropathic dysesthesias, including tactile allodynia, thermal hyperalgesia, and guarding of the affected paw. Rats were anesthetized with halothane and the vertebrae over the L4 to S2 region were exposed. The L5 and L6 spinal nerves were exposed, carefully isolated, and tightly ligated with 4-0 silk suture distal to the DRG. After ensuring homeostatic stability, the wounds were sutured, and the animals allowed to recover in individual cages. Sham-operated rats were prepared in an identical fashion except that the L5/L6 spinal nerves were not ligated. Any rats exhibiting signs of motor deficiency were euthanized. After a period of recovery following the surgical intervention, rats show enhanced sensitivity to painful and normally non-painful stimuli.

Figure 2:
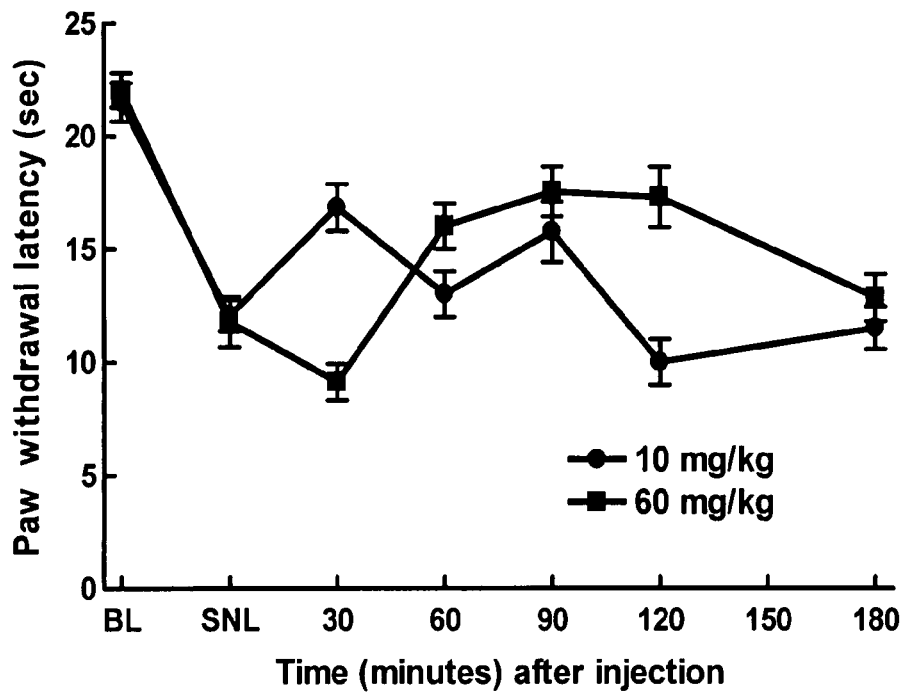
FIG. 2 shows the effect of 10 and 60 mg/kg i.p. administration of compound 107 on the reversal of thermal hyperalgesia in rats after L5/L6 spinal nerve ligation (Chung neuropathic pain model).

After one standard dose (10 or 60 mg/kg), injected i.p. according to the published procedure, there is a clear antihyperalgesic effect of nNOS selective compound 107 (see FIG. 2).

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:

1. A compound of the formula:

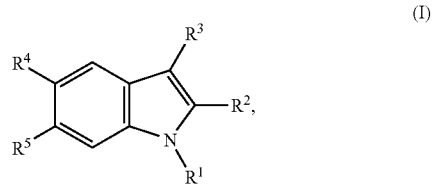

(I)

or a pharmaceutically acceptable salt or prodrug thereof, wherein, $R^1$ is H, optionally substituted $C_{1-6}$ alkyl, optionally substituted $C_{1-4}$ alkaryl, optionally substituted $C_{1-4}$ alkheterocyclyl, or optionally substituted $C_{2-9}$ heterocyclyl;

each of $R^2$ and $R^3$ is, independently, H, Hal, optionally substituted $C_{1-6}$ alkyl, optionally substituted $C_{6-10}$ aryl, optionally substituted $C_{1-6}$ alkaryl, optionally substituted $C_{2-9}$ heterocyclyl, or optionally substituted $C_{1-4}$ alkheterocyclyl;

$R^4$ is H, $R^{4A}C(NH)NH(CH_2)_{r4}$, or $R^{4B}NHC(S)NH(CH_2)_{r4}$, wherein r4 is an integer from 0 to 2, $R^{4A}$ is optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, optionally substituted $C_{1-4}$ thioalkheterocyclyl, or substituted amino; $R^{4B}$ is unsubstituted $C_{1-6}$ alkyl, optionally substituted $C_{6-10}$ aryl, optionally substituted $C_{2-9}$ heterocyclyl, optionally substituted $C_{1-6}$ thioalkoxy, optionally substituted $C_{1-4}$ thioalkaryl, optionally substituted aryloyl, optionally substituted $C_{1-4}$ thioalkheterocyclyl, or optionally substituted amino; and $R^5$ is H, $R^{5A}C(NH)NH(CH_2)_{r5}$, or $R^{5A}NHC(S)NH(CH_2)_{r5}$, wherein r5 is an integer from 0 to 2, $R^{5A}$ is optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, optionally substituted $C_{1-4}$ thioalkheterocyclyl, or optionally substituted amino;

wherein one, but not both, of $R^4$ and $R^5$ is H, and
when $R^4$ is H, $R^1$ is H, and
when $R^5$ is H, $R^3$ is H.

2. A compound of claim 1, wherein
$R^1$ is H, optionally substituted $C_{1-6}$ alkyl, or optionally substituted $C_{2-9}$ heterocyclyl,
each of $R^2$ and $R^3$ is, independently, H, optionally substituted $C_{1-6}$ alkaryl, optionally substituted $C_{6-10}$ aryl, or optionally substituted $C_{2-9}$ heterocyclyl;
$R^4$ is H or $R^{4A}C(NH)NH(CH_2)_{r4}$, wherein r4 is an integer from 0 to 1, and $R^{4A}$ is optionally substituted $C_{2-9}$ heterocyclyl, or substituted amino; and
$R^5$ is H or $R^{5A}C(NH)NH(CH_2)_{r5}$, wherein r5 is an integer from 0 to 1, and $R^{5A}$ is optionally substituted $C_{2-9}$ heterocyclyl, or optionally substituted amino.

3. A compound of claim 1, wherein
$R^1$ is H, optionally substituted $C_{1-6}$ alkyl, or optionally substituted $C_{2-9}$ heterocyclyl.
each of $R^2$ and $R^3$ is, independently, H, optionally substituted $C_{1-6}$ alkaryl, optionally substituted $C_{6-10}$ aryl, or optionally substituted $C_{2-9}$ heterocyclyl; and
each of $R^4$ and $R^5$ is, independently, H or the group

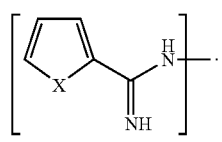

wherein X = O or S

4. A compound of claim 2, wherein
$R^1$ is H, optionally substituted $C_{1-6}$ alkyl, or optionally substituted $C_{2-9}$ heterocyclyl.

each of $R^2$ and $R^3$ is, independently, H, optionally substituted $C_{1-6}$ alkaryl, optionally substituted $C_{6-10}$ aryl, or optionally substituted $C_{2-9}$ heterocyclyl; and
each of $R^4$ and $R^5$ is, independently, H or the group

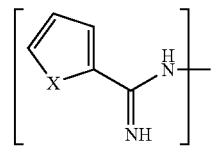

wherein X = O or S.

5. A compound of claim 1, wherein $R^3$ is H, $R^5$ is H, and $R^4$ is

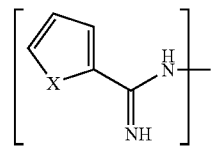

wherein X = O or S.

6. A compound of claim 5, wherein $R^1$ is optionally substituted $C_{1-4}$ alkheterocyclyl, optionally substituted $C_{2-9}$ heterocyclyl, or $C_{1-6}$ alkyl substituted with $NR^GR^H$, where each of $R^G$ and $R^H$ is, independently, selected from the group consisting of hydrogen; alkyl of one to six carbon atoms; cycloalkyl of three to eight carbon atoms; adamantly; and alkcycloalkyl, where the cycloalkyl group is of three to eight carbon atoms, and the alkylene group is of one to ten carbon atoms.

7. A compound of claim 5, wherein $R_2$ is H, $C_{1-6}$ alkyl, optionally substituted $C_{6-10}$ aryl, or optionally substituted $C_{1-6}$ alkaryl.

8. A compound of claim 1, wherein $R^1$ is H, $R^4$ is H, and $R^5$ is

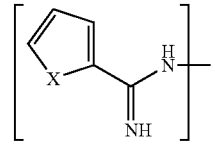

wherein X = O or S.

9. A compound of claim 8, wherein $R^3$ is optionally substituted $C_{2-9}$ heterocyclyl. or optionally substituted cycloalkyl.

10. A compound of claim 1, wherein $R^1$ or $R^3$ is

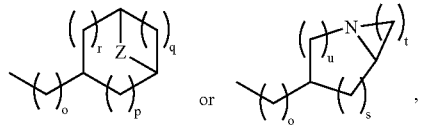

wherein Z is $NR^6$, $R^6$ is H or $C_{1-6}$ alkyl, o is an integer from 0 to 3, p is an integer from 1 to 2, q is an integer from 0 to 2, r is an integer from 0 to 1, s is an integer from 1 to 3, u is an integer from 0 to 1, and t is an integer from 5 to 7, and wherein said $R^1$ or $R^3$ substituent includes 0 to 6 carbon-carbon double bonds or 0 or 1 carbon-nitrogen double bonds.

11. A compound selected from the group consisting of:
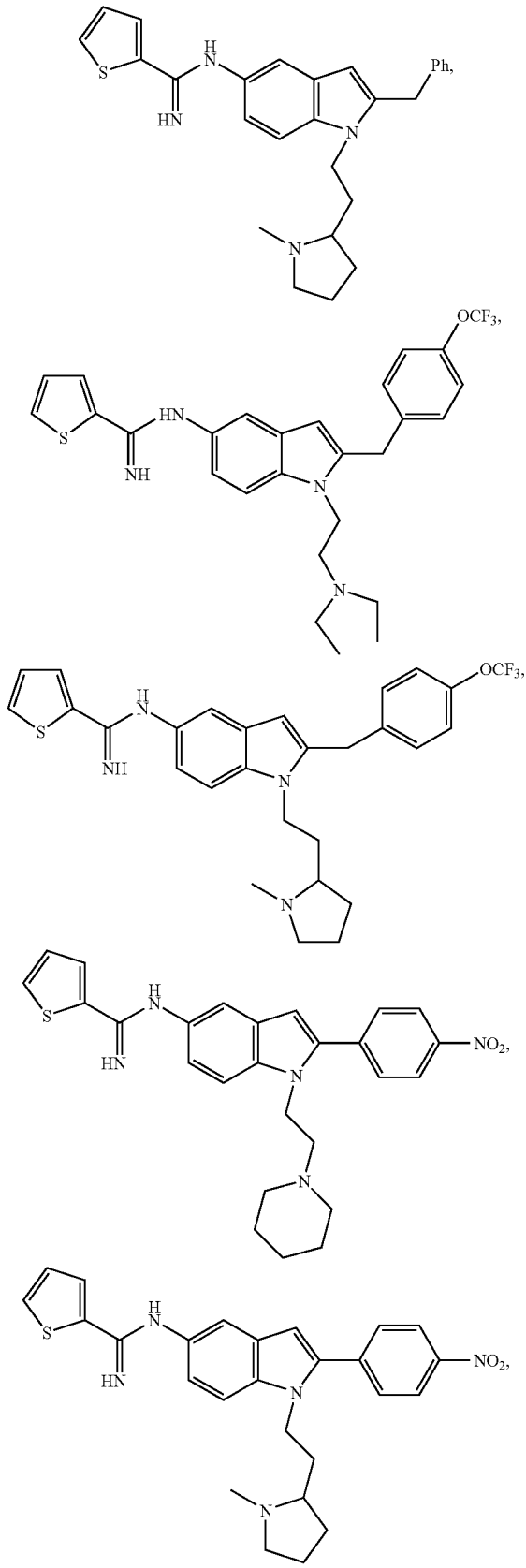
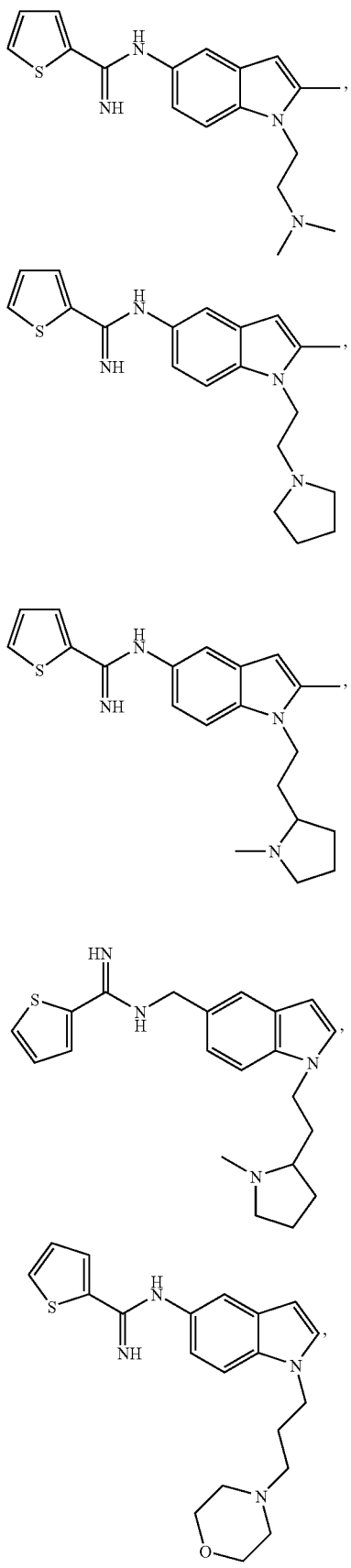

167
-continued
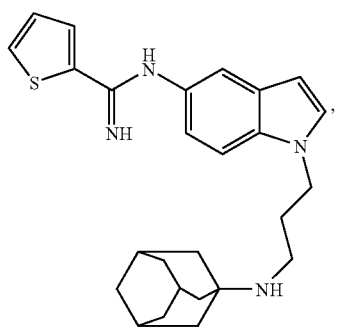
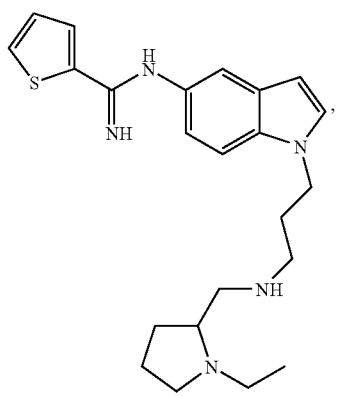
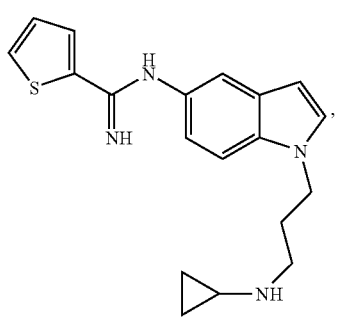
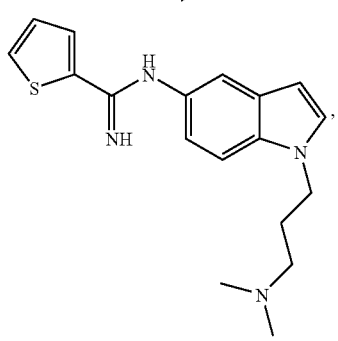
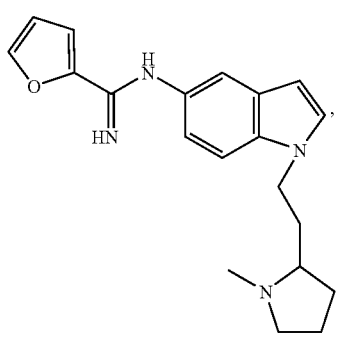
168
-continued
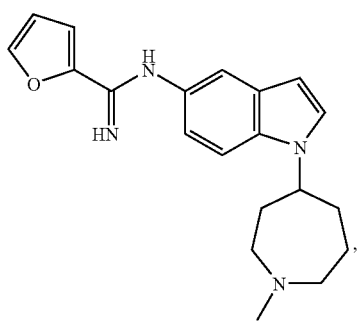
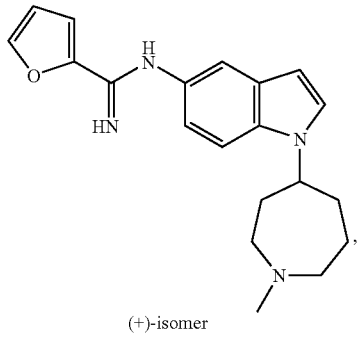
(+)-isomer
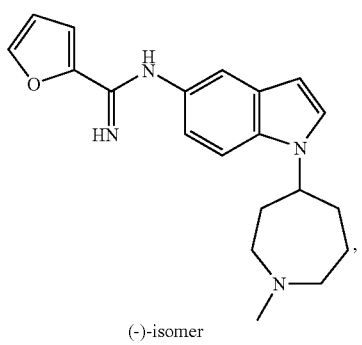
(−)-isomer
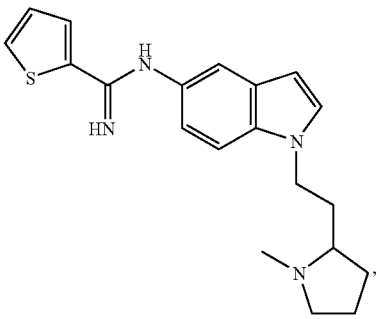
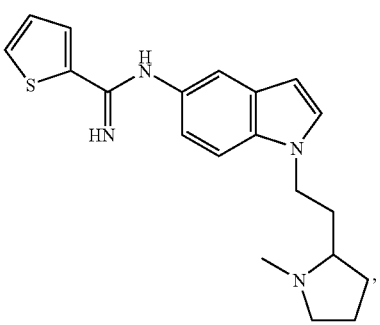
(+)-isomer

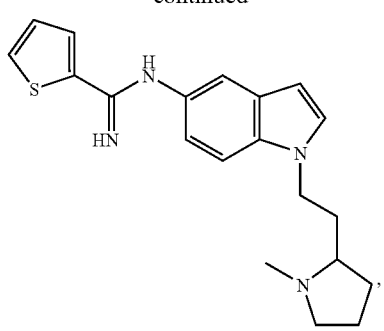
(-)-isomer
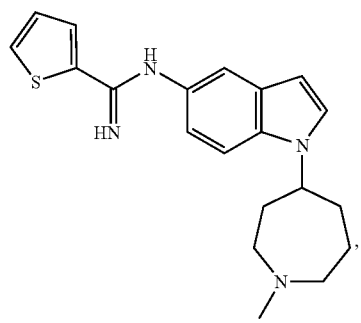
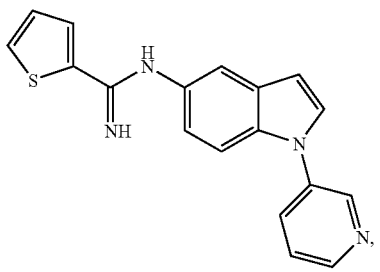
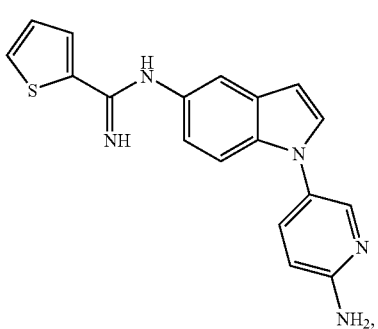
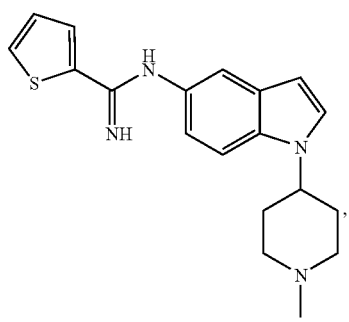
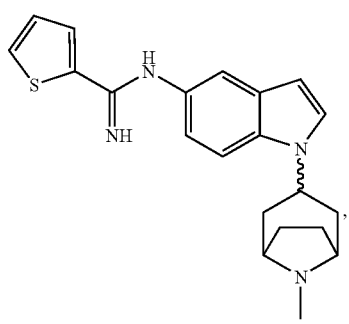
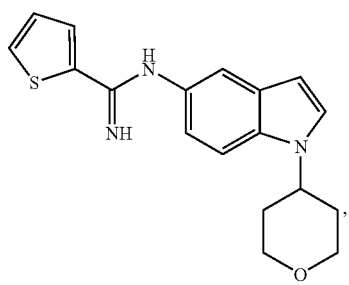

171
-continued
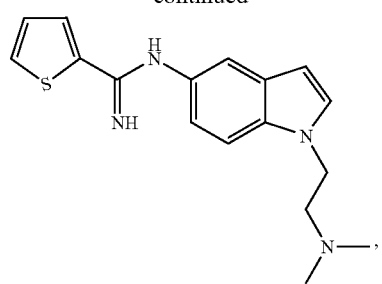
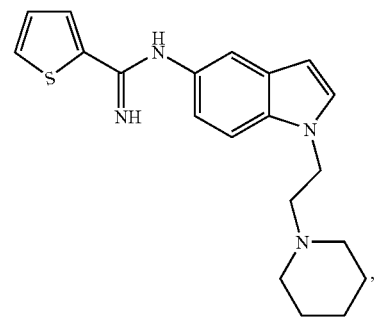
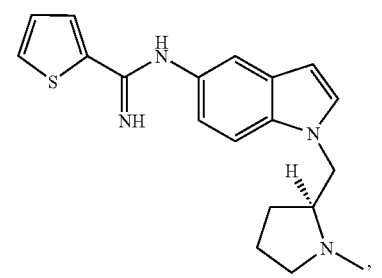
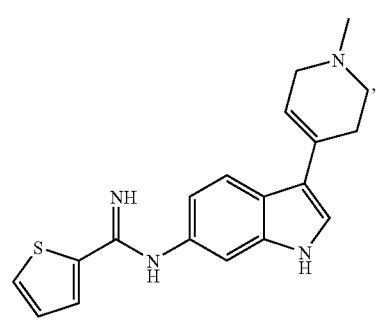
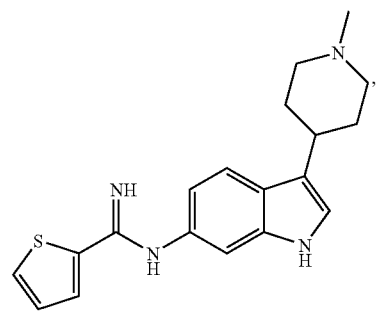
172
-continued
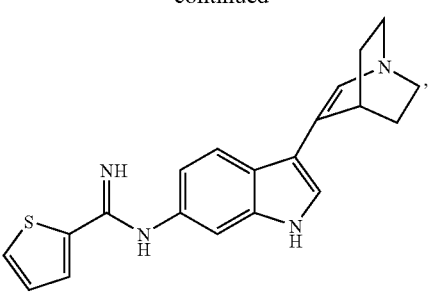
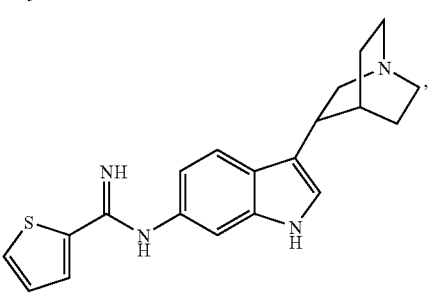
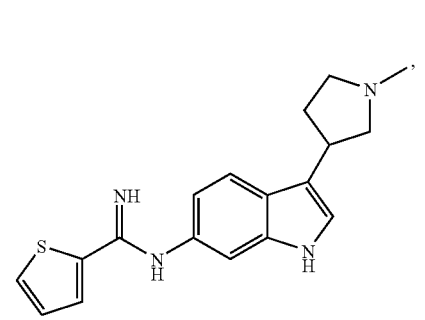
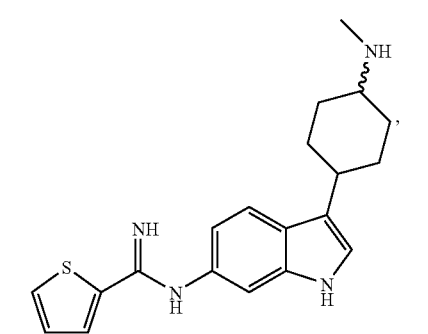
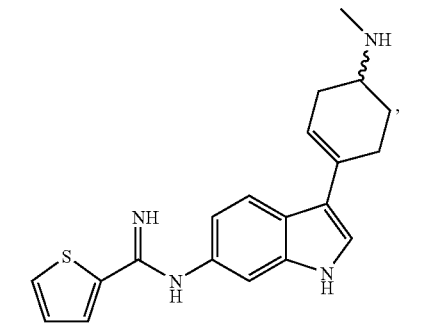

-continued

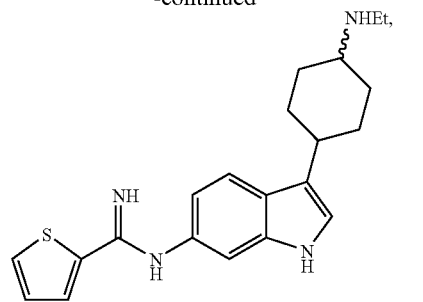

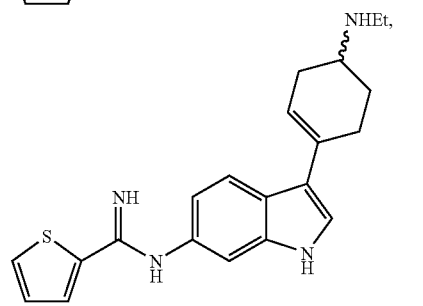

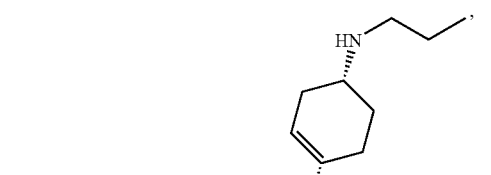

, and

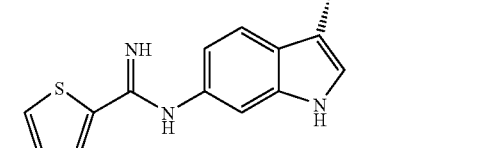

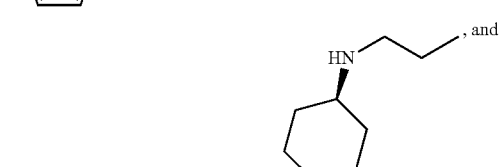

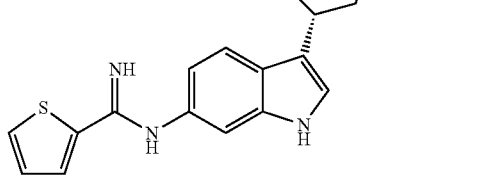

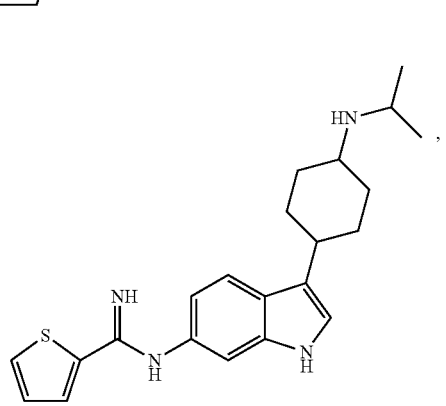

or an enantiomer, pharmaceutically acceptable salt, or prodrug thereof.

12. The compound of claim 1, wherein said compound selectively inhibits neuronal nitric oxide synthase (nNOS) over endothelial nitric oxide synthase (eNOS) or inducible nitric oxide synthase (iNOS).

13. The compound of claim 6, wherein said compound selectively inhibits nNOS over both eNOS and iNOS.

14. A pharmaceutical composition comprising a compound of claim 1 and a pharmaceutically acceptable excipient.

15. The compound of claim 1, wherein $R^2$ is H.

16. A compound of the formula

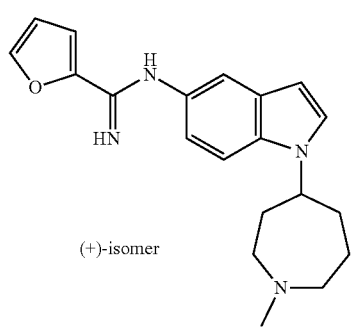

(+)-isomer or a pharmaceutically acceptable salt thereof.

17. A compound of the formula

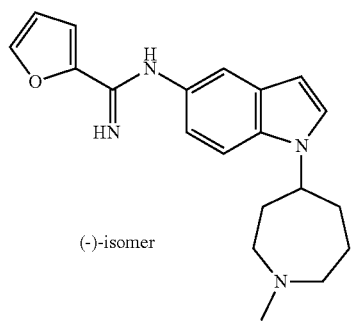

(-)-isomer or a pharmaceutically acceptable salt thereof.

18. A compound of the formula

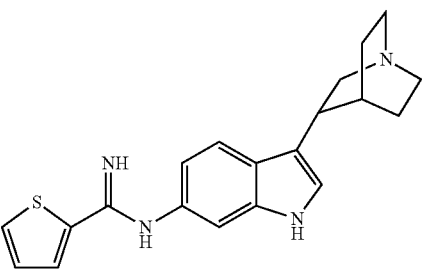

or an enantiomer or a pharmaceutically acceptable salt thereof.

19. A compound of the formula
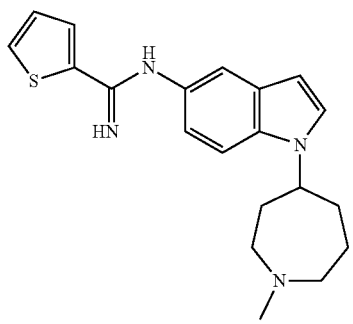
or an enantiomer or a pharmaceutically acceptable salt thereof.
20. A compound of the formula
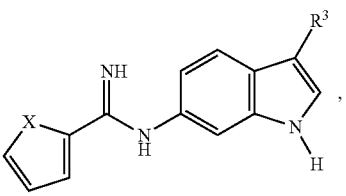
or a pharmaceutically acceptable salt or prodrug thereof, wherein X is O or S, and $R^3$ is cycloalkyl of three to eight carbon atoms substituted with an optionally substituted amino group.
* * * * *

UNITED STATES PATENT AND TRADEMARK OFFICE
CERTIFICATE OF CORRECTION

PATENT NO. : 7,989,447 B2
APPLICATION NO. : 11/787167
DATED : August 2, 2011
INVENTOR(S) : Maddaford et al.

It is certified that error appears in the above-identified patent and that said Letters Patent is hereby corrected as shown below:

Column 38, Under Scheme 8, replace "H3PO4A$_c$OH or
 pyrrolidine/ethanol" with
 --$H_3PO_4A_cOH$ or pyrrolidine/ethanol--.

Column 56, Line 14, replace "lomoxicam" with
 --lornoxicam--.

Column 75, Line 24, replace "layer washed" with
 --layer was washed--.

Column 95, Line 38, replace "pad washed" with
 --pad was washed--.

Column 102, Line 53-54, replace "pad washed" with
 --pad was washed--.

Column 121, Line 58, replace "bed and washed with" with
 --bed and was washed with--.

Column 122, Line 59, "bed and washed with" with
 --bed and was washed with--.

Column 127, Line 13, replace "layer washed" with
 --layer was washed--;

Line 50, replace "layer washed" with
 --layer was washed--.

Signed and Sealed this
Twelfth Day of March, 2013

Teresa Stanek Rea
*Acting Director of the United States Patent and Trademark Office*

Column 129, Line 17, replace "layer washed" with
--layer was washed--.

Column 130, Line 59, replace "layer washed" with
--layer was washed--.

Column 131, Line 36-37, replace "layer washed" with
--layer was washed--.

Column 138, Line 66, replace "layer washed" with
--layer was washed--.

Column 163, Claim 3, Line 63, replace "wherein X = O or S" with
--wherein X = O or S.--;

Claim 4, Line 67-68, replace "heterocyclyl." with
--heterocyclyl--.

Column 164, Claim 7, Line 36, replace "$R_2$" with
--$R^2$--;

Claim 9, Line 51-52, replace "$C_{2-9}$ heterocyclyl. or optionally substituted cycloalkyl." with --$C_{2-9}$ heterocyclyl.--.